*(12)* United States Patent
Chrusciel et al.

US009994521B2

(10) Patent No.: US 9,994,521 B2
(45) Date of Patent: *Jun. 12, 2018

(54) THERAPEUTIC COMPOUNDS AND COMPOSITIONS

(71) Applicant: eXIthera Pharmaceuticals Inc., Westborough, MA (US)

(72) Inventors: Robert A. Chrusciel, Portage, MI (US); Robert C. Gadwood, Portage, MI (US); Neil J. Hayward, Hudson, MA (US); Michael J. Melnick, Portage, MI (US); Manuel A. Navia, Boston, MA (US); Toni J. Poel, Plainwell, MI (US); Frans L. Stassen, Cambridge, MA (US); Catherine A. Stewart, Wayland, MI (US)

(73) Assignee: eXIthera Pharmaceuticals, Inc., Westborough, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/290,565

(22) Filed: Oct. 11, 2016

(65) Prior Publication Data

US 2017/0037003 A1 Feb. 9, 2017

Related U.S. Application Data

(63) Continuation of application No. 14/614,169, filed on Feb. 4, 2015, now Pat. No. 9,499,532.

(60) Provisional application No. 61/937,031, filed on Feb. 7, 2014.

(51) Int. Cl.
| | |
|---|---|
| *C07D 205/08* | (2006.01) |
| *C07D 417/06* | (2006.01) |
| *C07D 401/06* | (2006.01) |
| *C07D 405/14* | (2006.01) |

(52) U.S. Cl.
CPC ......... *C07D 205/08* (2013.01); *C07D 401/06* (2013.01); *C07D 405/14* (2013.01); *C07D 417/06* (2013.01)

(58) Field of Classification Search
None
See application file for complete search history.

(56) References Cited

U.S. PATENT DOCUMENTS

| | | |
|---|---|---|
| 4,595,532 A | 6/1986 | Miller |
| 6,335,324 B1 | 1/2002 | Bisacchi et al. |
| 7,501,404 B2 | 3/2009 | Bannister et al. |

FOREIGN PATENT DOCUMENTS

| | | | | |
|---|---|---|---|---|
| CA | 2536435 A1 | * | 3/2005 | ............. A61K 31/00 |
| EP | 1099690 A1 | * | 5/2001 | ........... C07D 205/08 |
| EP | 1099690 A4 | | 10/2001 | |
| WO | WO 2006108039 A2 | * | 10/2006 | ........... C07D 205/08 |

OTHER PUBLICATIONS

MedicineNet. MedicineNet.com. Deep Vein Thrombosis. (2015). < http://medicinenet.com/deep_vein_thrombosis/article.htm>.*
WebMd. Deep Vein Thrombosis Health Center: How to Prevent Deep Vein Thrombosis (DVT). (2015) < http://www.webmd.com/dvt/deep-vein-thrombosis-prevent-dvt>.*
The NIH. How Can Deep Vein Thrombosis be Prevented? (2011) < http://www.nhlbi.nih.gov/health/health-topics/topics/dvt/prevention#>.*
Meijers et al., "High Levels of Coagulation Factor XI as a Risk Factor for Venous Thrombosis," The New England Journal of Medicine, 342(10):696-701 (2000).
International Search Report and Written Opinion for PCT/US2015/014478, dated Jul. 23, 2015.

* cited by examiner

*Primary Examiner* — Deepak R Rao
*Assistant Examiner* — Laura M Daniel
(74) *Attorney, Agent, or Firm* — Goodwin Procter LLP

(57) ABSTRACT

The present invention provides compounds and compositions that inhibit Factor XIa or kallikrein and methods of using these compounds and composition.

18 Claims, 24 Drawing Sheets

Chart A.

| Compound Number | Structure | R²CH₂Br | R³OH | R⁴: Reagent Type for Urea Formation | MS (ESI+) m/z | HPLC (min) | HPLC Method |
|---|---|---|---|---|---|---|---|
| 1 | (structure with CO₂Bn, aminopyridine, ·TFA) | NBoc₂-pyridyl-CH₂Br | BnOH | PhCH(CH₃)N=C=O | 459.3 (M+H)⁺ | 3.40 | B |
| 2 | (structure with CO₂Me, chlorothienyl) | 5-chlorothienyl-CH₂Br | BnOH | PhCH(CH₃)N=C=O | 407.1/409.2 (M+H)⁺, 429.2/431.1 (M+Na)⁺ | 4.479 | A |
| 3 | (structure with CO₂Bn, chlorothienyl) | 5-chlorothienyl-CH₂Br | BnOH | PhCH(CH₃)N=C=O | 483.1/485.1 (M+H)⁺, 505.2/507.1 (M+Na)⁺ | 5.011 | A |
| 4 | (structure with CO₂Bn, chloropyridyl) | 6-chloropyridyl-CH₂Br | BnOH | PhCH(CH₃)N=C=O | 477.9 (M+H)⁺ | 4.390 | B |
| 5 | (structure with CO₂H, chlorothienyl) | 5-chlorothienyl-CH₂Br | PMBOH | PhCH(CH₃)N=C=O | 393.1/395.1 (M+H)⁺, 415.0/417.1 (M+Na)⁺ | 4.034 | A |
| 6 | (structure with CO₂H, chlorothienyl, diphenylmethyl) | 5-chlorothienyl-CH₂Br | PMBOH | Ph₂CHN=C=O | 455.1 (M+H)⁺ | 4.126 | A |

FIG. 1A

| # | Structure | Reagent | Alcohol | Isocyanate | MS | RT | Class |
|---|---|---|---|---|---|---|---|
| 31 | (structure) | N(Boc)PMB / Br-pyridine | PMBOH | diphenethyl isocyanate | 445.3 (M+H)+ | 3.46 | C |
| 32 | (structure) | N(Boc)PMB / Br-pyridine | BnOH | isopropyl isocyanate | 335.3 (M+H)+ | 2.45 | A |
| 36 | (structure) | N(Boc)PMB / Br-pyridine | PMBOH | phenethyl isocyanate | 383.3 (M+H)+ | 3.05 | C |
| 37 | (structure) | N(Boc)PMB / Br-pyridine | BnOH | 4-F-phenethyl isocyanate | 387.3 (M+H)+ | 2.84 | A |
| 38 | (structure) | N(Boc)PMB / Br-pyridine | BnOH | cyclohexyl isocyanate | 375.3 (M+H)+ | 3.21 | A |
| 40* | (structure) | N(Boc)PMB / Br-pyridine | PMBOH | pyridyl carbamate (4-NO2-phenyl) | 370.3 (M+H)+ | 1.37, 1.55 | C |
| 42* | (structure) | N(Boc)PMB / Br-pyridine | BnOH | 3-F-phenethyl isocyanate | 387.1 (M+H)+ | 2.70 | A |

FIG. 1C

| | | | | | | |
|---|---|---|---|---|---|---|
| 43 | ![structure] | N(Boc)PMB pyridine-Br | PMBOH | ![naphthyl-CH2-NCO] | 405.3 (M+H)+ | 3.18 | C |
| 44 | ![structure] | N(Boc)PMB pyridine-Br | PMBOH | ![Ph-CH(CF3)-NHC(O)O-C6H4-NO2] | 423.3 (M+H)+ | 3.24 | C |
| 45A** | ![structure] | N(Boc)PMB pyridine-Br | BnOH | ![pyridyl-CH(CH3)-NHC(O)O-C6H4-NO2] | 384.3 (M+H)+ | 1.27 | A |
| 45B** | ![structure] | N(Boc)PMB pyridine-Br | BnOH | ![pyridyl-CH(CH3)-NHC(O)O-C6H4-NO2] | 384.3 (M+H)+ | 1.54 | A |
| 47* | ![structure] | N(Boc)PMB pyridine-Br | BnOH | ![4-OCF3-C6H4-CH(CH3)-NCO] | 453.3 (M+H)+ | 3.17, 3.20 | A |
| 48 | ![structure] | N(Boc)PMB pyridine-Br | PMBOH | ![Bn-NCO] | 355.2 (M+H)+ | 2.368 | B |
| 49 | ![structure] | N(Boc)PMB pyridine-Br | BnOH | ![3-OCF3-C6H4-CH(CH3)-NCO] | 453.3 (M+H)+ | 3.47 | C |
| 50A** | ![structure] | N(Boc)PMB pyridine-Br | BnOH | ![isoquinolinyl-CH(CH3)-NHC(O)O-] | 420.3 (M+H)+ | 1.84 | A |

FIG. 1D

| | | | | | | |
|---|---|---|---|---|---|---|
| 50B** | 52 | 54 | 55 | 91 | 168 | 89 |
| [structure] | [structure] | [structure] | [structure] | [structure] | [structure] | [structure] |
| N(Boc)PMB / Br | N(Boc)PMB / Br | N(Boc)PMB / Br | N(Boc)PMB / Br | N(Boc)PMB / Br | N(Boc)PMB / Br | N(Boc)PMB / Br |
| BnOH | PMBOH | BnOH | PMBOH | PMBOH | PMBOH | PMBOH |
| [structure] | [structure] | [structure] | [structure] | [structure] | [structure] | [structure] |
| 420.3 (M+H)+ | 363.3 (M+H)+ | 370.3 (M+H)+ | 279.2 (M+H)+ | 449.2 (M+H)+ | 453.2 (M+H)+ | 477.2 (M+H)+ |
| 1.78 | 3.23 | 1.66 | 0.900 | 3.39 | 3.54 | 3.88 |
| A | C | C | B | C | C | C |

FIG. 1E

| | | | | | | |
|---|---|---|---|---|---|---|
| 68 | (structure) | N(Boc)PMB / Br | PMBOH | (structure) | 405.1 (M+H)+ | 2.721 | B |
| 123 | (structure) | Cl / Br | BnOH | (structure) | 416.1 (M+H)+ | 3.299 | A |
| 128 | (structure) | Cl / Br | PMBOH | (structure) | 468.0 (M+H)+ | 3.90 | A |
| 169 | (structure) | Cl / Br | PMBOH | (structure) | 434.0 (M+H)+ | 3.12 | A |
| 132 | (structure) | Cl / Br | PMBOH | (structure) | 496.1 (M+H)+ | 4.52 | A |
| 130 | (structure) | N(Boc)PMB / Br | BnOH | (structure) | 449.1 (M+H)+ | 3.57 | C |
| 170 | (structure) | Cl / Br | PMBOH | (structure) | 462.0 (M+H)+ | 3.53 | A |
| 166 | (structure) | N(Boc)PMB / Br | EtOH | (structure) | 477.1 (M+H)+ | 3.95 | C |

FIG. 1F

| | | | | | | |
|---|---|---|---|---|---|---|
| 88 | (structure) | N(Boc)PMB / pyridine-CH2Br | BnOH | (carbamate structure) | 429.1 (M+H)+ | 3.89 | C |
| 95 | (structure) | Cl-pyridine-CH2Br | PMBOH | (structure) | 462.0 (M+H)+ | 3.50 | A |
| 99 | (structure) | NBoc-pyridine-CH2Br | EtOH | (structure) | 491.1 (M+H)+ | 3.409 | B |
| 98 | (structure) | NBoc-pyridine-CH2Br | PMBOH | (structure) | 463.0 (M+H)+ | 3.072 | B |
| 102 | (structure) | thiazole-CH2Br | PMBOH | (structure) | 440.0 (M+H)+ | 3.312 | B |
| 108 | (structure) | Cl-pyridine-CH2Br | PMBOH | (structure) | 468.0 (M+H)+ | 3.77 | A |
| 133 | (structure) | Cl-pyridine-CH2Br | PMBOH | (structure) | 447.9 (M+H)+ | 4.09 | A |
| 131 | (structure) | Br-benzyl-Br | PMBOH | (structure) | 489 (M-H)− | 4.77 | A |

| | | | | | |
|---|---|---|---|---|---|
| 134 | 103 | 135 | 138 | 136 | 104 |
| structure | structure | structure | structure | structure | structure |
| 3-Cl-phenethyl Br | N(Boc)PMB pyridyl-CH2Br | 2-Cl-pyridyl-CH2Br | THPN-indole-CH2Br | benzodioxole-CH2Br | N(Boc)PMB pyridyl-CH2Br |
| PMBOH | EtOH | PMBOH | PMBOH | BnOH | BnOH |
| Cy-CH(CF3)-NHC(O)O-Ph | 4-OCF3-Ph-CH(CH3)-NHC(O)O-Ph | Cy-CH(CF3)-NHC(O)O-Ph | Cy-CH(CF3)-NHC(O)O-Ph | Cy-CH(CF3)-NHC(O)O-Ph | cyclooctyl-CH(CH3)-N=C=O |
| 459.0 (M-H)⁻ | 481.8 (M+H)⁺ | 414.0 (M+H)⁺ | 453.1 (M+H)⁺ | 456.9 (M+H)⁺ | 403.2 (M+H)⁺ |
| 4.91 | 3.428 | 3.45 | 3.92 | 4.238 | 3.65 |
| A | B | C | C | B | C |

| 147 | 149 | 151 | 154 | 155 | 156 |
|---|---|---|---|---|---|
| | | | | | |
| | N(Boc)PMB | N(Boc)PMB | Br, OMe | Br | Br, F, Cl |
| PMBOH | PMBOH | PMBOH | PMBOH | PMBOH | PMBOH |
| | | | | | |
| 430.2 (M+H)+ | 389.3 (M+H)+ | 417.4 (M+H)+ | 457.1 (M+H)+ | 441.2 (M+H)+ | 479.1 (M+H)+ |
| 3.68 | 3.27 | 3.757 | 4.83 | 5.045 | 5.07 |
| C | C | C | C | C | C |

| | | | | | | |
|---|---|---|---|---|---|---|
| 157 | (structure) | (3-Cl-phenethyl Br) | PMBOH | (Ph₂CH-N=C=O) | 461.1 (M-H)⁻ | 5.16 | A |
| 158 | (structure) | (3-Cl-phenethyl Br) | PMBOH | (structure) | 489.2 (M+H)⁺ | 6.12 | A |
| 159 | (structure) | (3-Cl-phenethyl Br) | PMBOH | (structure) | 479.1 (M-H)⁻ | 5.14 | A |
| 192 | (structure) | (3-Cl-phenethyl Br) | PMBOH | (structure) | 393.2 (M-H)⁻ | 5.23 | A |
| 193 | (structure) | (3-Cl-benzyl Br) | PMBOH | (structure) | 447.1 (M+H)⁺ | 5.22 | A |
| 194 | (structure) | (2-Cl-phenethyl Br) | PMBOH | (structure) | 459.1 (M-H)⁻ | 5.48 | A |

| | | | | | | |
|---|---|---|---|---|---|---|
| 97 | ![structure] | ![pyridine-CH2Br with Cl] | PMBOH | ![benzodioxole-CHMe-NHC(O)O-Ph] | 496.0 (M+H)+ | 4.5 | A |
| 107 | ![structure] | ![pyridine-CH2Br with Cl] | PMBOH | ![benzodioxole-CHMe-NHC(O)O-Ph] | 467.9 (M+H)+ | 3.74 | A |
| 171 | ![structure] | ![pyridine-CH2Br with Cl] | PMBOH | ![benzodioxole-CHMe-NHC(O)O-Ph] | 510.0 (M+H)+ | 4.63 | A |
| 114 | ![structure] TFA | ![pyridine-CH2Br with Cl] | PMBOH | ![benzodioxole-CHMe-NHC(O)O-Ph] | 434.0 (M+H)+ | 3.1 | A |
| 152 | ![structure] | ![PhCH2CH2Br] | PMBOH | ![cyclohexyl-CH(CF3)-NHC(O)O-Ph] | 441.4 (M+H)+ | 5.02 | C |
| 153 | ![structure] | ![4-Cl-C6H4-CH2Br] | PMBOH | ![cyclohexyl-CH(CF3)-NHC(O)O-Ph] | 461.3 | 5.09 | C |
| 196 | ![structure] | ![2-Cl-C6H4-CH2Br] | PMBOH | ![cyclohexyl-CH(CF3)-NHC(O)O-Ph] | 447.2 (M+H)+ | 5.187 | A |

\* Compound is a mixture of two diastereomers
\*\* XA, XB: Stereochemistry of diastereomers not assigned

FIG. 1M

Chart B. Nitriles

| Compound Number | Structure | R²Br | R⁴: Reagent Type for Urea Formation | MS (ESI+) m/z | HPLC (min) | HPLC Method |
|---|---|---|---|---|---|---|
| 28 | [structure: azetidinone with CN, CH₂-pyridinyl-NH₂, urea-CH(phenyl)₂, ·TFA] | N(Boc)PMB-pyridine-CH₂Br | O=C=N-CH(Ph)₂ | 412.4 (M+H)⁺ | 3.36 | A |
| 34 | [structure: azetidinone with CN, CH₂-pyridinyl-NH₂, urea-CH(CH₃)(phenyl), ·TFA] | N(Boc)PMB-pyridine-CH₂Br | O=C=N-CH(CH₃)(Ph) | 350.3 (M+H)⁺ | 2.85 | A |

FIG. 2

Chart C and D. Aminothiazoles

| Compound Number | Structure | R⁴: Reagent Type for Urea Formation | MS (ESI+) m/z | HPLC (min) | HPLC Method |
|---|---|---|---|---|---|
| 20 | 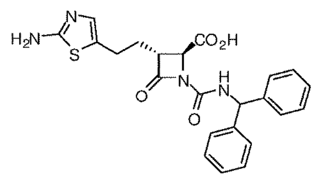 | | 451.0 (M+H)⁺ | 3.25 | A |
| 21 | 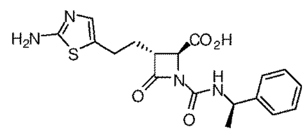 | | 389.1 (M+H)⁺ | 2.71 | A |
| 23 | 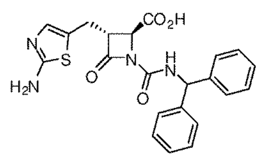 | | 437.1 (M+H)⁺ | 3.11 | A |
| 24 | 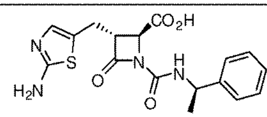 | | 375.3 (M+H)⁺ | 2.58 | A |

FIG. 3

Chart E. Amides

| Compound Number | Structure | R²Br | R⁴: Reagent Type for Urea Formation | MS (ESI+) m/z | HPLC (min) | HPLC Method |
|---|---|---|---|---|---|---|
| 22 | ![structure with H₂N-pyridine, CONH₂, phenyl groups, ·TFA] | ![NBoc₂-pyridine-CH₂Br] | ![diphenylmethyl isocyanate O=C=N-CH(Ph)₂] | 430.3 (M+H)⁺ | 3.089 | A |

FIG. 4

Chart F. Ethers

| Compound Number | Structure | R²Br | R⁵OH | R⁴: Reagent Type for Urea Formation | MS (ESI+) m/z | HPLC (min) | HPLC Method |
|---|---|---|---|---|---|---|---|
| 18 | 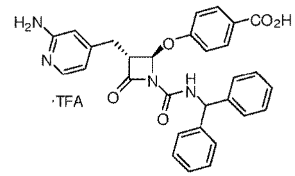 | NBoc₂ pyridine-CH₂Br | 4-hydroxybenzoate OBn | Ph₂CH-N=C=O | 523.1 (M+H)⁺ | 3.581 | A |
| 19 | 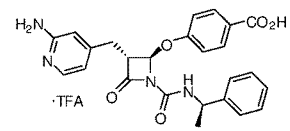 | NBoc₂ pyridine-CH₂Br | 4-hydroxybenzoate OBn | Ph(CH₃)CH-N=C=O | 461.1 (M+H)⁺ | 3.130 | A |
| 27 | 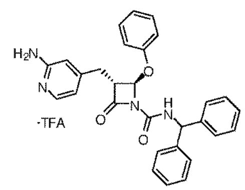 | N(Boc)Bn pyridine-CH₂Br | PhOH | Ph₂CH-N=C=O | 479.5 (M+H)⁺ | 3.845 | A |
| 33 | 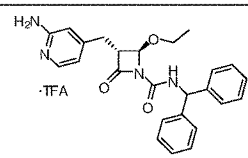 | N(Boc)PMB pyridine-CH₂Br | EtOH | Ph₂CH-N=C=O | 431.3 (M+H)⁺ | 3.405 | A |

FIG. 5

Chart G. Sulfones

| Compound Number | Structure | R²Br | R⁴: Reagent Type for Urea Formation | MS (ESI+) m/z | HPLC (min) | HPLC Method |
|---|---|---|---|---|---|---|
| 35 | (structure shown) ·TFA | N(Boc)PMB, CH₂Br pyridine | O=C=N-CHPh₂ | 465.3 (M+H)⁺ | 3.363 | A |

FIG. 6

Chart H.

| Compound Number | Structure | R²Br Reagent | R⁴: Reagent Type for Urea Formation | MS (ESI+) m/z | HPLC (min) | HPLC Method |
|---|---|---|---|---|---|---|
| 53 | (structure with OMe, phenyl, H₂N-pyridyl, TFA) | N(Boc)PMB pyridyl-CH₂Br | phenyl-CH(CH₃)-N=C=O | 382.3 (M+H)⁺ | 2.88 | A |

FIG. 7

Chart I.

| Compound Number | Structure | R²CH₂Br | R³OH or R³Br | R⁴: Reagent Type for Urea Formation | MS (ESI+) m/z | HPLC (min) | HPLC Method |
|---|---|---|---|---|---|---|---|
| 56 | 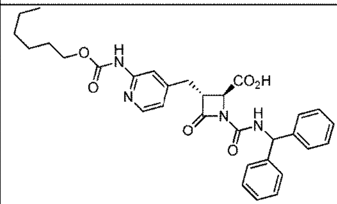 | N(Boc)PMB, pyridine-CH₂Br | | Ph₂CH-N=C=O | 559.0 (M+H)⁺ | 4.13 | A |
| 57 | 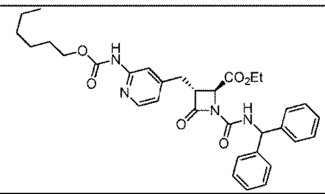 | N(Boc)PMB, pyridine-CH₂Br | EtOH | Ph₂CH-N=C=O | 587.0 (M+H)⁺ | 4.58 | A |
| 148 | 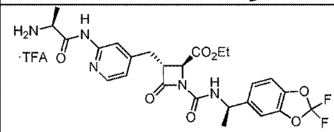 | N(Boc)PMB, pyridine-CH₂Br | EtOH | difluorobenzodioxole-CH(CH₃)-NHC(O)O-Ph | 548.1 (M+H)⁺ | 3.58 | C |
| 160 | 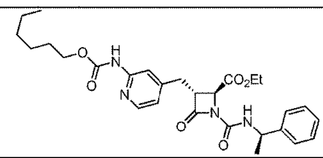 | N(Boc)PMB, pyridine-CH₂Br | EtOH | Ph-CH(CH₃)-N=C=O | 525.4 (M+H)⁺ | 4.195 | A |
| 175 | 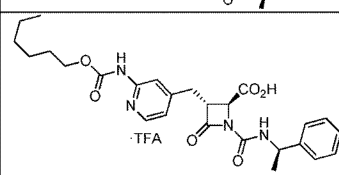 | N(Boc)PMB, pyridine-CH₂Br | | Ph-CH(CH₃)-N=C=O | 497.3 (M+H)⁺ | 3.772 | A |

FIG. 8

Chart J.

| Compound Number | Structure | R²CH₂Br | R³OH or R³Br | R⁴: Reagent Type for Urea Formation | MS (ESI+) m/z | HPLC (min) | HPLC Method |
|---|---|---|---|---|---|---|---|
| 100 | 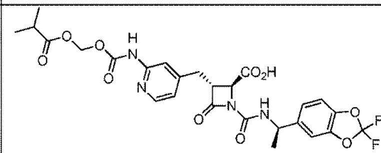 | N(Boc)PMB, Br | | | 593.2 (M+H)⁺ | 3.98 | C |
| 92 | 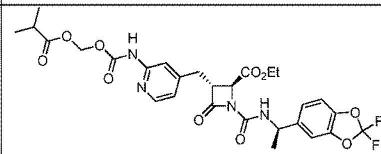 | N(Boc)PMB, Br | EtOH | | 621.1 (M+H)⁺ | 5.00 | C |
| 137 | 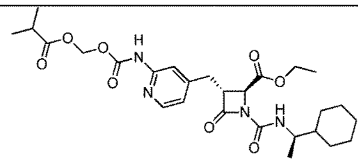 | N(Boc)PMB, Br | EtOH | O=C=N | 547.3 (M+H)⁺ | 4.129 | B |
| 140 | 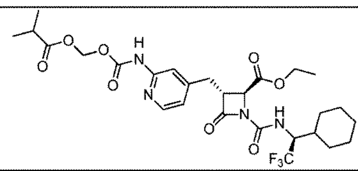 | N(Boc)PMB, Br | EtOH | | 601.3 (M+H)⁺ | 4.76 | C |
| 180 | 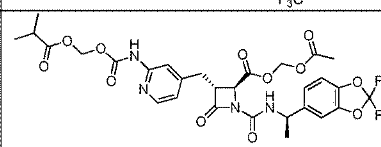 | N(Boc)PMB, Br | | | 665.3 (M+H)⁺ | 4.36 | C |

FIG. 9A

| 150 | 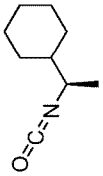 | EtOH | 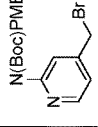 | 561.0 (M+H)⁺ | 4.607 | C |
FIG. 9B

Chart K.

| Compound Number | Structure | R² alkyl bromide | R³OH | R⁴: Reagent Type for Urea Formation | MS (ESI+) m/z | HPLC (min) | HPLC Method |
|---|---|---|---|---|---|---|---|
| 7 | 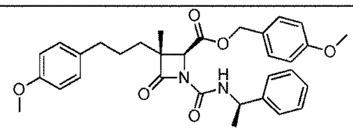 | Br-CH₂CH₂CH₂-C₆H₄-OMe | PMBOH | PhCH(CH₃)-N=C=O | 567.3 (M+Na)+ | 5.06 | B |
| 9 | 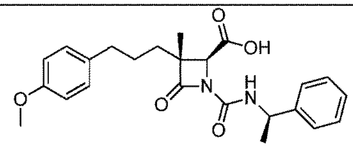 | Br-CH₂CH₂CH₂-C₆H₄-OMe | PMBOH | PhCH(CH₃)-N=C=O | 425.1 (M+H)+ | 4.177 | B |
| 11 | 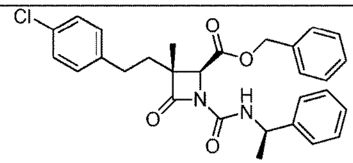 | Br-CH₂CH₂-C₆H₄-Cl | BnOH | PhCH(CH₃)-N=C=O | 504.9 (M+H)+ | 5.225 | B |
| 12 | 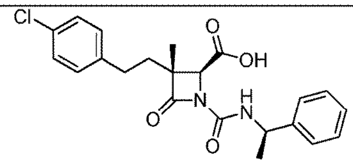 | Br-CH₂CH₂-C₆H₄-Cl | BnOH | PhCH(CH₃)-N=C=O | 414.9 (M+H)+ | 4.309 | B |

FIG. 10A

THERAPEUTIC COMPOUNDS AND COMPOSITIONS

RELATED APPLICATIONS

This application is a continuation of U.S. Ser. No. 14/614,169 filed Feb. 4, 2015 which claims priority under 35 U.S.C. § 119(e) to U.S. provisional patent application U.S. Ser. No. 61/937,031 filed Feb. 7, 2014, which is incorporated herein by reference.

BACKGROUND OF THE INVENTION

Blood coagulation is the first line of defense against blood loss following injury. The blood coagulation "cascade" involves a number of circulating serine protease zymogens, regulatory cofactors and inhibitors. Each enzyme, once generated from its zymogen, specifically cleaves the next zymogen in the cascade to produce an active protease. This process is repeated until finally thrombin cleaves the fibrinopeptides from fibrinogen to produce fibrin that polymerizes to form a blood clot. Although efficient clotting limits the loss of blood at a site of trauma, it also poses the risk of systemic coagulation resulting in massive thrombosis. Under normal circumstances, hemostasis maintains a balance between clot formation (coagulation) and clot dissolution (fibrinolysis). However, in certain disease states such as acute myocardial infarction and unstable angina, the rupture of an established atherosclerotic plaque results in abnormal thrombus formation in the coronary arterial vasculature.

Diseases that stem from blood coagulation, such as myocardial infarction, unstable angina, atrial fibrillation, stroke, pulmonary embolism, and deep vein thrombosis, are among the leading causes of death in developed countries. Current anticoagulant therapies, such as injectable unfractionated and low molecular weight (LMW) heparin and orally administered warfarin (coumadin), carry the risk of bleeding episodes and display patient-to-patient variability that results in the need for close monitoring and titration of therapeutic doses. Consequently, there is a large medical need for novel anticoagulation drugs that lack some or all of the side effects of currently available drugs.

Factor XIa is an attractive therapeutic target involved in the pathway associated with these diseases. Increased levels of Factor XIa or Factor XIa activity have been observed in several thromboembolic disorders, including venous thrombosis (Meijers et al., N. Engl. J. Med. 342:696, 2000), acute myocardial infarction (Minnema et al., Arterioscler Thromb Vasc Biol 20:2489, 2000), acute coronary syndrome (Butenas et al., Thromb Haemost 99:142, 2008), coronary artery disease (Butenas et al., Thromb Haemost 99:142, 2008), chronic obstructive pulmonary disease (Jankowski et al., Thromb Res 127:242, 2011), aortic stenosis (Blood Coagul Fibrinolysis, 22:473, 2011), acute cerebrovascular ischemia (Undas et al., Eur J Clin Invest, 42:123, 2012), and systolic heart failure due to ischemic cardiomyopathy (Zabcyk et al., Pol Arch Med Wewn. 120:334, 2010). Patients that lack Factor XI because of a genetic Factor XI deficiency exhibit few, if any, ischemic strokes (Salomon et al., Blood, 111:4113, 2008). At the same time, loss of Factor XIa activity, which leaves one of the pathways that initiate coagulation intact, does not disrupt hemostasis. In humans, Factor XI deficiency can result in a mild-to-moderate bleeding disorder, especially in tissues with high levels of local fibrinolytic activity, such as the urinary tract, nose, oral cavity, and tonsils. Moreover, hemostasis is nearly normal in Factor XI-deficient mice (Gailani, Blood Coagul Fibrinolysis, 8:134, 1997). Consequently, compounds that inhibit Factor XIa have the potential to prevent or treat a wide range of thromboembolic disorders while avoiding the side effects and therapeutic challenges that plague drugs that inhibit other components of the coagulation pathway. Moreover, due to the limited efficacy and adverse side effects of some current therapeutics for the inhibition of undesirable thrombosis (e.g., deep vein thrombosis and stroke), improved compounds and methods (e.g., those associated with Factor XIa) are needed for preventing or treating undesirable thrombosis.

Another therapeutic target is the enzyme kallikrein. Human plasma kallikrein is a serine protease that may be responsible for activating several downstream factors (e.g., bradykinin and plasmin) that are critical for coagulation and control of e.g., blood pressure, inflammation, and pain. Kallikreins are expressed e.g., in the prostate, epidermis, and the central nervous system (CNS) and may participate in e.g., the regulation of semen liquefaction, cleavage of cellular adhesion proteins, and neuronal plasticity in the CNS. Moreover, kallikreins may be involved in tumorigenesis and the development of cancer and angioedema, e.g., hereditary angioedema. Overactivation of the kallikrein-kinin pathway can result in a number of disorders, including angioedema, e.g., hereditary angioedema (Schneider et al., J. Allergy Clin. Immunol. 120:2, 416, 2007). To date, there are limited treatment options for HAE (e.g., WO2003/076458). As such, therapeutics are needed for preventing or treating these diseases.

SUMMARY OF THE INVENTION

The present invention features compounds that inhibit Factor XIa or kallikrein and methods for preventing or treating undesired thrombosis or angiodema (e.g., hereditary angiodema) by administering one or more of these compounds alone or in combination with other molecules to a mammal. The invention also provides methods for designing or selecting additional Factor XIa or kallikrein inhibitors using these structures. Desirably, these compounds have certain structural, physical, and spatial characteristics that enable the compounds to interact with specific residues of the active site of Factor XIa or kallikrein.

In one aspect, the present invention is directed to a compound of formula (I):

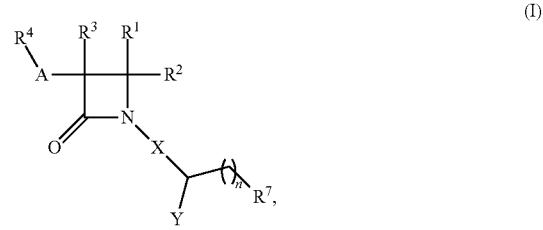

or a pharmaceutically acceptable salt thereof, wherein $R^1$ is H or $—C_{1-6}$ alkyl; $R^2$ is H, $—C_{1-6}$ alkyl, $—CO_2R^5$, $—C(O)NR^9R^{10}$, $—CN$, $—SO_qR^5$, $—OR^5$, $—CHN(OR^5)$, or a heteroaryl; $R^3$ is H or $—C_{1-6}$ alkyl; A is a bond, $C_{1-6}$ alkylene, $C_{2-6}$ alkenylene, or $C_{2-6}$ alkynylene; $R^4$ is cycloalkyl, aryl, heteroaryl or heterocyclyl (e.g., piperidonyl, piperidinyl, pyridonyl, benzodioxolyl e.g., difluorobenzodioxolyl), each of which is substituted with 0-3 occurrences of $R^6$; each $R^5$ is independently H, $—C_{1-6}$ alkyl, aralkyl, or aryl substituted with 0-3 occurrences of —NH$_2$ or R$^6$; each R$^6$ is independently halo, hydroxy, cyano, nitro, —C$_{1-6}$ alkyl (e.g., methyl, ethyl, haloalkyl (e.g., —CF$_3$)), —C$_{1-6}$ alkoxy (e.g., haloalkoxy (e.g., —OCF$_3$)), —NHR$^{10}$, —NR$^9$R$^{10}$, —C(O)R$^{11}$, —C(O)OR$^{11}$, —C(O)NR$^9$R$^{10}$, —C(NR$^8$)(N(R$^8$)$_2$), —SO$_q$R$^{11}$, —SO$_2$NR$^9$R$^{10}$, —NHC(O)OR$^{11}$, —NHC(O)R$^{11}$, —OC(O)R$^{11}$, aryl, heteroaryl, aralkyl, cycloalkyl, heteroaralkyl, heterocyclyl, or heterocyclylalkyl (e.g., 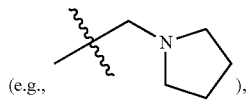), or two R$^6$ groups together with the atoms to which they are attached form a 5-7-membered ring (e.g., 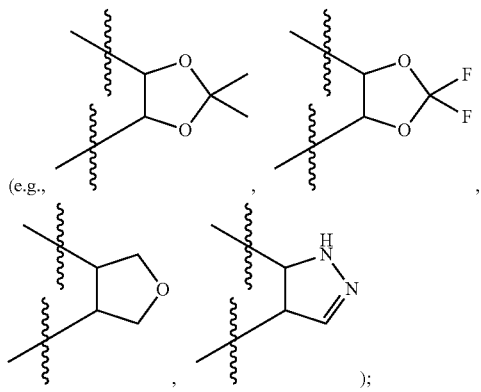);

X is —C(O)O—, —OC(O)—, —C(O)S(O)$_2$—, —S(O)$_2$C(O)—, — C(O)N(R$^5$)— or —N(R$^5$)C(O)—; Y is —C$_{1-6}$ alkyl, cycloalkyl (e.g., 3 to 8-membered cycloalkyl, e.g., 5 to 7-membered cycloalkyl), aryl, heteroaryl, or heterocyclyl (e.g., 3 to 8-membered heterocyclyl, e.g., 5 to 7-membered heterocyclyl), each of which is substituted with 0-3 occurrences of —NH$_2$ or R$^6$; R$^7$ is H, —C$_{1-6}$ alkyl (e.g., haloalkyl (e.g., —CF$_3$)), cycloalkyl, aryl, heteroaryl, or heterocyclyl, each of which is substituted with 0-3 occurrences of —NH$_2$ or R$^6$; each R$^8$ is independently H, —C$_{1-6}$ alkyl (e.g., haloalkyl (e.g., —CF$_3$)), —C(O)R$^5$, —C(O)OR$^5$, aryl, heteroaryl, aralkyl, heteroaralkyl, heterocyclyl, or heterocyclylalkyl; each of R$^9$ and R$^{10}$ is independently —C$_{1-6}$ alkyl, cycloalkyl, heterocyclyl, aryl, or heteroaryl, or R$^9$ and R$^{10}$ together form an optionally substituted 5-7-membered ring (e.g., 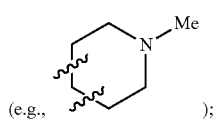);

each R$^{11}$ is independently H, —C$_{1-6}$ alkyl (e.g., substituted alkyl (e.g., 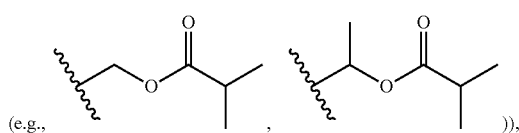)), aralkyl, or aryl; q is an integer from 0 to 2; and n is an integer from 0 to 2.

In some embodiments, R$^1$ is H.

In some embodiments, R$^2$ is —CO$_2$R$^5$ and R$^5$ is H, —C$_{1-6}$ alkyl, aralkyl, or aryl substituted with 1 occurrence of —NH$_2$ or R$^6$. In some embodiments, R$^5$ is H, methyl, ethyl, isopropyl, or benzyl substituted with 1 occurrence of R$^6$. In some embodiments, R$^5$ is H. In some embodiments, R$^5$ is ethyl.

In some embodiments, A is C$_{1-6}$ alkylene (e.g., ethylene or propylene).

In some embodiments, R$^4$ is aryl or heteroaryl. In some embodiments, R$^4$ is phenyl with 0 occurrences of R$^6$. In some embodiments, R$^4$ is phenyl substituted with 1-2 occurrences of R$^6$. In some embodiments, R$^6$ is halo, —C$_{1-6}$ alkoxy or —C(NR$^8$)(N(R$^8$)$_2$). In some embodiments, R$^6$ is —C(NR$^8$)(N(R$^8$)$_2$) and each R$^8$ is H. In some embodiments, R$^6$ is —C(NR$^8$)(N(R$^8$)$_2$) and each R$^8$ is independently H or —C(O)OR$^5$. In some embodiments, R$^6$ is —C(NR$^8$)(N(R$^8$)$_2$) and R$^5$ is —C$_{1-6}$ alkyl (e.g., hexyl). In some embodiments, R$^4$ is heteroaryl (e.g., a 6-membered heteroaryl or 5-membered heteroaryl) substituted with 0-3 occurrences of R$^6$. In some embodiments, R$^4$ is a 6-membered heteroaryl (e.g., pyridyl) substituted with 0-3 occurrences of R$^6$. In some embodiments, R$^4$ is a nitrogen-containing heteroaryl (e.g., pyridyl). In some embodiments, R$^4$ is pyridyl substituted with 1-2 occurrences of R$^6$. In some embodiments, R$^6$ is halo (e.g., chloro, bromo, fluoro). In some embodiments, R$^6$ is —NHR$^{10}$ and R$^{10}$ is —C$_{1-6}$ alkyl. In some embodiments, R$^6$ is —NHC(O)OR$^{11}$, and R$^{11}$ is —C$_{1-6}$ alkyl (e.g., substituted alkyl (e.g., (e.g., 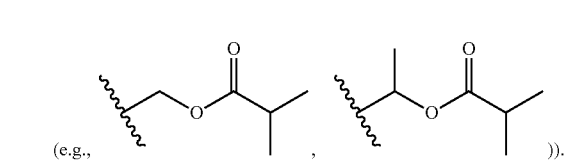)).

In some embodiments, X is —C(O)N(R$^5$)— or —N(R$^5$)C(O)—. In some embodiments, X is —C(O)N(R$^5$)— and R$^5$ is H.

In some embodiments, n is 0.

In some embodiments, R$^7$ is —C$_{1-6}$ alkyl (e.g., methyl, ethyl, propyl, —CF$_3$).

In some embodiments, Y is cycloalkyl (e.g., cyclohexyl). In some embodiments, Y is aryl or heteroaryl substituted with 0-3 occurrences of R$^6$. In some embodiments, Y is phenyl substituted with 0 occurrences of R$^6$. In some embodiments, Y is phenyl substituted with 1 occurrence of R$^6$. In some embodiments, Y is phenyl substituted with 2 occurrences of R$^6$.

In some embodiments, Y is aryl or heteroaryl and R$^6$ is haloalkoxy (e.g., —OCF$_3$). In some embodiments, Y is aryl or heteroaryl and two R$^6$ groups taken together with the atoms to which they are attached form a 5-7 membered ring. In some embodiments, Y is aryl or heteroaryl and two R$^6$ groups taken together with the atoms to which they are attached form a 5-7 membered ring selected from:

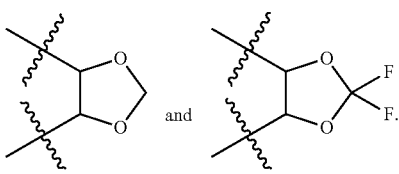 and 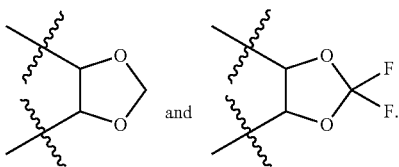 [SMILES: *C1OCOC1* ; *C1OC(F)(F)OC1*]

In some embodiments, Y is phenyl and $R^6$ is haloalkoxy (e.g., —$OCF_3$). In some embodiments, Y is phenyl and two $R^6$ groups taken together with the atoms to which they are attached form a 5-7 membered ring. In some embodiments, Y is phenyl and two $R^6$ groups taken together with the atoms to which they are attached form a 5-7 membered ring selected from:

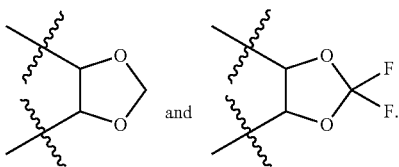 [SMILES: *C1OCOC1* ; *C1OC(F)(F)OC1*]

In some embodiments, the compound of formula (I) is selected from a compound of formula (Ia):

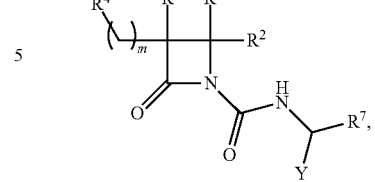

(Ia)

wherein $R^1$, $R^2$, $R^3$, $R^4$, $R^7$, and Y are as described for formula (I), and m is an integer from 1 to 6.

In some embodiments, the compound of formula (Ia) is selected from a compound of formula (Ib):

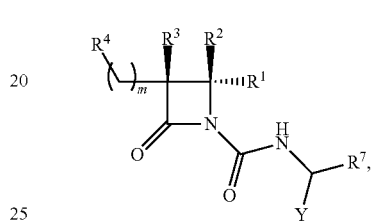

(Ib)

wherein $R^1$, $R^2$, $R^3$, $R^4$, $R^7$, Y and m are as described for formula (Ia).

In some embodiments, the compound of formula (Ib) is:

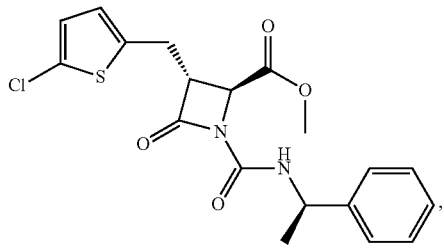

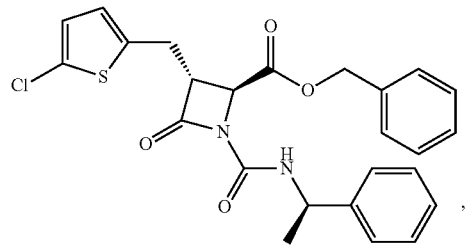

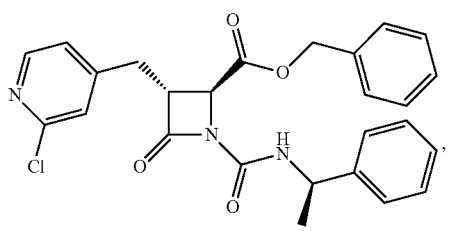

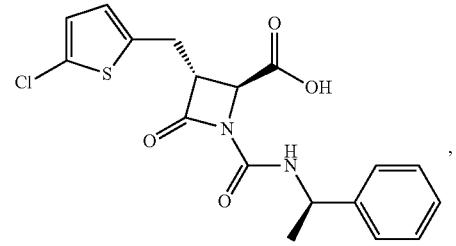

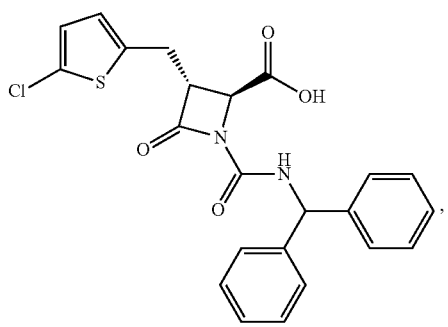

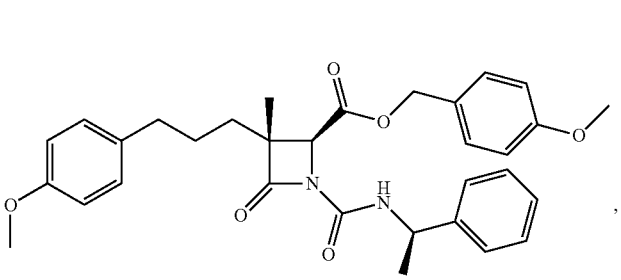

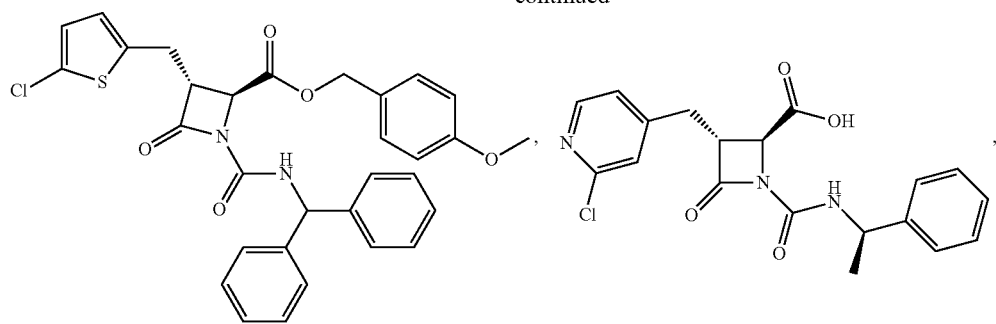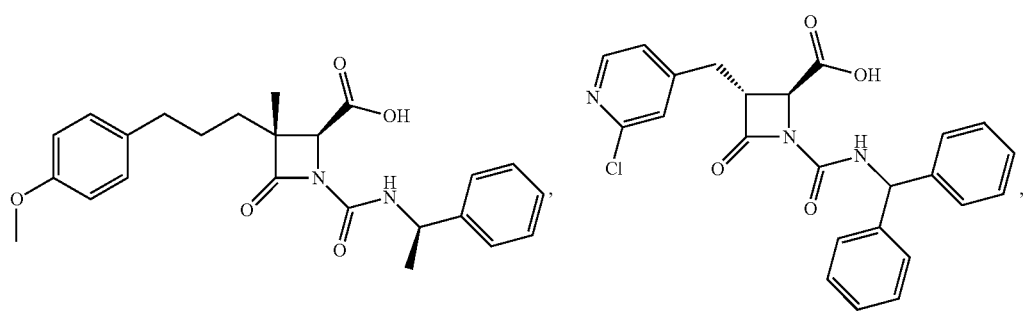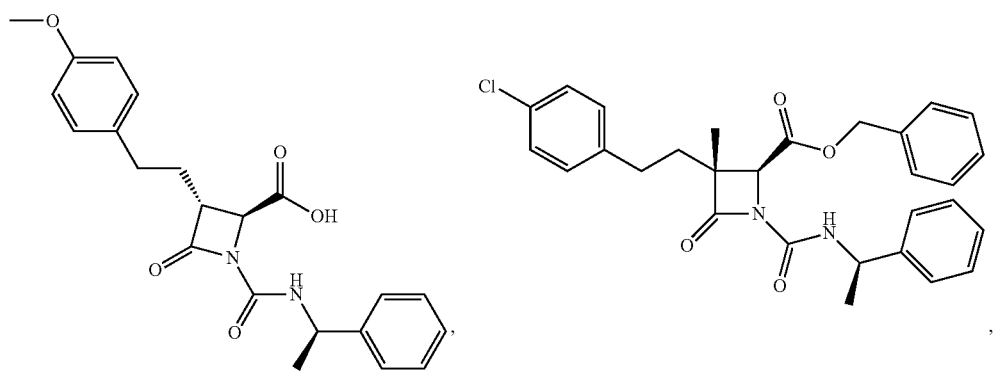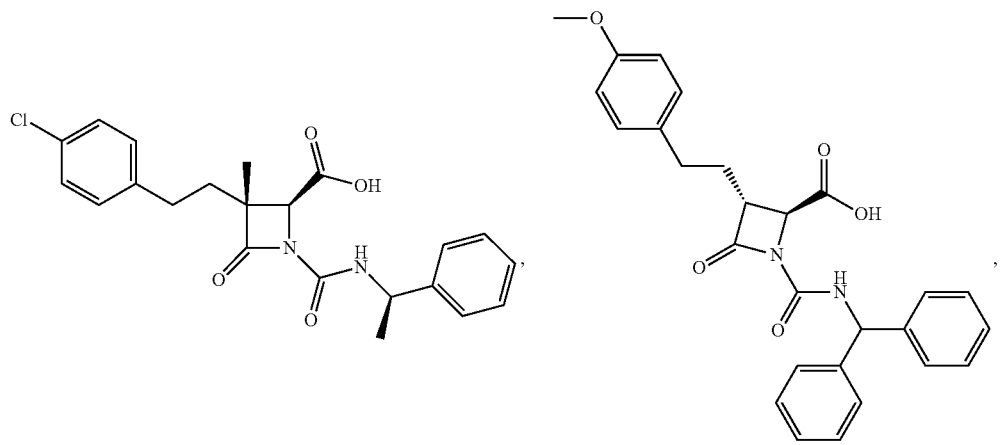

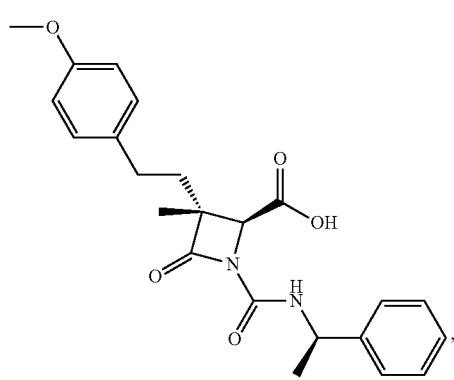
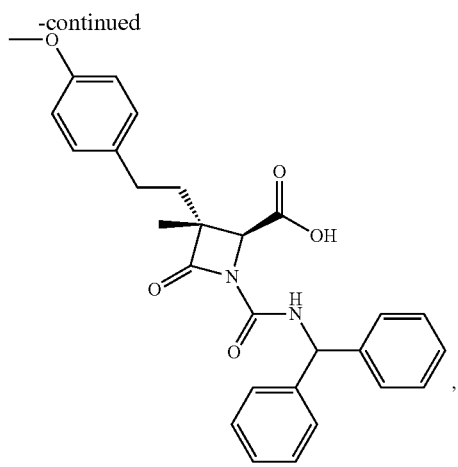
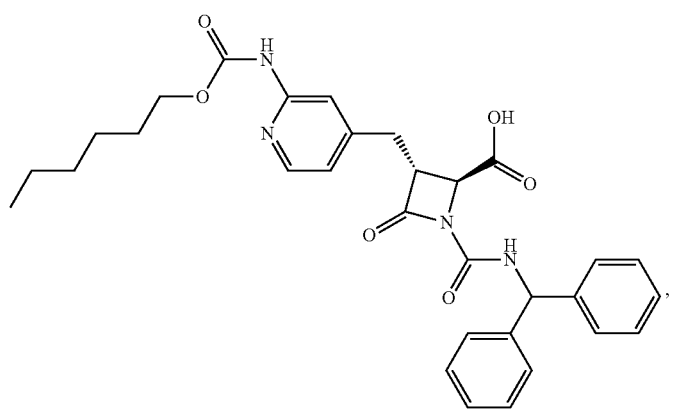
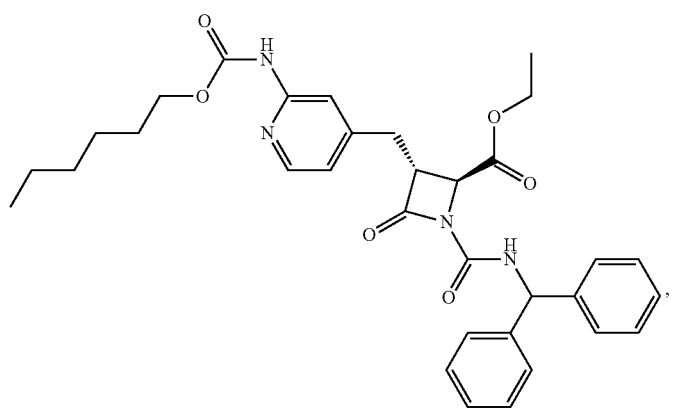
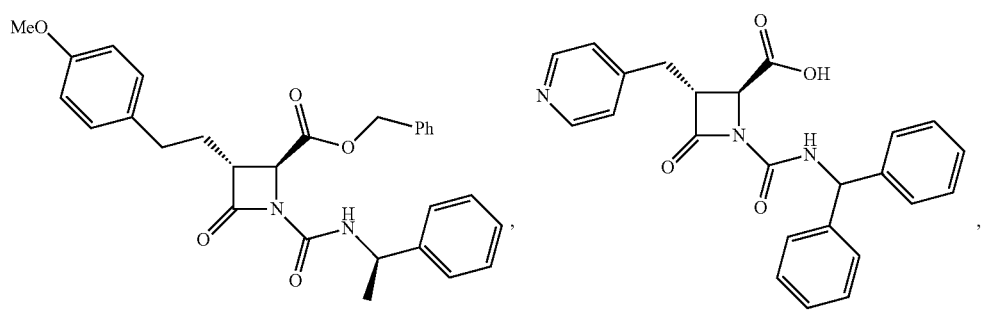

-continued
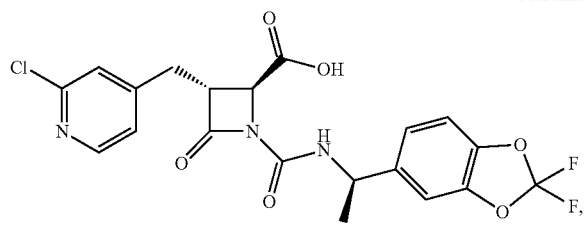
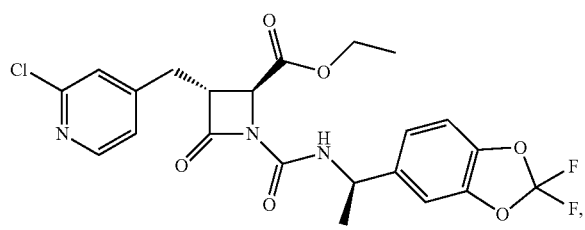
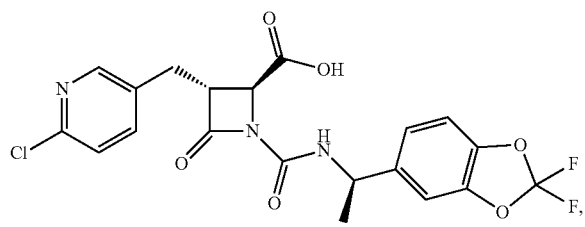
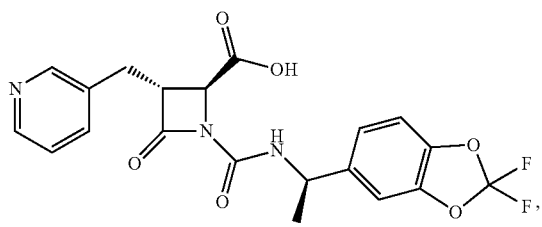
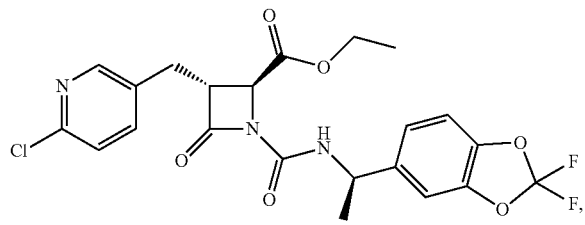
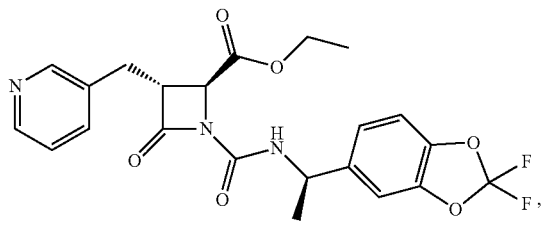
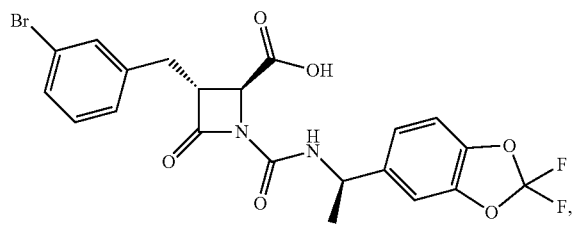
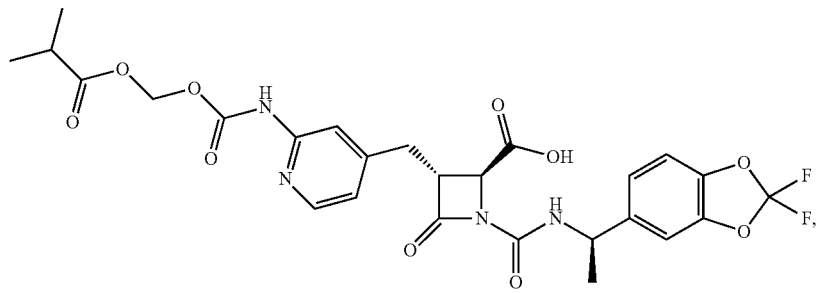
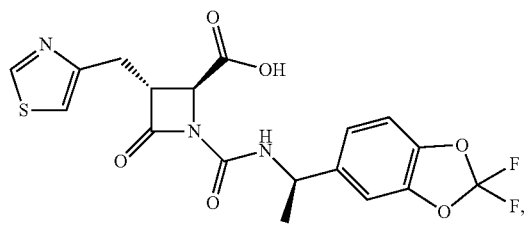

-continued
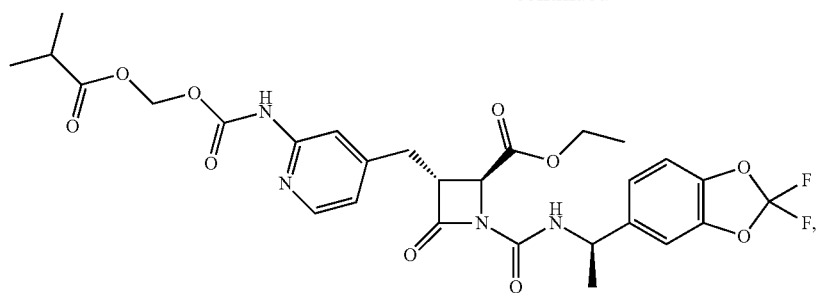
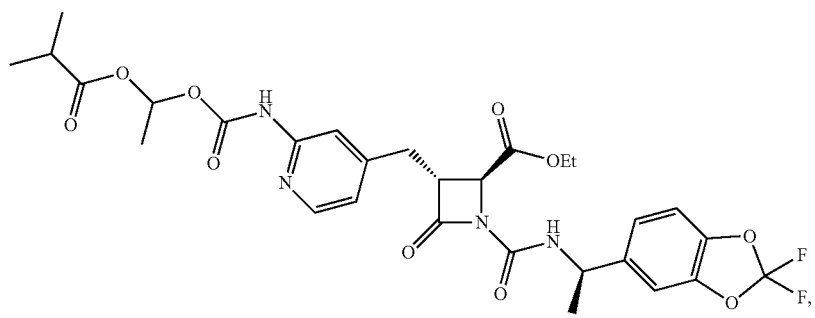
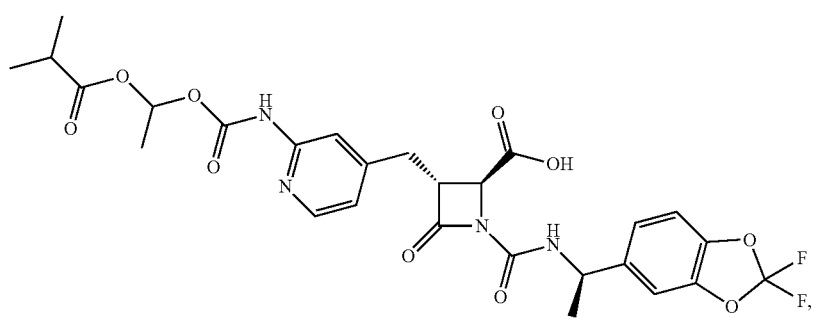
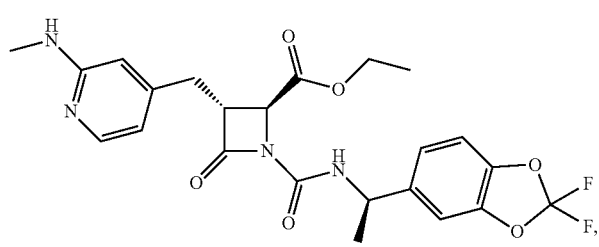
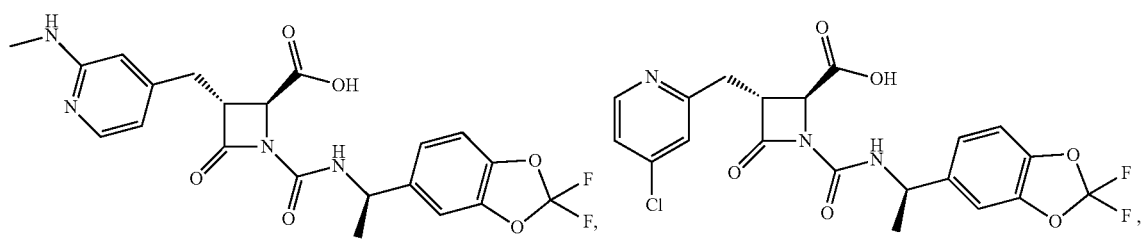
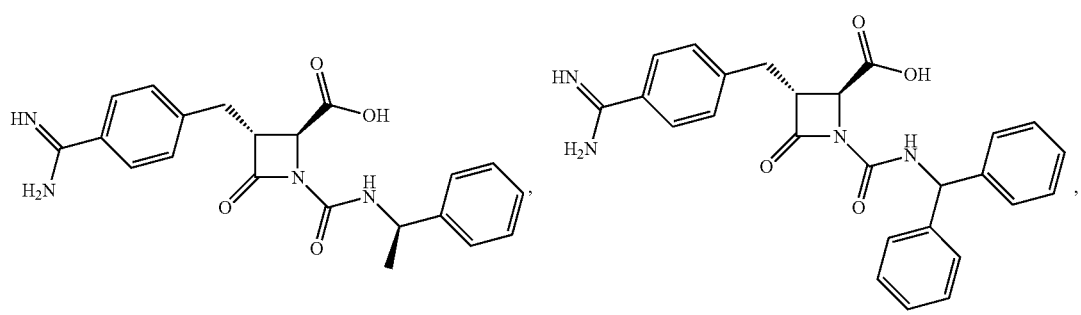

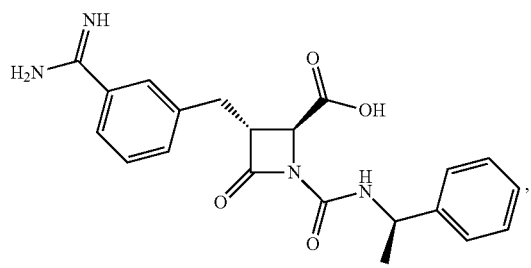
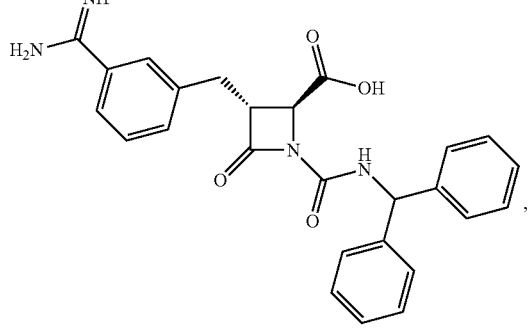
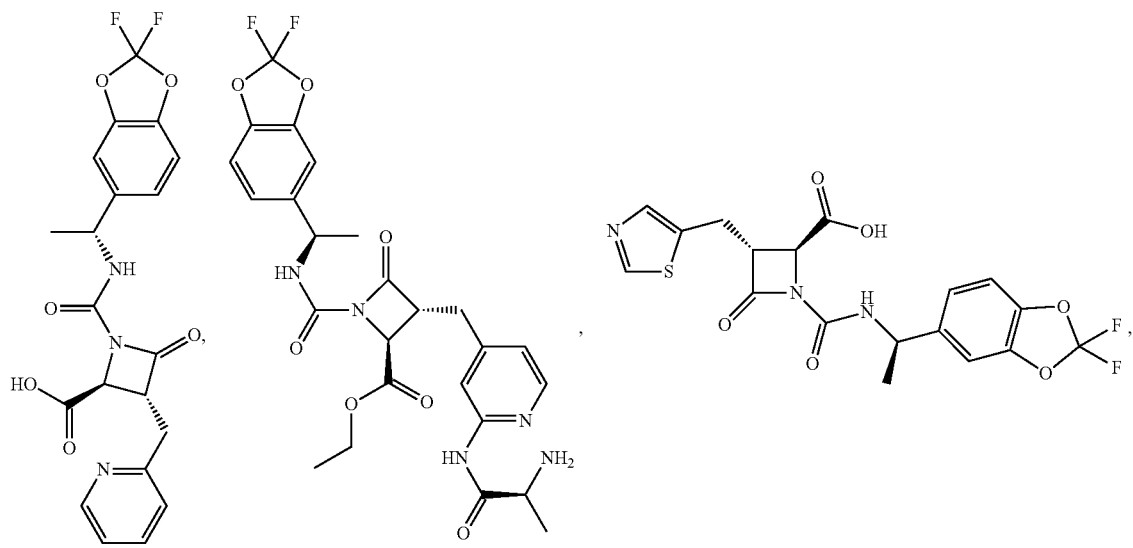
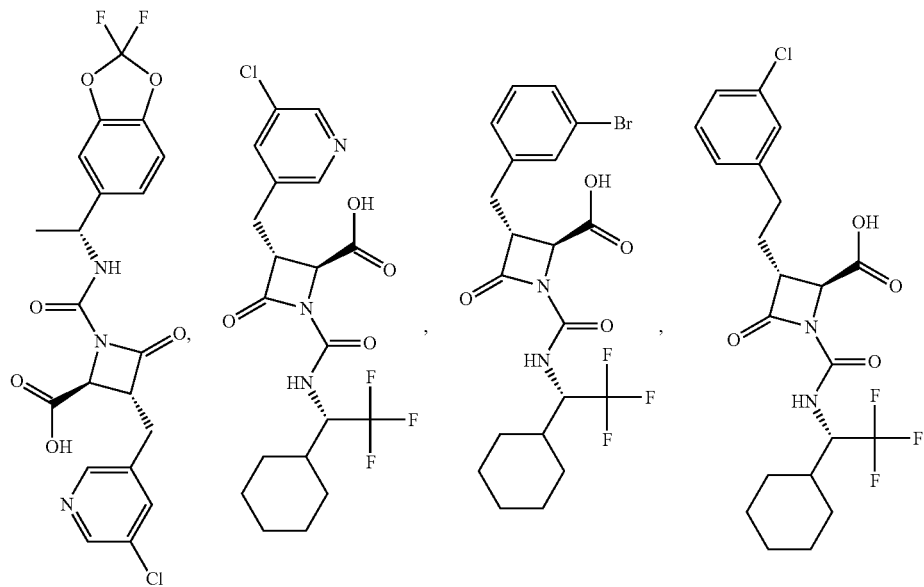

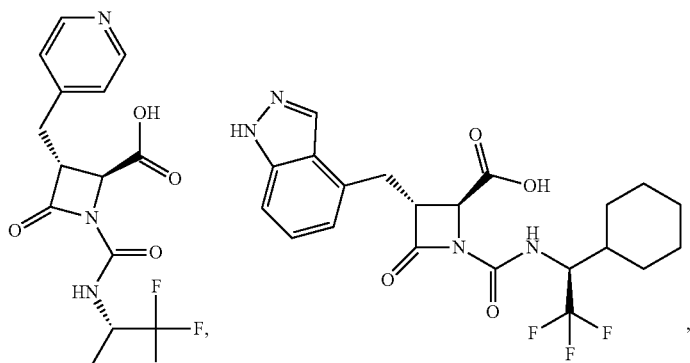
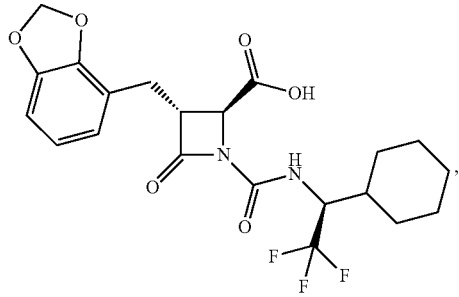
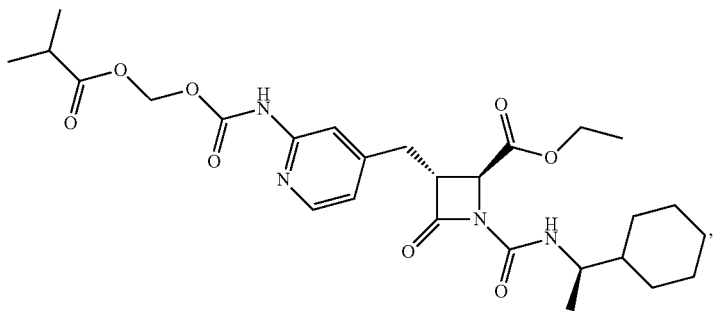
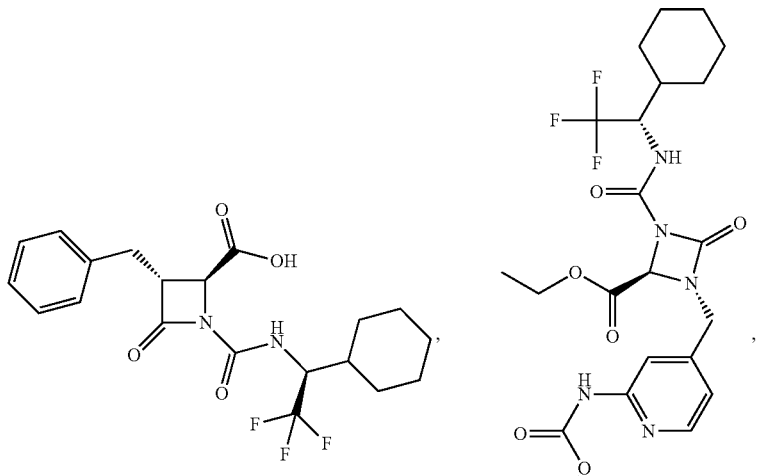

-continued
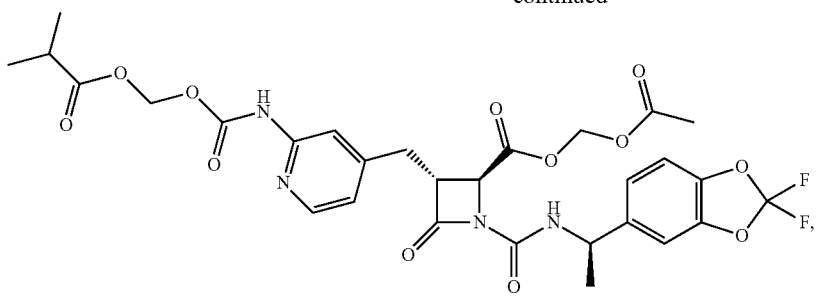
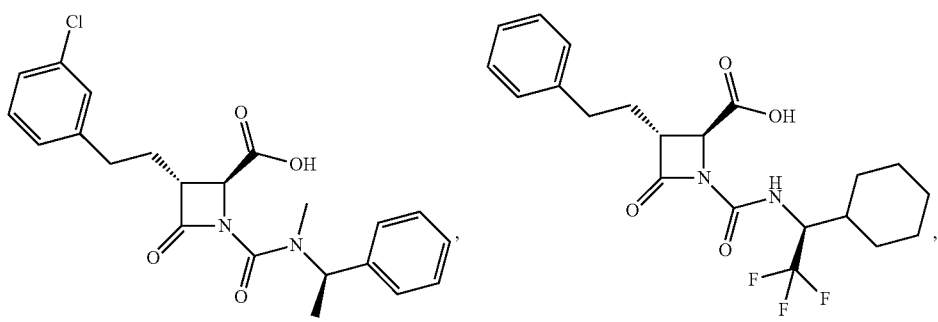
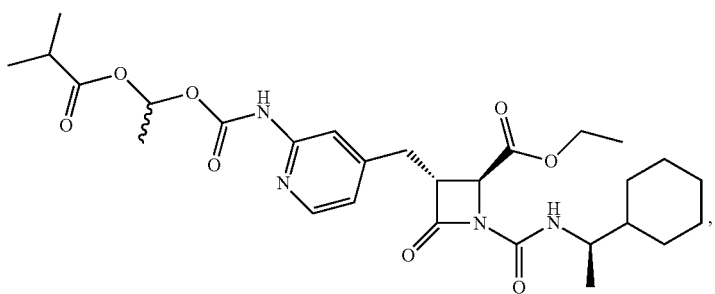
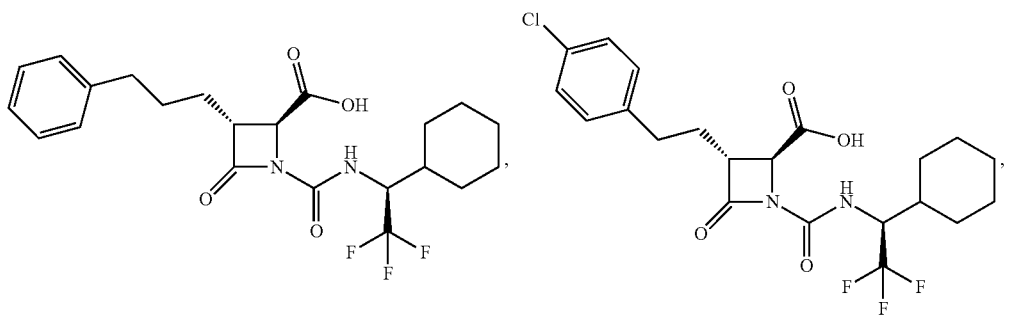
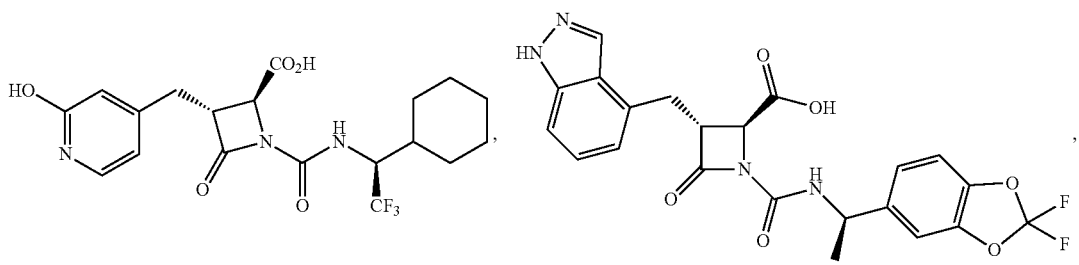

-continued
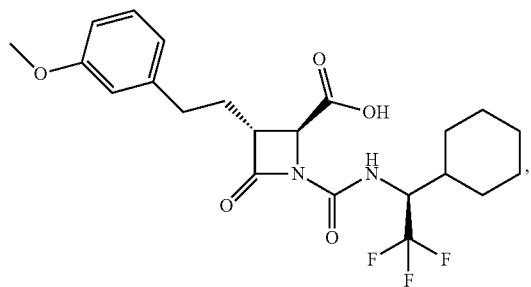
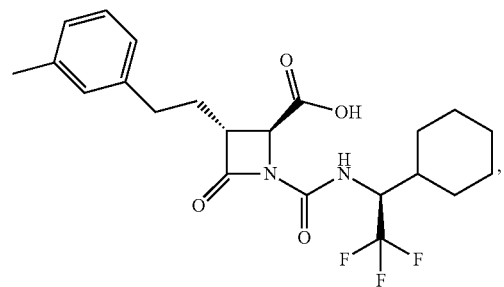
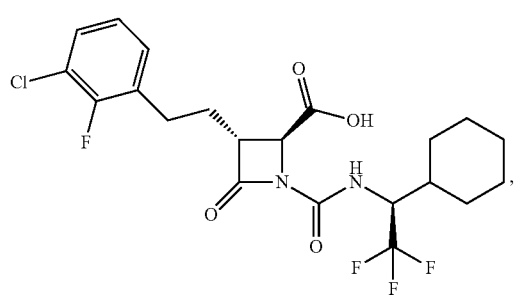
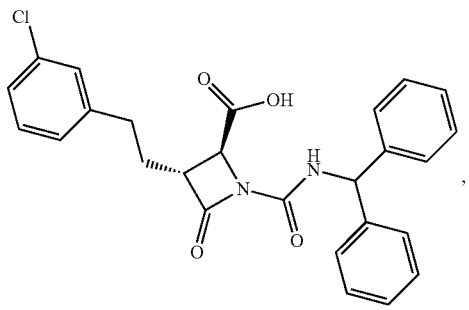
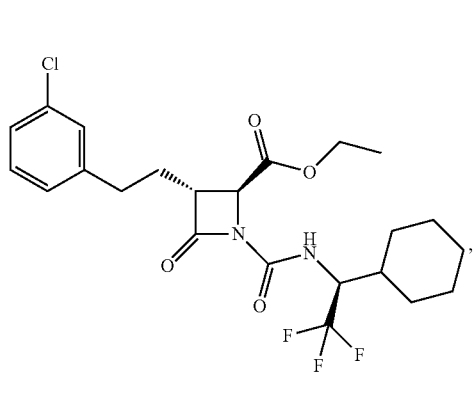
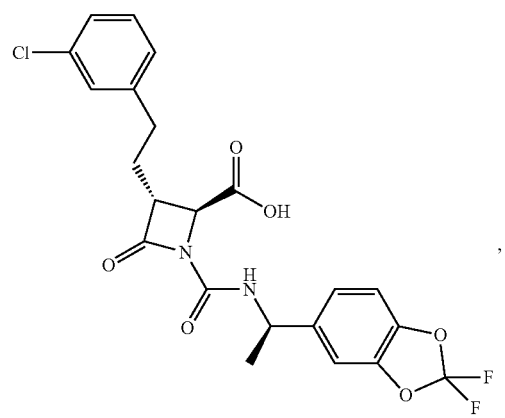
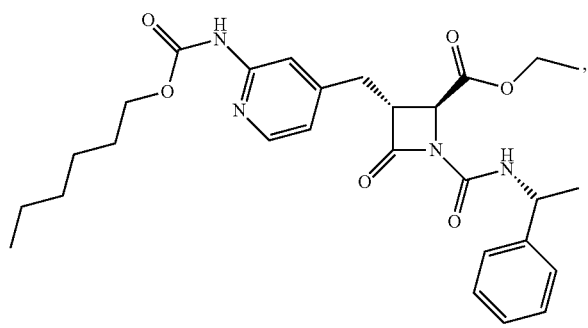
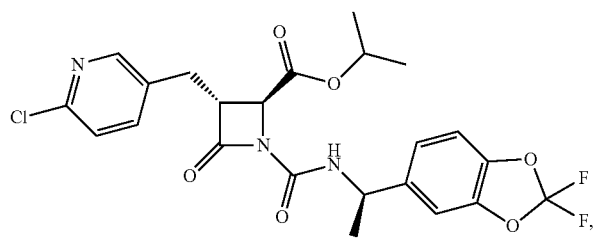

-continued
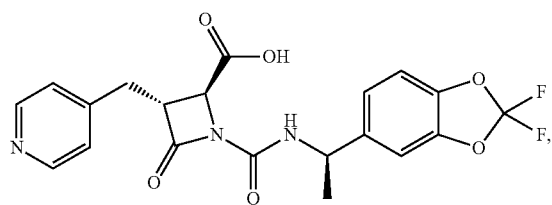
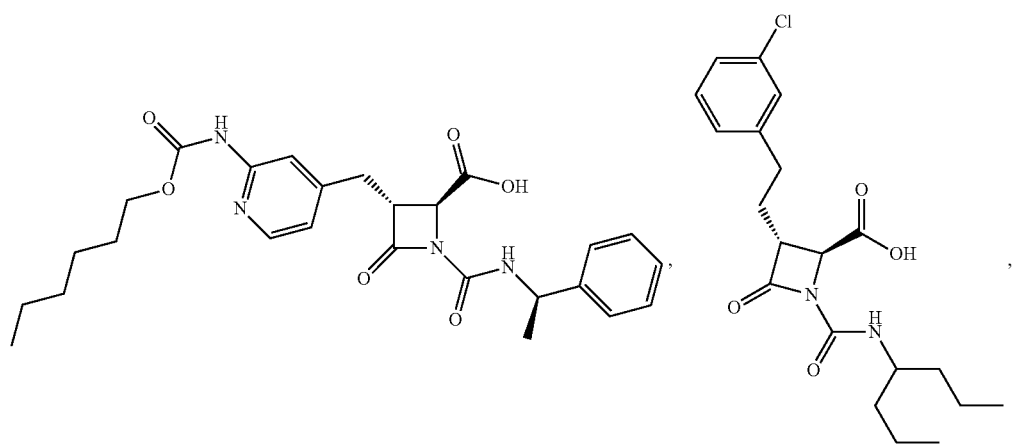
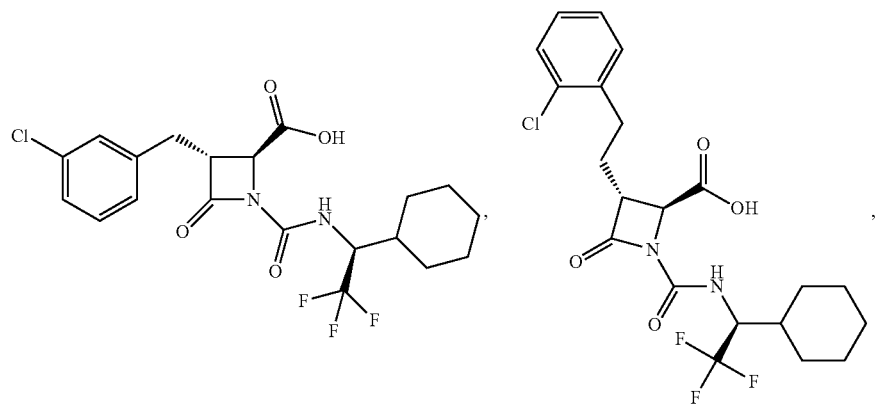
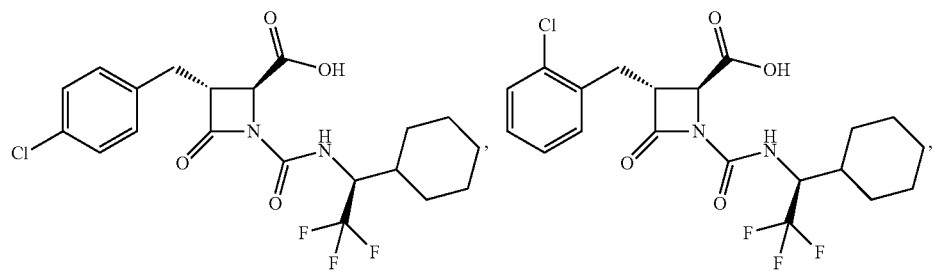

-continued

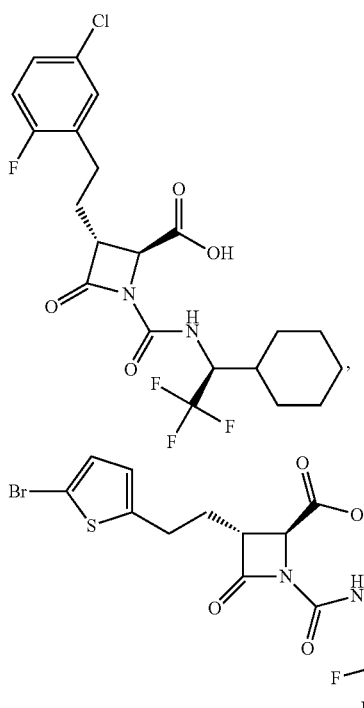

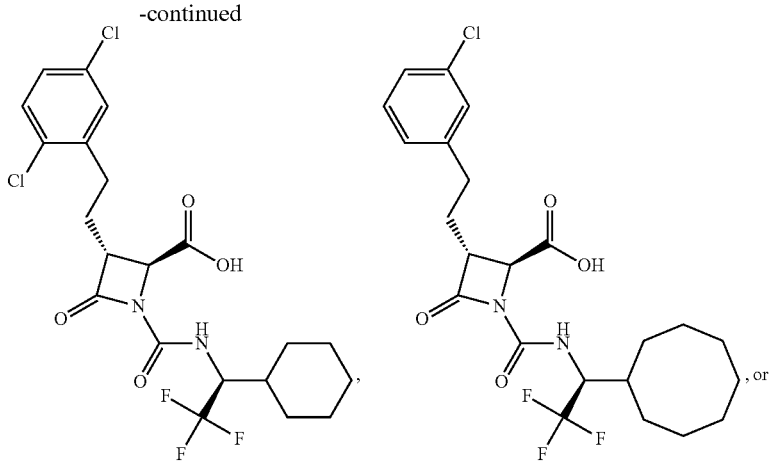

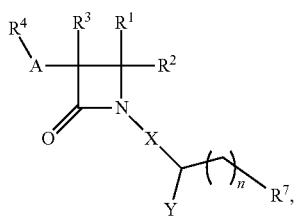

In one aspect, the present invention is directed to a compound of formula (II):

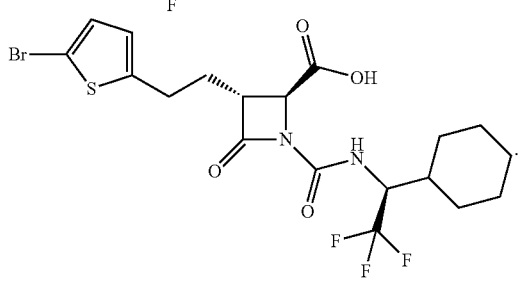
(II)

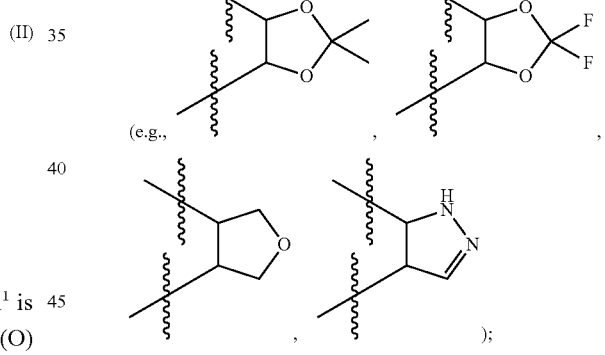
(e.g., ... );

or a pharmaceutically acceptable salt thereof, wherein $R^1$ is H or —$C_{1-6}$ alkyl; $R^2$ is H, —$C_{1-6}$ alkyl, —$CO_2R^5$, —C(O)$NR^9R^{10}$, —CN, —$SO_qR$, —$OR^5$, —CHN($OR^5$) or a heteroaryl; $R^3$ is H or —$C_{1-6}$ alkyl; A is a bond, $C_{1-6}$ alkylene, $C_{2-6}$ alkenylene or $C_{2-6}$ alkynylene; $R^4$ is cycloalkyl, aryl, heteroaryl or heterocyclyl, each of which is substituted with 0-3 occurrences of —$NH_2$ or $R^6$; each $R^5$ is independently H, —$C_{1-6}$ alkyl, aralkyl, or aryl substituted with 0-3 occurrences of —$NH_2$ or $R^6$; each $R^6$ is independently halo, hydroxy, cyano, nitro, —$C_{1-6}$ alkyl (e.g., methyl, ethyl, haloalkyl (e.g., —$CF_3$)), —$C_{1-6}$ alkoxy (e.g., haloalkoxy (e.g., —$OCF_3$)), —$NR^9R^{10}$, —$NHR^{10}$, —C(O)$R^{11}$, —C(O)$OR^{11}$, —C(O)$NR^9R^{10}$, —C($NR^8$)(N($R^8$)$_2$), —$SO_qR^{11}$, —$SO_2NR^9R^{10}$, —NHC(O)$OR^{11}$, —NHC(O)$R^{11}$, aryl, heteroaryl, aralkyl, cycloalkyl, heteroaralkyl, heterocyclyl or heterocyclylalkyl, or two $R^6$ groups together with the atoms to which they are attached form a 5-7-membered ring X is —C(O)O—, —OC(O)—, —C(O)S(O)$_2$—, —S(O)$_2$C(O)—, —C(O)N($R^5$)— or —N($R^5$)C(O)—; Y is cycloalkyl (e.g., 3 to 8-membered cycloalkyl, e.g., 5 to 7-membered cycloalkyl), heteroaryl, or heterocyclyl (e.g., 3 to 8-membered heterocyclyl, e.g., 5 to 7-membered heterocyclyl), each of which is substituted with 0-3 occurrences of —$NH_2$ or $R^6$; or substituted —$C_{1-6}$ alkyl or substituted aryl (e.g., substituted with 1-3 $R^6$); $R^7$ is H, —$C_{1-6}$ alkyl (e.g., methyl, haloalkyl (e.g., —$CF_3$)), cycloalkyl, aryl, heteroaryl or heterocyclyl, each of which is substituted with 0-3 occurrences of —$NH_2$ or $R^6$; each $R^8$ is independently H, —$C_{1-6}$ alkyl (e.g., haloalkyl (e.g., —$CF_3$)), —C(O)$R^5$, —C(O)$OR^5$, aryl, heteroaryl, aralkyl, heteroaralkyl, heterocyclyl or heterocyclylalkyl; each of $R^9$ and $R^{10}$ is independently —$C_{1-6}$ alkyl, cycloalkyl, heterocyclyl, aryl, or heteroaryl, or $R^9$ and $R^{10}$ together form an optionally substituted 5-7-membered ring; each $R^{11}$ is independently H, —$C_{1-6}$ alkyl (e.g., substituted alkyl (e.g., 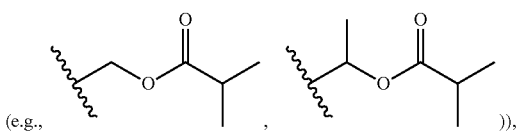), aralkyl, or aryl; q is an integer from 0 to 2; and n is an integer from 0 to 2.

In some embodiments, $R^1$ is H.

In some embodiments, R is —$CO_2R^5$ and R is H, —$C_{1-6}$ alkyl, aralkyl, or aryl substituted with 1 occurrence of —$NH_2$ or $R^6$. In some embodiments, $R^5$ is H, methyl, ethyl, isopropyl, or benzyl substituted with 1 occurrence of $R^6$. In some embodiments, $R^5$ is H. In some embodiments, $R^5$ is ethyl.

In some embodiments, A is $C_{1-6}$ alkylene (e.g., ethylene or propylene).

In some embodiments, $R^4$ is aryl or heteroaryl. In some embodiments, $R^4$ is phenyl substituted with 1 occurrence of $R^6$. In some embodiments, $R^6$ is halo, $C_{1-6}$ alkoxy or —$C(NR^8)(N(R^8)_2)$. In some embodiments, $R^6$ is —$C(NR^8)(N(R^8)_2)$ and each $R^8$ is H. In some embodiments, $R^8$ is independently H or —$CO_2R^5$. In some embodiments, $R^5$ is —$C_{1-6}$ alkyl (e.g., hexyl). In some embodiments, $R^4$ is heteroaryl (e.g., a 6-membered heteroaryl or 5-membered heteroaryl) substituted with 0-3 occurrences of —$NH_2$ or $R^6$. In some embodiments, $R^4$ is a 6-membered heteroaryl (e.g., pyridyl) substituted with 0-3 occurrences of —$NH_2$ or $R^6$. In some embodiments, $R^4$ is a nitrogen-containing heteroaryl (e.g., pyridyl) substituted with 0-3 occurrences of —$NH_2$ or $R^6$. In some embodiments, $R^4$ is pyridyl substituted with 1 occurrence of $R^6$. In some embodiments, $R^6$ is halo (e.g., chloro, bromo, fluoro). In some embodiments, $R^4$ is pyridyl substituted with 1 occurrence of —$NH_2$. In some embodiments, $R^6$ is —$NHR^{10}$ and $R^{10}$ is —$C_{1-6}$ alkyl. In some embodiments, $R^6$ is —$NHC(O)OR^{11}$, and $R^{11}$ is —$C_{1-6}$ alkyl (e.g., substituted alkyl (e.g., 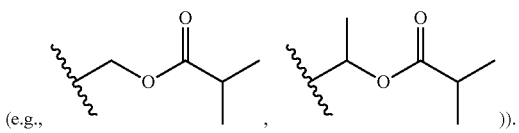).

In some embodiments, X is —$C(O)N(R^5)$— or —$N(R^5)C(O)$—. In some embodiments, X is —$C(O)N(R^5)$— and $R^5$ is H.

In some embodiments, n is 0.

In some embodiments, $R^7$ is —$C_{1-6}$ alkyl (e.g., methyl, ethyl, propyl, —$CF_3$). In some embodiments, $R^7$ is methyl. In some embodiments, $R^7$ is —$CF_3$.

In some embodiments, Y is cycloalkyl, heteroaryl, or heterocyclyl, each of which is substituted with 0-3 occurrences of —$NH_2$ or $R^6$, or substituted aryl. In some embodiments, Y is cycloalkyl (e.g., cyclohexyl). In some embodiments, Y is heteroaryl (e.g., pyridyl, pyrazinyl, pyrimidinyl, quinolinyl, isoquinolinyl, thiazolyl, indazolyl). In some embodiments, Y is substituted aryl (e.g., substituted phenyl, naphthyl). In some embodiments, Y is substituted phenyl substituted with 1-2 occurrences of $R^6$. In some embodiments, Y is phenyl substituted with 1 occurrence of $R^6$. In some embodiments, Y is phenyl and $R^6$ is haloalkoxy (e.g., —$OCF_3$). In some embodiments, Y is phenyl and $R^6$ is halo (e.g., chloro, bromo, fluoro). In some embodiments, Y is phenyl substituted with 2 occurrences of $R^6$.

In some embodiments, $R^6$ is haloalkoxy (e.g., —$OCF_3$). In some embodiments, two $R^6$ groups taken together with the atoms to which they are attached form a 5-7 membered ring. In some embodiments, two $R^6$ groups taken together with the atoms to which they are attached form a 5-7 membered ring and the ring is selected from:

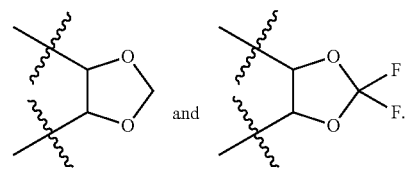 [SMILES: *C1OCOC1* ; *C1OC(F)(F)OC1*]

In some embodiments, the compound of formula (II) is selected from a compound of formula (IIa):

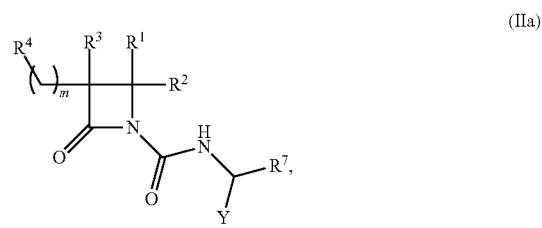

(IIa)

wherein $R^1$, $R^2$, $R^3$, $R^4$, $R^7$, and Y are as described for formula (II), and m is an integer from 1 to 6.

In some embodiments, the compound of formula (IIa) is selected from a compound of formula (IIb):

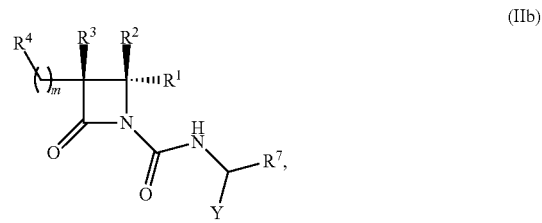

(IIb)

wherein $R^1$, $R^2$, $R^3$, $R^4$, $R^7$, Y and m are as described for formula (IIa).

In some embodiments, the compound of formula (IIb) is:
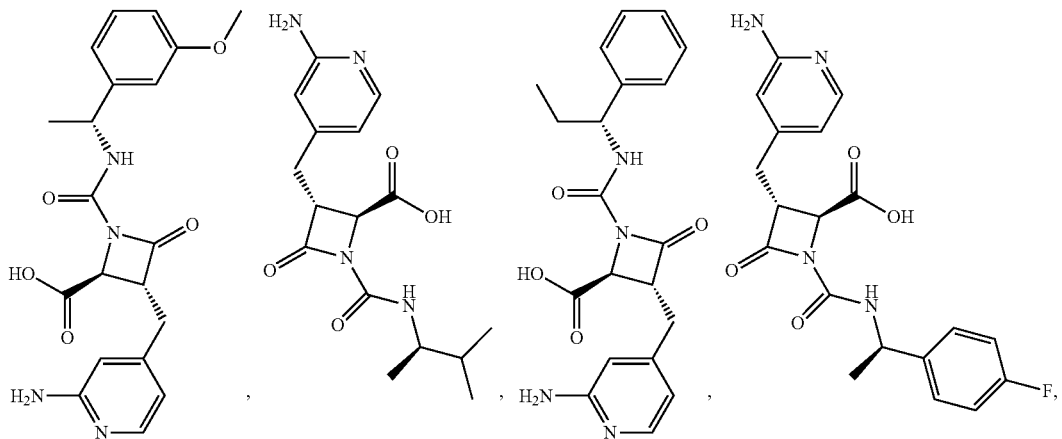
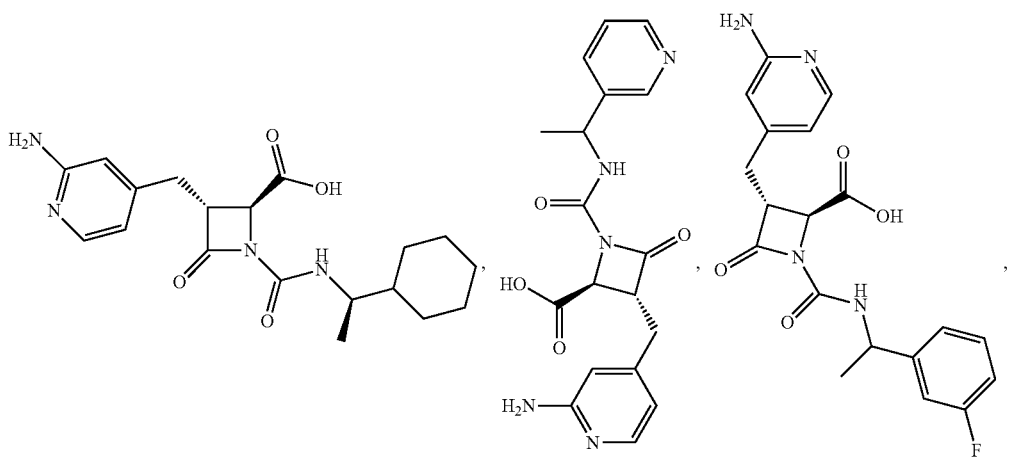
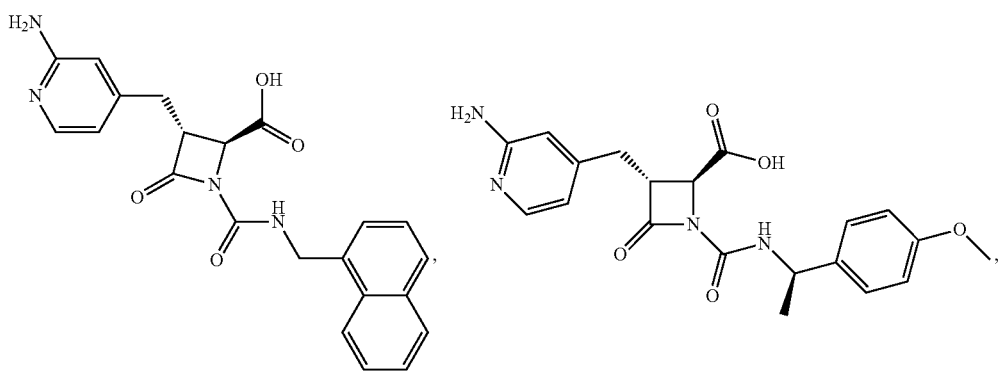

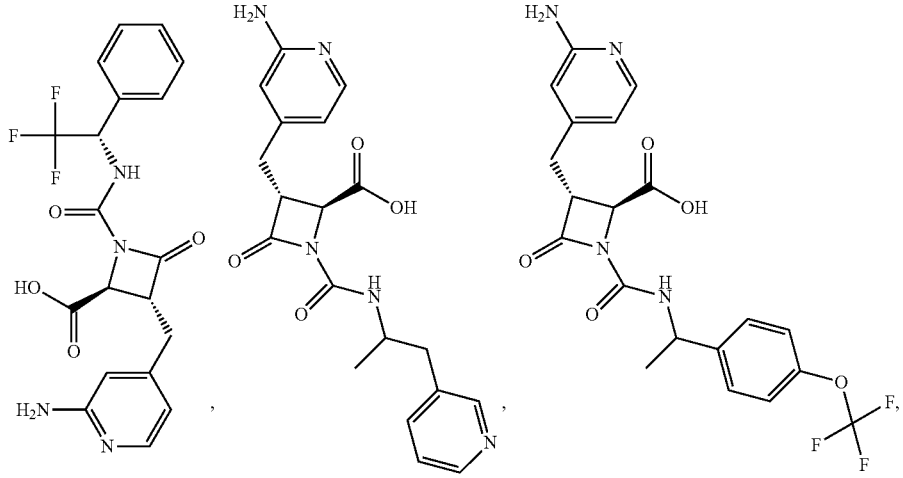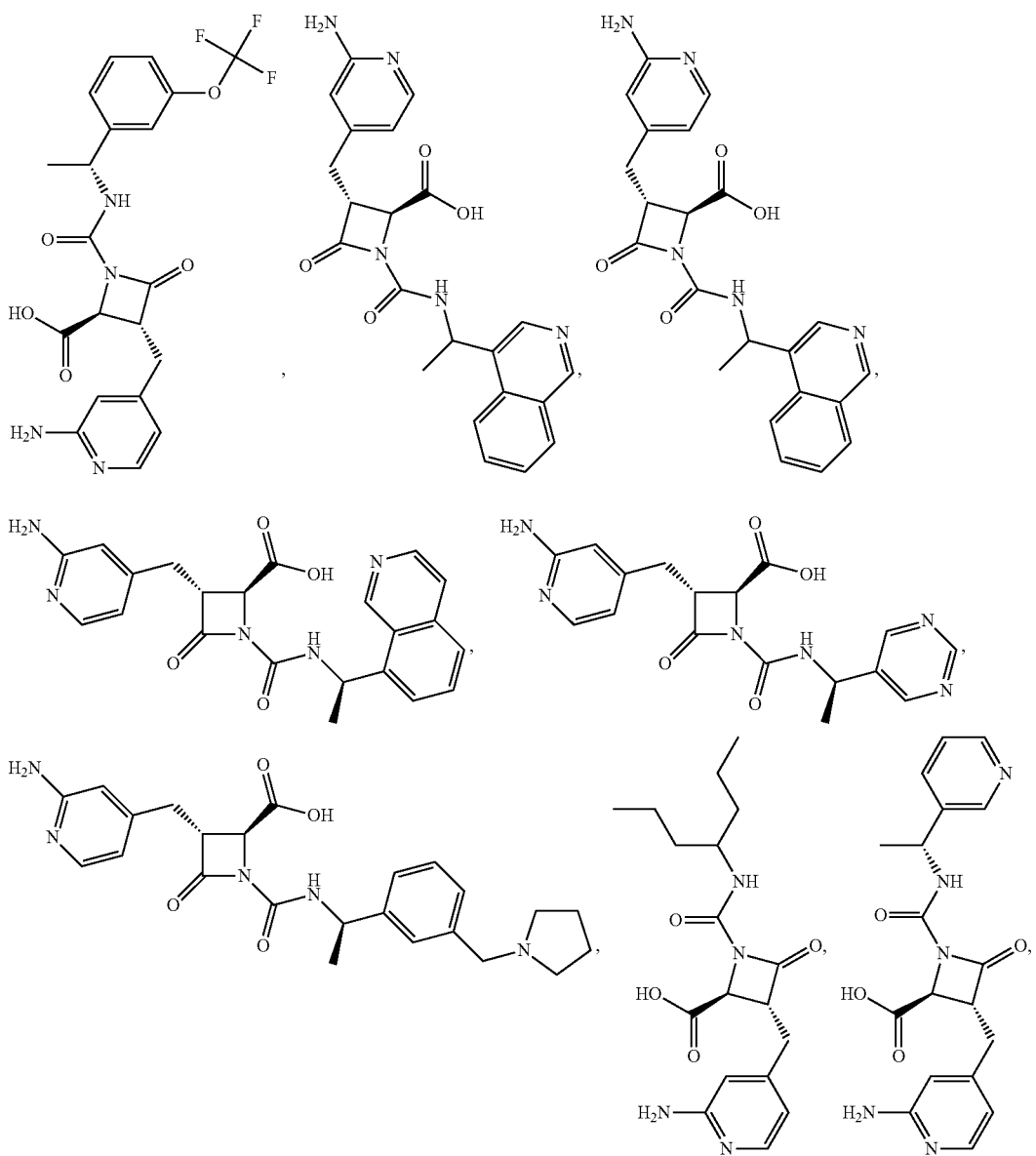

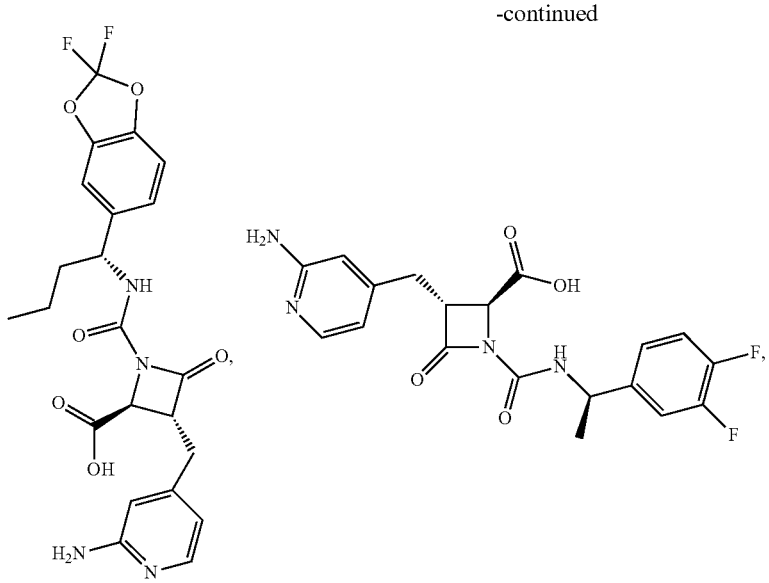
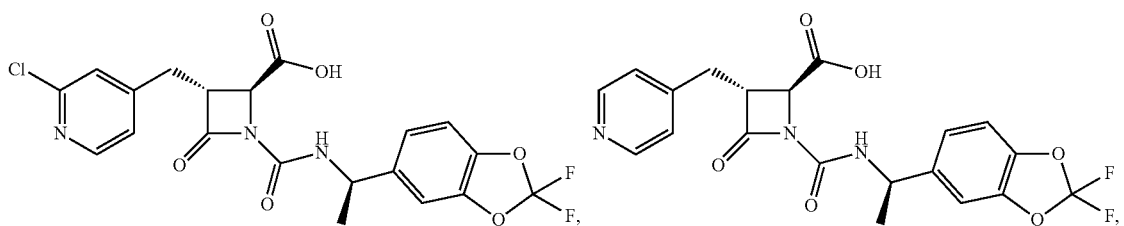
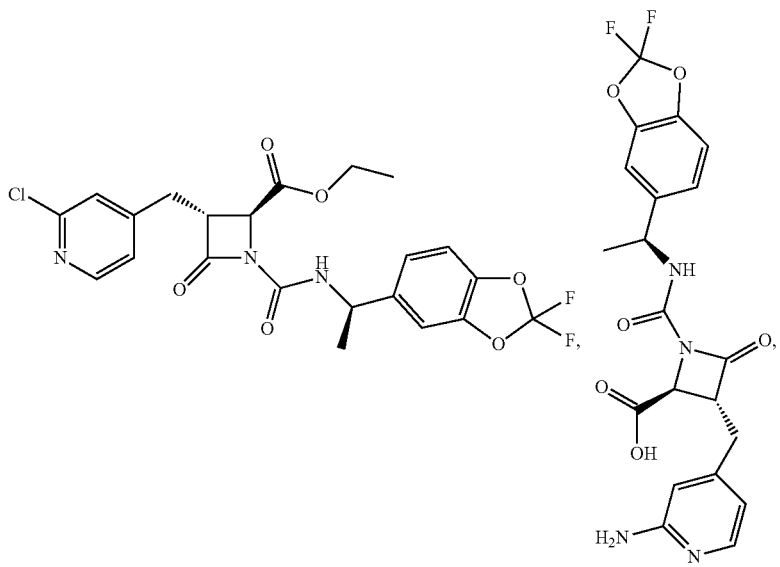
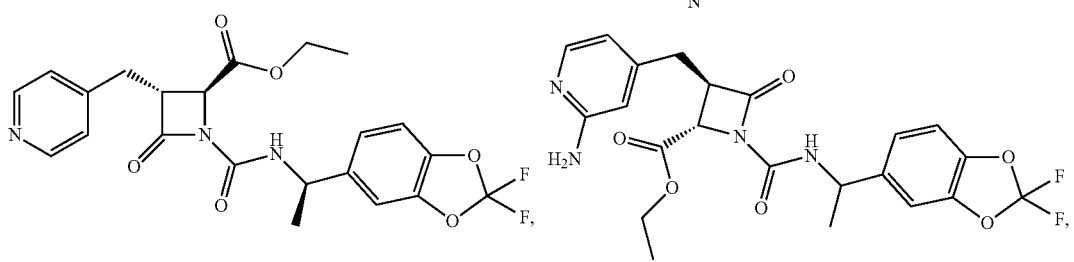

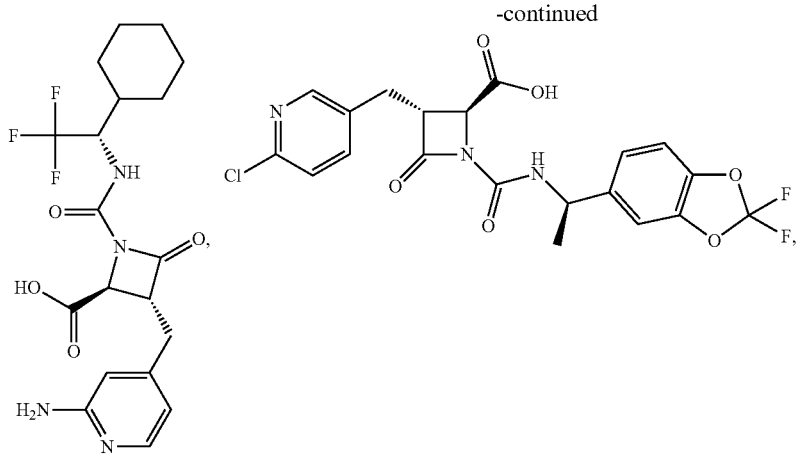
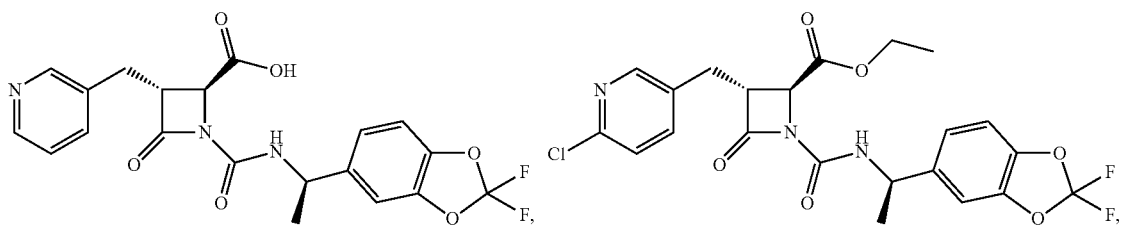
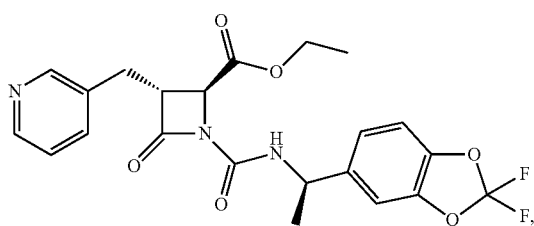
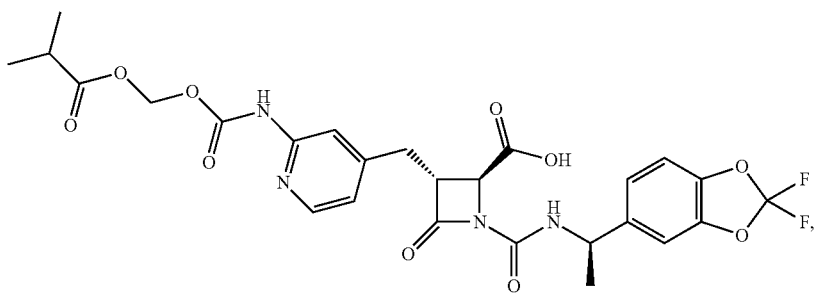
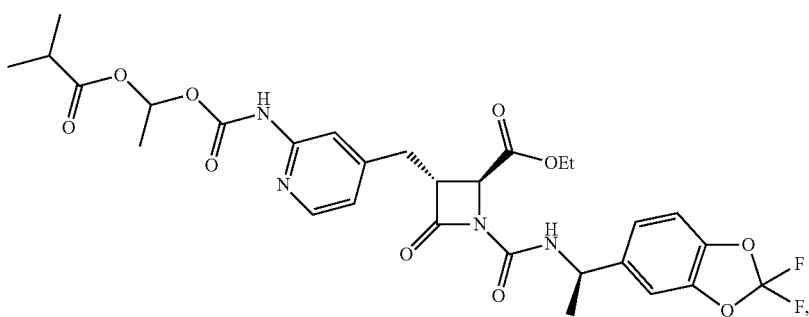

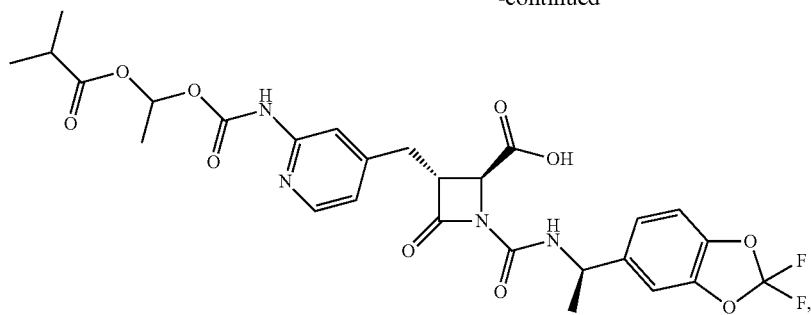
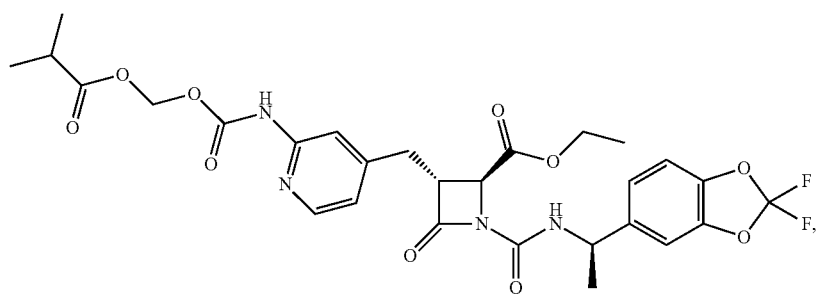
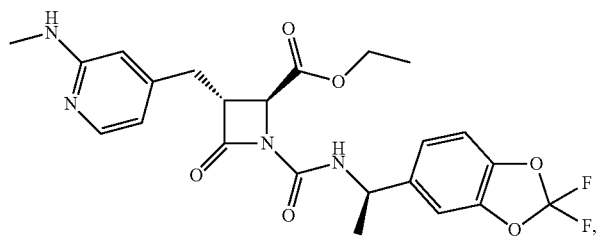
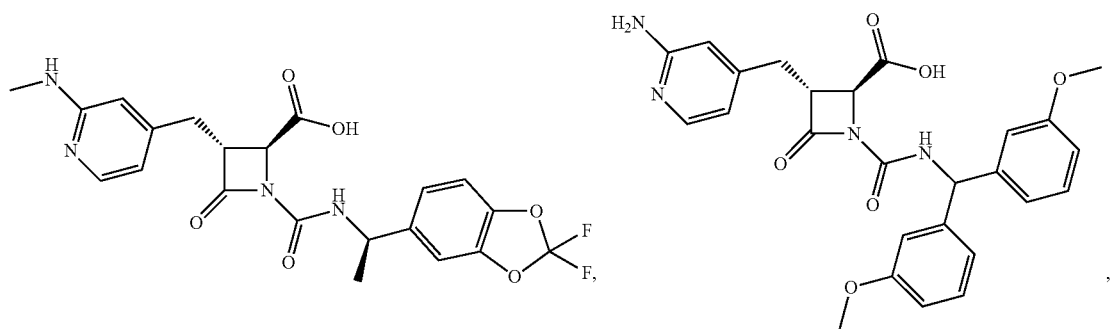
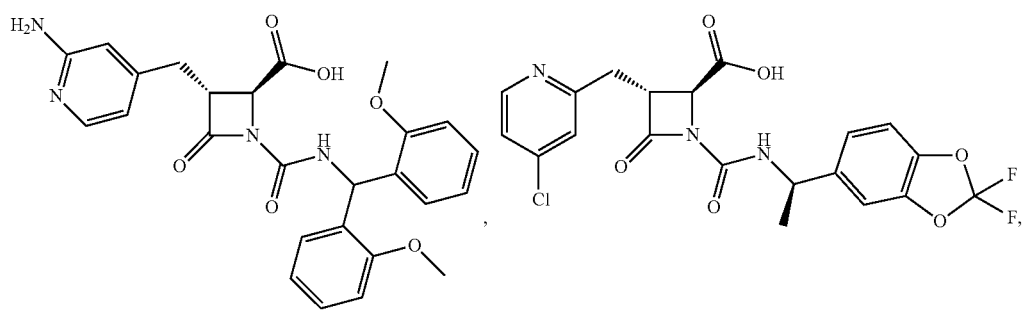

-continued
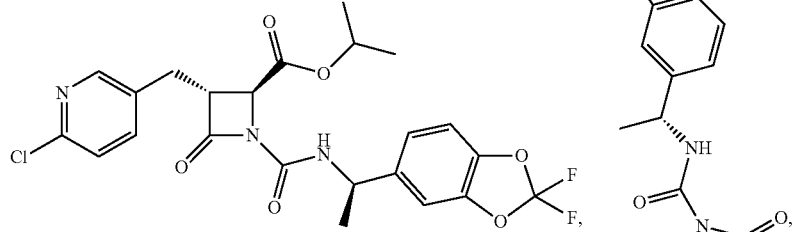
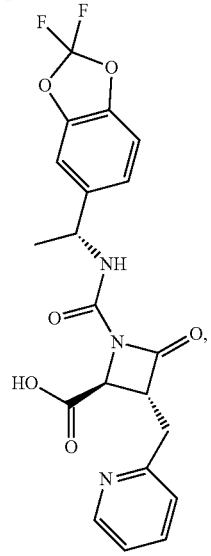
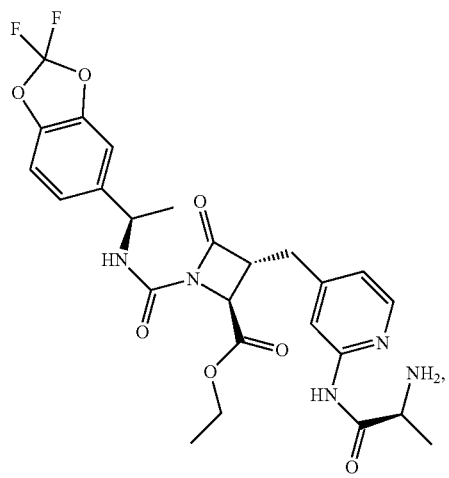
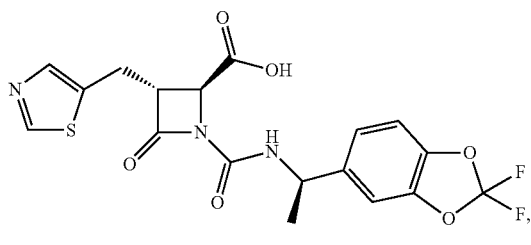
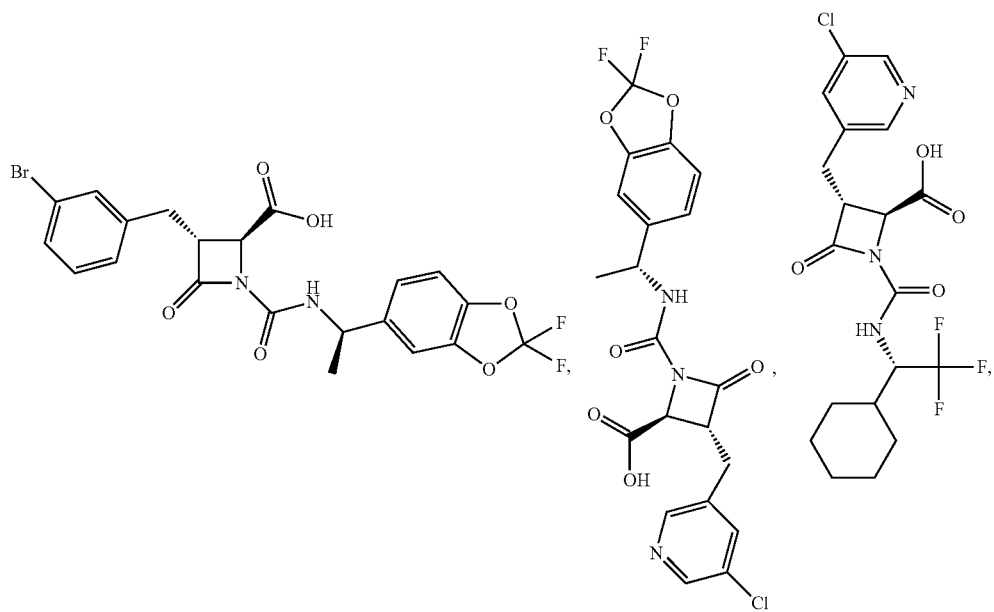

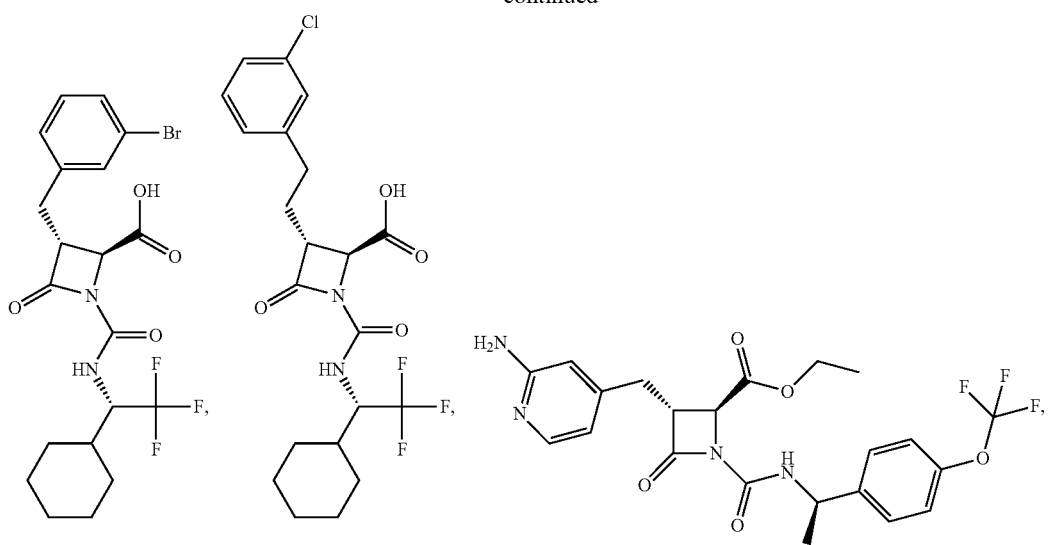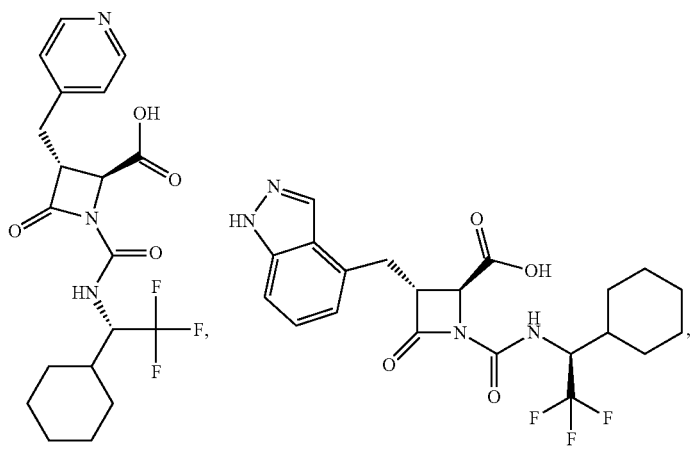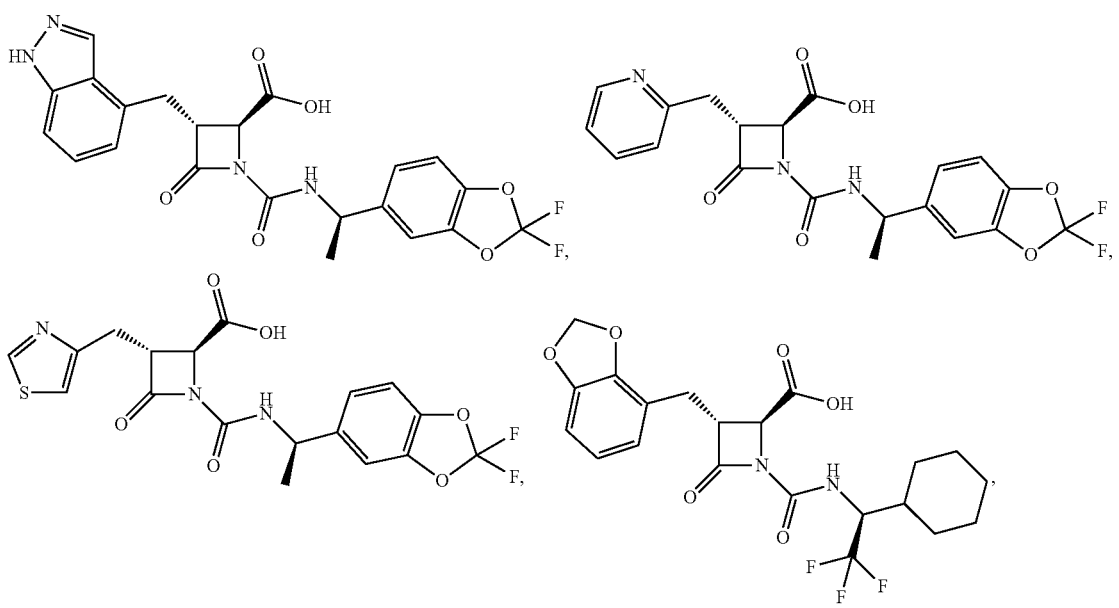

-continued
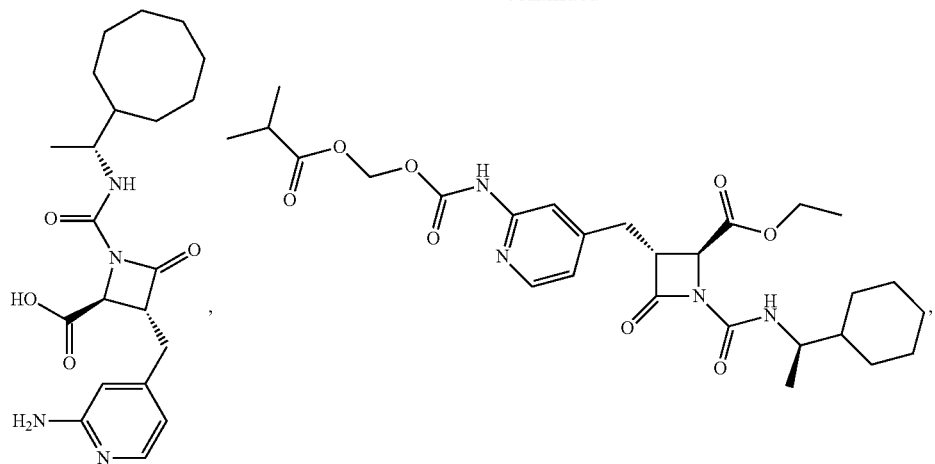
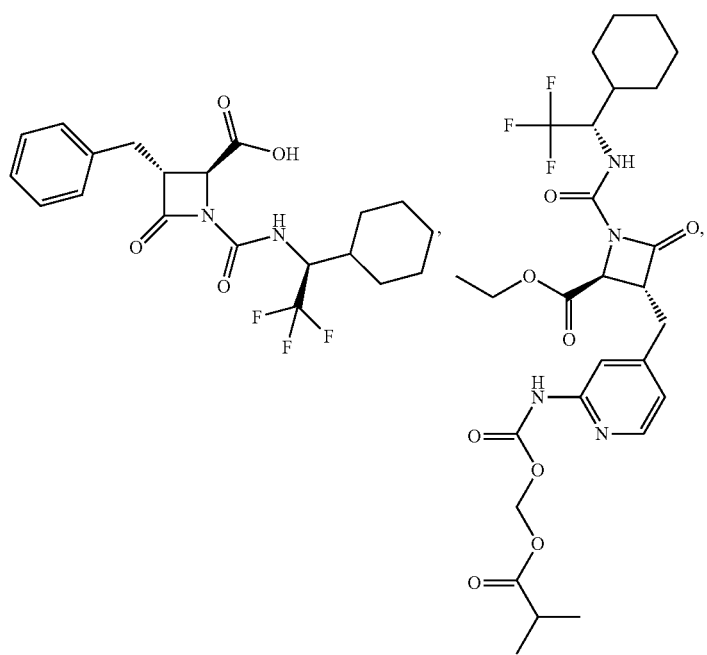
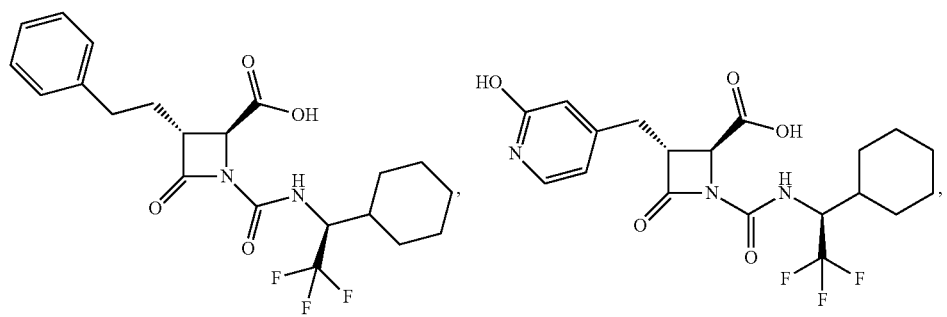

-continued
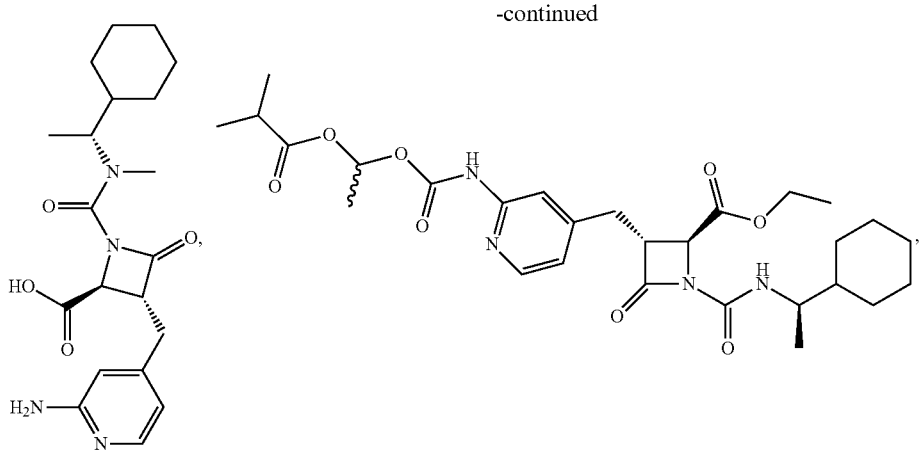
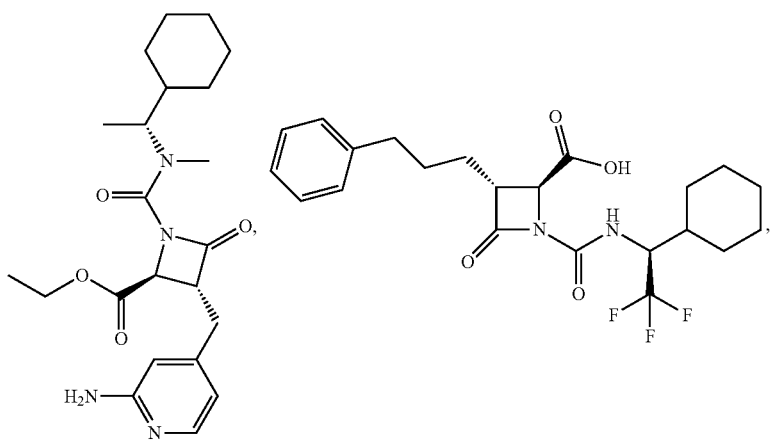
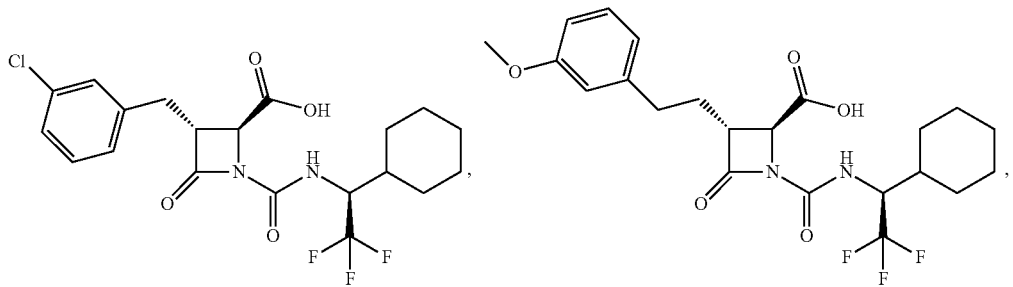
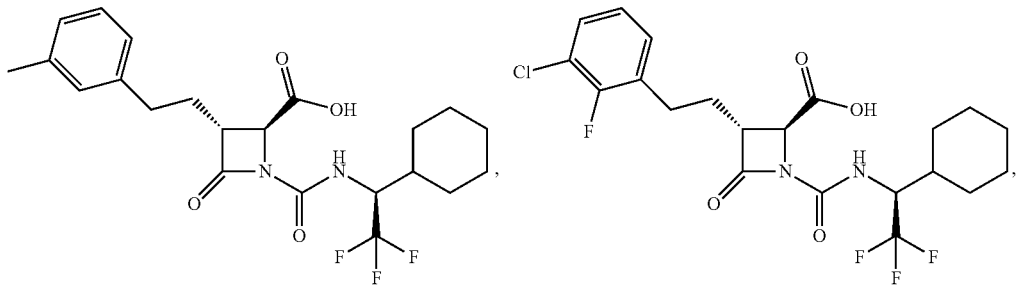

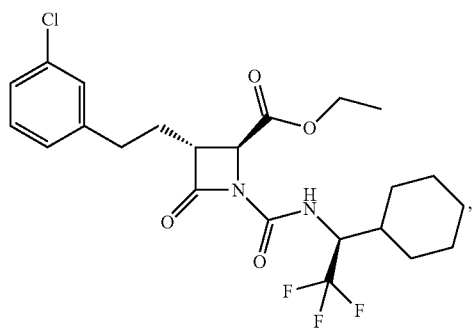
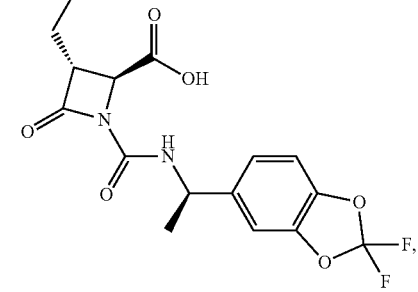
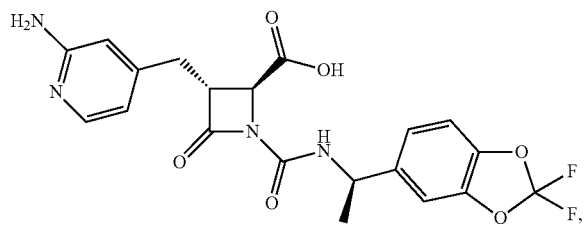
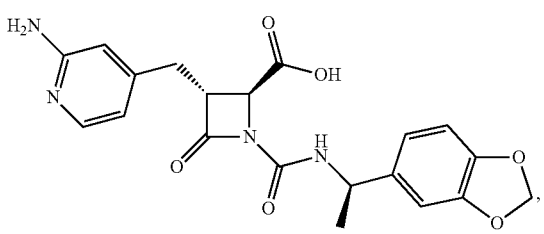
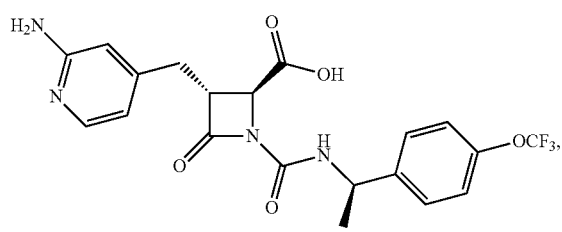
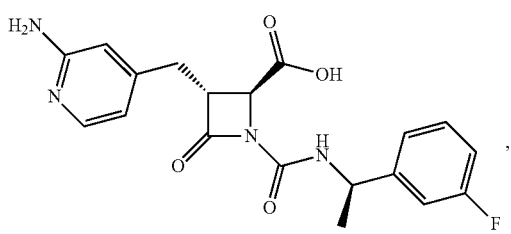
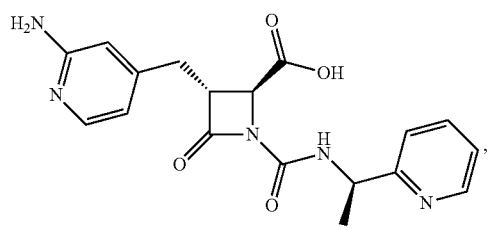
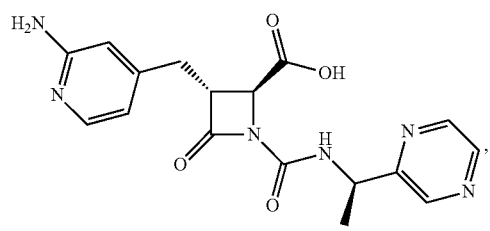
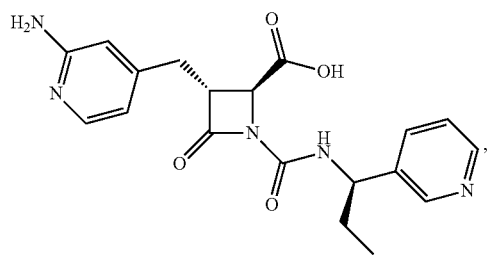
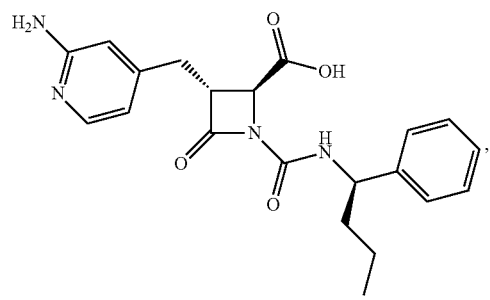

-continued
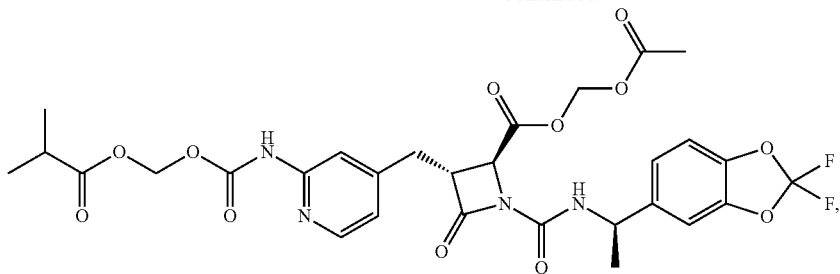
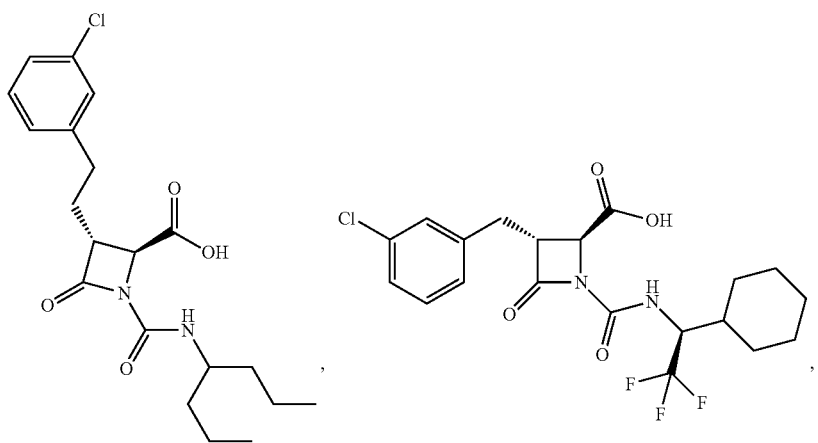
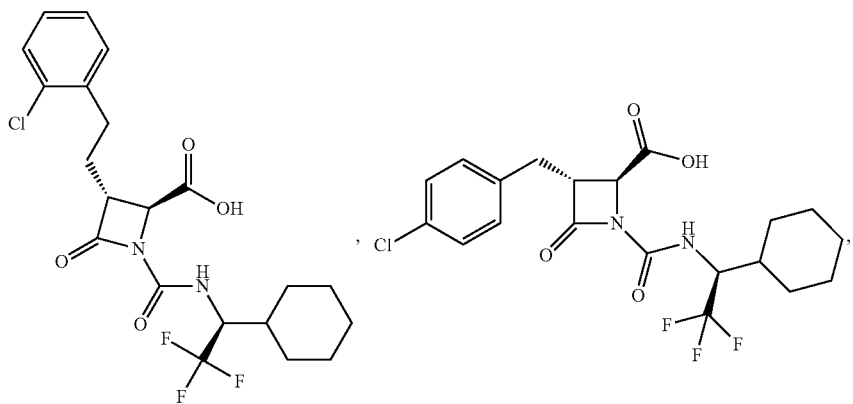
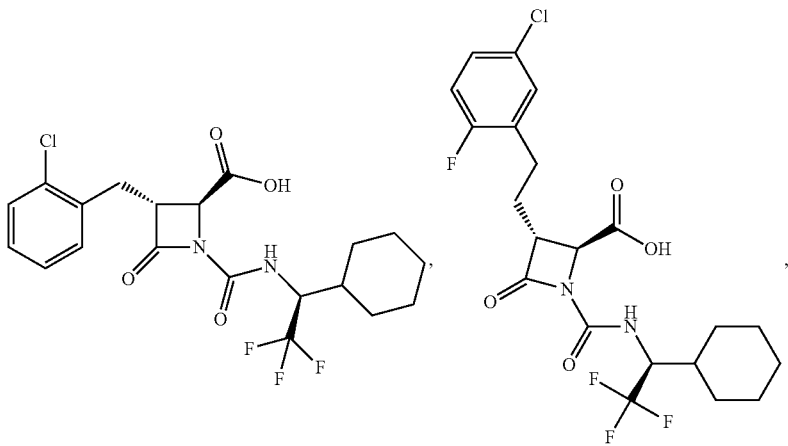

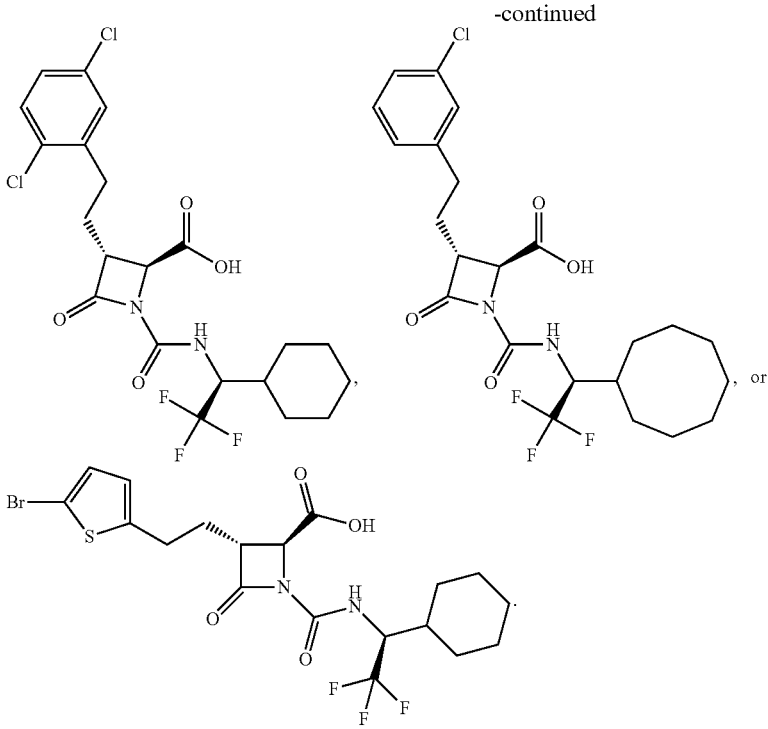

In some embodiments, the compound of formula (IIb) is selected from a compound of formula (IIc):

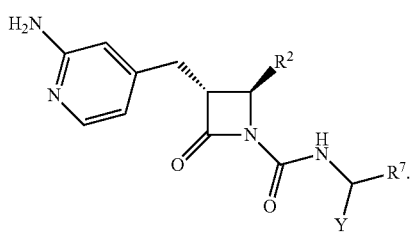

In one aspect, the present invention is directed to a compound of formula (III):

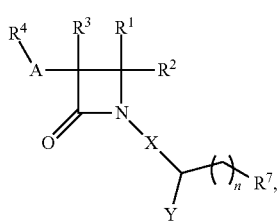

or a pharmaceutically acceptable salt thereof, wherein R is H or —$C_{2-6}$ alkyl; R is H, —$C_{2-6}$ alkyl, haloalkyl, —$CO_2R^{12}$, —$C(O)NH_2$, —CN, —$SO_qR^5$, —$OR^5$, —CHN($OR^5$), or a heteroaryl; $R^3$ is H or —$C_{1-6}$ alkyl; A is a bond, $C_{1-6}$ alkylene, $C_{2-6}$ alkenylene or $C_{2-6}$ alkynylene; $R^4$ is cycloalkyl, aryl, heteroaryl or heterocyclyl, each of which is substituted with 0-3 occurrences of —$NH_2$ or $R^6$ each $R^5$ is independently H, —$C_{1-6}$ alkyl, aralkyl, or aryl substituted with 0-3 occurrences of —$NH_2$ or $R^6$; each $R^6$ is independently halo, hydroxy, cyano, nitro, —$C_{1-6}$ alkyl, —$C_{1-6}$ alkoxy, —$NHR^{10}$, —$NR^9R^{10}$, —$C(O)R^{11}$, —$C(O)OR^1$, —$C(O)NR^9R^{10}$, —$C(NR^8)(N(R^8)_2)$, —$SO_qR^{11}$, —$SO_2NR^9R^{10}$, —$NHC(O)OR^{11}$, —$NHC(O)R^{11}$, aryl, heteroaryl, aralkyl, cycloalkyl, heteroaralkyl, heterocyclyl or heterocyclylalkyl, or two $R^6$ groups together with the atoms to which they are attached form a 5-7-membered ring; X is —C(O)O—, —OC(O)—, —C(O)S(O)$_2$—, —S(O)$_2$C(O)—, —C(O)N($R^5$)— or —N($R^5$)C(O)—; Y is —$C_{1-6}$ alkyl, cycloalkyl, aryl, heteroaryl, or heterocyclyl, each of which is substituted with 0-3 occurrences of —$NH_2$ or $R^6$; $R^7$ is H, —$C_{1-6}$ alkyl, cycloalkyl, aryl, heteroaryl or heterocyclyl, each of which is substituted with 0-3 occurrences of —$NH_2$ or $R^6$; each $R^8$ is independently H, —$C_{1-6}$ alkyl, —$C(O)R^5$, —$C(O)OR^5$, aryl, heteroaryl, aralkyl, heteroaralkyl, heterocyclyl, or heterocyclylalkyl; each of $R^9$ and $R^{10}$ is independently —$C_{1-6}$ alkyl, cycloalkyl, heterocyclyl, aryl, or heteroaryl, or $R^9$ and $R^{10}$ together form an optionally substituted 5-7-membered ring; each $R^1$ is independently H, —$C_{1-6}$ alkyl, aralkyl, or aryl; each $R^{12}$ is independently haloalkyl, optionally substituted —$C_{3-6}$ alkyl, or aralkyl; q is an integer from 0 to 2; and n is an integer from 0 to 2.

In some embodiments, $R^1$ is H.

In some embodiments, $R^2$ is haloalkyl (e.g., —$CH_2F$, —$CHF_2$, —$CF_3$), —$CO_2R^{12}$, —$C(O)NH_2$, —CN, —$SO_qR^5$ (e.g., —$SO_2R^5$), —$OR^5$, —$CHN(OR^5)$, or a heteroaryl (e.g., triazolyl, tetrazolyl, optionally substituted oxazolyl, optionally substituted isoxazolyl). In some embodiments, $R^{12}$ is haloalkyl, propyl, or aralkyl (e.g., benzyl). In some embodiments, $R^5$ is H, —$C_{1-6}$ alkyl (e.g., methyl, ethyl, propyl) or aryl (e.g., phenyl).

In some embodiments, A is $C_{1-6}$ alkylene (e.g., ethylene or propylene).

In some embodiments, $R^4$ is aryl or heteroaryl. In some embodiments, $R^4$ is phenyl substituted with 1 occurrence of $R^6$. In some embodiments, $R^6$ is $C_{1-6}$ alkoxy or —$C(NR^8)$ ($N(R^8)_2$). In some embodiments, $R^6$ is —$C(NR^8)(N(R^8)_2)$ and each $R^8$ is H. In some embodiments, $R^8$ is independently H or —$C(O)OR^5$. In some embodiments, $R^5$ is —$C_{1-6}$ alkyl (e.g., hexyl).

In some embodiments, $R^4$ is heteroaryl (e.g., a 6-membered heteroaryl or 5-membered heteroaryl) substituted with 0-3 occurrences of —$NH_2$ or $R^6$. In some embodiments, $R^4$ is a 6-membered heteroaryl (e.g., pyridyl) substituted with 0-3 occurrences of —$NH_2$ or $R^6$. In some embodiments, $R^6$ is halo (e.g., chloro). In some embodiments, $R^4$ is pyridyl substituted with 1 occurrence of —$NH_2$.

In some embodiments, X is —$C(O)N(R^8)$— or —$N(R^5)C(O)$—. In some embodiments, X is —$C(O)N(R^5)$— and $R^5$ is H.

In some embodiments, n is 0.

In some embodiments, $R^7$ is —$C_{1-6}$ alkyl (e.g., methyl). In some embodiments, $R^7$ is aryl (e.g., phenyl).

In some embodiments, Y is cycloalkyl, aryl, heteroaryl, or heterocyclyl, each of which is substituted with 0-3 occurrences of —$NH_2$ or $R^6$. In some embodiments, Y is phenyl substituted with 0 occurrences of $R^6$. In some embodiments, Y is phenyl substituted with 1 occurrence of $R^6$. In some embodiments, of $R^6$ is —$C_{1-6}$ alkoxy.

In some embodiments, the compound of formula (III) is selected from a compound of formula (IIIa):

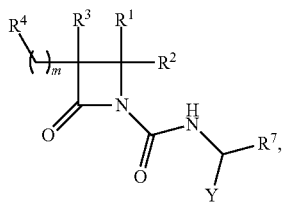

(IIIa)

wherein $R^1$, $R^2$, $R^3$, $R^4$, $R^7$, and Y are as described for formula (III), and m is an integer from 1 to 6.

In some embodiments, the compound of formula (IIIa) is selected from a compound of formula (IIIb):

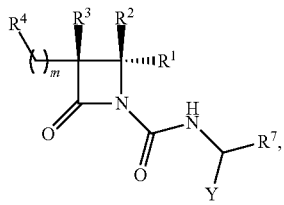

(IIIb)

wherein $R^1$, $R^2$, $R^3$, $R^4$, $R^7$, Y and m are as described for formula (IIIa).

In some embodiments, the compound of formula (IIIb) is:

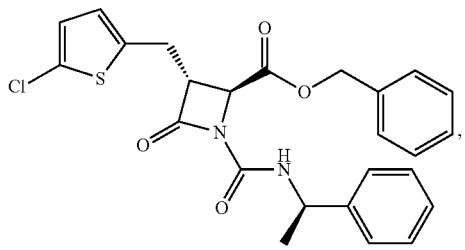

-continued

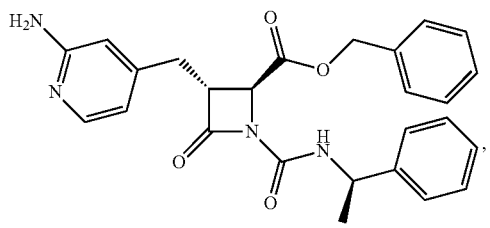

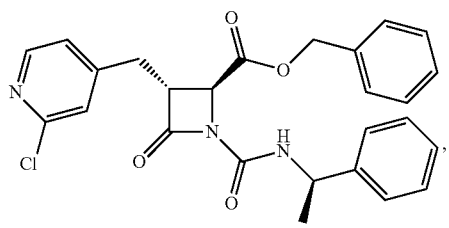

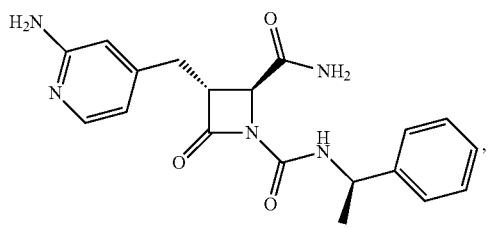

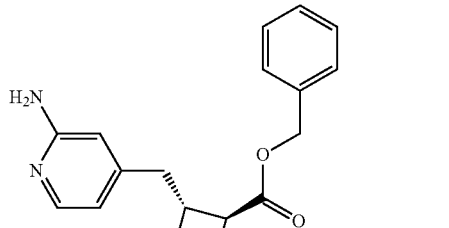

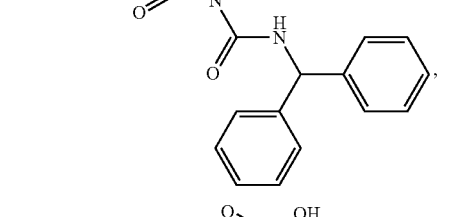

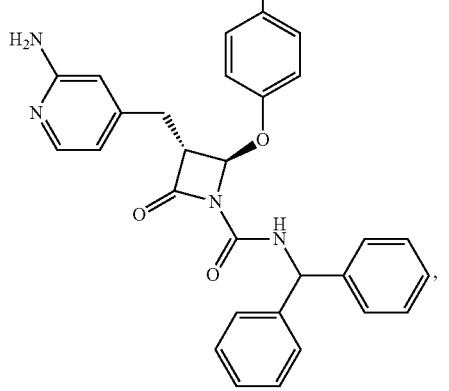

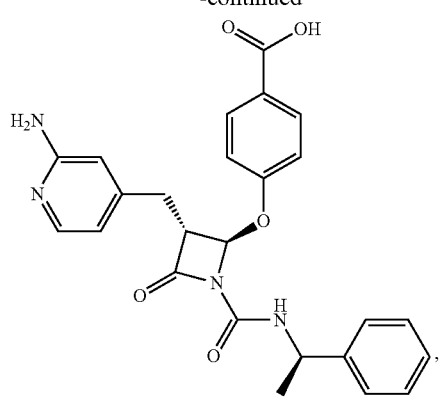
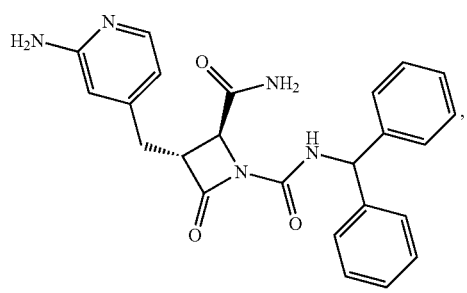
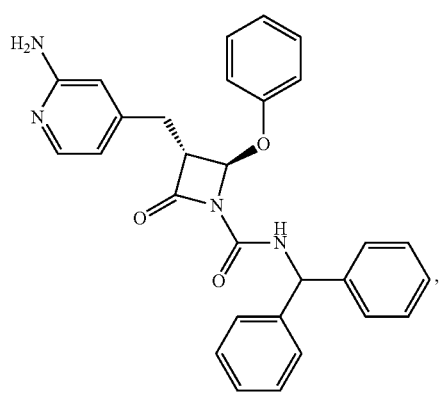
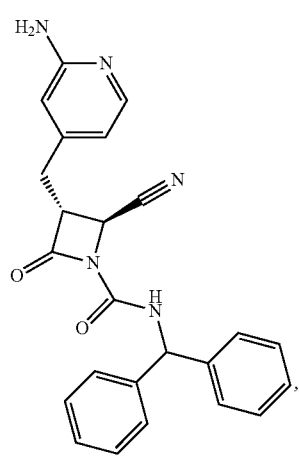
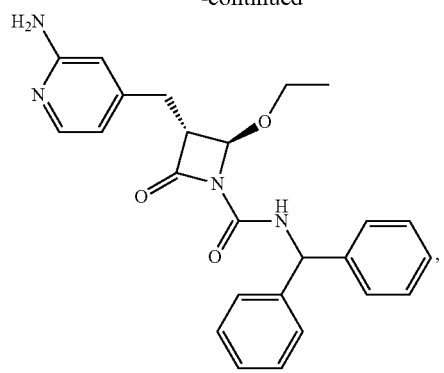
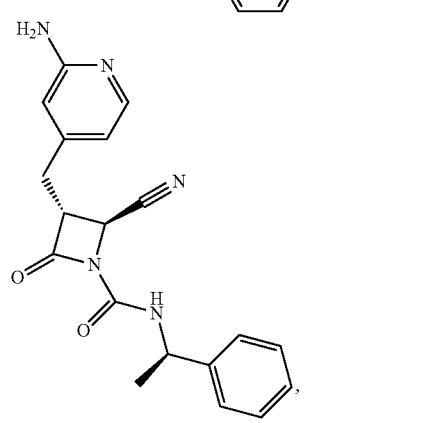
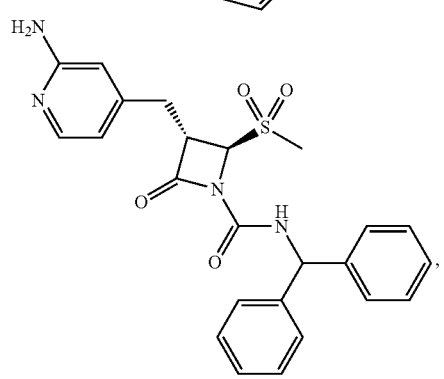
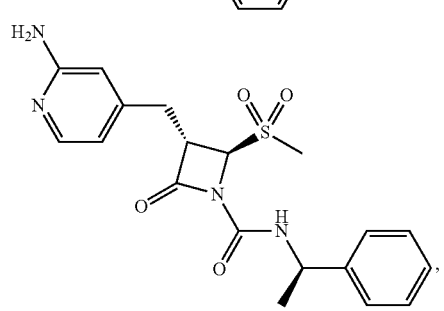
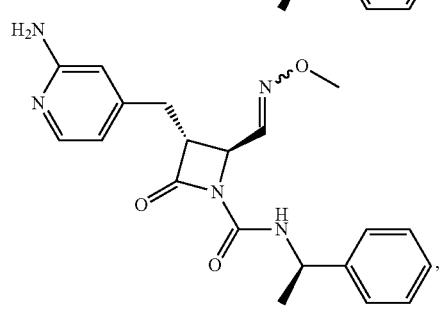

57
-continued
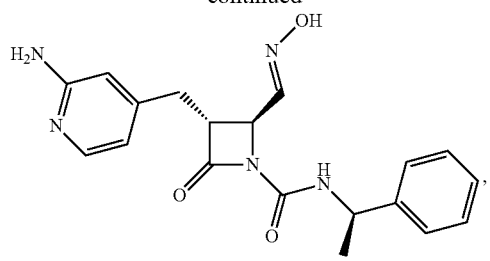
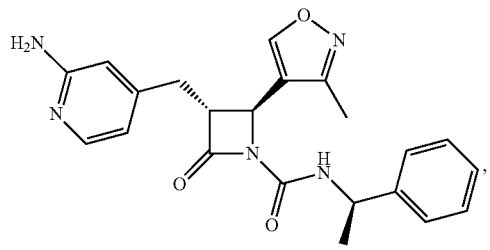
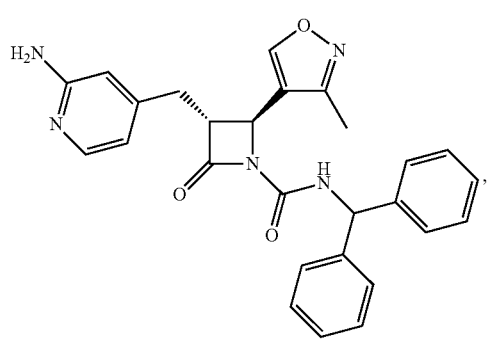
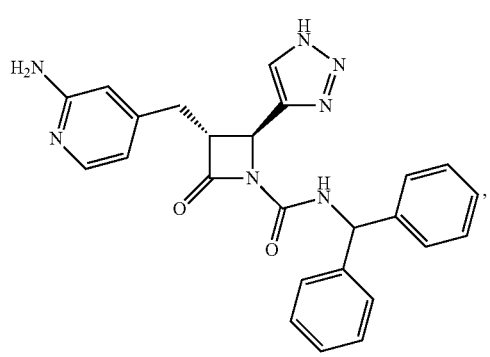
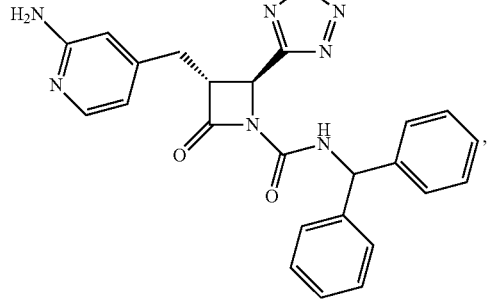
58
-continued
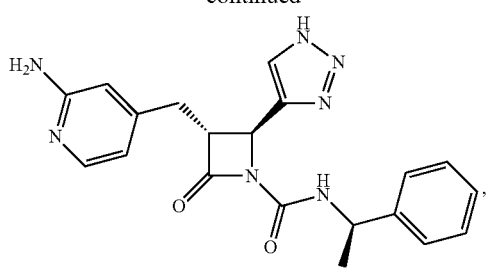
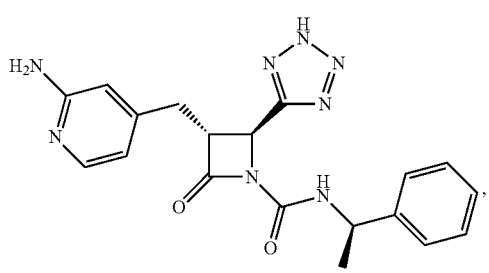
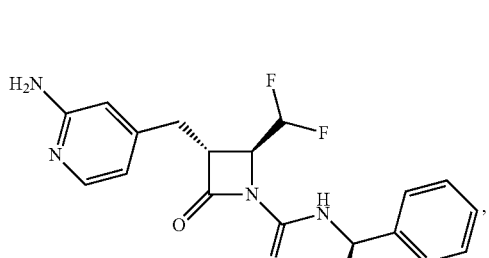
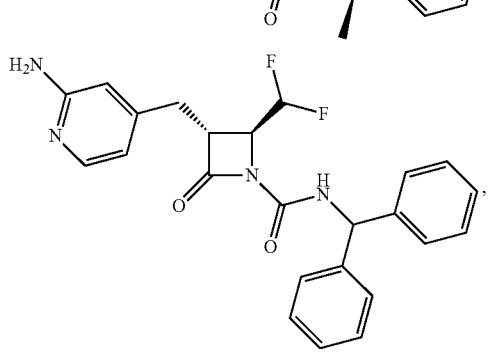
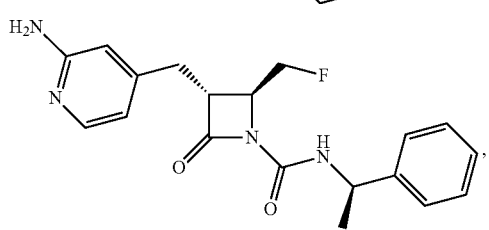
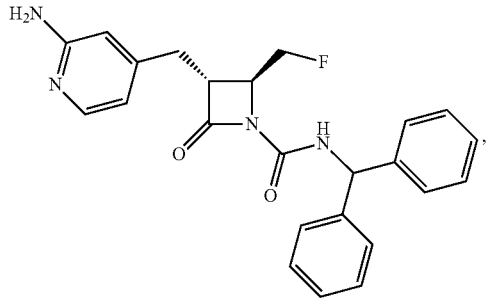

-continued

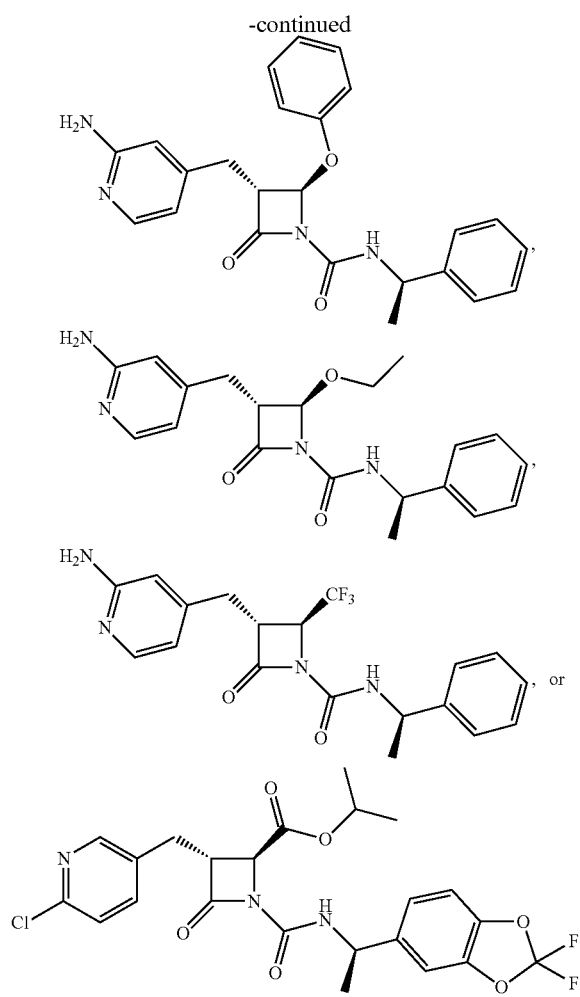

In one aspect, the present invention is directed to a compound of formula (IV):

(IV)

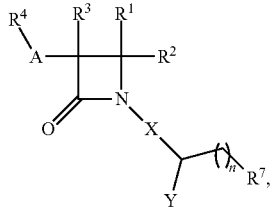

or a pharmaceutically acceptable salt thereof, wherein $R^1$ is H or —$C_{1-6}$ alkyl; $R^2$ is H, —$C_{1-6}$ alkyl, —$CO_2R^5$, —C(O) $NR^9R^{10}$, —CN, —$SO_qR^5$, —$OR^5$, —$CHN(OR^5)$ or a heteroaryl; $R^3$ is H or —$C_{1-6}$ alkyl; A is a bond, $C_{1-6}$ alkylene, $C_{2-6}$ alkenylene or $C_{2-6}$ alkynylene; $R^4$ is cycloalkyl, aryl, heteroaryl or heterocyclyl, each of which is substituted with 0-3 occurrences of —$NH_2$ or $R^6$; each $R^5$ is independently H, —$C_{1-6}$ alkyl, aralkyl, or aryl substituted with 0-3 occurrences of —$NH_2$ or $R^6$; each $R^6$ is independently halo, —$C_{1-6}$ alkyl, —$C_{1-6}$ alkoxy, —$NR^9R^{10}$, —$C(O)R^1$, —C(O) OR, —$C(O)NR^9R^{10}$, —$C(NR^8)(N(R^8)_2)$, —$SO_qR^{11}$, —$SO_2NR^9R^{10}$, —$NHC(O)OR^{11}$, aryl, heteroaryl, aralkyl, cycloalkyl, heteroarylkyl, heterocyclyl or heterocyclylalkyl, or two $R^6$ groups together with the atoms to which they are attached form a 5-7-membered ring; X is —C(O)O—, —OC(O)—, —C(O)S(O)_2—, —S(O)_2C(O)—, —C(O)N (R^5)— or —N(R^5)C(O)—; Y is H, —$C_{1-6}$ alkyl, cycloalkyl, aryl, heteroaryl, or heterocyclyl, each of which is substituted with 0-3 occurrences of —$NH_2$ or $R^6$; $R^7$ is H, —$C_{2-6}$ alkyl, haloalkyl, cycloalkyl, heteroaryl or heterocyclyl, each of which is substituted with 0-3 occurrences of —$NH_2$ or $R^6$, or substituted aryl; each $R^8$ is independently H, —$C_{1-6}$ alkyl, —$C(O)R^5$, —$C(O)OR^5$, aryl, heteroaryl, aralkyl, heteroaralkyl, heterocyclyl or heterocyclylalkyl; each of $R^9$ and $R^{10}$ is independently —$C_{1-6}$ alkyl, cycloalkyl, heterocyclyl, aryl, or heteroaryl, or $R^9$ and $R^{10}$ together form an optionally substituted 5-7-membered ring; each $R^{11}$ is independently H, —$C_{1-6}$ alkyl, aralkyl, or aryl; q is an integer from 0 to 2; and n is an integer from 0 to 2.

In some embodiments, $R^1$ is H.
In some embodiments, $R^2$ is —$CO_2R$, wherein $R^5$ is H or —$C_{1-6}$ alkyl (e.g., ethyl).
In some embodiments, A is $C_{1-6}$ alkylene (e.g., ethylene or propylene).
In some embodiments, $R^4$ is aryl or heteroaryl. In some embodiments, $R^4$ is phenyl substituted with 1 occurrence of $R^6$. In some embodiments, $R^6$ is halo, $C_{1-6}$ alkoxy or —$C(NR^8)(N(R^8)_2)$. In some embodiments, $R^6$ is —$C(NR^8)$ $(N(R^8)_2)$ and each $R^8$ is H. In some embodiments, $R^4$ is heteroaryl (e.g., a 6-membered heteroaryl or 5-membered heteroaryl) substituted with 0-3 occurrences of —$NH_2$ or $R^6$. In some embodiments, $R^4$ is a 6-membered heteroaryl (e.g., pyridyl) substituted with 0-3 occurrences of —$NH_2$ or $R^6$. In some embodiments, $R^6$ is halo (e.g., chloro, bromo, fluoro). In some embodiments, $R^6$ is —$NHC(O)OR^{11}$, and $R^{11}$ is —$C_{1-6}$ alkyl (e.g., substituted alkyl (e.g., 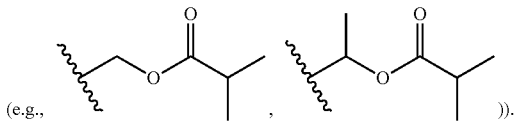 )).

In some embodiments, X is —$C(O)N(R^5)$— or —$N(R^5)$ $C(O)$—. In some embodiments, X is —$C(O)N(R^5)$— and $R^5$ is H.
In some embodiments, $R^7$ is H, —$C_{2-6}$ alkyl, haloalkyl, cycloalkyl, or substituted aryl.
In some embodiments, n is 0.
In some embodiments, Y is H, —$C_{1-6}$ alkyl, cycloalkyl, aryl, heteroaryl, or heterocyclyl, each of which is substituted with 0-3 occurrences of —$NH_2$ or $R^6$. In some embodiments, Y is aryl (e.g., aryl, naphthyl). In some embodiments, Y is phenyl substituted with 0 occurrences of $R^6$. In some embodiments, Y is phenyl substituted with 1 occurrence of $R^6$. In some embodiments, $R^6$ is haloalkoxy (e.g., —$OCF_3$) or halo (e.g., chloro). In some embodiments, Y is aryl or heteroaryl and two $R^6$ groups taken together with the atoms to which they are attached form a 5-7 membered ring selected from:

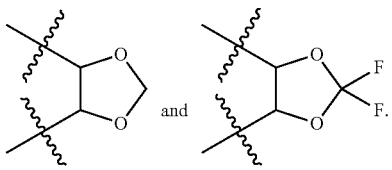 [SMILES: *C1OCOC1* ; *C1OC(F)(F)OC1*]

In some embodiments, Y is phenyl and two R⁶ groups taken together with the atoms to which they are attached form a 5-7 membered ring. In some embodiments, Y is phenyl and two R⁶ groups taken together with the atoms to which they are attached form a 5-7 membered ring selected from:

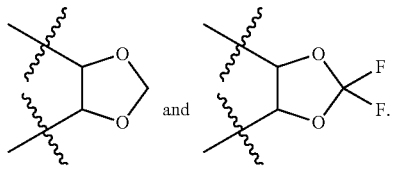 [SMILES: *C1OCOC1* ; *C1OC(F)(F)OC1*]

In some embodiments, Y is heteroaryl (e.g., pyridyl, pyrazinyl, pyrimidinyl, quinolinyl, isoquinolinyl, thiazolyl, indazolyl) substituted with 0-3 occurrences of R⁶. In some embodiments, Y is cycloalkyl (e.g., cyclohexyl). In some embodiments, Y is —$C_{1-6}$ alkyl substituted with 0 occurrences of R⁶. In some embodiments, Y is —$C_{1-6}$ alkyl substituted with 1-3 occurrences of R⁶, and R⁶ is aryl. In some embodiments, Y is —$C_{1-6}$ alkyl substituted with 2 occurrences of R⁶, and R⁶ is aryl (e.g., phenyl).

In some embodiments, the compound of formula (IV) is selected from a compound of formula (IVa):

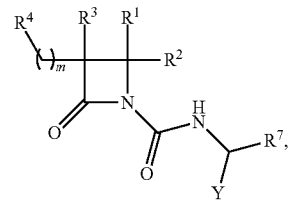

(IVa)

wherein R¹, R², R³, R⁴, R⁷, and Y are as described for formula (IV), and m is an integer from 1 to 6.

In some embodiments, the compound of formula (IVa) is selected from a compound of formula (IVb):

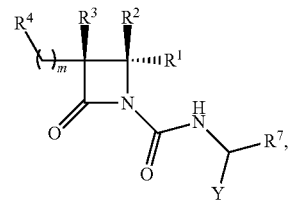

(IVb)

wherein R¹, R², R³, R⁴, R⁷, Y and m are as described for formula (IVa).

In some embodiments, the compound of formula (IV) is:

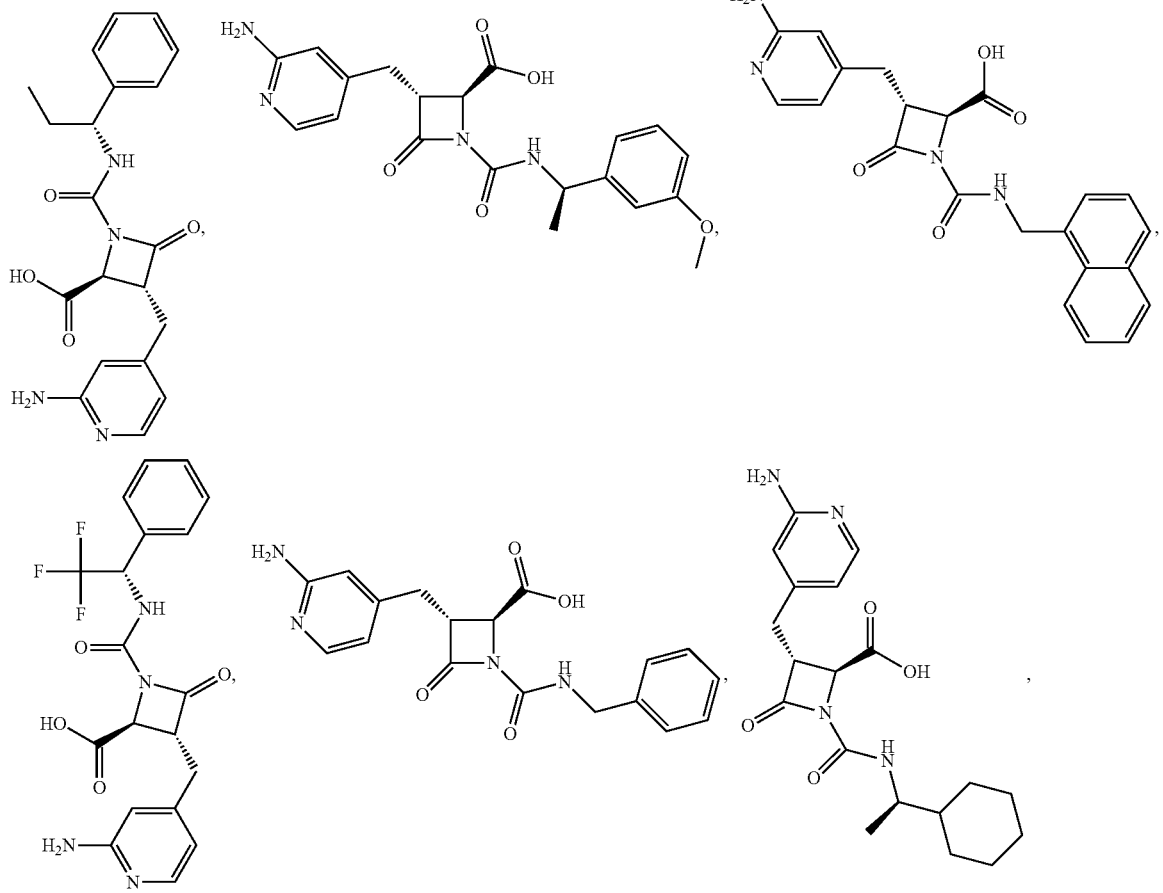

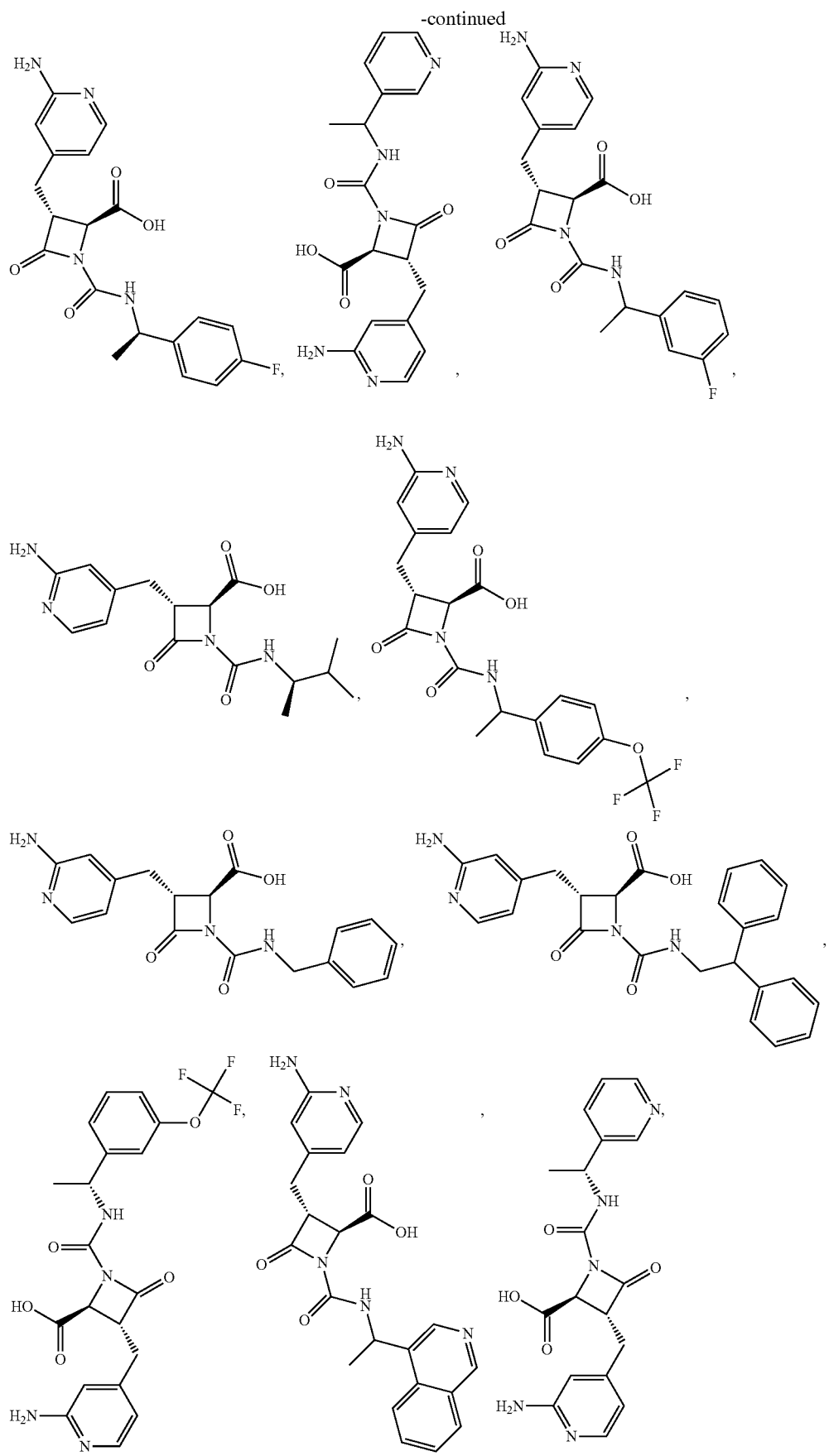

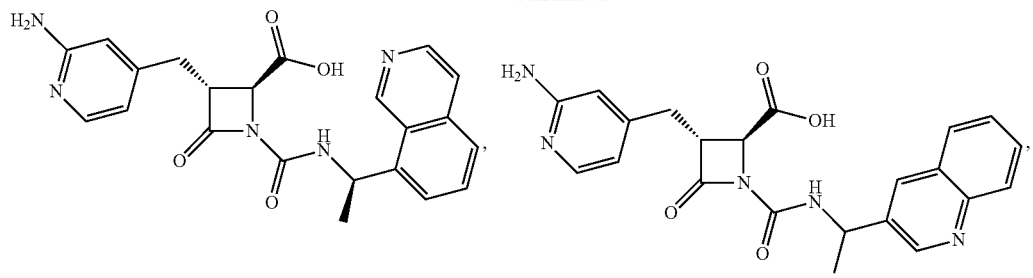
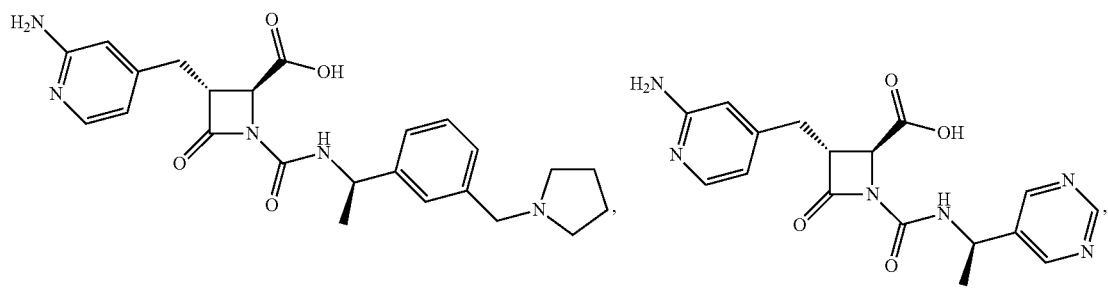
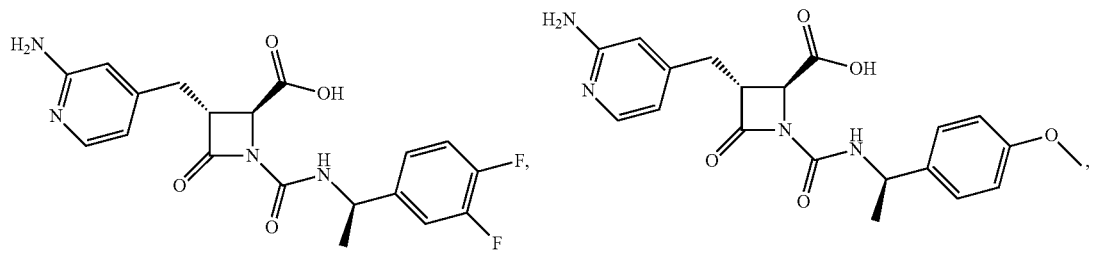
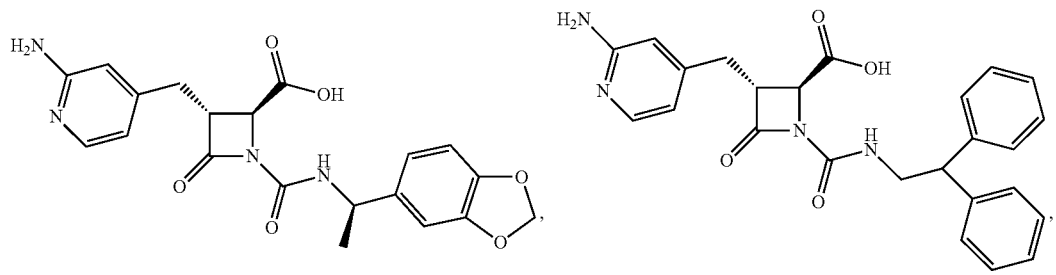
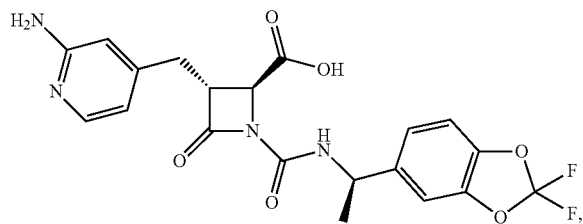
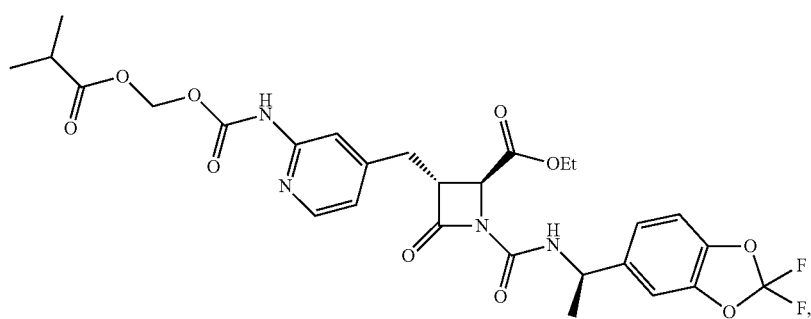

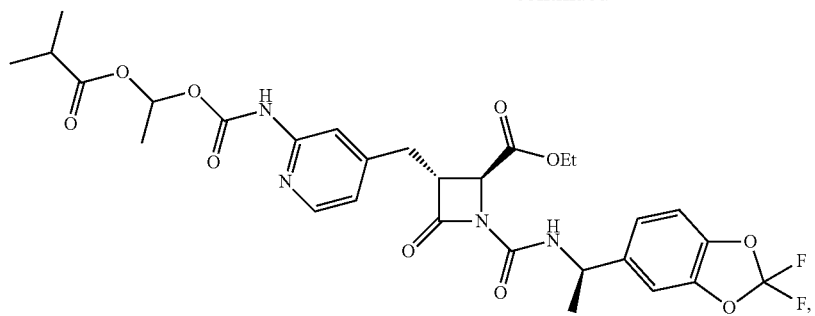
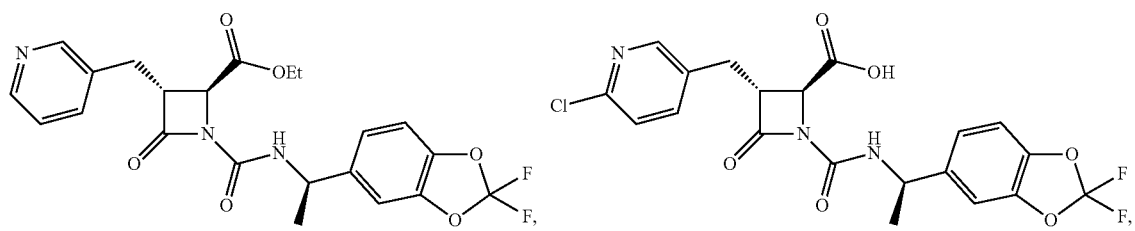
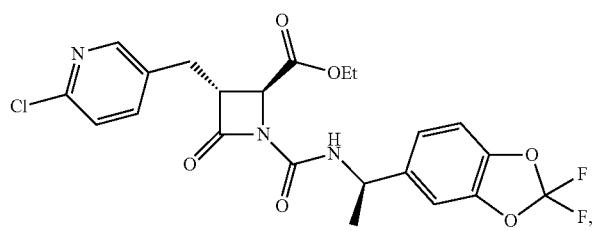
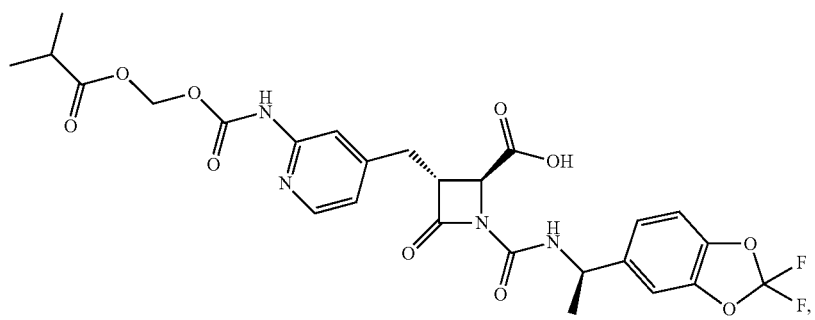
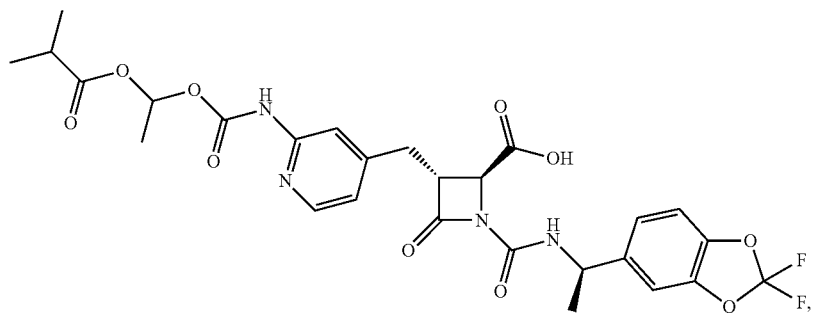
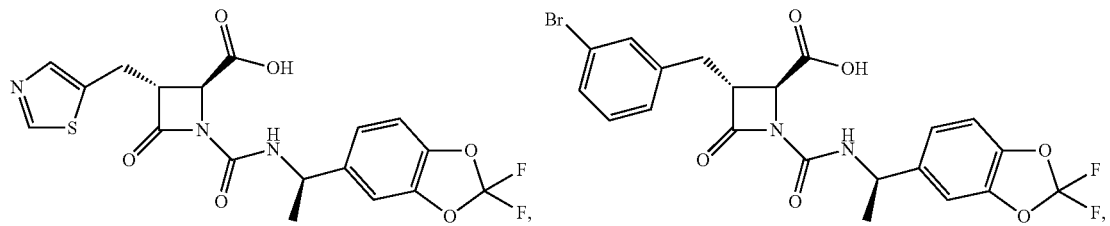

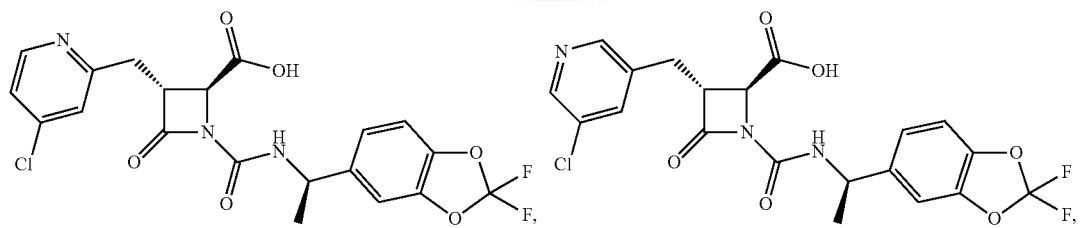
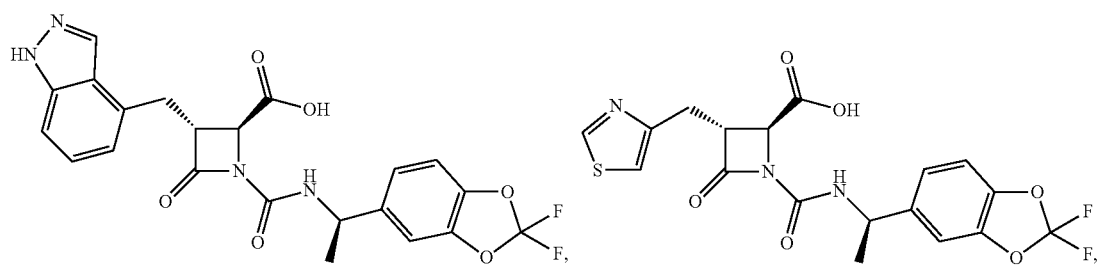
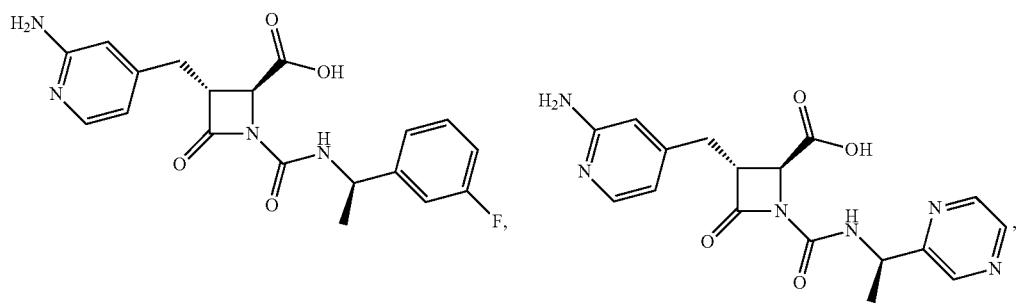
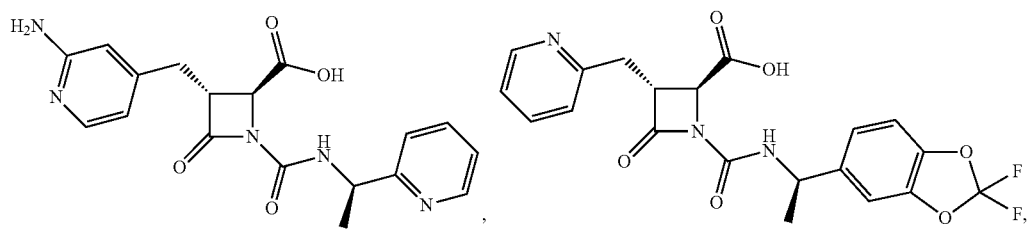
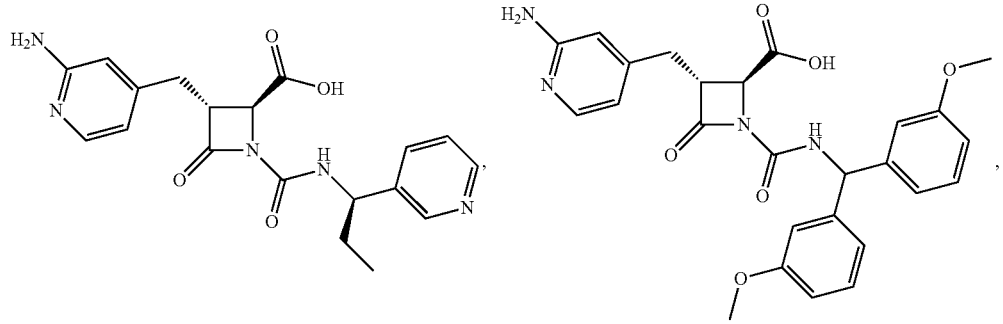
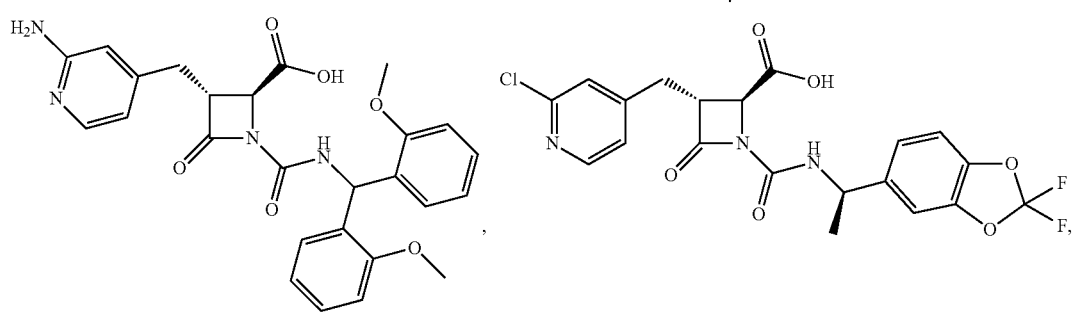

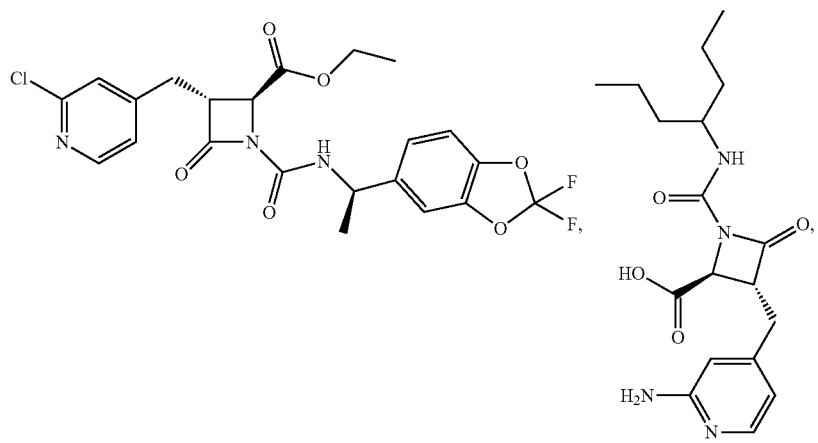
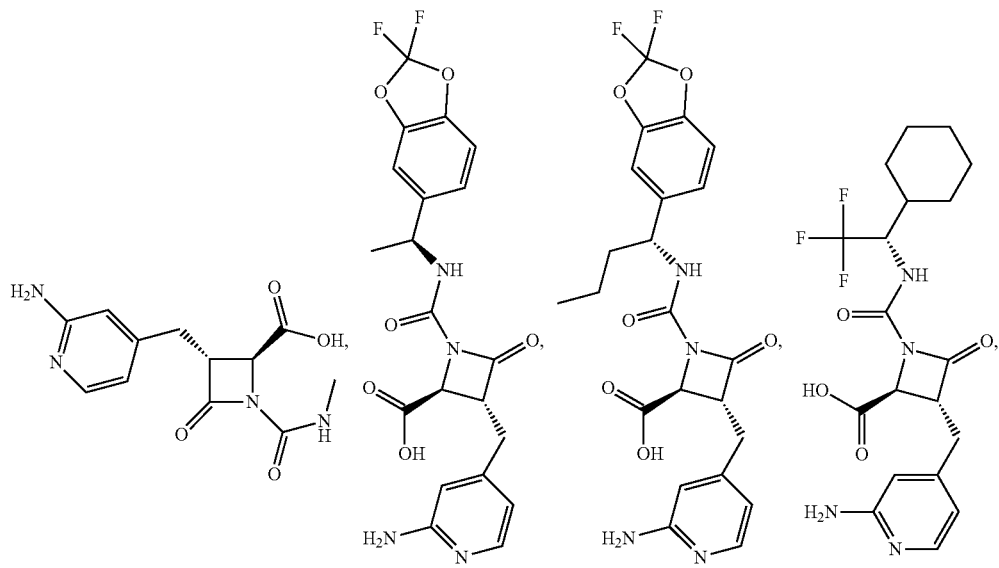
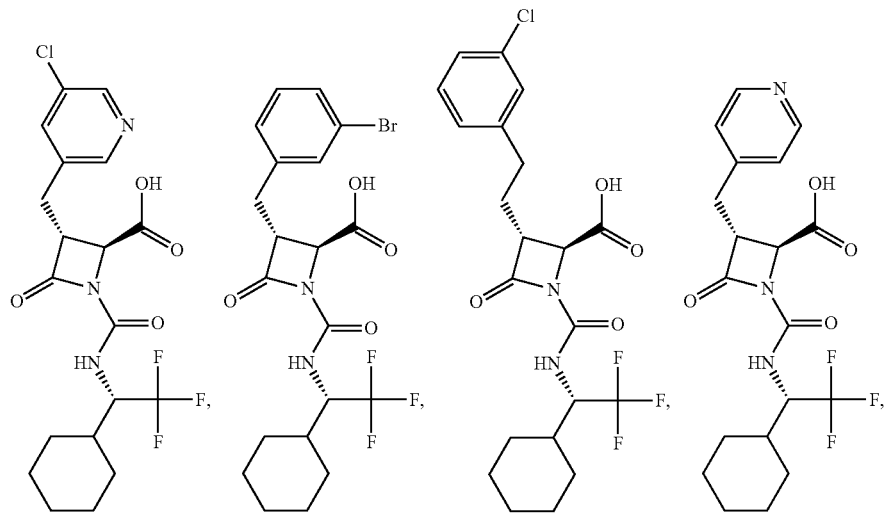

-continued
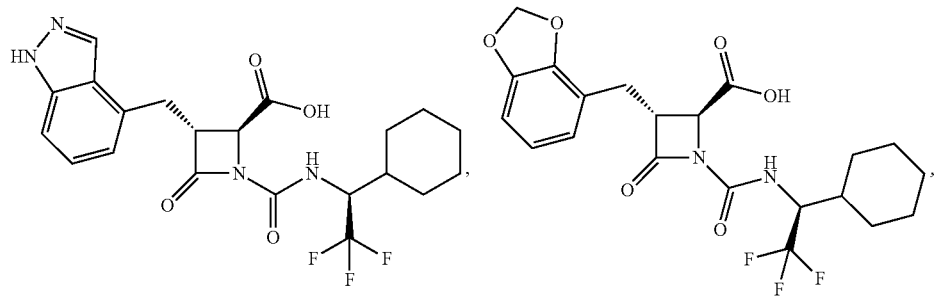
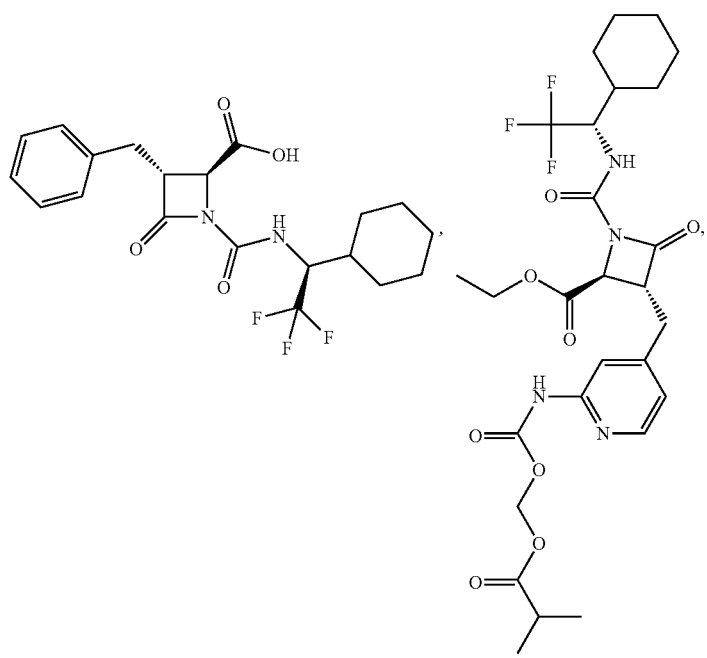
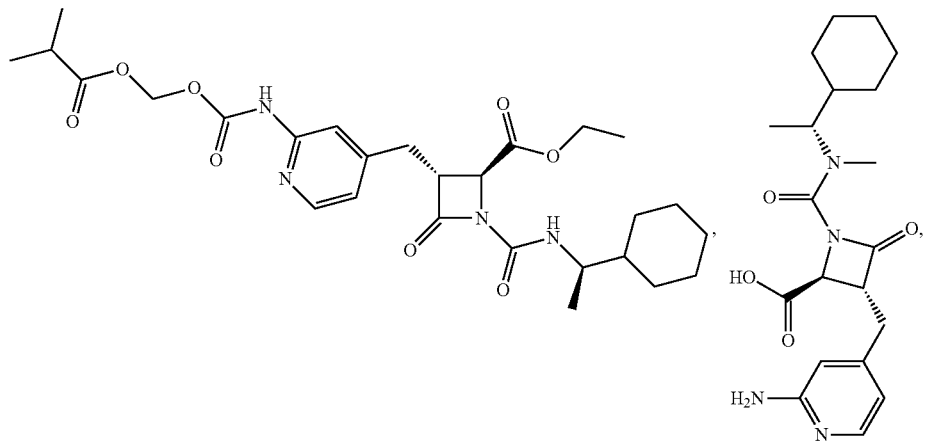

75 76
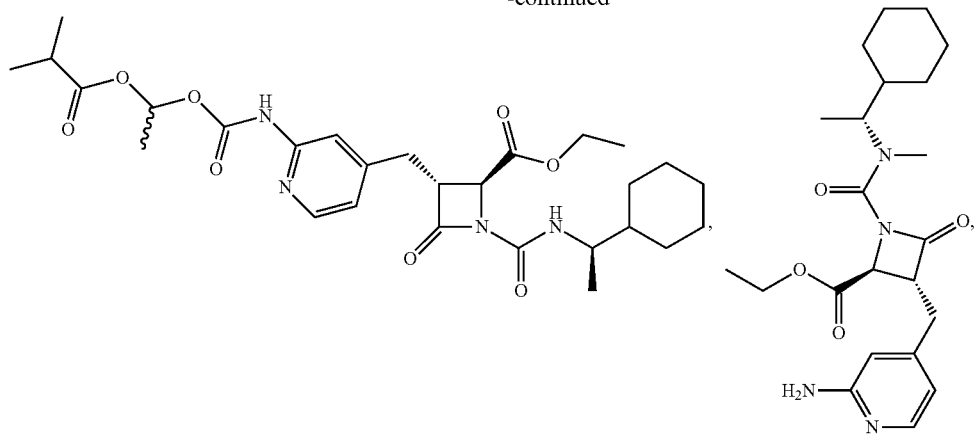
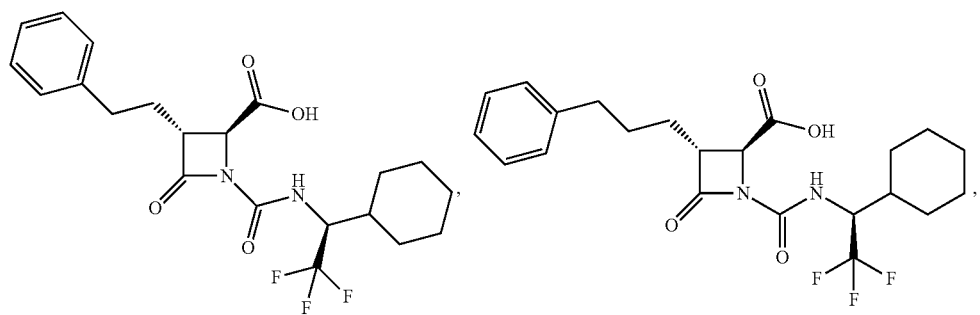
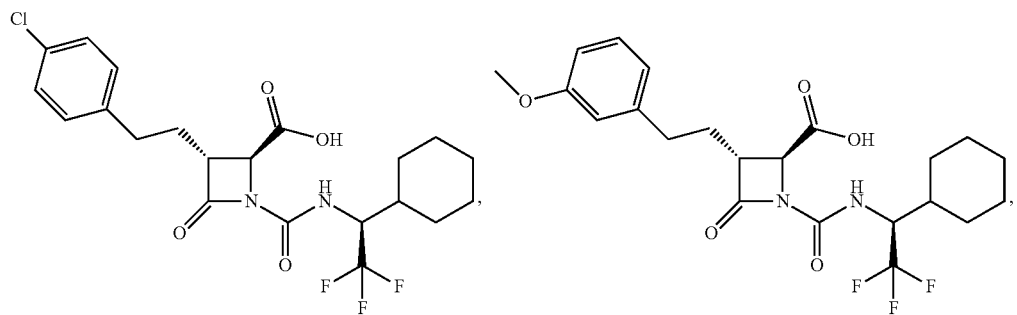
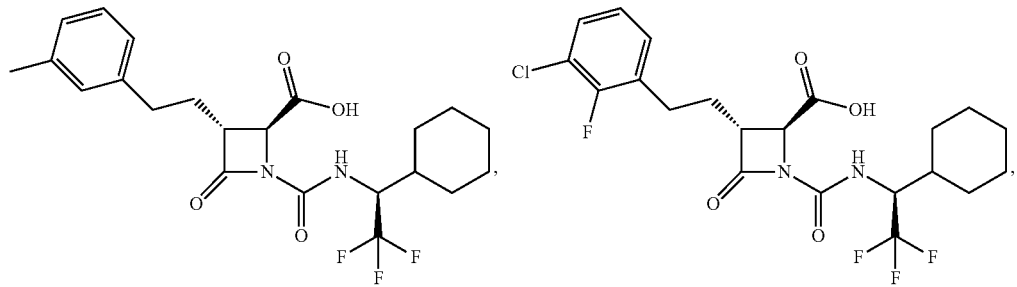

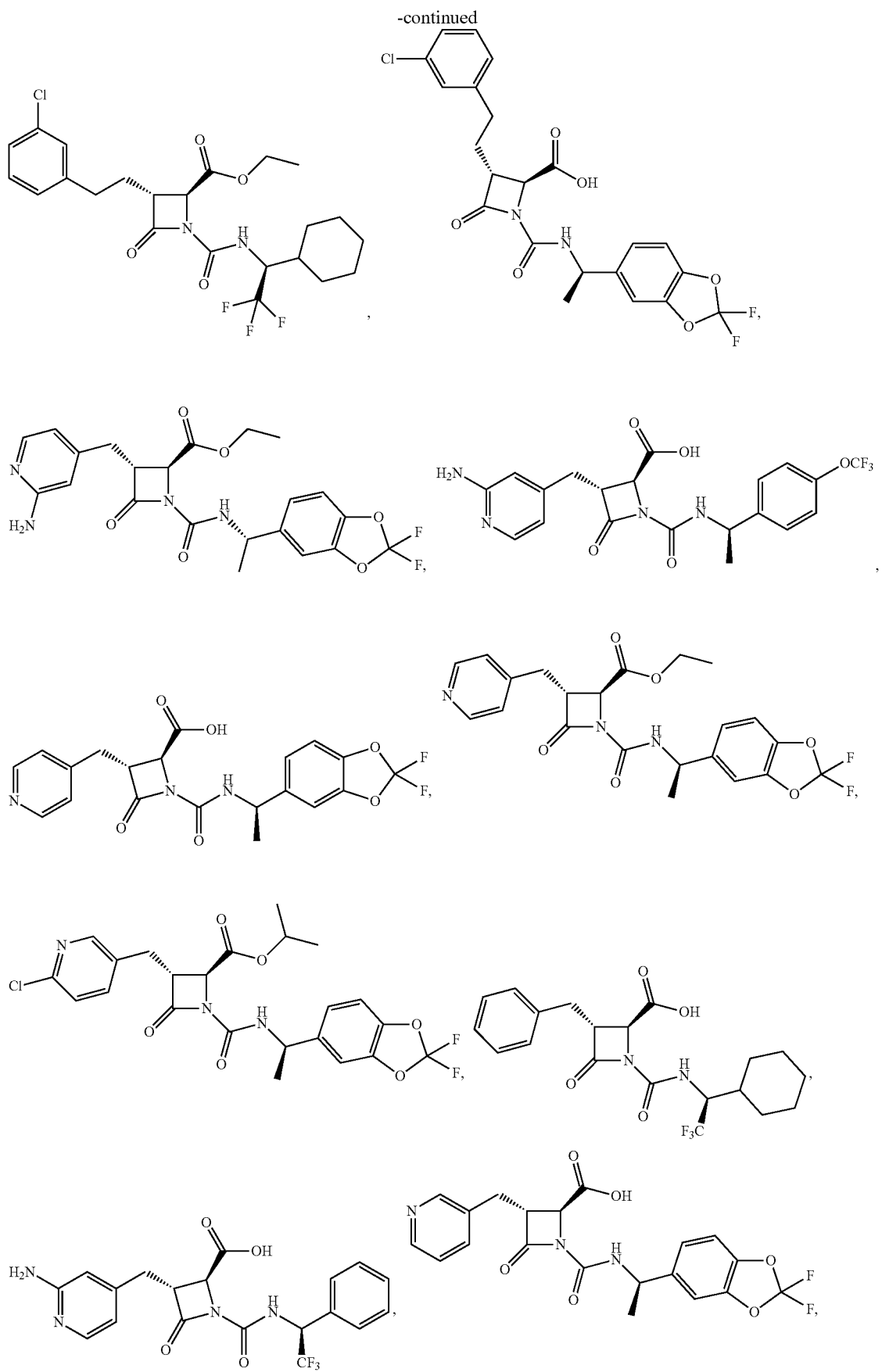

-continued
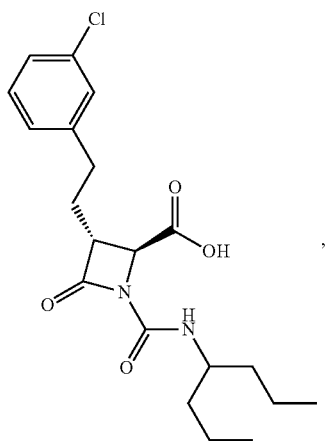 , 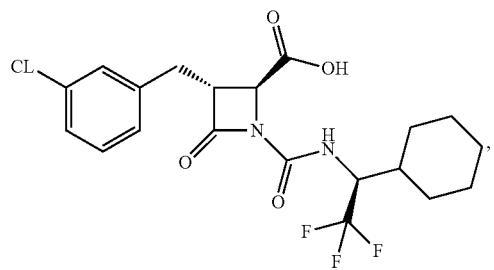 ,
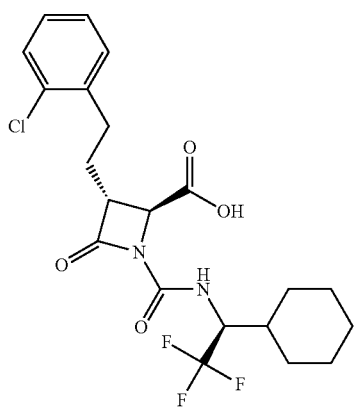 , 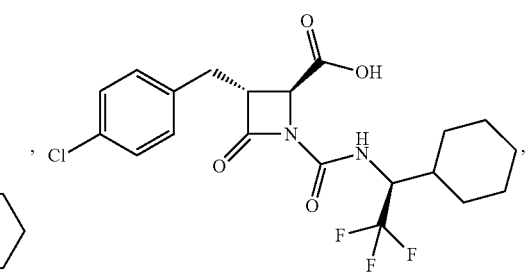 ,
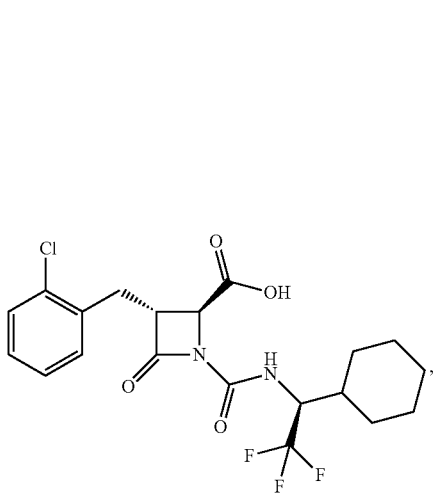 , 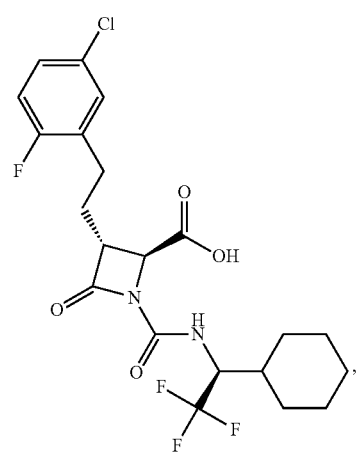 , 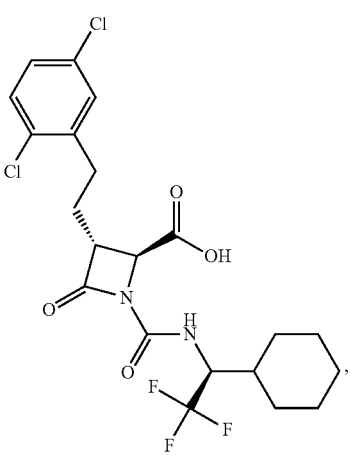 ,

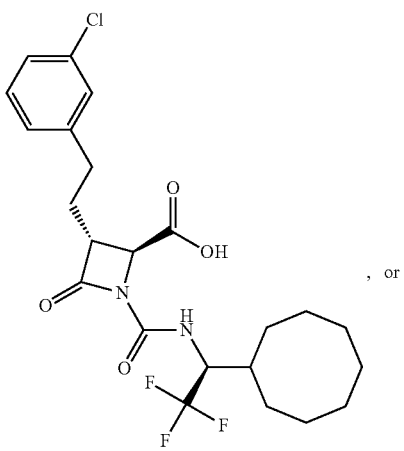, or 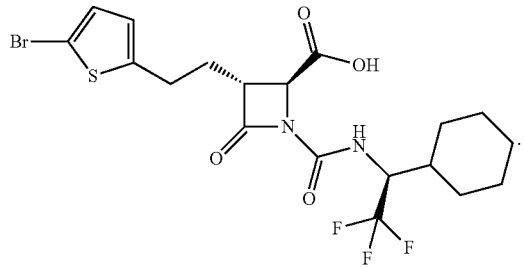

In one aspect, the present invention is directed to a compound of formula (V):

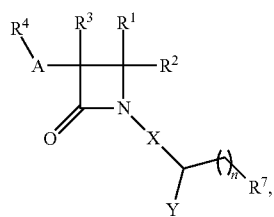

or a pharmaceutically acceptable salt thereof, wherein $R^1$ is H or —$C_{1-6}$ alkyl; $R^2$ is H, —$C_{1-6}$ alkyl, —$CO_2R^5$, —C(O)NR$^9$R$^{10}$, —CN, —SO$_q$R$^5$, —OR$^5$, —CHN(OR$^5$) or a heteroaryl; $R^3$ is H or —$C_{1-6}$ alkyl; A is $C_{2-6}$ alkylene, $C_{2-6}$ alkenylene, or $C_{2-6}$ alkynylene; $R^4$ is cycloalkyl, aryl, heteroaryl or heterocyclyl, each of which is substituted with 0-3 occurrences of —NH$_2$ or $R^6$; each $R^5$ is independently H, —$C_{1-6}$ alkyl, aralkyl, or aryl substituted with 0-3 occurrences of —NH$_2$ or $R^6$; each $R^6$ is independently halo, hydroxy, cyano, nitro, —$C_{1-6}$ alkyl, —$C_{1-6}$ alkoxy, —NHR$^{10}$, —NR$^9$R$^{10}$, —C(O)R$^{11}$, —C(O)OR$^{11}$, —C(O)NR$^9$R$^{10}$, —C(NR$^8$)(N(R$^8$)$_2$), —SO$_q$R$^{11}$, —SO$_2$NR$^9$R$^{10}$, —NHC(O)OR$^{11}$, —NHC(O)R$^{11}$, aryl, heteroaryl, aralkyl, cycloalkyl, heteroaralkyl, heterocyclyl or heterocyclylalkyl, or two $R^6$ groups together with the atoms to which they are attached form a 5-7-membered ring; X is —C(O)O—, —OC(O)—, —C(O)S(O)$_2$—, —S(O)$_2$C(O)—, —C(O)N(R$^5$)— or —N(R$^5$)C(O)—; Y is —$C_{1-6}$ alkyl, cycloalkyl, aryl, heteroaryl, or heterocyclyl, each of which is substituted with 0-3 occurrences of —NH$_2$ or $R^6$; $R^7$ is H, —$C_{1-6}$ alkyl, cycloalkyl, aryl, heteroaryl or heterocyclyl, each of which is substituted with 0-3 occurrences of —NH$_2$ or $R^6$; each $R^8$ is independently H, —$C_{1-6}$ alkyl, —C(O)R$^5$, —C(O)OR$^5$, aryl, heteroaryl, aralkyl, heteroaralkyl, heterocyclyl or heterocyclylalkyl; each of $R^9$ and $R^{10}$ is independently —$C_{1-6}$ alkyl, cycloalkyl, heterocyclyl, aryl, or heteroaryl, or $R^9$ and $R^{10}$ together form an optionally substituted 5-7-membered ring; each $R^{11}$ is independently H, —$C_{1-6}$ alkyl, aralkyl, or aryl; q is an integer from 0 to 2; and n is an integer from 0 to 2.

In some embodiments, $R^1$ is H.
In some embodiments, $R^2$ is —$CO_2R$, wherein $R^5$ is H, —$C_{1-6}$ alkyl (e.g., ethyl), or aralkyl (e.g., benzyl).

In some embodiments, A is $C_{2-6}$ alkylene (e.g., ethylene or propylene).

In some embodiments, $R^4$ is aryl or heteroaryl. In some embodiments, $R^4$ is aryl. In some embodiments, $R^4$ is phenyl substituted with 1 occurrence of $R^6$. In some embodiments, $R^6$ is —$C_{1-6}$ alkyl, halo (e.g., chloro, bromo, fluoro), haloalkoxy (e.g., —OCF$_3$) or —C(NR$^8$)(N(R$^8$)$_2$). In some embodiments, $R^6$ is —C(NR$^8$)(N(R$^8$)$_2$) and each $R^8$ is H. In some embodiments, $R^6$ is —C(NR$^8$)(N(R$^8$)$_2$) and each $R^8$ is H. In some embodiments, $R^8$ is H or —C(O)OR$^5$. In some embodiments, $R^5$ is —$C_{1-6}$ alkyl (e.g., hexyl).

In some embodiments, $R^4$ is heteroaryl (e.g., a 6-membered heteroaryl or 5-membered heteroaryl) substituted with 0-3 occurrences of —NH$_2$ or $R^6$. In some embodiments, $R^4$ is a 6-membered heteroaryl (e.g., pyridyl) substituted with 0-3 occurrences of —NH$_2$ or $R^6$. In some embodiments, $R^6$ is halo (e.g., chloro).

In some embodiments, X is —C(O)N(R$^5$)— or —N(R$^5$)C(O)—. In some embodiments, X is —C(O)N(R$^5$)— and $R^5$ is H.

In some embodiments, n is 0.
In some embodiments, $R^7$ is —$C_{1-6}$ alkyl (e.g., methyl, —CF$_3$).

In some embodiments, Y is —$C_{1-6}$ alkyl (e.g., ethyl, propyl), cycloalkyl, aryl, heteroaryl, or heterocyclyl, each of which is substituted with 0-3 occurrences of —NH$_2$ or $R^6$. In some embodiments, Y is cycloalkyl (e.g., cyclohexyl). In some embodiments, Y is phenyl substituted with 0 occurrences of $R^6$. In some embodiments, Y is phenyl substituted with 1 occurrence of $R^6$. In some embodiments, $R^6$ is —$C_{1-6}$ alkyl, halo (e.g., chloro, bromo, fluoro) or haloalkoxy (e.g., —OCF$_3$). In some embodiments, Y is phenyl substituted with 2 occurrences of $R^6$. In some embodiments, two $R^6$ groups taken together with the atoms to which they are attached form a 5-7 membered ring. In some embodiments, two $R^6$ groups taken together with the atoms to which they are attached form a 5-7 membered ring and the ring is selected from:

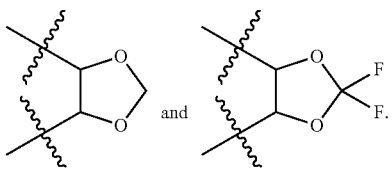 [SMILES: *C1OCOC1* ; *C1OC(F)(F)OC1*]

In some embodiments, the compound of formula (V) is selected from a compound of formula (Va):

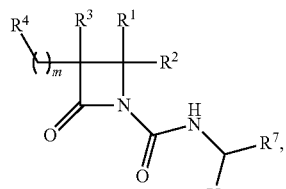
(Va)

wherein $R^1$, $R^2$, $R^3$, $R^4$, $R^7$, and Y are as described for formula (V), and m is an integer from 2 to 6.

In some embodiments, the compound of formula (Va) is selected from a compound of formula (Vb):

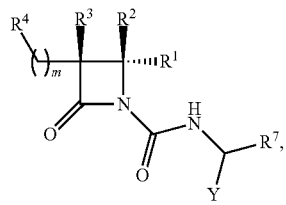
(Vb)

wherein $R^1$, $R^2$, $R^3$, $R^4$, $R^7$, Y and m are as described for formula (Va).

In some embodiments, the compound of formula (Vb) is:

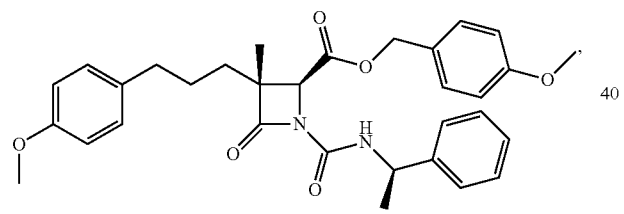

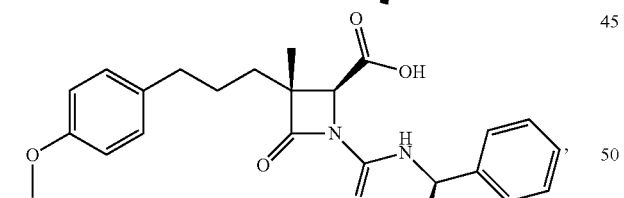

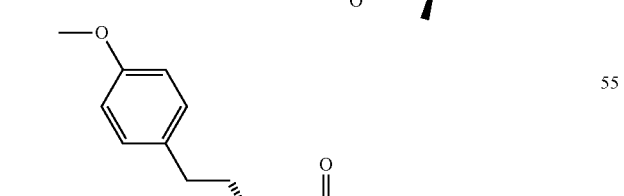

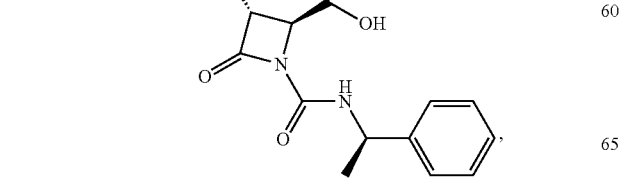

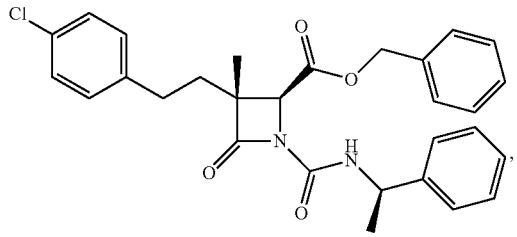

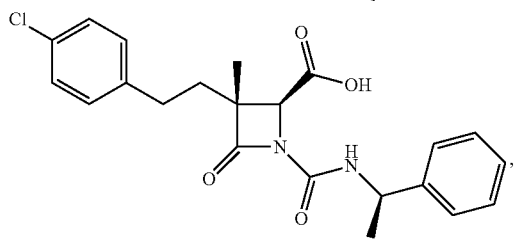

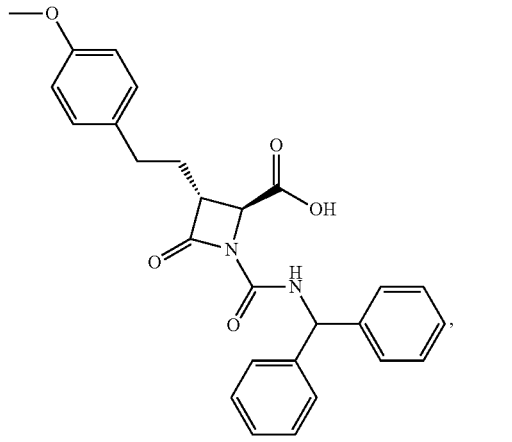

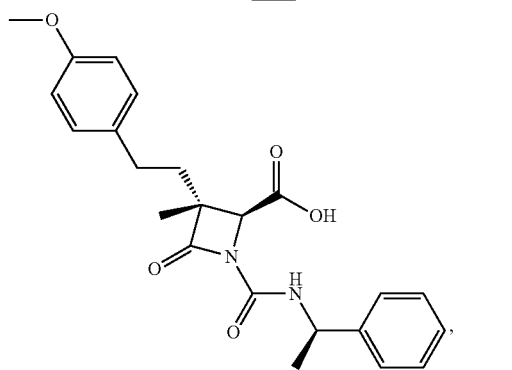

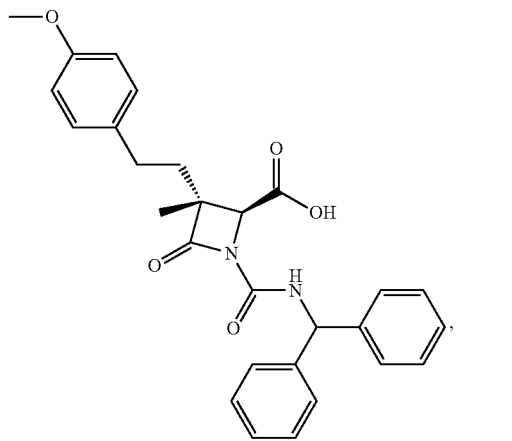

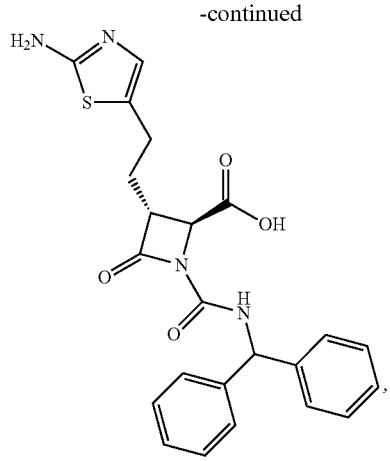
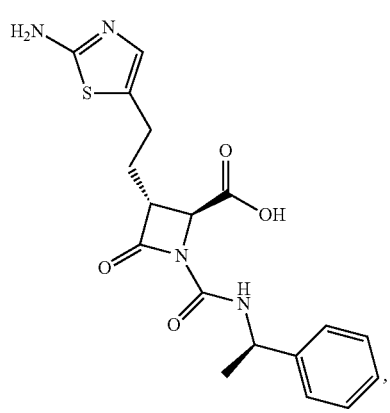
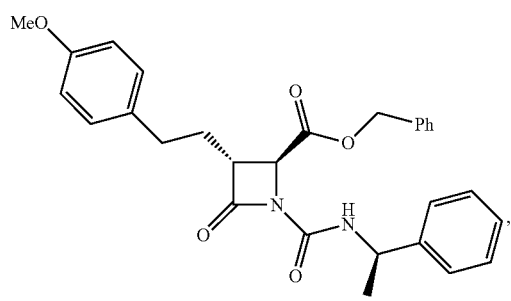
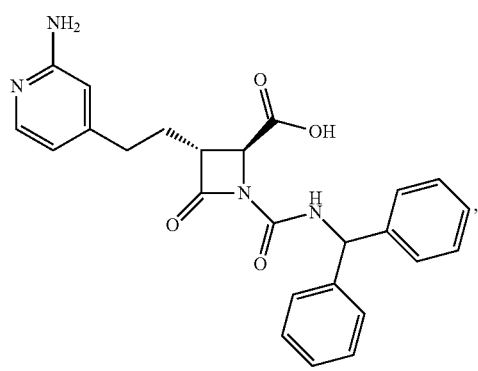
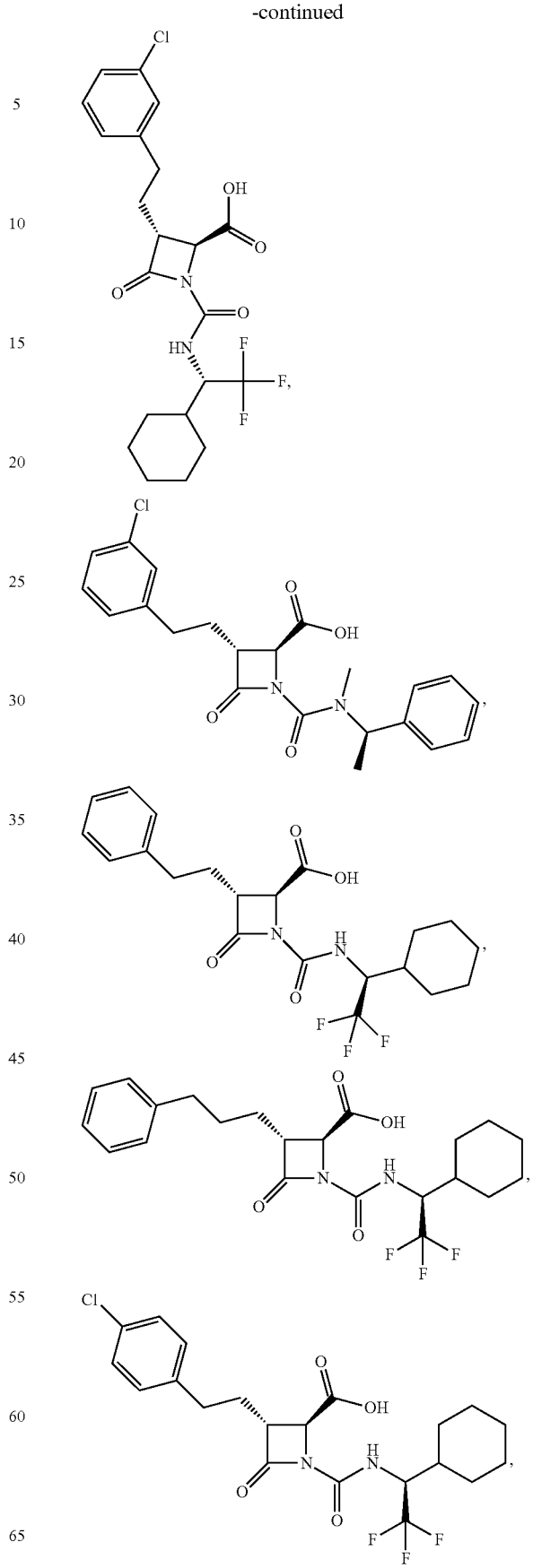

87
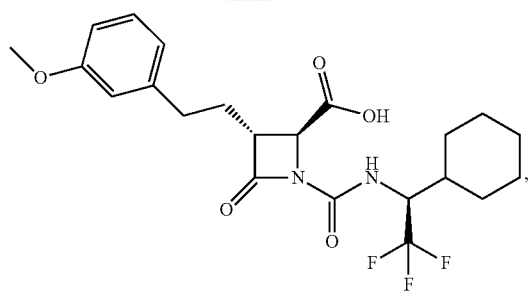
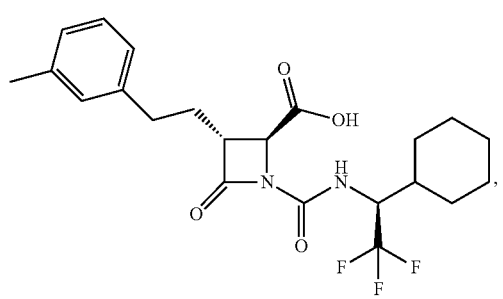
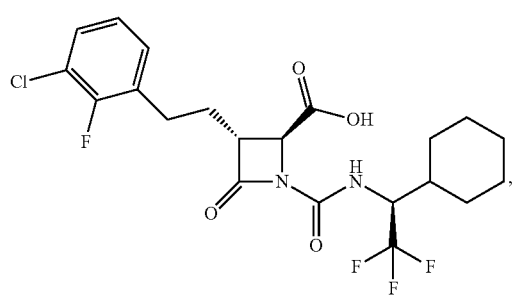
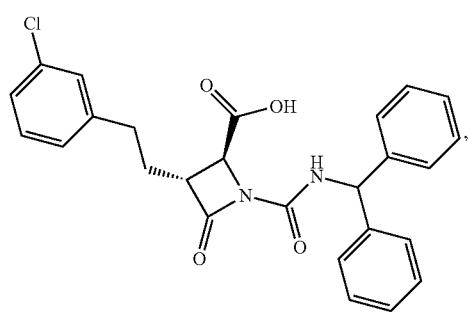
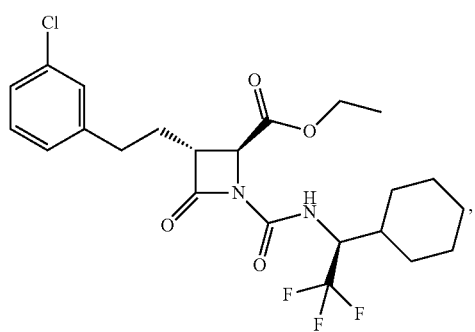
88
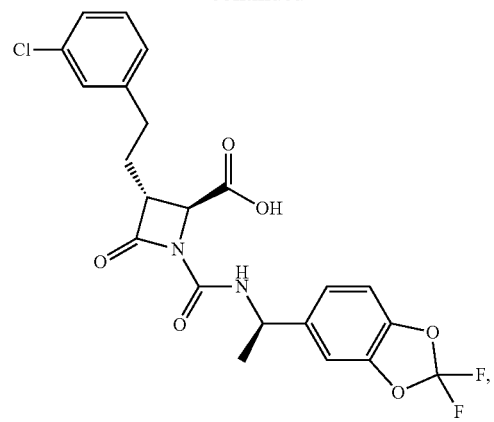
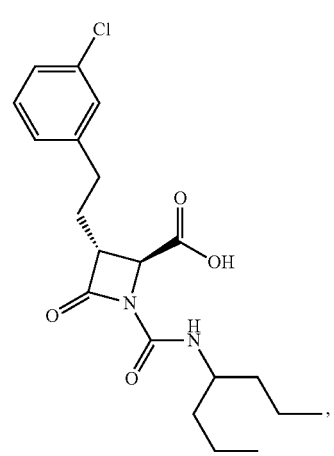
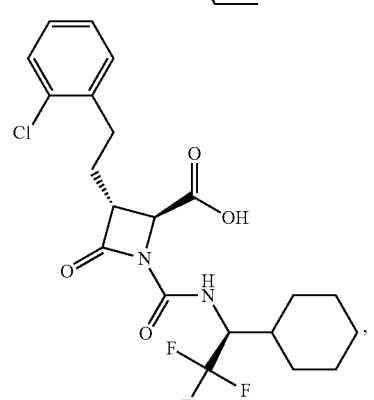
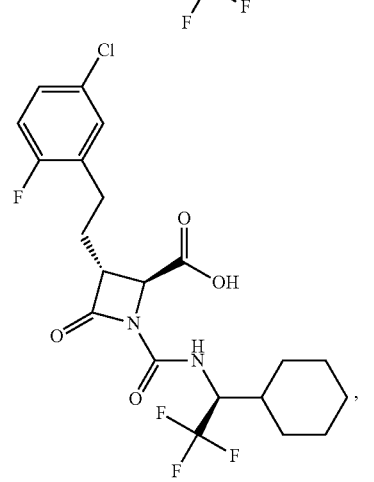

-continued

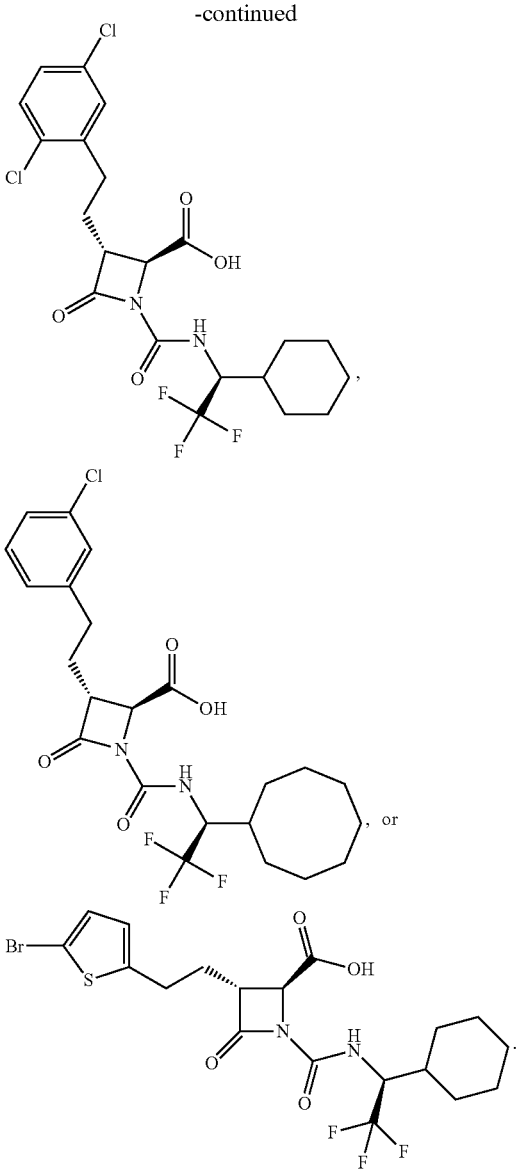

In one aspect, the present invention is directed to a compound of formula (VI):

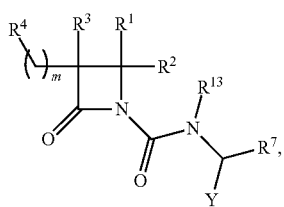
(VI)

or a pharmaceutically acceptable salt thereof, wherein $R^1$ is H or —$C_{1-6}$ alkyl; $R^2$ is H, —$C_{1-6}$ alkyl, —$CO_2R^5$, —$C(O)NR^9R^{10}$, —CN, —$SO_qR$, —$OR^5$, —$CHN(OR^5)$ or a heteroaryl; $R^3$ is H or —$C_{1-6}$ alkyl; $R^4$ is cycloalkyl, aryl, heteroaryl or heterocyclyl, each of which is substituted with 0-3 occurrences of —$NH_2$ or $R^6$; each $R^5$ is independently H, —$C_{1-6}$ alkyl, aralkyl, or aryl substituted with 0-3 occurrences of —$NH_2$ or $R^6$; each $R^6$ is independently halo, hydroxy, cyano, nitro, —$C_{1-6}$ alkyl, —$C_{1-6}$ alkoxy, —$NHR^{10}$, —$NR^9R^{10}$, —$C(O)R^{11}$, —$C(O)OR^{11}$, —$C(O)NR^9R^{10}$, —$C(NR^8)(N(R^8)_2)$, —$SO_qR^1$, —$SO_2NR^9R^{10}$, —$NHC(O)OR^{11}$, —$NHC(O)R^{11}$, aryl, heteroaryl, aralkyl, cycloalkyl, heteroaralkyl, heterocyclyl or heterocyclylalkyl, or two $R^6$ groups together with the atoms to which they are attached form a 5-7-membered ring; Y is —$C_{1-6}$ alkyl, cycloalkyl, aryl, heteroaryl, or heterocyclyl, each of which is substituted with 0-3 occurrences of —$NH_2$ or $R^6$; $R^7$ is H, —$C_{1-6}$ alkyl, cycloalkyl, aryl, heteroaryl or heterocyclyl, each of which is substituted with 0-3 occurrences of —$NH_2$ or $R^6$; each $R^8$ is independently H, —$C_{1-6}$ alkyl, —$C(O)R^5$, —$C(O)OR^5$, aryl, heteroaryl, aralkyl, heteroaralkyl, heterocyclyl or heterocyclylalkyl; each of $R^9$ and $R^{10}$ is independently —$C_{1-6}$ alkyl, cycloalkyl, heterocyclyl, aryl, or heteroaryl, or $R^9$ and $R^{10}$ together form an optionally substituted 5-7-membered ring; each $R^{11}$ is independently H, —$C_{1-6}$ alkyl, aralkyl, or aryl; $R^{13}$ is —$C_{1-6}$ alkyl; q is an integer from 0 to 2; and m is an integer from 1 to 6.

In some embodiments, $R^1$ is H.

In some embodiments, $R^2$ is —$CO_2R^5$, wherein $R^5$ is H or —$C_{1-6}$ alkyl (e.g., ethyl).

In some embodiments, A is $C_{1-6}$ alkylene (e.g., ethylene or propylene).

In some embodiments, $R^4$ is aryl or heteroaryl. In some embodiments, $R^4$ is phenyl substituted with 1 occurrence of $R^6$. In some embodiments, $R^6$ is halo (e.g., chloro).

In some embodiments, $R^4$ is heteroaryl (e.g., a 6-membered heteroaryl or 5-membered heteroaryl) substituted with 0-3 occurrences of —$NH_2$ or $R^6$. In some embodiments, $R^4$ is a 6-membered heteroaryl (e.g., pyridyl) substituted with 0-3 occurrences of —$NH_2$ or $R^6$. In some embodiments, $R^6$ is halo (e.g., chloro). In some embodiments, $R^4$ is a pyridyl substituted with 1 occurrence of —$NH_2$.

In some embodiments, X is —$C(O)N(R^5)$— or —$N(R^5)C(O)$—. In some embodiments, X is —$C(O)N(R^5)$— and $R^5$ is H.

In some embodiments, n is 0.

In some embodiments, $R^7$ is —$C_{1-6}$ alkyl (e.g., methyl).

In some embodiments, Y is cycloalkyl, aryl, heteroaryl, or heterocyclyl, each of which is substituted with 0-3 occurrences of —$NH_2$ or $R^6$. In some embodiments, Y is cycloalkyl (e.g., cyclohexyl). In some embodiments, Y is phenyl substituted with 0 occurrences of $R^6$. In some embodiments, Y is phenyl substituted with 1 occurrence of $R^6$.

In some embodiments, $R^{13}$ is methyl.

In some embodiments, the compound of formula (VI) is selected from a compound of formula (VIa):

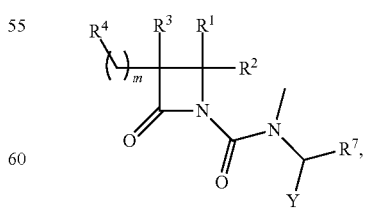
(VIa)

wherein $R^1$, $R^2$, $R^3$, $R^4$, $R^7$, and Y are as described for formula (VI), and m is an integer from 1 to 6.

In some embodiments, the compound of formula (VIa) is selected from a compound of formula (VIb):

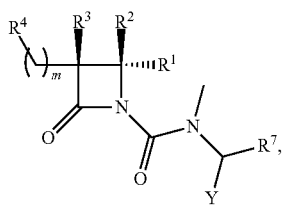

(VIb)

wherein R¹, R², R³, R⁴, R⁷, Y and m are as described for formula (VIa).

In some embodiments, the compound of formula (VIb) is:

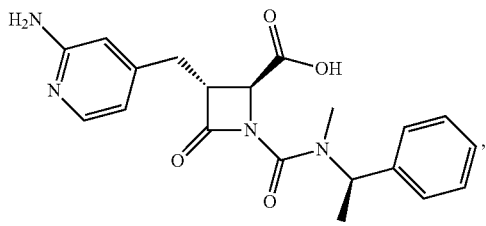

,

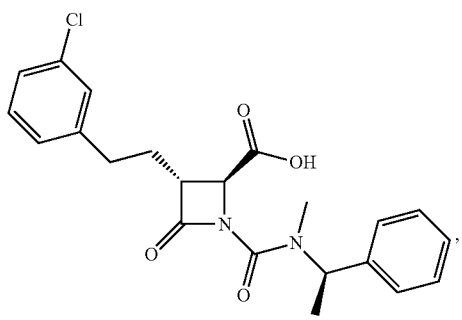

,

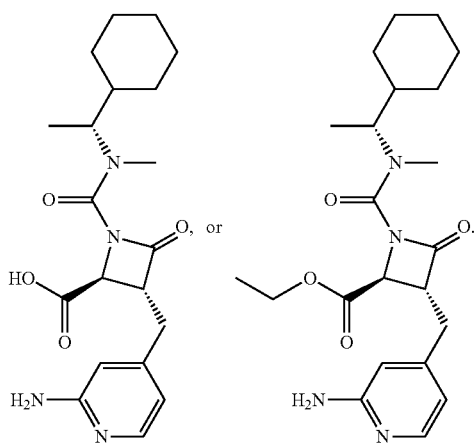

In one aspect, the present invention is directed to a compound of formula (VII):

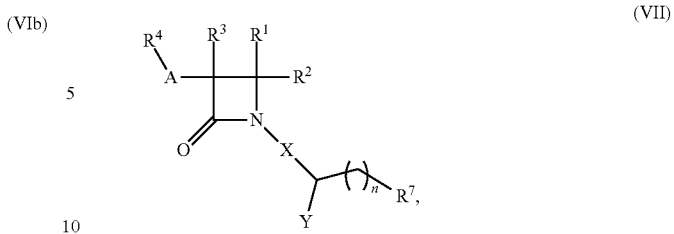

(VII)

or a pharmaceutically acceptable salt thereof, wherein $R^1$ is H or —$C_{1-6}$ alkyl; $R^2$ is H, —$C_{1-6}$ alkyl, —$CO_2R^5$, —$C(O)NR^9R^{10}$, —CN, —$SO_qR^5$, —$OR^5$, —$CHN(OR^5)$ or a heteroaryl; $R^3$ is —$C_{1-6}$ alkyl; A is a bond, $C_{1-6}$ alkylene, $C_{2-6}$ alkenylene or $C_{2-6}$ alkynylene; $R^4$ is cycloalkyl, aryl, heteroaryl or heterocyclyl, each of which is substituted with 0-3 occurrences of —$NH_2$ or $R^6$; each $R^5$ is independently H, —$C_{1-6}$ alkyl, aralkyl, or aryl substituted with 0-3 occurrences of —$NH_2$ or $R^6$; each $R^6$ is independently halo, hydroxy, cyano, nitro, —$C_{1-6}$ alkyl, —$C_{1-6}$ alkoxy, —$NHR^{10}$, —$NR^9R^{10}$, —$C(O)R^{11}$, —$C(O)OR^{11}$, —$C(O)NR^9R^{10}$, —$C(NR^8)(N(R^8)_2)$, —$SO_qR^{11}$, —$SO_2NR^9R^{10}$, —$NHC(O)OR^{11}$, —$NHC(O)R^{11}$, aryl, heteroaryl, aralkyl, cycloalkyl, heteroaralkyl, heterocyclyl or heterocyclylalkyl, or two $R^6$ groups together with the atoms to which they are attached form a 5-7-membered ring; X is —$C(O)O$—, —$OC(O)$—, —$C(O)S(O)_2$—, —$S(O)_2C(O)$—, —$C(O)N(R^5)$— or —$N(R^5)C(O)$—; Y is H, —$C_{1-6}$ alkyl, cycloalkyl, aryl, heteroaryl, or heterocyclyl, each of which is substituted with 0-3 occurrences of —$NH_2$ or $R^6$; $R^7$ is H, —$C_{1-6}$ alkyl, cycloalkyl, aryl, heteroaryl or heterocyclyl, each of which is substituted with 0-3 occurrences of —$NH_2$ or $R^6$; each $R^8$ is independently H, —$C_{1-6}$ alkyl, —$C(O)R^5$, —$C(O)OR^5$, aryl, heteroaryl, aralkyl, heteroaralkyl, heterocyclyl or heterocyclylalkyl; each of $R^9$ and $R^{10}$ is independently —$C_{1-6}$ alkyl, cycloalkyl, heterocyclyl, aryl, or heteroaryl, or $R^9$ and $R^{10}$ together form an optionally substituted 5-7-membered ring; each $R^{11}$ is independently H, —$C_{1-6}$ alkyl, aralkyl, or aryl; q is an integer from 0 to 2; and n is an integer from 0 to 2.

In some embodiments, $R^1$ is H.

In some embodiments, $R^2$ is —$CO_2R^5$, wherein $R^5$ is H, —$C_{1-6}$ alkyl, or aralkyl (e.g., benzyl).

In some embodiments, $R^3$ is methyl.

In some embodiments, A is $C_{1-6}$ alkylene (e.g., ethylene or propylene).

In some embodiments, $R^4$ is aryl or heteroaryl. In some embodiments, $R^4$ is phenyl substituted with 1 occurrence of $R^6$. In some embodiments, $R^6$ is halo (e.g., chloro) or $C_{1-6}$ alkoxy.

In some embodiments, $R^4$ is heteroaryl (e.g., a 6-membered heteroaryl or 5-membered heteroaryl) substituted with 0-3 occurrences of —$NH_2$ or $R^6$. In some embodiments, $R^4$ is a 6-membered heteroaryl (e.g., pyridine) substituted with 0-3 occurrences of —$NH_2$ or $R^6$. In some embodiments, $R^6$ is halo (e.g., chloro).

In some embodiments, X is —$C(O)N(R^5)$— or —$N(R^5)C(O)$—. In some embodiments, X is —$C(O)N(R^5)$— and $R^5$ is H.

In some embodiments, n is 0.

In some embodiments, $R^7$ is —$C_{1-6}$ alkyl (e.g., methyl) or aryl (e.g., phenyl).

In some embodiments, Y is aryl, heteroaryl, or heterocyclyl, each of which is substituted with 0-3 occurrences of —$NH_2$ or $R^6$. In some embodiments, Y is aryl. In some embodiments, Y is phenyl substituted with 0 occurrences of R⁶. In some embodiments, Y is phenyl substituted with 1 occurrence of R⁶.

In some embodiments, the compound of formula (VII) is selected from a compound of formula (VIIa):

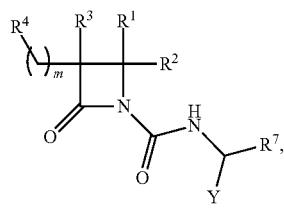

(VIIa)

wherein
R¹, R², R³, R⁴, R⁷, and Y are as described for formula (VII), and
m is an integer from 1 to 6.

In some embodiments, the compound of formula (VIIa) is selected from a compound of formula (VIIb):

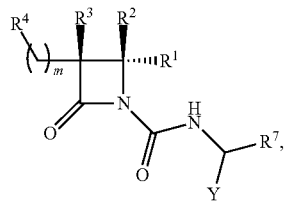

(VIIb)

wherein R¹, R², R³, R⁴, R⁷, Y and m are as described for formula (VIIa).

In some embodiments, the compound of formula (VIIb) is:

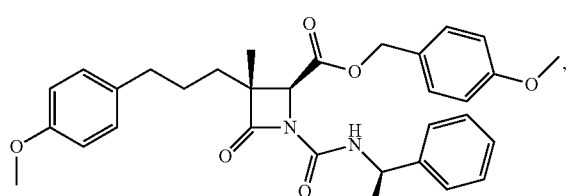

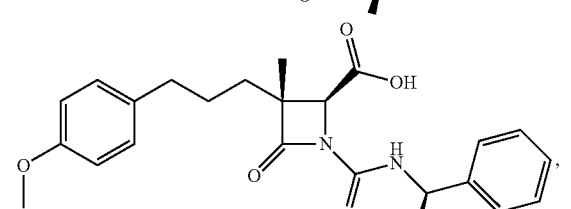

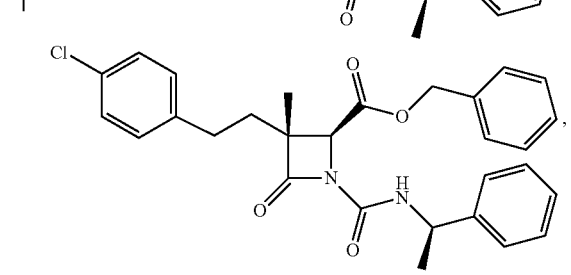

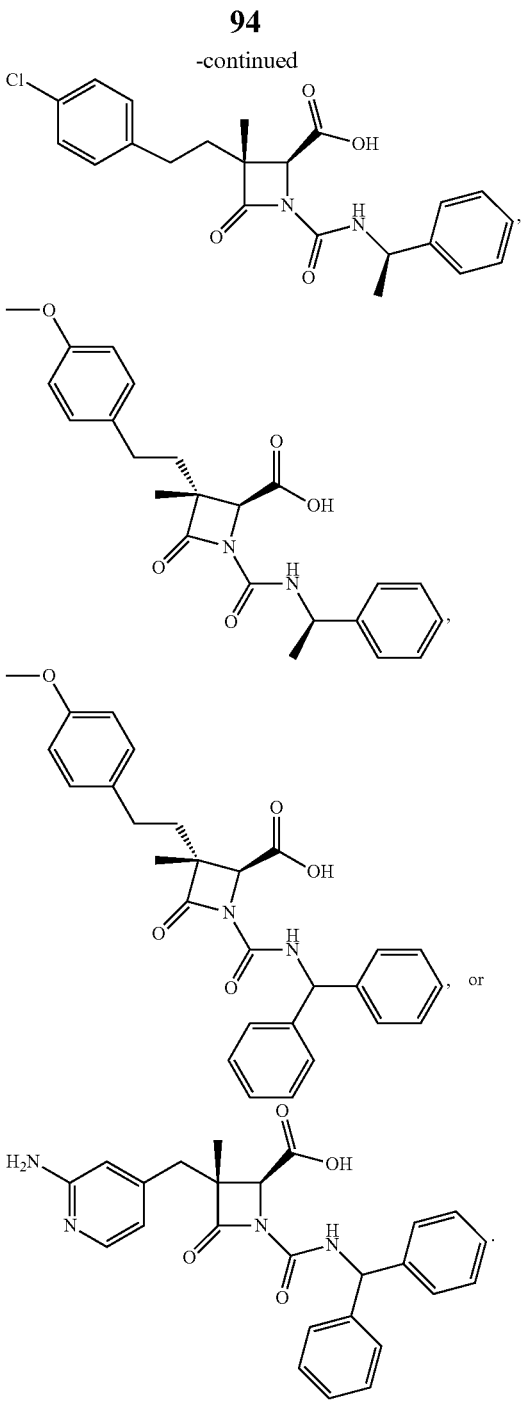

In some embodiments, the compound of formula (VIIb) is selected from a compound of formula (VIIc):

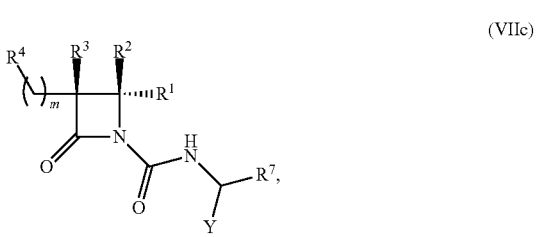

(VIIc)

wherein $R^1$, $R^2$, $R^3$, $R^7$, Y and m are as described for formula (VIIb), and $R^4$ is cycloalkyl, aryl, heteroaryl or heterocyclyl, each of which is substituted with 0-3 occurrences of $R^6$.

In one aspect, the present invention is directed to a pharmaceutical composition comprising a compound of the formula (I)-(VII) or a pharmaceutically acceptable salt thereof and one or more pharmaceutically acceptable excipients.

In some embodiments, the composition is provided as a solution.

In one aspect, the present invention is directed to a method of reducing the risk of stroke (e.g., ischemia, e.g., a transient ischemic event) in a subject that has suffered an ischemic event (e.g., a transient ischemic event), comprising administering to the subject an effective amount of a compound of the formula (I)-(VII) or a pharmaceutically acceptable salt thereof, or of a composition described herein (e.g., a composition comprising a compound of the formula (I)-(VII)).

In some embodiments, the administering reduces the risk of stroke in a subject as compared to a subject who is not administered with the compound.

In one aspect, the present invention is directed to a method of reducing non-central nervous system systemic embolism (e.g., ischemia, e.g., a transient ischemic event) in a subject that has suffered an ischemic event (e.g., a transient ischemic event), comprising administering to the subject an effective amount of a compound of the formula (I)-(VII) or a pharmaceutically acceptable salt thereof, or of a composition described herein (e.g., a composition comprising a compound of the formula (I)-(VII)).

In some embodiments, the administering reduces non-central nervous system systemic embolism in a subject as compared to a subject who is not administered with the compound.

In one aspect, the present invention is directed to a method of treating deep vein thrombosis comprising administering to the subject that has suffered an ischemic event (e.g., a transient ischemic event), an effective amount of a compound of the formula (I)-(VII) or a pharmaceutically acceptable salt thereof, or of a composition described herein (e.g., a composition comprising a compound of the formula (I)-(VII)).

In one aspect, the present invention is directed to a method of reducing the risk of recurrence of deep vein thrombosis comprising administering to the subject that has suffered deep vein thrombosis, an effective amount of a compound of the formula (I)-(VII) or a pharmaceutically acceptable salt thereof, or of a composition described herein (e.g., a composition comprising a compound of the formula (I)-(VII)). In some embodiments, the administering reduces the risk of recurrence of deep vein thrombosis in a subject as compared to a subject who is not administered with the compound.

In one aspect, the present invention is directed to a method of reducing the risk of recurrence of pulmonary embolism (e.g., symptomatic pulmonary embolism) comprising administering to the subject that has suffered a pulmonary embolism, an effective amount of a compound of the formula (I)-(VII) or a pharmaceutically acceptable salt thereof, or of a composition described herein (e.g., a composition comprising a compound of the formula (I)-(VII)).

In some embodiments, the administering reduces the risk of recurrence of pulmonary embolism in a subject as compared to a subject who is not administered with the compound.

In one aspect, the present invention is directed to a method of prophylaxis of pulmonary embolism in a subject that has suffered a pulmonary embolism, comprising administering to the subject an effective amount of a compound of the formula (I)-(VII) or a pharmaceutically acceptable salt thereof, or of a composition described herein (e.g., a composition comprising a compound of the formula (I)-(VII)).

In one aspect, the present invention is directed to a method of treating a subject that has had an ischemic event (e.g., transient ischemia), comprising: administering a compound of the formula (I)-(VII) or a pharmaceutically acceptable salt thereof, or of a composition described herein (e.g., a composition comprising a compound of the formula (I)-(VII)) to the subject. In some embodiments, the compound is administered to the subject within 24 hours or less, e.g., 12, 10, 9, 8, 7, 6 hours or less, after the onset of the ischemic event in the subject.

In one aspect, the present invention is directed to a method of treating a subject that has had an ischemic event (e.g., transient ischemia), comprising: administering a compound of the formula (I)-(VII) or a pharmaceutically acceptable salt thereof, or of a composition described herein (e.g., a composition comprising a compound of the formula (I)-(VII)) to the subject. In some embodiments, the compound is administered to the subject within more than 2 hours to 12 hours, e.g., more than 2 hours to 10 hours or less, more than 2 hours to 8 hours or less, after the onset of the ischemic event in the subject.

In one aspect, the present invention is directed to a method of inhibiting Factor XIa in a subject, comprising administering to the subject that has suffered ischemia an effective amount of a compound of the formula (I)-(VII) or a pharmaceutically acceptable salt thereof, or of a composition described herein (e.g., a composition comprising a compound of the formula (I)-(VII)).

In some embodiments, the subject is a mammal (e.g., a human). In some embodiments, the subject is undergoing surgery (e.g., knee replacement surgery, hip replacement surgery). In some embodiments, the subject is a subject with nonvalvular atrial fibrillation. In some embodiments, the subject has one or more of the following risk factors for stroke: a prior stroke (e.g., ischemic, unknown, hemorrhagic), transient ischemic attack, or non-CNS systemic embolism. In some embodiments, the subject has one or more of the following risk factors for stroke: 75 years or older of age, hypertension, heart failure or left ventricular ejection fraction (e.g., less than or equal to 35%), or diabetes mellitus.

In some embodiments, the compound is administered by oral or parenteral (e.g., intravenous) administration.

In some embodiments, the compound is administered prior to an ischemic event (e.g., to a subject is at risk of an ischemic event).

In some embodiments, the compound is administered after an ischemic event (e.g., a transient ischemic event).

In some embodiments, the compound is administered about 1, 2, 3, 4, 5, 6, 7, 8, 9, 10, 11, 12, 13, or 14 days or more after an ischemic event (e.g., a transient ischemic event).

In some embodiments, the compound is administered about 1, 2, 3, 4, 5, 6, 7, or 8 weeks or more after an ischemic event (e.g., a transient ischemic event).

In some embodiments, the compound is administered in combination with an additional therapeutic agent. In some embodiments, the additional therapeutic agent is administered after administration of the compound. In some embodiments, the additional therapeutic agent is administered orally. In some embodiments, the additional therapeutic agent is administered at least 1, 2, 3, 4, 5, 6, 7, 8, 10, 12, 14, 16, 18, 20, or 24 hours or more after administration of the compound. In some embodiments, the additional therapeutic agent is administered at least 1, 2, 3, 4, 5, 6, 7, 14, 21, or 28 days or more after administration of the compound. In some embodiments, the additional therapeutic agent is administered about 1 day, about 2 days, about 3 days, about 4 days, about 5 days, about 6 days, about 7 days or more after administration of the compound.

In some embodiments, the additional therapeutic agent is administered chronically (e.g., for about 1 day, about 2 days, about 3 days, about 4 days, about 5 days, about 6 days, about 7 days, about 8 days, about 9 days, about 10 days, about 11 days, about 12 days, about 13 days, or about 14 days or more) after administration of the compound.

In some embodiments, the additional therapeutic agent treats a side effect (e.g., active pathological bleeding or severe hypersensitivity reactions (e.g., anaphylactic reactions), spinal and or epidural hematoma, gastrointestinal disorder (e.g., abdominal pain upper, dyspepsia, toothache), general disorders and administration site conditions (e.g., fatigue), infections and infestations (e.g., sinusitis, urinary tract infection), musculoskeletal and connective tissues disorders (e.g., back pain, osteoarthritis), respiratory, thoracic and mediastinal disorders (e.g., oropharyngeal pain), injury, poisoning, and procedural complications (e.g., wound secretion), musculoskeletal and connective tissues disorders (e.g., pain in extremity, muscle spasm), nervous system disorders (e.g., syncope), skin and subcutaneous tissue disorders (e.g., pruritus, blister), blood and lymphatic system disorders (e.g., agranulocytosis), gastrointestinal disorders (e.g., retroperitoneal hemorrhage), hepatobiliary disorders (e.g., jaundice, cholestasis, cytolytic hepatitis), immune system disorders (e.g., hypersensitivity, anaphylactic reaction, anaphylactic shock, angioedema), nervous system disorders (e.g., cerebral hemorrhage, subdural hematoma, epidural hematoma, hemiparesis), skin and subcutaneous tissue disorders (e.g., Stevens-Johnson syndrome).

In some embodiments, the additional therapeutic agent is a NSAID (e.g., aspirin, naproxen), platelet aggregation inhibitor (e.g., clopidogrel), or anticoagulant (e.g., warfarin, enoxaparin).

In some embodiments, the additional therapeutic agent results in an additive therapeutic effect.

In some embodiments, the additional therapeutic agent results in a synergistic therapeutic effect.

In another aspect, the invention features a pharmaceutical composition comprising a compound described herein (e.g., a compound of formula (I)-(VII)) and a pharmaceutically acceptable excipient.

In another aspect, the invention features a method of modulating (e.g., inhibiting) Factor XIa in a patient. The method comprises the step of administering an effective amount of a compound described herein (e.g., a compound of formula (I)-(VII)) to a patient in need thereof, thereby modulating (e.g., inhibiting) Factor XIa.

In another aspect, the invention features a method of treating a subject in need thereof for a thromboembolic disorder. The method comprises administering to the subject a therapeutically effective amount of a compound described herein (e.g., a compound of formula (I)-(VII)).

The thromboembolic disorder can be arterial cardiovascular thromboembolic disorders, venous cardiovascular thromboembolic disorders, and thromboembolic disorders in the chambers of the heart; including unstable angina, an acute coronary syndrome, first myocardial infarction, recurrent myocardial infarction, ischemia (e.g., ischemic sudden death or transient ischemic attack), stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another aspect, the invention features a method of treating a subject identified as being at risk for stroke or thrombosis thereby reducing the likelihood of stroke or thrombosis in the subject. In some embodiments, the subject is further identified as being at risk for bleeding (e.g., excessive bleeding) or sepsis. In some embodiments, the treatment is effective without bleeding liabilities. In some embodiments, the treatment is effective to maintain the patency of infusion ports and lines. In addition, the compounds described herein (e.g., compounds of formula (I)-(VII)) are useful in the treatment and prevention of other diseases in which the generation of thrombin has been implicated as playing a physiologic role. For example, thrombin has been implicated in contributing to the morbidity and mortality of chronic and degenerative diseases, such as cancer, arthritis, atherosclerosis, vascular dementia, and Alzheimer's disease, by its ability to regulate many different cell types through specific cleavage and activation of a cell surface thrombin receptor, mitogenic effects, diverse cellular functions such as cell proliferation, for example, abnormal proliferation of vascular cells resulting in restenosis or angiogenesis, release of PDGF, and DNA synthesis. Inhibition of Factor XIa effectively blocks thrombin generation and therefore neutralizes any physiologic effects of thrombin on various cell types.

The representative indications discussed above include some, but not all, of the potential clinical situations amenable to treatment with a Factor XIa inhibitor.

In another aspect, the invention features a method of treating a subject that has edema (e.g., angioedema, e.g., hereditary angioedema), comprising administering a compound of the formula (I)-(VII) or a pharmaceutically acceptable salt thereof, or of a composition described herein (e.g., a composition comprising a compound of the formula (I)-(VII)) to the subject.

In another aspect, the invention features a method of inhibiting kallikrein in a subject, comprising administering to the subject with edema (e.g., angioedema, e.g., hereditary angioedema), an effective amount of a compound of the formula (I)-(VII) or a pharmaceutically acceptable salt thereof, or of a composition described herein (e.g., a composition comprising a compound of the formula (I)-(VII)) to the subject.

BRIEF DESCRIPTION OF THE DRAWINGS

FIGS. 1A-1M depict Chart A and the synthesis of Structures A-8 and A-9.
FIG. 2 depicts Chart B and the synthesis of Structure B-5.
FIG. 3 depicts Chart C and D and the synthesis of Structure D-8.
FIG. 4 depicts Chart E and the synthesis of Structure E-6.
FIG. 5 depicts Chart F and the synthesis of Structure F-8.
FIG. 6 depicts Chart G and the synthesis of Structure G-4.
FIG. 7 depicts Chart H and the synthesis of Structure H-9.

FIG. 8 depicts Chart I and the synthesis of Structures I-4 through I-7.

FIGS. 9A-9B depict Chart J and the synthesis of Structures J-3 and J-4.

FIGS. 10A-10B depict Chart K and the synthesis of Structure K-9.

DETAILED DESCRIPTION

Definitions

Figure 1B:
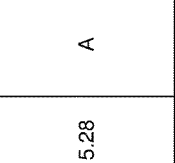
Figure 1I:
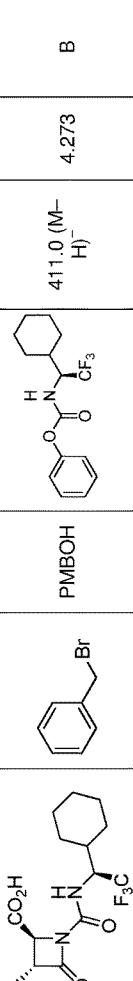
Figure 1L:
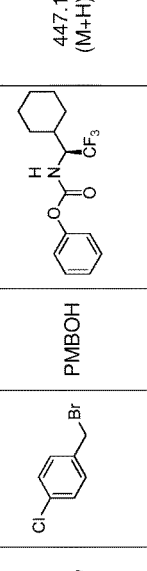

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl". Unless otherwise specified, each instance of an alkyl group is independently optionally substituted, i.e., unsubstituted (an "unsubstituted alkyl") or substituted (a "substituted alkyl") with one or more substituents; e.g., for instance from 1 to 5 substituents, 1 to 3 substituents, or 1 substituent. In certain embodiments, the alkyl group is unsubstituted $C_{1-10}$ alkyl (e.g., —$CH_3$). In certain embodiments, the alkyl group is substituted $C_{1-10}$ alkyl. Common alkyl abbreviations include Me (—$CH_3$), Et (—$CH_2CH_3$), nPr (—$CH(CH_3)_2$), nPr (—$CH_2CH_2CH_3$), n-Bu (—$CH_2CH_2CH_2CH_3$), or i-Bu (—$CH_2CH(CH_3)_2$).

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "alkenyl" refers to a straight or branched hydrocarbon chain containing 2-12 carbon atoms (unless otherwise noted) and having one or more double bonds. Examples of alkenyl groups include, but are not limited to, allyl, propenyl, 2-butenyl, 3-hexenyl and 3-octenyl groups. One of the double bond carbons may optionally be the point of attachment of the alkenyl substituent.

The term "alkenylene" refers to a divalent alkenyl, e.g. —CH=CH—, —$CH_2$—CH=CH—, and —CH=CH—$CH_2$—.

The term "alkynyl" refers to a straight or branched hydrocarbon chain containing 2-12 carbon atoms (unless otherwise noted) and characterized in having one or more triple bonds.

Examples of alkynyl groups include, but are not limited to, ethynyl, propargyl, and 3-hexynyl.

One of the triple bond carbons may optionally be the point of attachment of the alkynyl substituent.

The term "alkynylene" refers to a divalent alkynyl, e.g. —CH≡CH—, —$CH_2$—CH≡CH—, and —CH≡CH—$CH_2$—.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The terms "cyano" and "nitrile" refer to the radical —CN.

The terms "cycloalkyl", "heterocycloalkyl" or "heterocyclyl", by themselves or in combination with other terms, represent, unless otherwise stated, cyclic versions of "alkyl" and "heteroalkyl", respectively. Additionally, for heterocycloalkyl or heterocyclyl, a heteroatom can occupy the position at which the heterocycle is attached to the remainder of the molecule.

Examples of cycloalkyl include, but are not limited to, cyclopropyl, cyclobutyl, cyclopentyl, cyclohexyl, 1-cyclohexenyl, 3-cyclohexenyl, cycloheptyl, cyclooctanyl, and the like. Examples of heterocycloalkyl and heterocyclyl include, but are not limited to, 1-1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "heteroalkyl," as used herein, refers to an alkyl group, as defined herein, which further comprises 1 or more (e.g., 1, 2, 3, or 4) heteroatoms (e.g., oxygen, sulfur, nitrogen, boron, silicon, phosphorus) within the parent chain, wherein the one or more heteroatoms is inserted between adjacent carbon atoms within the parent carbon chain and/or one or more heteroatoms is inserted between a carbon atom and the parent molecule, i.e., between the point of attachment. In certain embodiments, a heteroalkyl group refers to a saturated group having from 1 to 10 carbon atoms and 1, 2, 3, or 4 heteroatoms ("hetero$C_{1-10}$ alkyl"). In some embodiments, a heteroalkyl group is a saturated group having 1 to 9 carbon atoms and 1, 2, 3, or 4 heteroatoms ("hetero$C_{1-9}$ alkyl"). In some embodiments, a heteroalkyl group is a saturated group having 1 to 8 carbon atoms and 1, 2, 3, or 4 heteroatoms ("hetero$C_{1-8}$ alkyl"). In some embodiments, a heteroalkyl group is a saturated group having 1 to 7 carbon atoms and 1, 2, 3, or 4 heteroatoms ("hetero$C_{1-7}$ alkyl"). In some embodiments, a heteroalkyl group is a group having 1 to 6 carbon atoms and 1, 2, or 3 heteroatoms ("hetero$C_{1-6}$ alkyl"). In some embodiments, a heteroalkyl group is a saturated group having 1 to 5 carbon atoms and 1 or 2 heteroatoms ("hetero$C_{1-5}$ alkyl"). In some embodiments, a heteroalkyl group is a saturated group having 1 to 4 carbon atoms and 1 or 2 heteroatoms ("hetero$C_{1-4}$ alkyl"). In some embodiments, a heteroalkyl group is a saturated group having 1 to 3 carbon atoms and 1 heteroatom ("hetero$C_{1-3}$ alkyl"). In some embodiments, a heteroalkyl group is a saturated group having 1 to 2 carbon atoms and 1 heteroatom ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted heteroC$_{1-10}$ alkyl. In certain embodiments, the heteroalkyl group is a substituted heteroC$_{1-10}$ alkyl.

The terms "heterocyclyl" when used in combination with other terms (e.g., heterocyclylalkyl) includes heterocyclyl rings as defined above. Thus, the term "heterocyclylalkyl" is meant to include those radicals in which a heterocyclyl group is attached to an alkyl group including those alkyl groups in which a carbon atom (e.g., a methylene group) has been replaced by, for example, an oxygen atom.

The terms "halo" or "halogen," by themselves or as part of another substituent, mean, unless otherwise stated, a fluorine, chlorine, bromine, or iodine atom.

The term "haloalkyl," as used herein, refers to an alkyl group, as defined herein, which further comprises 1 or more (e.g., 1, 2, 3, or 4) halogen atoms (e.g., fluorine, chlorine, bromine, or iodine), wherein the alkyl group is substituted with one or more halogen atoms. In certain embodiments, a haloalkyl group refers to a saturated group having from 1 to 10 carbon atoms and 1, 2, 3, or 4 halogen atoms ("haloC$_{1-10}$ alkyl"). Additionally, the term "haloalkyl," is meant to include monohaloalkyl and polyhaloalkyl. For example, the term "haloalkyl" is mean to include, but not be limited to, trifluoromethyl, 2,2,2-trifluoroethyl, 4-chlorobutyl, 3-bromopropyl, and the like.

The terms "haloalkoxy" or "haloalkoxyl" as used herein, refer to an alkoxy group, as defined herein, which further comprises 1 or more (e.g., 1, 2, 3, or 4) halogen atoms (e.g., fluorine, chlorine, bromine, or iodine), wherein the alkoxy group is substituted with one or more halogen atoms.

The term "hydroxy" refers to the radical —OH.

The term "aryl" means, unless otherwise stated, a polyunsaturated, aromatic, hydrocarbon substituent that can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl, aralkyl, heteroaralkyl) includes both aryl and heteroaryl rings as defined above. Thus, the terms "arylalkyl", "aralkyl" and "heteroaralkyl" are meant to include those radicals in which an aryl or heteroaryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "nitro" refers to the radical —NO$_2$.

"Protecting group," as used herein refers to a portion of a substrate that is substantially stable under a particular reaction condition, but which is cleaved from the substrate under a different reaction condition. A protecting group can also be selected such that it participates in the direct oxidation of the aromatic ring component of the compounds of the invention. For examples of useful protecting groups, see, for example, Greene et al., *Protective Groups in Organic Synthesis*, John Wiley & Sons, New York, 1991.

Alkyl, alkenyl, alkynyl, cycloalkyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" cycloalkyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds described herein that results in the formation of a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^a$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(O)R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ cycloalkyl, 3-14 membered heterocyclyl, C$_{6-14}$ aryl, and 5-14 membered heteroaryl, wherein each alkyl, alkenyl, alkynyl, cycloalkyl, heterocyclyl, aryl, and heteroaryl is independently substituted with 0, 1, 2, 3, 4, or 5 R$^{dd}$ groups;

each instance of R$^a$ is, independently, selected from C$_{1-10}$ alkyl, C$_{1-10}$ perhaloalkyl, C$_{2-10}$ alkenyl, C$_{2-10}$ alkynyl, C$_{3-10}$ cycloalkyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 $R^{dd}$ groups;

each instance of $R^{bb}$ is, independently, selected from hydrogen, —OH, —OR$^{aa}$, —N(R$^{cc}$)$_2$, —CN, —C(=O)R$^a$, —C(=O)N(R$^{cc}$)$_2$, —CO$_2$R, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R, —P(=O)(R$^a$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ cycloalkyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 $R^{dd}$ groups;

each instance of $R^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3^+$X, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, $C_{1-6}$ alkyl, $C_{1-6}$ perhaloalkyl, $C_{2-6}$ alkenyl, $C_{2-6}$ alkynyl, $C_{3-10}$ cycloalkyl, 3-10 membered heterocyclyl, $C_6$10 aryl, 5-10 membered heteroaryl, wherein each alkyl, alkenyl, alkynyl, cycloalkyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ cycloalkyl, $C_{6-10}$ aryl, 3-10 membered heterocyclyl, and 3-10 membered heteroaryl, wherein each alkyl, alkenyl, alkynyl, cycloalkyl, heterocyclyl, aryl, and heteroaryl is independently substituted with 0, 1, 2, 3, 4, or 5 $R^{gg}$ groups; each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ cycloalkyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, cycloalkyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{3-10}$ cycloalkyl, C$_{6-10}$ aryl, 3-10 membered heterocyclyl, 5-10 membered heteroaryl; or two geminal $R^{gg}$ substituents can be joined to form =O or =S; wherein X is a counterion.

These and other exemplary substituents are described in more detail in the Detailed Description, Examples, and claims. The invention is not intended to be limited in any manner by the above exemplary listing of substituents.

Compounds

Described herein are compounds that inhibit Factor XIa or kallikrein, for example the compounds described herein (e.g., a compound of formula (I)-(VII)).

Exemplary compounds include, but are not limited to the compounds described in Table 1 below:

TABLE 1

Exemplary compounds of the present invention.

| ID # | Structure | ID # | Structure |
|---|---|---|---|
| 1 | 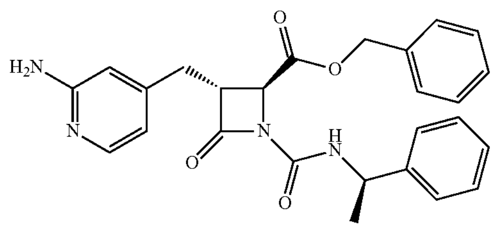 [SMILES: C[C@@H](NC(=O)N1C(=O)[C@H](Cc2ccnc(N)c2)[C@H]1C(=O)OCc1ccccc1)c1ccccc1] | 3 | 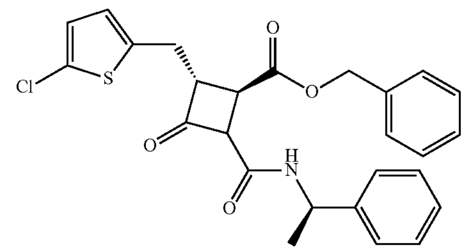 [SMILES: C[C@@H](NC(=O)C1C(=O)[C@H](Cc2ccc(Cl)s2)[C@H]1C(=O)OCc1ccccc1)c1ccccc1] |
| 2 | 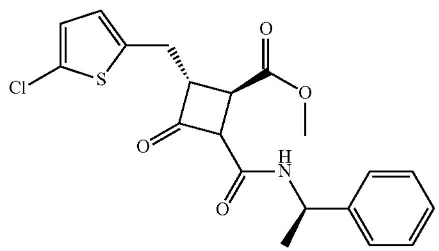 [SMILES: COC(=O)[C@H]1C(C(=O)N[C@H](C)c2ccccc2)C(=O)[C@@H]1Cc1ccc(Cl)s1] | 4 | 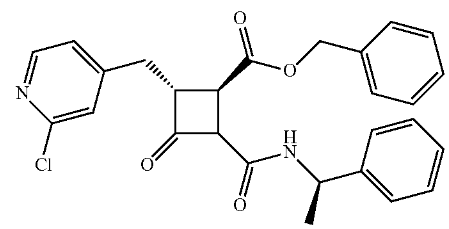 [SMILES: C[C@@H](NC(=O)C1C(=O)[C@H](Cc2ccnc(Cl)c2)[C@H]1C(=O)OCc1ccccc1)c1ccccc1] |
| 5 | 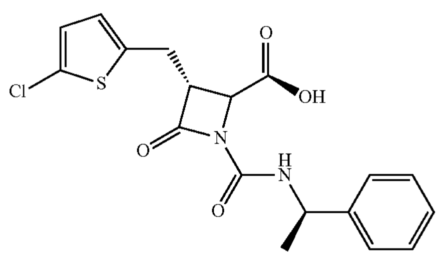 | 7 | 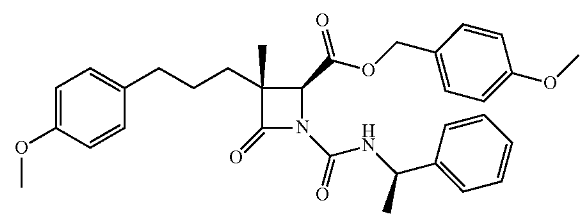 [SMILES: COc1ccc(CCC[C@@]2(C)C(=O)N(C(=O)N[C@H](C)c3ccccc3)[C@@H]2C(=O)OCc2ccc(OC)cc2)cc1] |

TABLE 1-continued
Exemplary compounds of the present invention.
| ID # | Structure | ID # | Structure |
|---|---|---|---|
| 6 | 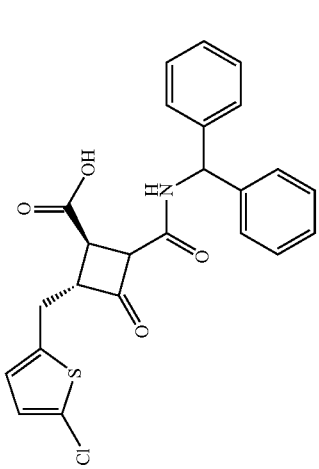 | 8 | 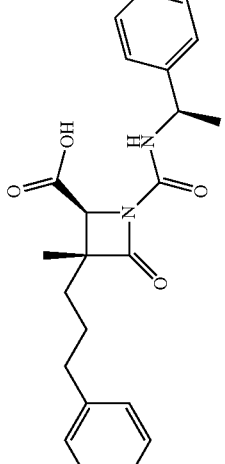 |
| 9 | 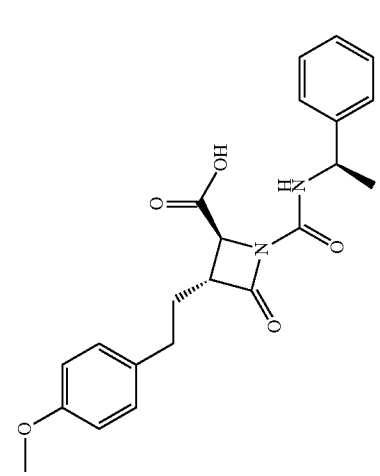 | 11 | 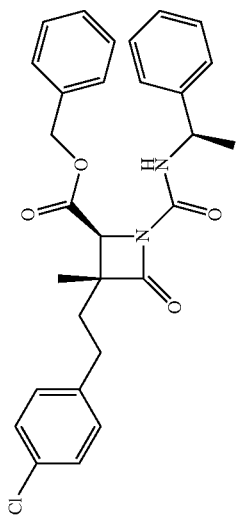 |
| 10 | 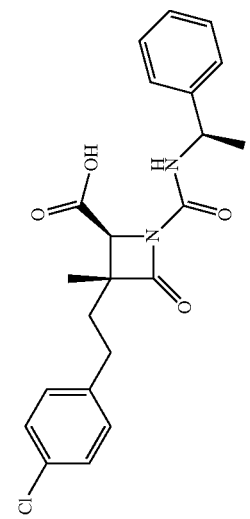 | 12 | 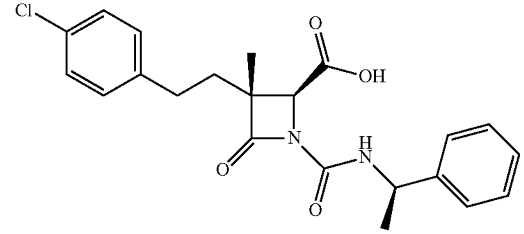 [SMILES: C[C@@H](NC(=O)N1C(=O)[C@](C)(CCc2ccc(Cl)cc2)[C@H]1C(=O)O)c1ccccc1] |

TABLE 1-continued

Exemplary compounds of the present invention.

| ID # | Structure | ID # | Structure |
|---|---|---|---|
| 13 | 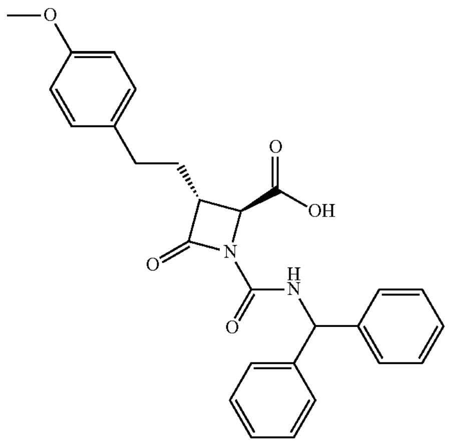 [SMILES: COc1ccc(CC[C@H]2C(=O)N(C(=O)NC(c3ccccc3)c3ccccc3)[C@@H]2C(=O)O)cc1] | 15 | 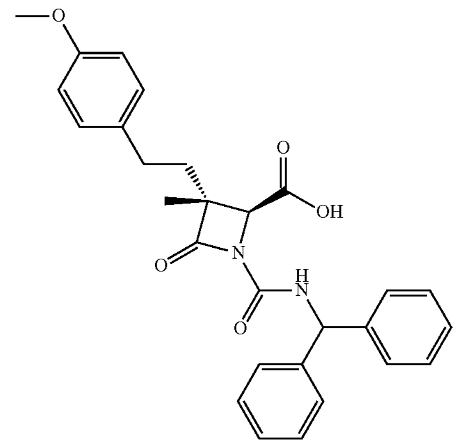 [SMILES: COc1ccc(CC[C@@]2(C)C(=O)N(C(=O)NC(c3ccccc3)c3ccccc3)[C@@H]2C(=O)O)cc1] |
| 14 | 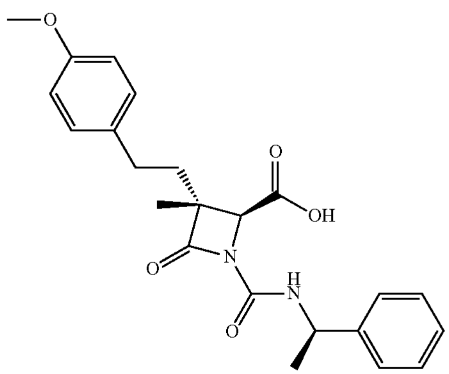 [SMILES: COc1ccc(CC[C@@]2(C)C(=O)N(C(=O)N[C@H](C)c3ccccc3)[C@@H]2C(=O)O)cc1] | 16 | 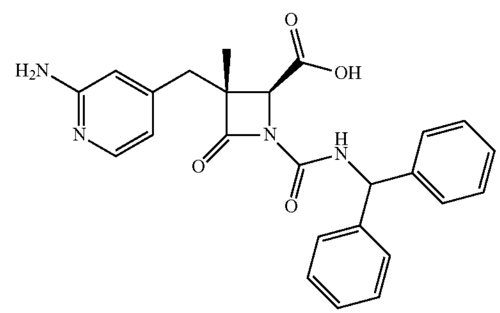 [SMILES: C[C@]1(Cc2ccnc(N)c2)C(=O)N(C(=O)NC(c2ccccc2)c2ccccc2)[C@@H]1C(=O)O] |

TABLE 1-continued

Exemplary compounds of the present invention.

| ID # | Structure |
|---|---|
| 17 | |
| 18 | |
| 21 | |
| 22 | |

TABLE 1-continued
Exemplary compounds of the present invention.
| ID # | Structure | ID # | Structure |
|---|---|---|---|
| 19 | 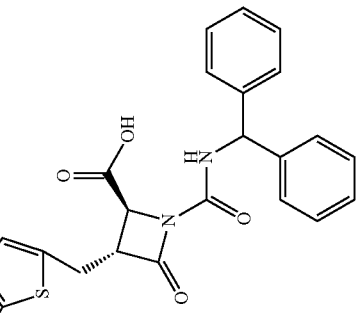 | 23 | 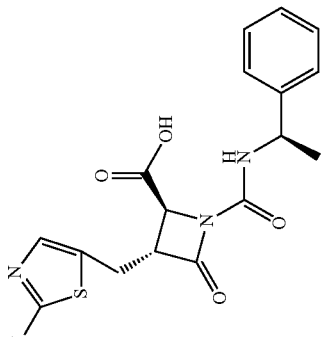 |
| 20 | 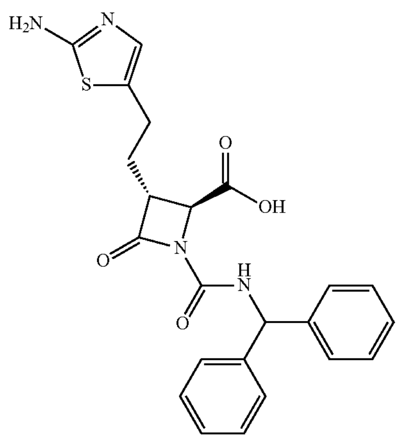 [SMILES: Nc1ncc(CC[C@H]2C(=O)N(C(=O)NC(c3ccccc3)c3ccccc3)[C@@H]2C(=O)O)s1] | 24 | 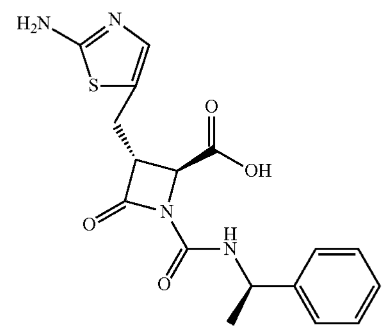 [SMILES: C[C@@H](NC(=O)N1C(=O)[C@H](Cc2cnc(N)s2)[C@H]1C(=O)O)c1ccccc1] |

TABLE 1-continued
Exemplary compounds of the present invention.
| ID # | Structure | ID # | Structure |
|---|---|---|---|
| 25 | 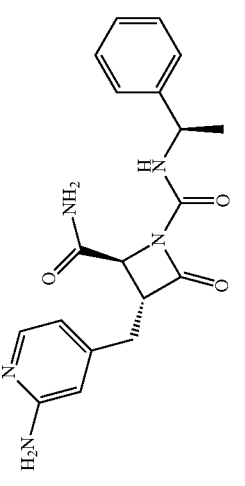 | 29 | 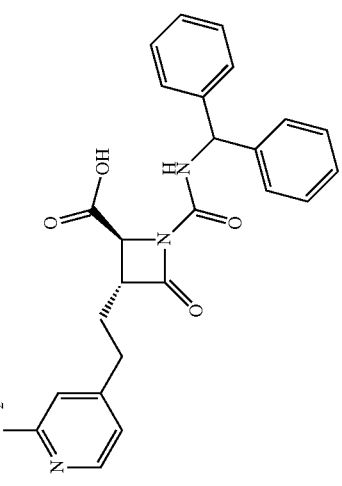 |
| 26 | 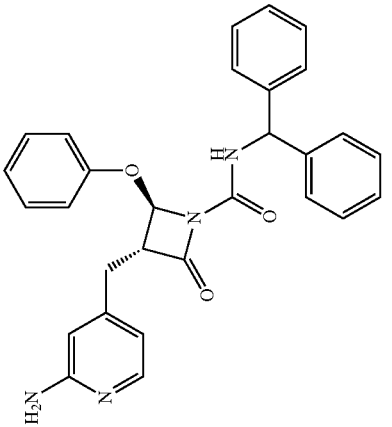 | 27 | 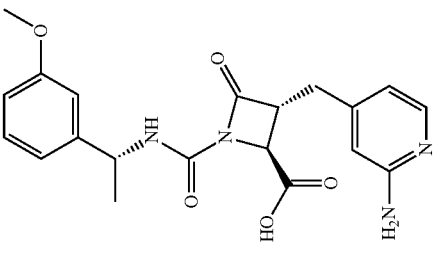 |

TABLE 1-continued

Exemplary compounds of the present invention.

| ID # | Structure | ID # | Structure |
|---|---|---|---|
| 28 | 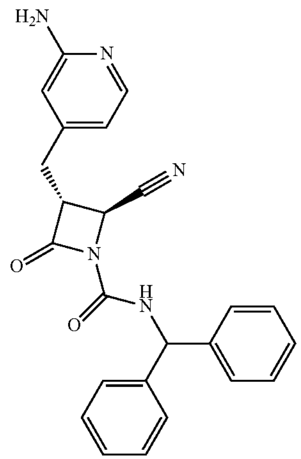 [SMILES: N#C[C@@H]1[C@@H](Cc2ccnc(N)c2)C(=O)N1C(=O)NC(c1ccccc1)c1ccccc1] | 34 | 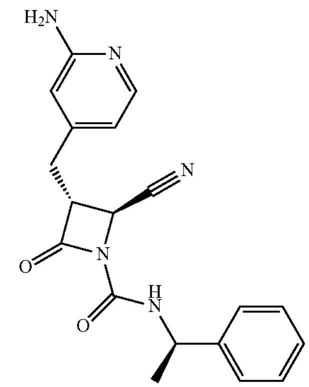 [SMILES: C[C@@H](NC(=O)N1C(=O)[C@H](Cc2ccnc(N)c2)[C@H]1C#N)c1ccccc1] |
| 31 | 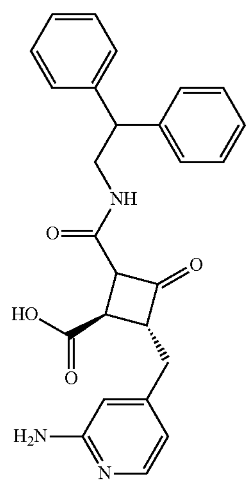 [SMILES: Nc1cc(C[C@H]2C(=O)C(C(=O)NCC(c3ccccc3)c3ccccc3)[C@@H]2C(=O)O)ccn1] | 35 | 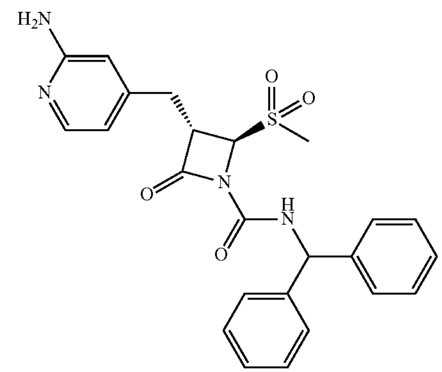 [SMILES: CS(=O)(=O)[C@@H]1[C@@H](Cc2ccnc(N)c2)C(=O)N1C(=O)NC(c1ccccc1)c1ccccc1] |

TABLE 1-continued

Exemplary compounds of the present invention.

| ID # | Structure | ID # | Structure |
|---|---|---|---|
| 32 | 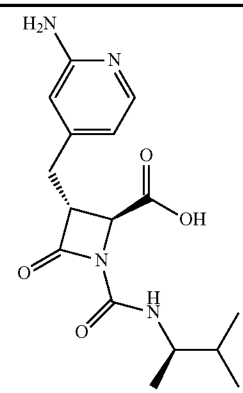 | 36 | 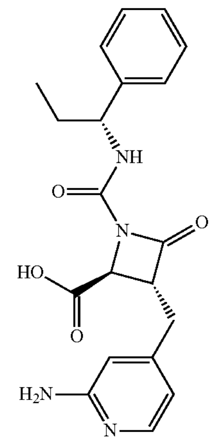 [SMILES: CC[C@@H](NC(=O)N1C(=O)[C@H](Cc2ccnc(N)c2)[C@H]1C(=O)O)c1ccccc1] |
| 33 | 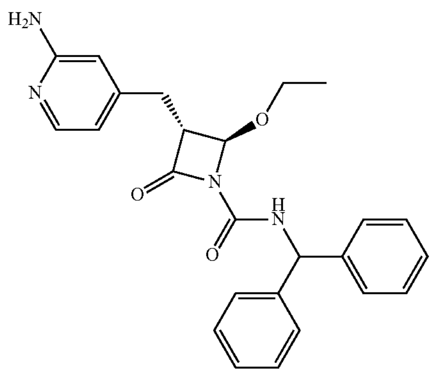 [SMILES: CCO[C@@H]1[C@@H](Cc2ccnc(N)c2)C(=O)N1C(=O)NC(c1ccccc1)c1ccccc1] | 37 | 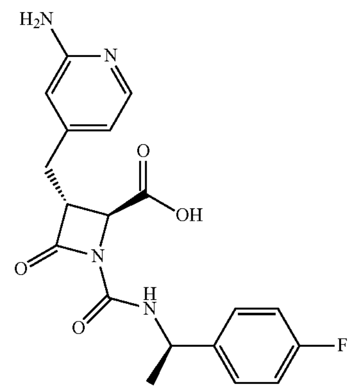 [SMILES: C[C@@H](NC(=O)N1C(=O)[C@H](Cc2ccnc(N)c2)[C@H]1C(=O)O)c1ccc(F)cc1] |

TABLE 1-continued

Exemplary compounds of the present invention.

| ID # | Structure |
|---|---|
| 38 | |
| 39 | |
| 43 | |
| 44 | |

TABLE 1-continued
Exemplary compounds of the present invention.
| ID # | Structure |
|---|---|
| 45 | 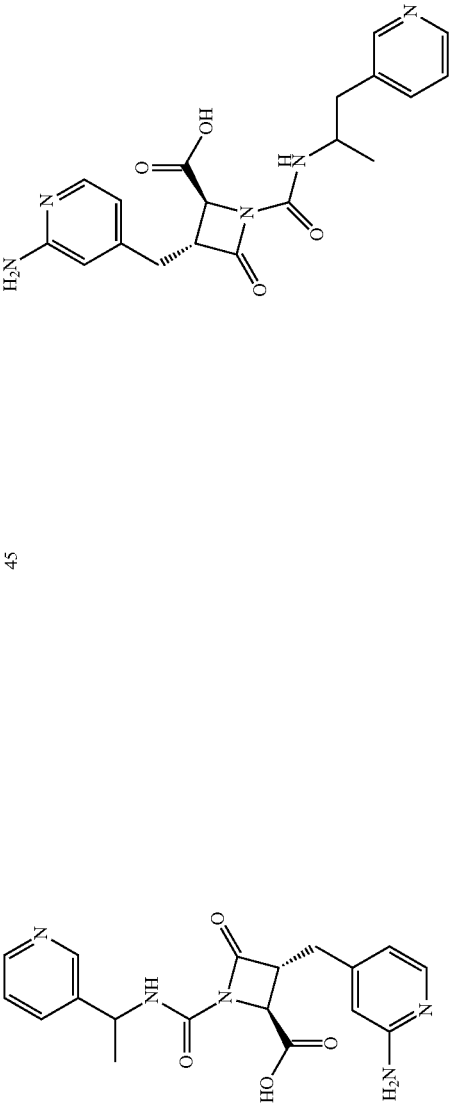 |
| 46 | 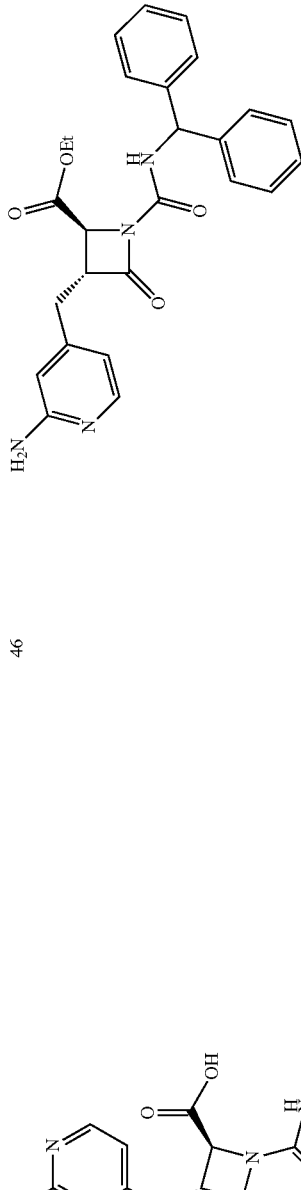 |
| 40 |  |
| 42 | |

TABLE 1-continued
Exemplary compounds of the present invention.
| ID # | Structure |
|---|---|
| 51 | 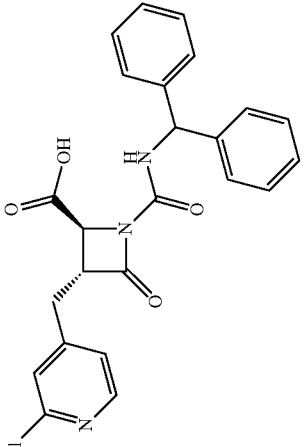 |
| 52 | 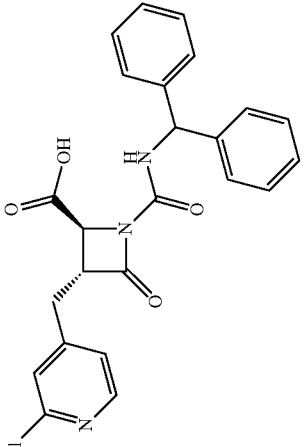 |
| ID # | Structure |
|---|---|
| 47 | 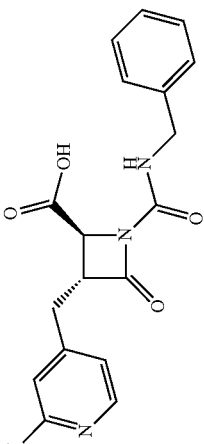 |
| 48 | 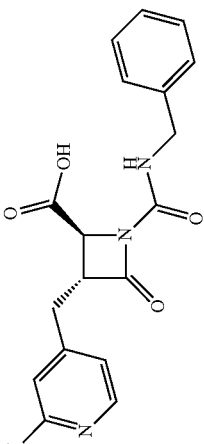 |

TABLE 1-continued
Exemplary compounds of the present invention.
| ID # | Structure | ID # | Structure |
|---|---|---|---|
| 49 | 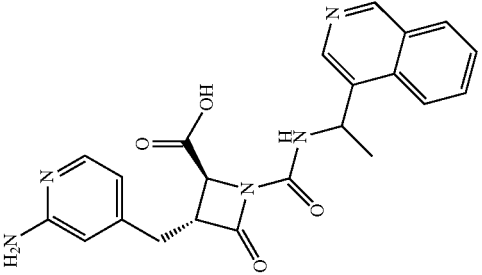 | 53 | 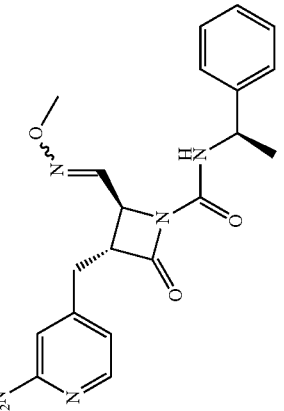 |
| 50 | 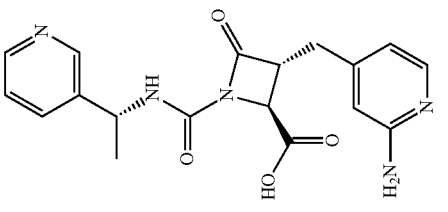 | 54 | 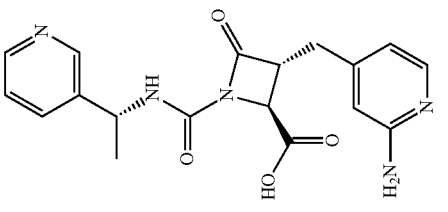 |

TABLE 1-continued

Exemplary compounds of the present invention.

| ID # | Structure |
|---|---|
| 55 | |
| 56 | |
| 59 | |
| 60 | |

TABLE 1-continued

Exemplary compounds of the present invention.

| ID # | Structure |
|---|---|
| 57 | |
| 58 | |
| 61 | |
| 62 | |
| 63 | |
| 67 | |

TABLE 1-continued

Exemplary compounds of the present invention.

| ID # | Structure | ID # | Structure |
|---|---|---|---|
| 64 | 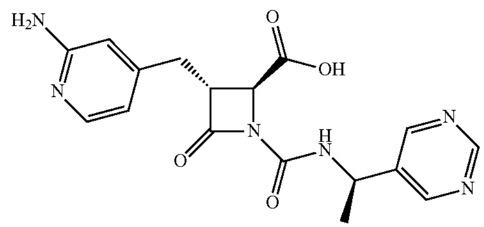 | 68 | 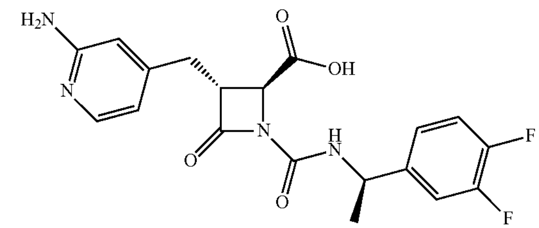 [SMILES: C[C@@H](NC(=O)N1C(=O)[C@H](Cc2ccnc(N)c2)[C@H]1C(=O)O)c1ccc(F)c(F)c1] |
| 65 | 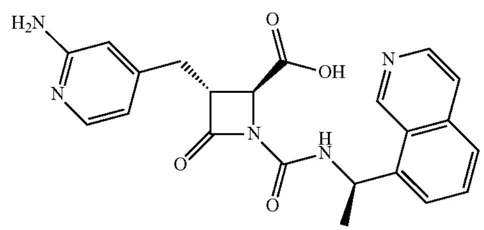 [SMILES: C[C@@H](NC(=O)N1C(=O)[C@H](Cc2ccnc(N)c2)[C@H]1C(=O)O)c1cccc2ccncc12] | 69 | 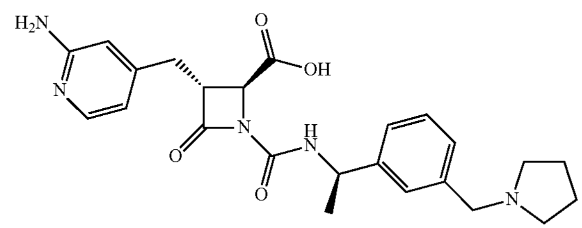 [SMILES: C[C@@H](NC(=O)N1C(=O)[C@H](Cc2ccnc(N)c2)[C@H]1C(=O)O)c1cccc(CN2CCCC2)c1] |
| 66 | 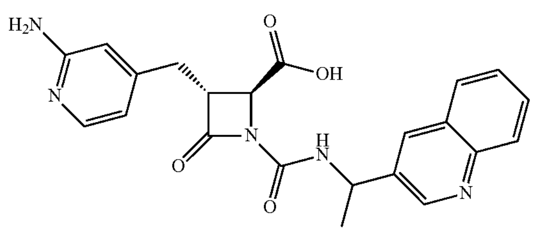 [SMILES: CC(NC(=O)N1C(=O)[C@H](Cc2ccnc(N)c2)[C@H]1C(=O)O)c1cnc2ccccc2c1] | 70 | 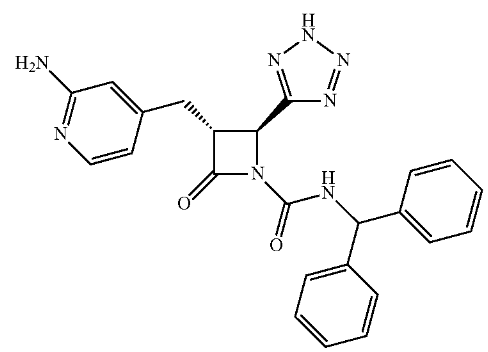 [SMILES: Nc1cc(C[C@H]2C(=O)N(C(=O)NC(c3ccccc3)c3ccccc3)[C@@H]2c2nn[nH]n2)ccn1] |

TABLE 1-continued

Exemplary compounds of the present invention.

| ID # | Structure |
|---|---|
| 71 | |
| 72 | |
| 73 | |
| 75 | |
| 76 | |
| 77 | |

TABLE 1-continued
Exemplary compounds of the present invention.
| ID # | Structure |
|---|---|
| 74 | 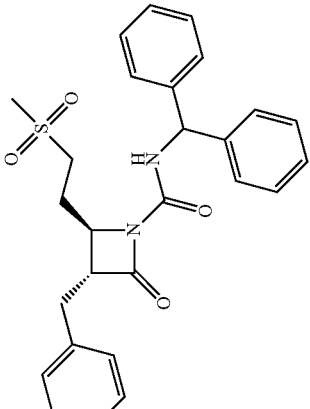 |
| 78 | 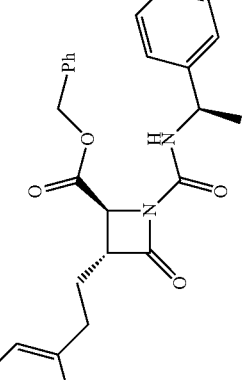 |
| 79 | 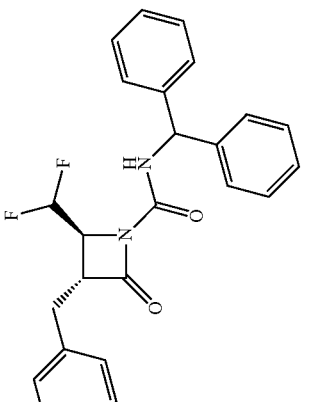 |
| 86 | 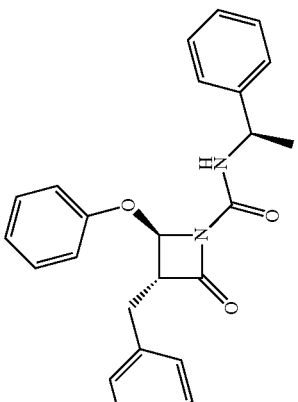 |
| 80 | 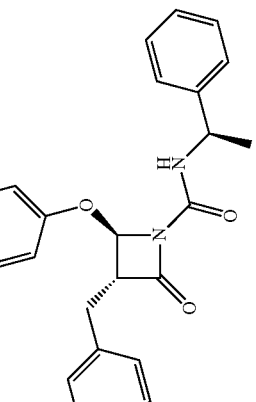 |
| 88 | 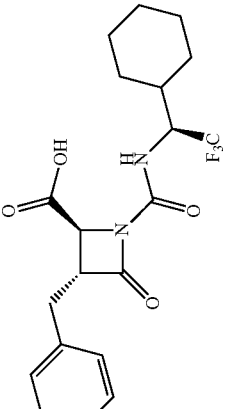 |

TABLE 1-continued

Exemplary compounds of the present invention.

| ID # | Structure | ID # | Structure |
|---|---|---|---|
| 83 | 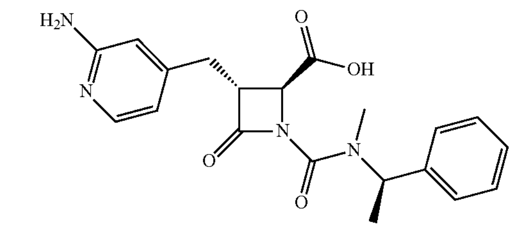 [SMILES: C[C@H](c1ccccc1)N(C)C(=O)N1C(=O)[C@H](Cc2ccnc(N)c2)[C@H]1C(=O)O] | 89 | 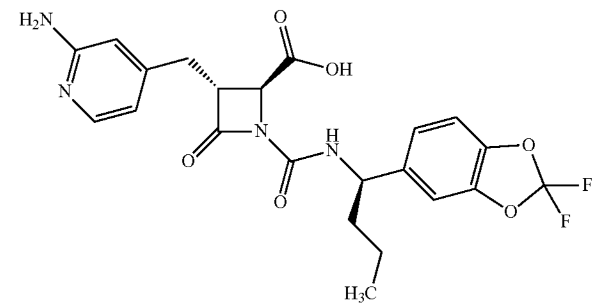 [SMILES: CCC[C@@H](NC(=O)N1C(=O)[C@H](Cc2ccnc(N)c2)[C@H]1C(=O)O)c1ccc2c(c1)OC(F)(F)O2] |
| 84 | 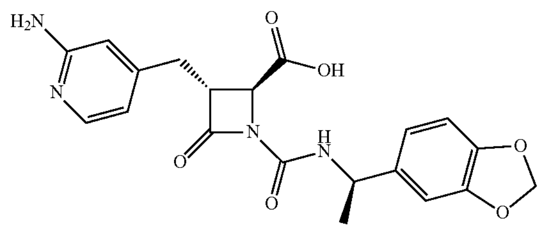 [SMILES: C[C@@H](NC(=O)N1C(=O)[C@H](Cc2ccnc(N)c2)[C@H]1C(=O)O)c1ccc2c(c1)OCO2] | 91 | 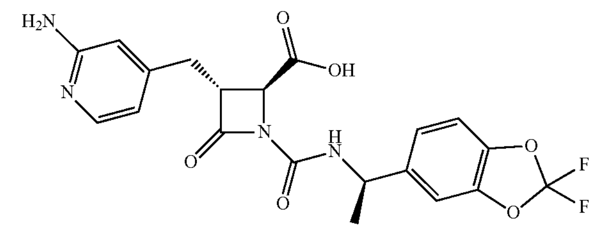 [SMILES: C[C@@H](NC(=O)N1C(=O)[C@H](Cc2ccnc(N)c2)[C@H]1C(=O)O)c1ccc2c(c1)OC(F)(F)O2] |
| 92 | 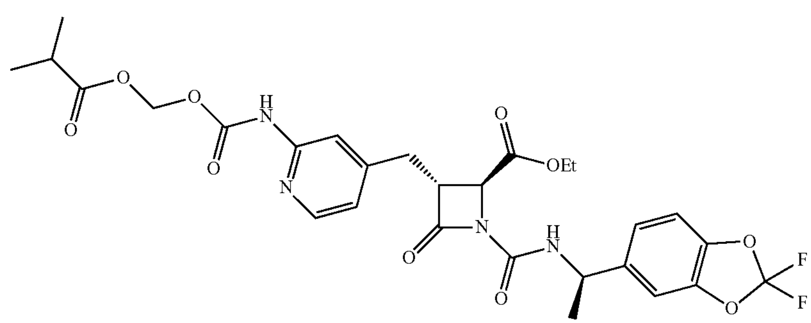 [SMILES: CCOC(=O)[C@@H]1[C@@H](Cc2ccnc(NC(=O)OCOC(=O)C(C)C)c2)C(=O)N1C(=O)N[C@H](C)c1ccc2c(c1)OC(F)(F)O2] | 98 | 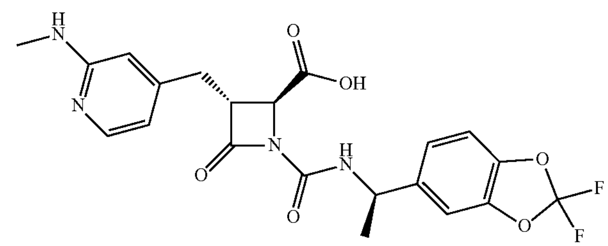 [SMILES: CNc1cc(C[C@H]2C(=O)N(C(=O)N[C@H](C)c3ccc4c(c3)OC(F)(F)O4)[C@@H]2C(=O)O)ccn1] |

TABLE 1-continued

Exemplary compounds of the present invention.

| ID # | Structure | ID # | Structure |
|---|---|---|---|
| 93 | 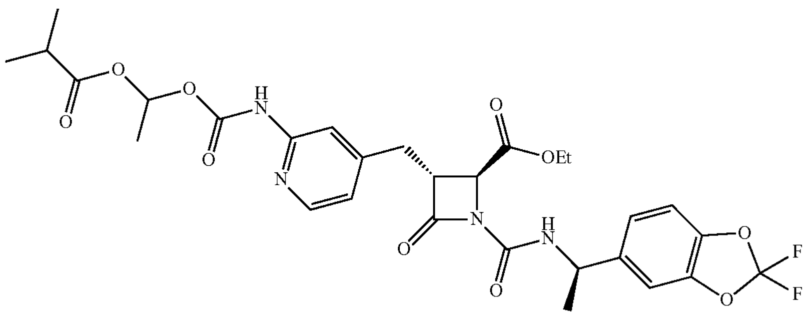 [SMILES: CCOC(=O)[C@@H]1[C@@H](Cc2ccnc(NC(=O)OC(C)OC(=O)C(C)C)c2)C(=O)N1C(=O)N[C@H](C)c1ccc2c(c1)OC(F)(F)O2] | 99 | 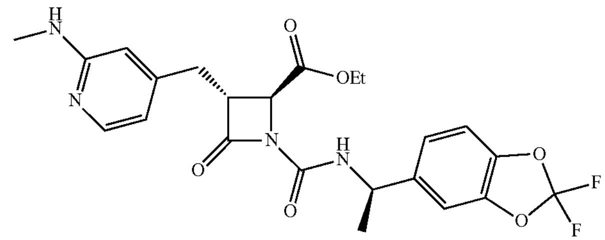 |
| 95 | 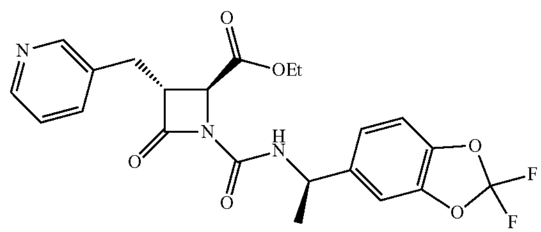 [SMILES: CCOC(=O)[C@@H]1[C@@H](Cc2cccnc2)C(=O)N1C(=O)N[C@H](C)c1ccc2c(c1)OC(F)(F)O2] | 100 | 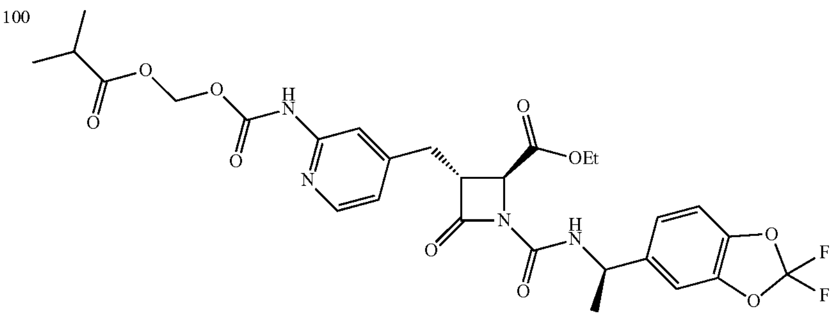 |
| 96 | 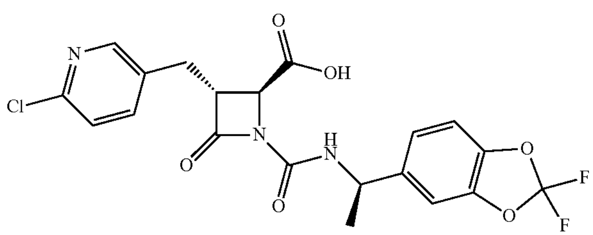 [SMILES: C[C@@H](NC(=O)N1C(=O)[C@H](Cc2ccc(Cl)nc2)[C@H]1C(=O)O)c1ccc2c(c1)OC(F)(F)O2] | 101 | 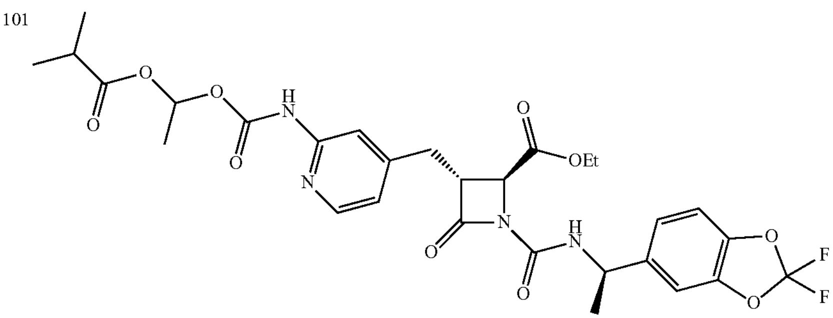 |

TABLE 1-continued

Exemplary compounds of the present invention.

| ID # | Structure | ID # | Structure |
|---|---|---|---|
| 97 | (chemical structure) | 102 | (chemical structure) |
| 103 | (chemical structure) | 108 | (chemical structure) |
| 104 | (chemical structure) | 109 | (chemical structure) |

TABLE 1-continued

Exemplary compounds of the present invention.

| ID # | Structure | ID # | Structure |
|---|---|---|---|
| 105 | 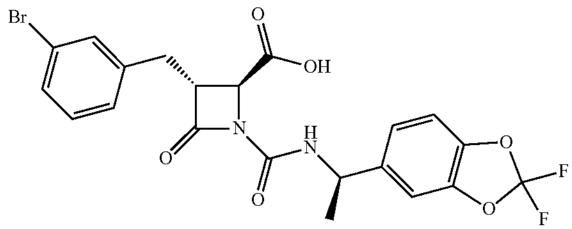 [SMILES: C[C@@H](NC(=O)N1C(=O)[C@H](Cc2cccc(Br)c2)[C@H]1C(=O)O)c1ccc2c(c1)OC(F)(F)O2] | 110 | 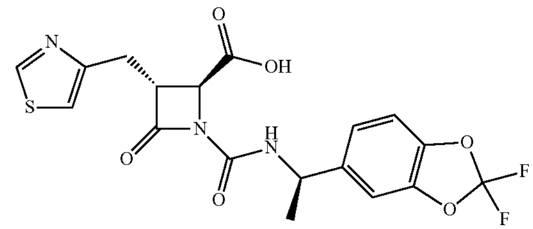 [SMILES: C[C@@H](NC(=O)N1C(=O)[C@H](Cc2cscn2)[C@H]1C(=O)O)c1ccc2c(c1)OC(F)(F)O2] |
| 107 | 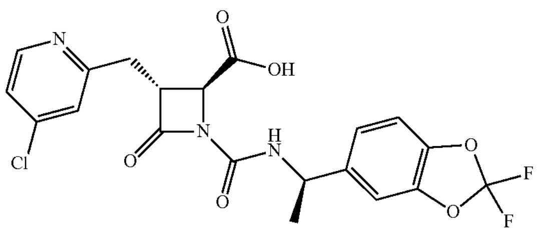 [SMILES: C[C@@H](NC(=O)N1C(=O)[C@H](Cc2cc(Cl)ccn2)[C@H]1C(=O)O)c1ccc2c(c1)OC(F)(F)O2] | 111 | 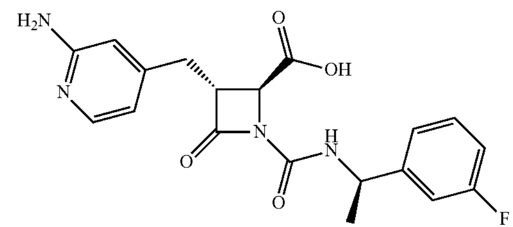 [SMILES: C[C@@H](NC(=O)N1C(=O)[C@H](Cc2ccnc(N)c2)[C@H]1C(=O)O)c1cccc(F)c1] |
| 112 | 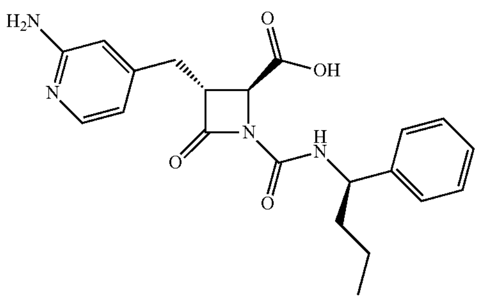 [SMILES: CCC[C@@H](NC(=O)N1C(=O)[C@H](Cc2ccnc(N)c2)[C@H]1C(=O)O)c1ccccc1] | 119 | 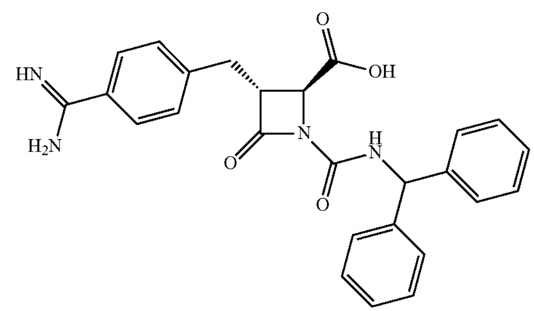 [SMILES: N=C(N)c1ccc(C[C@H]2C(=O)N(C(=O)NC(c3ccccc3)c3ccccc3)[C@@H]2C(=O)O)cc1] |
| 113 | 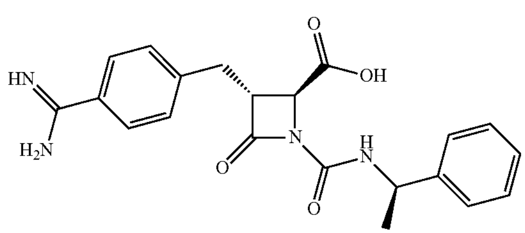 [SMILES: C[C@@H](NC(=O)N1C(=O)[C@H](Cc2ccc(C(=N)N)cc2)[C@H]1C(=O)O)c1ccccc1] | 120 | 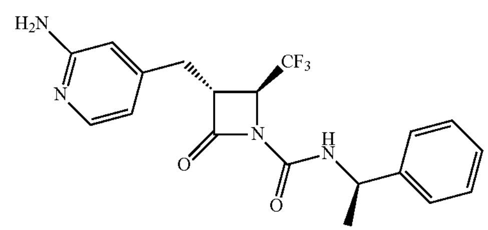 [SMILES: C[C@@H](NC(=O)N1C(=O)[C@H](Cc2ccnc(N)c2)[C@H]1C(F)(F)F)c1ccccc1] |

TABLE 1-continued

Exemplary compounds of the present invention.

| ID # | Structure |
|---|---|
| 114 | |
| 117 | |
| 118 | |
| 123 | |
| 124 | |
| 126 | |

TABLE 1-continued
Exemplary compounds of the present invention.
| ID # | Structure | ID # | Structure |
|---|---|---|---|
| 127 | 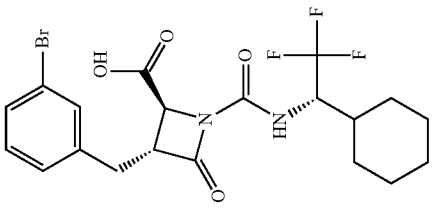 | 131 | 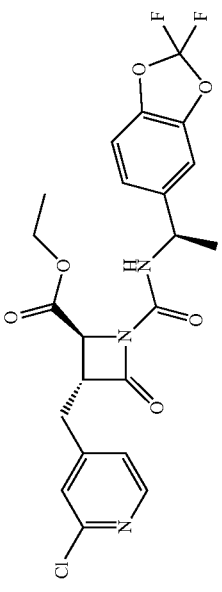 |
| 128 | 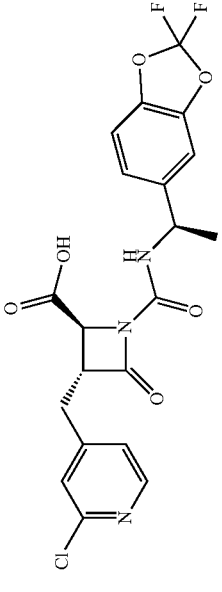 | 132 | 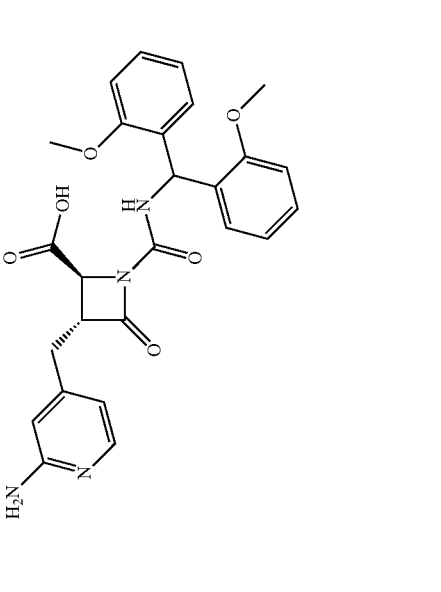 |

TABLE 1-continued

Exemplary compounds of the present invention.

| ID # | Structure |
|---|---|
| 130 | (structure) |
| 133 | (structure) |

TABLE 1-continued

Exemplary compounds of the present invention.

| ID # | Structure |
|---|---|
| 134 | (structure) |
| 135 | (structure) |
| 137 | (structure) |
| 138 | (structure) |

TABLE 1-continued

Exemplary compounds of the present invention.

| ID # | Structure |
|---|---|
| 139 | (structure) |
| 147 | (structure) |
| 136 | (structure) |
| 140 | (structure) |

TABLE 1-continued

Exemplary compounds of the present invention.

| ID # | Structure | ID # | Structure |
|------|-----------|------|-----------|
| 144 | 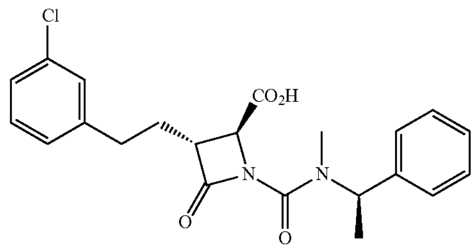 [SMILES: C[C@H](c1ccccc1)N(C)C(=O)N1C(=O)[C@H](CCc2cccc(Cl)c2)[C@H]1C(=O)O] | 148 | 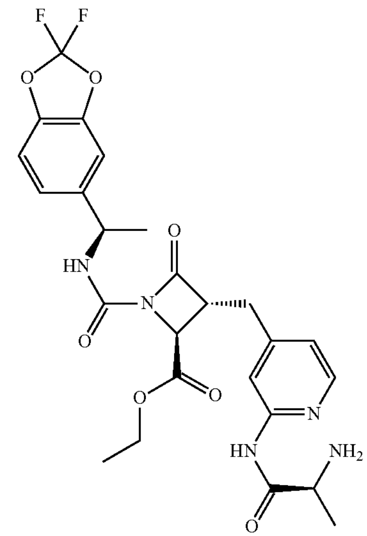 [SMILES: CCOC(=O)[C@@H]1[C@@H](Cc2ccnc(NC(=O)[C@H](C)N)c2)C(=O)N1C(=O)N[C@H](C)c1ccc2c(c1)OC(F)(F)O2] |
| 145 | 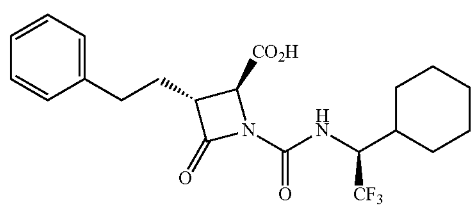 [SMILES: O=C(O)[C@@H]1[C@@H](CCc2ccccc2)C(=O)N1C(=O)N[C@@H](C1CCCCC1)C(F)(F)F] | 150 | 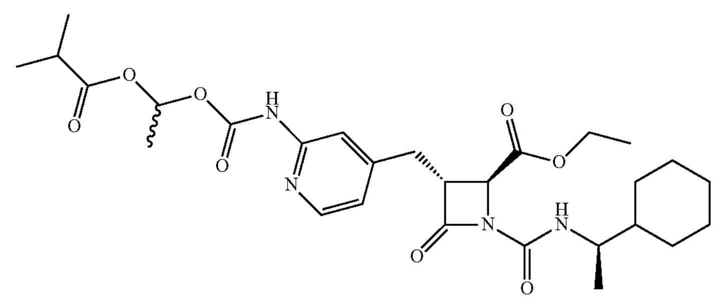 [SMILES: CCOC(=O)[C@@H]1[C@@H](Cc2ccnc(NC(=O)OC(C)OC(=O)C(C)C)c2)C(=O)N1C(=O)N[C@H](C)C1CCCCC1] |

TABLE 1-continued
Exemplary compounds of the present invention.
| ID # | Structure | ID # | Structure |
|---|---|---|---|
| 149 | 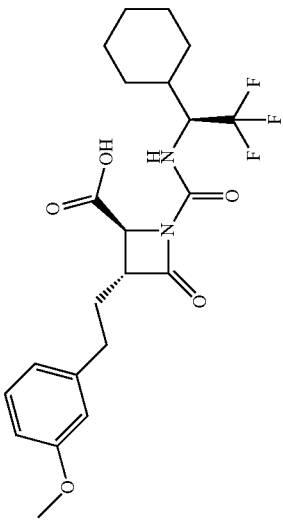 | 154 | 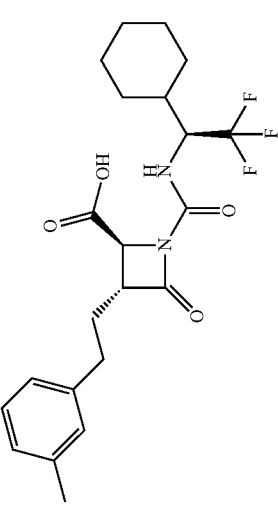 |
| 151 | 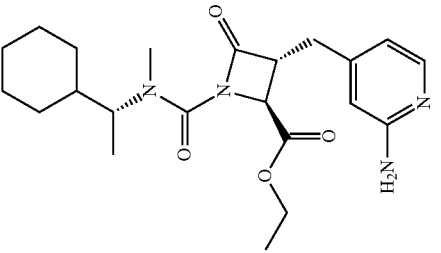 | 155 | 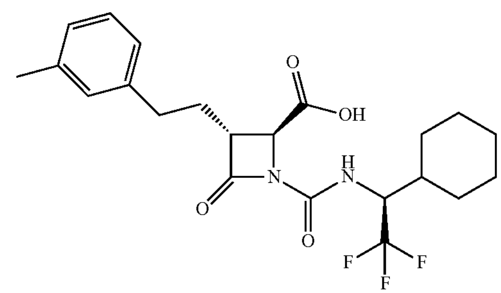 [SMILES: Cc1cccc(CC[C@H]2C(=O)N(C(=O)N[C@@H](C3CCCCC3)C(F)(F)F)[C@@H]2C(=O)O)c1] |

TABLE 1-continued

Exemplary compounds of the present invention.

| ID # | Structure | ID # | Structure |
|---|---|---|---|
| 152 | 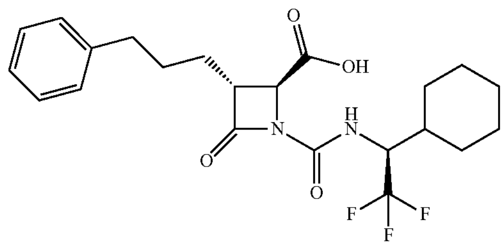 [SMILES: O=C(O)[C@@H]1[C@@H](CCCc2ccccc2)C(=O)N1C(=O)N[C@@H](C1CCCCC1)C(F)(F)F] | 156 | 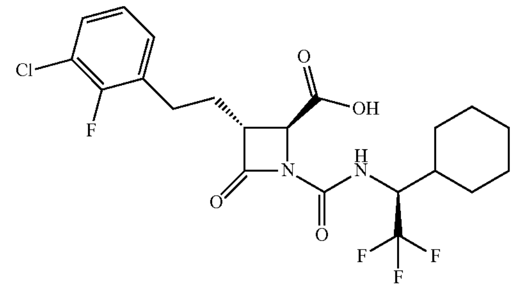 [SMILES: O=C(O)[C@@H]1[C@@H](CCc2cccc(Cl)c2F)C(=O)N1C(=O)N[C@@H](C1CCCCC1)C(F)(F)F] |
| 153 | 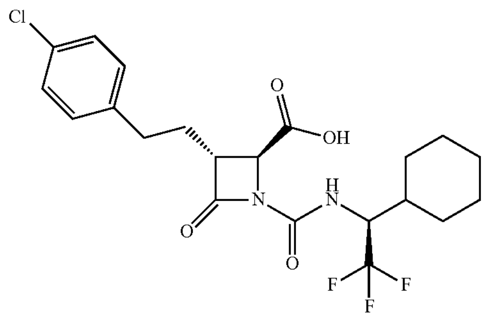 [SMILES: O=C(O)[C@@H]1[C@@H](CCc2ccc(Cl)cc2)C(=O)N1C(=O)N[C@@H](C1CCCCC1)C(F)(F)F] | 157 | 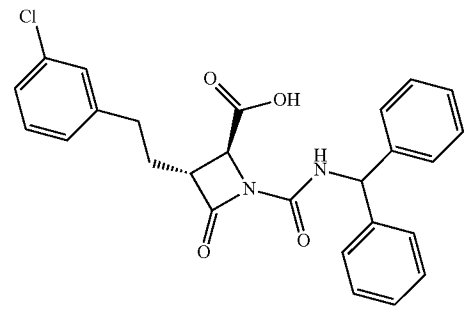 [SMILES: O=C(O)[C@@H]1[C@@H](CCc2cccc(Cl)c2)C(=O)N1C(=O)NC(c1ccccc1)c1ccccc1] |
| 158 | 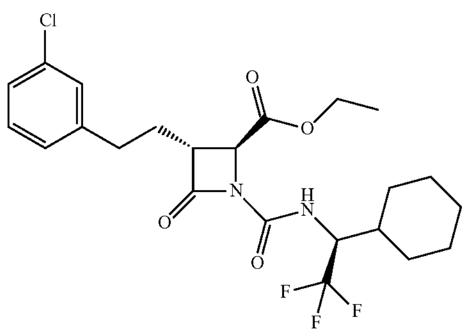 [SMILES: CCOC(=O)[C@@H]1[C@@H](CCc2cccc(Cl)c2)C(=O)N1C(=O)N[C@@H](C1CCCCC1)C(F)(F)F] | 168 | 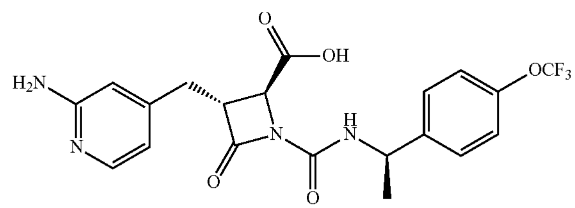 [SMILES: C[C@@H](NC(=O)N1C(=O)[C@H](Cc2ccnc(N)c2)[C@H]1C(=O)O)c1ccc(OC(F)(F)F)cc1] |

TABLE 1-continued

Exemplary compounds of the present invention.

| ID # | Structure |
|---|---|
| 159 | |
| 160 | |
| 166 | |
| 169 | |
| 170 | |
| 171 | |

TABLE 1-continued
Exemplary compounds of the present invention.
| ID # | Structure | ID # | Structure |
|---|---|---|---|
| 175 | 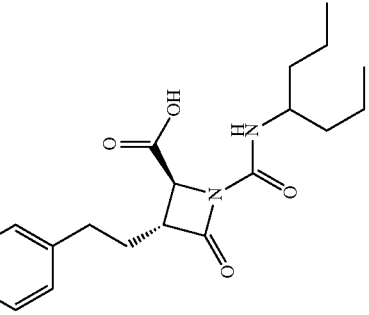 | 192 | 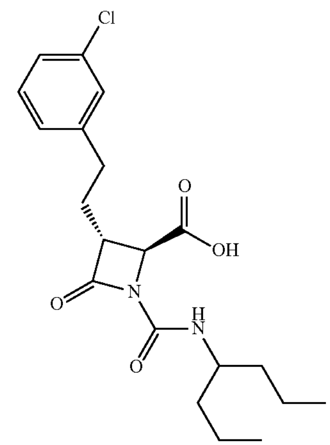 [SMILES: CCCC(CCC)NC(=O)N1C(=O)[C@H](CCc2cccc(Cl)c2)[C@H]1C(=O)O] |
| 180 | 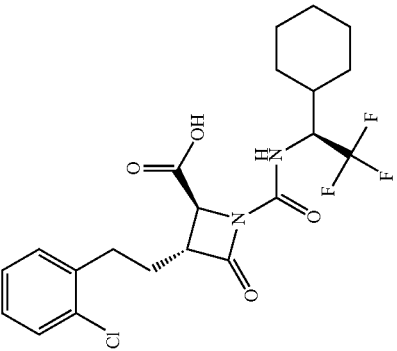 | 194 | 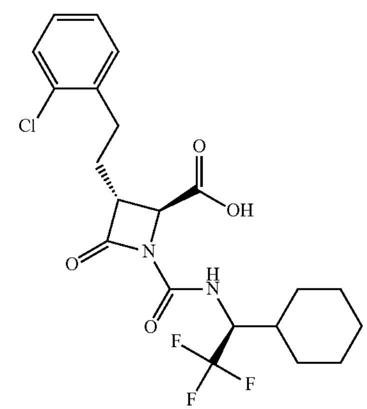 [SMILES: O=C(O)[C@@H]1[C@@H](CCc2ccccc2Cl)C(=O)N1C(=O)N[C@@H](C1CCCCC1)C(F)(F)F] |

TABLE 1-continued

Exemplary compounds of the present invention.

| ID # | Structure | ID # | Structure |
|---|---|---|---|
| 190 | 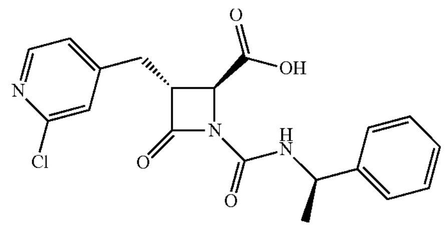 [SMILES: C[C@@H](NC(=O)N1C(=O)[C@H](Cc2ccnc(Cl)c2)[C@H]1C(=O)O)c1ccccc1] | 197 | 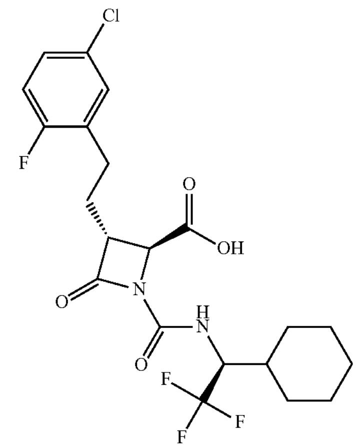 [SMILES: O=C(O)[C@@H]1[C@@H](CCc2cc(Cl)ccc2F)C(=O)N1C(=O)N[C@@H](C1CCCCC1)C(F)(F)F] |
| 191 | 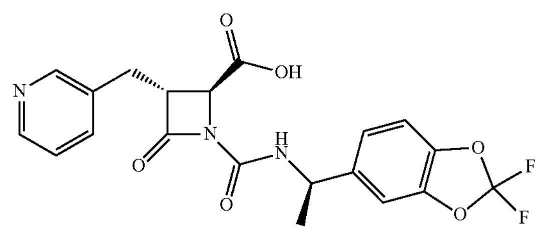 [SMILES: C[C@@H](NC(=O)N1C(=O)[C@H](Cc2cccnc2)[C@H]1C(=O)O)c1ccc2c(c1)OC(F)(F)O2] | 193 | 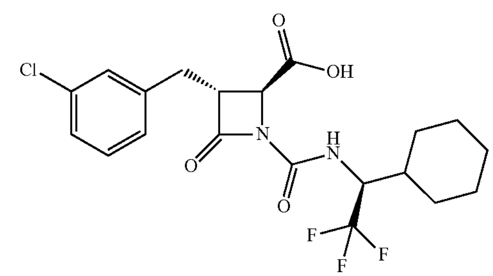 [SMILES: O=C(O)[C@@H]1[C@@H](Cc2cccc(Cl)c2)C(=O)N1C(=O)N[C@@H](C1CCCCC1)C(F)(F)F] |
| 195 | 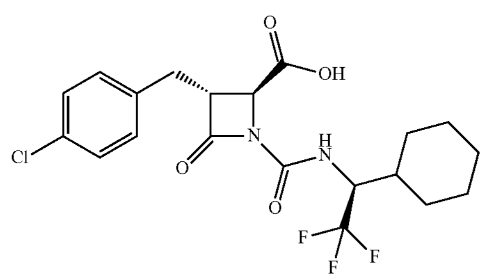 [SMILES: O=C(O)[C@@H]1[C@@H](Cc2ccc(Cl)cc2)C(=O)N1C(=O)N[C@@H](C1CCCCC1)C(F)(F)F] | 200 | 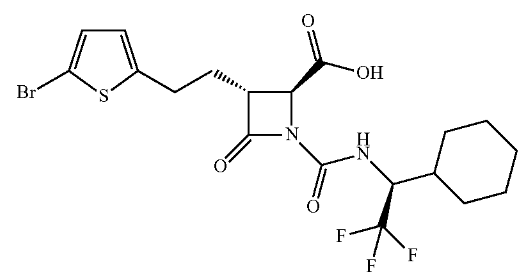 [SMILES: O=C(O)[C@@H]1[C@@H](CCc2ccc(Br)s2)C(=O)N1C(=O)N[C@@H](C1CCCCC1)C(F)(F)F] |

TABLE 1-continued

Exemplary compounds of the present invention.

| ID # | Structure | ID # | Structure |
|---|---|---|---|
| 196 | 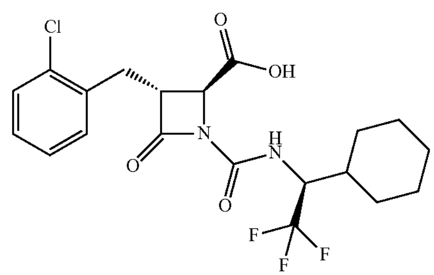 [SMILES: O=C(O)[C@@H]1[C@@H](Cc2ccccc2Cl)C(=O)N1C(=O)N[C@@H](C1CCCCC1)C(F)(F)F] | | |
| 198 | 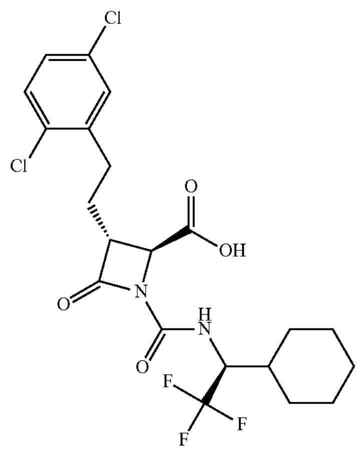 [SMILES: O=C(O)[C@@H]1[C@@H](CCc2cc(Cl)ccc2Cl)C(=O)N1C(=O)N[C@@H](C1CCCCC1)C(F)(F)F] | | |

TABLE 1-continued
Exemplary compounds of the present invention.
| ID # | Structure | ID # | Structure |
|---|---|---|---|
| 199 | 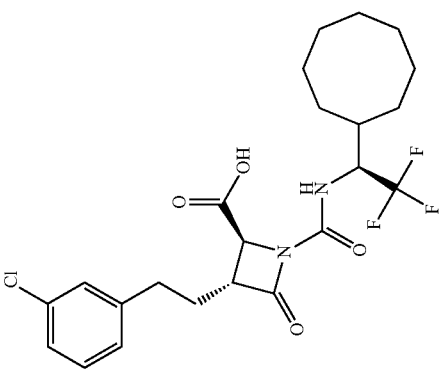 | | |

In some embodiments, a compound described herein is formed into a salt. A compound described herein can be administered as a free acid, a zwitterion or as a salt. A salt can also be formed between a cation and a negatively charged substituent on a compound described herein. Suitable cationic counterions include sodium ions, potassium ions, magnesium ions, calcium ion, and ammonium ions (e.g., a tetraalkyl ammonium cation such as tetramethylammonium ion). In compounds including a positively charged substituent or a basic substituent, a salt can be formed between an anion and a positively charged substituent (e.g., amino group) or basic substituent (e.g., pyridyl) on a compound described herein. Suitable anions include chloride, bromide, iodide, sulfate, nitrate, phosphate, citrate, methanesulfonate, trifluoroacetate, and acetate.

Pharmaceutically acceptable salts of the compounds described herein (e.g., a compound of formula (I)-(VII)) also include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate, trifluoroacetate, and undecanoate.

Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

As used herein, the compounds of this invention, including the compounds of formula (I)-(VII), are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood), or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

Any formula or a compound described herein is also intended to represent unlabeled forms as well as isotopically labeled forms of the compounds, isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{51}P$, $^{32}P$, $^{35}S$, $^{36}Cl$, $^{125}I$ respectively. The invention includes various isotopically labeled compounds as defined herein, for example, those into which radioactive isotopes, such as $^3H$, $^{13}C$, and $^{14}C$ are present. Such isotopically labelled compounds are useful in metabolic studies (with $^{14}C$), reaction kinetic studies (with, for example 'H or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies, isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of a formula described herein. The concentration of such a heavier isotope, specifically deuterium, may be defined by the isotopic enrichment factor. The term "isotopic enrichment factor" as used herein means the ratio between the isotopic abundance and the natural abundance of a specified isotope If a substituent m a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 8633.3 (99.5% deuterium incorporation).

Isotopically-labelled compounds described herein can generally be prepared by conventional techniques known to those skilled in the art or by processes analogous to those described in the accompanying Examples and Preparations using an appropriate isotopically-labeled reagents in place of the non-labeled reagent previously employed. Pharmaceutically acceptable solvates in accordance with the invention include those wherein the solvent of crystallization may be isotopically substituted, e.g, $D_2O$, $D_2$-acetone, $D_2$-DMSO.

Any asymmetric atom (e.g., carbon or the like) of the compound(s) of the present invention can be present in racemic or enantiomerically enriched, for example the (R)-(S)- or (RS)-configuration, in certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form Accordingly, as used herein a compound of the present invention can be in the form of one of the possible isomers, rotamers, atropisomers, tautoroers or mixtures thereof, for example, as substantially pure geometric (cis or trans) isomers, diastereorners, optical isomers (antipodes), racemates or mixtures thereof. Any resulting mixtures of isomers can be separated on the basis of the physicochemical differences of the constituents, into the pure or substantially pure geometric or optical isomers, diastereomers, racemates, for example, by chromatography or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, (+)—O,O'-Di-p-toluoyl-D-tartaric acid, mandelic acid, malic acid or camphor-10-sulfonic acid. Racemic products can also be resolved by chiral chromatography, e.g., high pressure liquid chromatography (HPLC) using a chiral adsorbent.

The compounds described herein (e.g., a compound of formula (I)-(VII)) may also be represented in multiple tautomeric forms, for example, a compound of formula (I), (II), (III), (IV), (V), (VI), or (VII). In such instances, the invention expressly includes all tautomeric forms of the compounds described herein. All crystal forms of the compounds described herein are expressly included in this invention.

A compound described herein (e.g., a compound of formula (I)-(VII)) can be evaluated for its ability to modulate (e.g., inhibit) Factor XIa or kallikrein.

Methods of Synthesizing Compounds

The compounds described herein can be synthesized by conventional methods using commercially available starting materials and reagents. For example, compounds can be synthesized utilizing the methods set forth in U.S. Pat. No. 7,501,404, or as described in the methods described herein.

Methods of Treatment

The compounds described herein (e.g., compounds of formula (I)-(VII)) can inhibit Factor XIa or kallikrein. In some embodiments, a compound described herein can inhibit both Factor XIa and kallikrein. As a result, these compounds can be useful in the treatment or prevention of a disorder described herein. Exemplary disorders include thrombotic events associated with coronary artery and cerebrovascular disease, venous or arterial thrombosis, coagulation syndromes, ischemia and angina (stable and unstable), deep vein thrombosis (DVT), disseminated intravascular coagulopathy, Kasabach-Merritt syndrome, pulmonary embolism, myocardial infarction, cerebral infarction, cerebral thrombosis, transient ischemic attacks, atrial fibrillation, cerebral embolism, thromboembolic complications of surgery (such as hip or knee replacement, introduction of artificial heart valves and endarterectomy) and peripheral arterial occlusion and may also be useful in treating or preventing myocardial infarction, stroke, angina and other consequences of atherosclerotic plaque rupture. The compounds of the invention possessing Factor XIa or kallikrein inhibition activity may also be useful in preventing thrombosis in cancer patients and to prevent thromboembolic events at or following tissue plasminogen activator-based or mechanical restoration of blood vessel patency. The compounds of the invention possessing Factor XIa or kallikrein inhibition activity may also be useful as inhibitors of blood coagulation such as during the preparation, storage and fractionation of whole blood.

Factor XIa inhibition, according to the present invention, can be a more effective and safer method of inhibiting thrombosis compared to inhibiting other coagulation serine proteases such as thrombin or Factor Xa. Administration of a small molecule Factor XIa inhibitor should have the effect of inhibiting thrombin generation and clot formation with no or substantially no effect on bleeding times and little or no impairment of haemostasis. These results differ substantially from that of other "direct acting" coagulation protease inhibitors (e.g., active-site inhibitors of thrombin and Factor Xa), which demonstrate prolongation of bleeding time and less separation between antithrombotic efficacy and bleeding time prolongation. A preferred method according to the invention comprises administering to a mammal a pharmaceutical composition containing at least one compound of the invention.

The compounds described herein (e.g., any of a compound of formula (I)-(VII)) can inhibit kallikrein, for example, a compound of formula (I), (II), (III), (IV), (V), (VI), or (VII). As a result, these compounds can be useful in the treatment or prevention of diseases involved in inflammation, such as edema (e.g., cerebral edema, macular edema, and angioedema (e.g., hereditary angioedema)). In some embodiments, the compounds of the invention can be useful in the treatment or prevention of hereditary angioedema. The compounds described herein (e.g., compounds of formula (I)-(VII)) can also be useful in the treatment of e.g., stroke, ischemia, and perioperative blood loss for example, a compound of formula (I), (II), (III), (IV), (V), (VI), or (VII).

The methods of the present invention are useful for treating or preventing those conditions which involve the action of Factor XIa or kallikrein. Accordingly, the methods of the present invention are useful in treating consequences of atherosclerotic plaque rupture including cardiovascular diseases associated with the activation of the coagulation cascade in thrombotic or thrombophilic states. As used herein, the terms "treating" or "treatment" encompass responsive or prophylaxis measures, e.g., measures designed to inhibit or delay the onset of the disease, achieve a full or partial reduction of the symptoms or disease state, or to alleviate, lessen, or cure the disease or disorder or its symptoms.

More particularly, the methods of the present invention may be used to treat acute coronary syndromes such as coronary artery disease, myocardial infarction, unstable angina (including crescendo angina), ischemia (e.g., ischemia resulting from vascular occlusion), and cerebral infarction. The methods of the present invention further may be useful in treating stroke and related cerebral vascular diseases (including cerebrovascular accident, vascular dementia, and transient ischemic attack); venous thrombosis and thrombo-embolism, such as deep vein thrombosis (DVT) and pulmonary embolism; thrombosis associated with atrial fibrillation, ventricular enlargement, dilated cardiac myopathy, or heart failure; peripheral arterial disease and intermittent claudication; the formation of atherosclerotic plaques and transplant atherosclerosis; restenosis following arterial injury induced endogenously (by rupture of an atherosclerotic plaque), or exogenously (by invasive cardiological procedures such as vessel wall injury resulting from angioplasty); disseminated intravascular coagulopathy, Kasabach-Merritt syndrome, cerebral thrombosis, and cerebral embolism.

Additionally, the methods of the present invention may be useful in treating thrombo-embolic consequences or complications associated with cancer; surgery (such as hip replacement, endarterectomy, introduction of artificial heart valves, vascular grafts, mechanical organs, and implantation or transplantation of organ, tissue or cells); medications (such as tissue plasminogen activator or similar agents and surgical restoration of blood vessel patency) in patients suffering myocardial infarction, stroke, pulmonary embolism and like conditions; medications (such as oral contraceptives, hormone replacement, and heparin, e.g., for treating heparin-induced thrombocytopenia); sepsis (such as sepsis related to disseminated intravascular coagulation); and pregnancy or childbirth. The methods of the present invention may be used to treat thrombosis due to confinement (i.e. immobilization, hospitalization, bed rest, limb immobilization, e.g., with immobilizing casts, etc.).

The methods of the present invention may also be used to maintain blood vessel patency, for example, in patients undergoing transluminal coronary angioplasty, or in connection with vascular surgery such as bypass grafting, arterial reconstruction, atherectomy, vascular grafts, stent patency, and organ, tissue or cell implantation and transplantation. The inventive methods may be used to inhibit blood coagulation in connection with the preparation, storage, fractionation, or use of whole blood. For example, the inventive methods may be used in maintaining whole and fractionated blood in the fluid phase such as required for analytical and biological testing, e.g., for ex vivo platelet and other cell function studies, bioanalytical procedures, and quantitation of blood-containing components, or for maintaining extracorpeal blood circuits, as in dialysis or surgery (e.g., coronary artery bypass surgery).

In addition, the methods of the present invention may be useful in treating and preventing the prothrombotic complications of cancer. The methods may be useful in treating tumor growth, as an adjunct to chemotherapy, for preventing angiogenesis, and for treating cancer, more particularly, cancer of the lung, prostate, colon, breast, ovaries, and bone.

Ischemia

"Ischemia" or an "ischemic event" is a vascular disease generally involving vascular occlusion or a restriction in blood supply to tissues. Ischemia can cause a shortage of oxygen and glucose needed for cellular metabolism. Ischemia is generally caused by problematic blood vessels that result in damage or dysfunction of tissue. Ischemia can also refer to a local loss in blood or oxygen in a given part of the body resulting from congestion (e.g., vasoconstriction, thrombosis, or embolism). Causes include embolism, thrombosis of an atherosclerosis artery, trauma, venous problems, aneurysm, heart conditions (e.g., myocardial infarction, mitral valve disease, chronic arterial fibrillation, cardiomyopathies, and prosthesis), trauma or traumatic injury (e.g., to an extremity producing partial or total vessel occlusion), thoracic outlet syndrome, atherosclerosis, hypoglycemia, tachycardia, hypotension, outside compression of a blood vessel (e.g., by a tumor), sickle cell disease, localized extreme cold (e.g., by frostbite), tourniquet application, glutamate receptor stimulation, arteriovenous malformations, rupture of significant blood vessels supplying a tissue or organ, and anemia.

A transient ischemic event generally refers to a transient (e.g., short-lived) episode of neurologic dysfunction caused by loss of blood flow (e.g., in the focal brain, spinal cord, or retinal) without acute infarction (e.g., tissue death). In some embodiments, the transient ischemic event lasts for less than 72 hours, 48 hours, 24 hours, 12 hours, 10 hours, 8 hours, 4 hours, 2 hours, 1 hour, 45 minutes, 30 minutes, 20 minutes, 15 minutes, 10 minutes, 5 minutes, 4 minutes, 3 minutes, 2 minutes, or 1 minute.

Angioedema

Angioedema is the rapid swelling of the dermis, subcutaneous tissue, mucosa, and submucosal tissues. Angioedema is typically classified as either hereditary or acquired.

"Acquired angioedema" can be immunologic, non-immunologic, or idiopathic; caused by e.g., allergy, as a side effect of medications, e.g., ACE inhibitor medications.

"Hereditary angioedema" or "HAE" refers to a genetic disorder that results in acute periods of edema (e.g., swelling) that may occur in nearly all parts of the body, including the face, limbs, neck, throat, larynx, extremities, gastrointestinal tract, and genitalia. Attacks of HAE can often be life-threatening, with severity depending on the area affected, e.g., abdominal attacks may result in intenstinal obstruction, while swelling of the larynx and upper airway can lead to asphyxiation. Pathogenesis of hereditary angioedema may be related to unopposed activation of the contact pathway by the initial generation of kallikrein or clotting factors (e.g., Factor XII).

Signs and symptoms include swelling, e.g., of the skill of the face, mucosa of the mouth or throat, and tongue. Itchiness, pain, decreased sensation in the affected areas, urticaria (i.e., hives), or stridor of the airway may also be a sign of angioedema. However, there can be no associated itch, or urticaria, e.g., in hereditary angioedema. HAE subjects can experience abdominal pain (e.g., abdominal pain lasting one to five days, abdominal attacks increasing a subject's white blood cell count), vomiting, weakness, watery diarrhea, or rash.

Bradykinin plays an important role in angioedema, particularly hereditary angioedema. Bradykinin is released by various cell types in response to numerous different stimuli and is a pain mediator. Interfering with bradykinin production or degradation can lead to angioedema. In hereditary angioedema, continuous production of enzyme kallikrein can facilitate bradykinin formation. Inhibition of kallikrein can interfere with bradykinin production; and treat or prevent angioedema.

Pharmaceutical Compositions

The compositions described herein include the compound described herein (e.g., a compound of formula (I)-(VII), e.g., a compound of formula (I), (II), (III), (IV), (V), (VI), or (VII)), as well as additional therapeutic agents, if present, in amounts effective for achieving the treatment of a disease or disease symptoms (e.g., such as a disease associated with Factor XIa or kallikrein).

Pharmaceutically acceptable carriers, adjuvants and vehicles that may be used in the pharmaceutical compositions provided herewith include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

Routes of Administration

The pharmaceutical compositions provided herewith may be administered orally, rectally, or parenterally (e.g., intravenous infusion, intravenous bolus injection, inhalation, implantation).

The term parenteral as used herein includes subcutaneous, intracutaneous, intravenous (e.g., intravenous infusion, intravenous bolus injection), intranasal, inhalation, pulmonary, transdermal, intramuscular, intraarticular, intraarterial, intrasynovial, intrasternal, intrathecal, intralesional and intracranial injection or other infusion techniques. The pharmaceutical compositions provided herewith may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The pharmaceutical compositions may be in the form of a sterile injectable preparation, for example, as a sterile injectable aqueous or oleaginous solution or suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans or other similar emulsifying agents or bioavailability enhancers which are commonly used in the manufacture of pharmaceutically acceptable solid, liquid, or other dosage forms may also be used for the purposes of formulation.

The pharmaceutical compositions provided herewith may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient may be suspended or dissolved in an oily phase is combined with emulsifying or suspending agents. If desired, certain sweetening or flavoring or coloring or taste masking agents may be added.

The compounds described herein can, for example, be administered by injection, intravenously (e.g., intravenous infusion, intravenous bolus injection), intraarterially, subdermally, intraperitoneally, intramuscularly, or subcutaneously; or orally, buccally, nasally, transmucosally, topically with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions provided herewith will be administered from about 1 to about 6 times per day (e.g., by intravenous bolus injection) or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Combinations

In carrying out the methods of the present invention, it may be desired to administer the compounds of the invention (Factor XIa or kallikrein inhibitors) in combination with each other and one or more other agents for achieving a therapeutic benefit such as antithrombotic or anticoagulant agents, anti-hypertensive agents, anti-ischemic agents, anti-arrhythmic agents, platelet function inhibitors, and so forth. For example, the methods of the present invention may be carried out by administering the small molecule Factor XIa or kallikrein inhibitors in combination with a small molecule Factor XIa or kallikrein inhibitor. More particularly, the inventive methods may be carried out by administering the small molecule Factor XIa or kallikrein inhibitors in combination with aspirin, clopidogrel, ticlopidine or CS-747, warfarin, low molecular weight heparins (such as LOVENOX), GPIIb/GPIIIa blockers, PAI-1 inhibitors such as XR-330 and T-686, P2Y1 and P2Y12 receptor antagonists; thromboxane receptor antagonists (such as ifetroban), prostacyclin mimetics, thromboxane A synthetase inhibitors (such as picotamide), serotonin-2-receptor antagonists (such as ketanserin); compounds that inhibit other coagulation factors such as FVII, FVIII, FIX, FX, prothrombin, TAFI, and fibrinogen, or other compounds that inhibit FXI or kallikrein; fibrinolytics such as TPA, streptokinase, PAI-1 inhibitors, and inhibitors of α-2-antiplasmin such as anti-α-2-antiplasmin antibody fibrinogen receptor antagonists, inhibitors of α-1-antitrypsin, hypolipidemic agents, such as HMG-CoA reductase inhibitors (e.g., pravastatin, simvastatin, atorvastatin, fluvastatin, cerivastatin, AZ4522, and itavastatin), and microsomal triglyceride transport protein inhibitors (such as disclosed in U.S. Pat. Nos. 5,739,135, 5,712,279 and 5,760,246); antihypertensive agents such as angiotensin-converting enzyme inhibitors (e.g., captopril, lisinopril or fosinopril); angiotensin-II receptor antagonists (e.g., irbesartan, losartan or valsartan); ACE/NEP inhibitors (e.g., omapatrilat and gemopatrilat); or β-blockers (such as propranolol, nadolol and carvedilol). The inventive methods may be carried out by administering the small molecule Factor XIa or kallikrein inhibitors in combination with anti-arrhythmic agents such as for atrial fibrillation, for example, amiodarone or dofetilide.

In carrying out the methods of the present invention, it may be desired to administer the compounds of the invention (Factor XIa or kallikrein inhibitors) in combination with agents that increase the levels of cAMP or cGMP in cells for a therapeutic benefit. For example, the compounds of the invention may have advantageous effects when used in combination with phosphodiesterase inhibitors, including PDE1 inhibitors (such as those described in Journal of Medicinal Chemistry, Vol. 40, pp. 2196-2210 [1997]), PDE2 inhibitors, PDE3 inhibitors (such as revizinone, pimobendan, or olprinone), PDE4 inhibitors (such as rolipram, cilomilast, or piclamilast), PDE7 inhibitors, or other PDE inhibitors such as dipyridamole, cilostazol, sildenafil, denbutyline, theophylline (1,2-dimethylxanthine), ARIFLOT™ (i.e., cis-4-cyano-4-[3-(cyclopentylox-y)-4-methoxyphenyl] cyclohexane-1-carboxyl-ic acid), arofyline, roflumilast, C-11294A, CDC-801, BAY-19-8004, cipamfylline, SCH351591, YM-976, PD-189659, mesiopram, pumafentrine, CDC-998, IC-485, and KW-4490.

The inventive methods may be carried out by administering the compounds of the invention in combination with prothrombolytic agents, such as tissue plasminogen activator (natural or recombinant), streptokinase, reteplase, activase, lanoteplase, urokinase, prourokinase, anisolated streptokinase plasminogen activator complex (ASPAC), animal salivary gland plasminogen activators, and the like.

The inventive methods may be carried out by administering the compounds of the invention in combination with β-adrenergic agonists such as albuterol, terbutaline, formoterol, salmeterol, bitolterol, pilbuterol, or fenoterol; anticholinergics such as ipratropium bromide; anti-inflammatory cortiocosteroids such as beclomethasone, triamcinolone, budesonide, fluticasone, flunisolide or dexamethasone; and anti-inflammatory agents such as cromolyn, nedocromil, theophylline, zileuton, zafirlukast, monteleukast and pranleukast.

Small molecule Factor XIa or kallikrein inhibitors may act synergistically with one or more of the above agents. Thus, reduced doses of thrombolytic agent(s) may be used, therefore obtaining the benefits of administering these compounds while minimizing potential hemorrhagic and other side effects.

Course of Treatment

The compositions described herein include a therapeutically effective amount of a compound of the invention (e.g., a Factor XIa or kallikrein inhibitor) in combination and one or more other agents (e.g., an additional therapeutic agent) such as antithrombotic or anticoagulant agents, anti-hypertensive agents, anti-ischemic agents, anti-arrhythmic agents, platelet function inhibitors, and so forth for achieving a therapeutic benefit.

In some embodiments, the additional therapeutic agent is administered following administration of the compound of the invention (e.g., a Factor XIa or kallikrein inhibitor). In some embodiments, the additional therapeutic agent is administered 15 minutes, 30 minutes, 1 hour, 2 hours, 4 hours, 6 hours, 8 hours, 10 hours, 12 hours, 14 hours, 18 hours, 24 hours, 48 hours, 72 hours or longer after administration of the compound of the invention (e.g., a Factor XIa or kallikrein inhibitor). In some embodiments, the additional therapeutic agent is administered (e.g., orally) after discharge from a medical facility (e.g., a hospital).

In some embodiments, the compound of the invention (e.g., a Factor XIa or kallikrein inhibitor) and additional therapeutic agent are co-formulated into a single composition or dosage.

In some embodiments, the compound of the invention (e.g., a Factor XIa or kallikrein inhibitor) and additional therapeutic agent are administered separately. In some embodiments, the compound of the invention (e.g., a Factor XIa or kallikrein inhibitor) and additional therapeutic agent are administered sequentially. In some embodiments, the compound of the invention (e.g., a Factor XIa or kallikrein inhibitor) and additional therapeutic agent are administered separately and sequentially. In general, at least one of the compound of the invention (e.g., a Factor XIa or kallikrein inhibitor) and additional therapeutic agent is administered parenterally (e.g., intranasally, intramuscularly buccally, inhalation, implantation, transdermal, intravenously (e.g., intravenous infusion, intravenous bolus injection), subcutaneous, intracutaneous, intranasal, pulmonary, transdermal, intraarticular, intraarterial, intrasynovial, intrasternal, intrathecal, intralesional and intracranial injection or other infusion techniques); orally; or rectally, for example, intramuscular injection or intravenously (e.g., intravenous infusion, intravenous bolus injection)). In some embodiments, compound of the invention is administered parenterally (e.g., intranasally, buccally, intravenously (e.g., intravenous infusion, intravenous bolus injection) or intramuscularly). In some embodiments, additional therapeutic agent is administered orally. In some embodiments, the compound of the invention (e.g., a Factor XIa or kallikrein inhibitor) is administered parenterally (e.g., intranasally, buccally, intravenously (e.g., intravenous infusion, intravenous bolus injection) or intramuscularly) and the additional therapeutic agent is administered orally.

In some embodiments, the compound of the invention (e.g., a Factor XIa or kallikrein inhibitor) may be administered once or several times a day. A duration of treatment may follow, for example, once per day for a period of about 1, 2, 3, 4, 5, 6, 7 days or more. In some embodiments, the treatment is chronic (e.g., for a lifetime). In some embodiments, the treatment is administered orally. In some embodiments, either a single dose in the form of an individual dosage unit or several smaller dosage units or by multiple administrations of subdivided dosages at certain intervals is administered. For instance, a dosage unit can be administered from about 0 hours to about 1 hr, about 1 hr to about 24 hr, about 1 to about 72 hours, about 1 to about 120 hours, or about 24 hours to at least about 120 hours post injury. Alternatively, the dosage unit can be administered from about 0.5, 1, 1.5, 2, 3, 4, 5, 6, 7, 8, 9, 10, 11, 12, 13, 14, 15, 16, 17, 18, 19, 20, 21, 22, 23, 24, 30, 40, 48, 72, 96, 120 hours or longer post injury. Subsequent dosage units can be administered any time following the initial administration such that a therapeutic effect is achieved. In some embodiments, the initial dose is administered orally. In some embodiments, doses subsequent to the initial dose are administered parenterally (e.g., intranasally, intramuscularly buccally, inhalation, implantation, transdermal, intravenously (e.g., intravenous infusion, intravenous bolus injection), subcutaneous, intracutaneous, intranasal, pulmonary, transdermal, intraarticular, intraarterial, intrasynovial, intrasternal, intrathecal, intralesional and intracranial injection or other infusion techniques); orally; or rectally.

Where a subject undergoing therapy exhibits a partial response, or a relapse following completion of the first cycle of the therapy, subsequent courses of therapy may be needed to achieve a partial or complete therapeutic response (e.g., chronic treatment, e.g., for a lifetime).

In some embodiments, the compound of the invention (e.g., a Factor XIa or kallikrein inhibitor) is administered intravenously, e.g., as an intravenous infusion or intravenous bolus injection, for about 5 minutes to about 1 week; about 30 minutes to about 24 hours, about 1 hour to about 12 hours, about 2 hours to about 12 hours, about 4 hours to about 12 hours, about 6 hours to about 12 hours, about 6 hours to about 10 hours; about 5 minutes to about 1 hour, about 5 minutes to about 30 minutes; about 12 hours to about 1 week, about 24 hours to about 1 week, about 2 days to about 5 days, or about 3 days to about 5 days. In one embodiment, the compound of the invention (e.g., a Factor XIa or kallikrein inhibitor) is administered as an intravenous infusion for about 5, 10, 15, 30, 45, or 60 minutes or longer; about 1, 2, 4, 6, 8, 10, 12, 16, or 24 hours or longer; about 1, 2, 3, 4, 5, 6, 7, 8, 9, or 10 days or longer.

Dosages and Dosing Regimens

The effective amount of a small molecule Factor XIa or kallikrein inhibitor administered according to the present invention may be determined by one of ordinary skill in the art. The specific dose level and frequency of dosage for any particular subject may vary and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Upon improvement of a patient's condition, a maintenance dose of a compound, composition or combination provided herewith may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

EXAMPLES

The compounds of the present invention are prepared as described in the Charts, Schemes, Preparation of Intermediates and Examples below, or prepared by methods analogous thereto, which are readily known and available to one of ordinary skill in the art of organic synthesis.

Synthesis of the Compounds of the Invention

Temperatures are given in degrees Celsius (° C.). Unless otherwise stated, operations are carried out at room or ambient temperature, that is, at a temperature in the range of 18-25° C. under an inert atmosphere with the exclusion of moisture. Chromatography means flash chromatography on silica gel as described in Still, W. C, Kahn, M.; Mitra, A. *J. Org. Chem.* 1978, 43, 2923; thin layer chromatography (TLC) is carried out on silica gel plates. NMR data is given in parts per million (ppm) relative to the deuterium lock signal of the deuterated solvent utilized. Conventional abbreviations for signal shape are used. For mass spectra (MS), the lowest mass major ion is reported for molecules where isotope splitting results in multiple mass spectral peaks. Solvent mixture compositions are given as volume percentages or volume ratios. In cases where the NMR spectra are complex, only diagnostic signals are reported.

Analytical HPLC

Method A: Agilent 1100 HPLC, Zorbax Eclipse XDB-C18 50×4.6 mm column, 1.5 mL/min, Solvent A-Water (0.1% TFA), Solvent B-Acetonitrile (0.07% TFA), Gradient −5 min 95% A to 90% B; 1 min. hold; then recycle (to 95% A over 1 min), UV Detection @ 214 and 254 nm.

Method B: Agilent 1100 HPLC, Zorbax Eclipse XDB-C18 50×4.6 mm column, 1.5 mL/min, Solvent A-Water (0.1% TFA), Solvent B-Acetonitrile (0.07% TFA), Gradient −5 min 95% A to 90% B; 1 min. hold; then recycle (to 95% A over 1 min), UV Detection @ 210 and 254 nm.

Method C: Agilent 1100 HPLC, Zorbax Eclipse XDB-C18 50×4.6 mm column, 1.5 mL/min, Solvent A-Water (0.1% TFA), Solvent B-Acetonitrile (0.07% TFA), Gradient −6 min 95% A to 95% B; 1 min. hold; then recycle (to 95% A over 1 min), UV Detection @ 210 and 254 nm.

TERMS AND ABBREVIATIONS

ACN=acetonitrile,
BOC=Boc=tert-butoxycarbonyl,
br=broad,
t-BuOH=tert-butyl alcohol,
Cat.=catalytic,
Conc.=concentrated,
d=doublet,
dd=doublet of doublets,
ddd=doublet of doublet of doublets,
dt=doublet of triplets,
DCM=dichloromethane,
Dess-Martin periodinane=1,1,1-Tris(acetyloxy) 1,1-dihydro-1,2-benziodoxol-3(1H)-one,
DIAD=diisopropyl azodicarboxylate,
DMF=N,N-dimethylforamide,
DMSO=dimethyl sulfoxide,
$Et_2O$=diethyl ether,
$Et_3N$=triethylamine,
EtOAc=ethyl acetate,
EtOH=ethyl alcohol,
equiv.=equivalent(s),
h=hour(s),
$H_2O$=water,
HCl=hydrochloric acid
HPLC=high performance liquid chromatography,
HOAc=acetic acid,
IPA=isopropyl alcohol,
ISCO=normal phase silica gel cartridges supplied by Teledyne ISCO,
$K_2CO_3$=potassium carbonate,
$LiBH_4$=lithium tetrahydroborate,
LiBr=lithium bromide,
LiCl=lithium chloride,
LAH=lithium tetrahydroaluminate,
m=multiplet,
min.=min=minute(s)
$MgCl_2$=magnesium chloride
MeOH=methanol,
MsCl=methanesulfonyl chloride,
MTBE=methyl tert-butyl ether,
$NaHCO_3$=sodium bicarbonate,
$Na_2SO_4$=sodium sulfate,
$NH_4OH$=ammonium hydroxide,
$NH_4OAc$=ammonium acetate,
$NH_4Cl$=ammonium chloride,
NMR=nuclear magnetic resonance,
NMP=N-methylpyrrolidinone,
Pd—C=palladium on activated carbon
p=pentet,
PMB=p-methoxybenzyl,
PMBCl=p-methoxybenzyl chloride,
ret=retention
rt=room temperature,
s=singlet,
sat=saturated,
t=triplet,
TFA=trifluoroacetic acid,
TBDPS=t-butyldiphenylsilyl,
TBS=t-butyldimethylsilyl,
THF=tetrahydrofuran,
THP=tetrahydropyran,
TLC=thin layer chromatography Example 1. General Synthetic Schemes and Methods In general, in the instances when the compound of the invention contains a basic substituent (e.g., an amino group, pyridyl), an acidic substitutent (e.g., a carboxylic acid), or is zwitterionic (i.e., containing both a basic substituent and an acidic substituent), for ease of isolation and handling, it is preferred to isolate the compound as a salt. This salt form facilitates characterization and is used directly in biological assays.

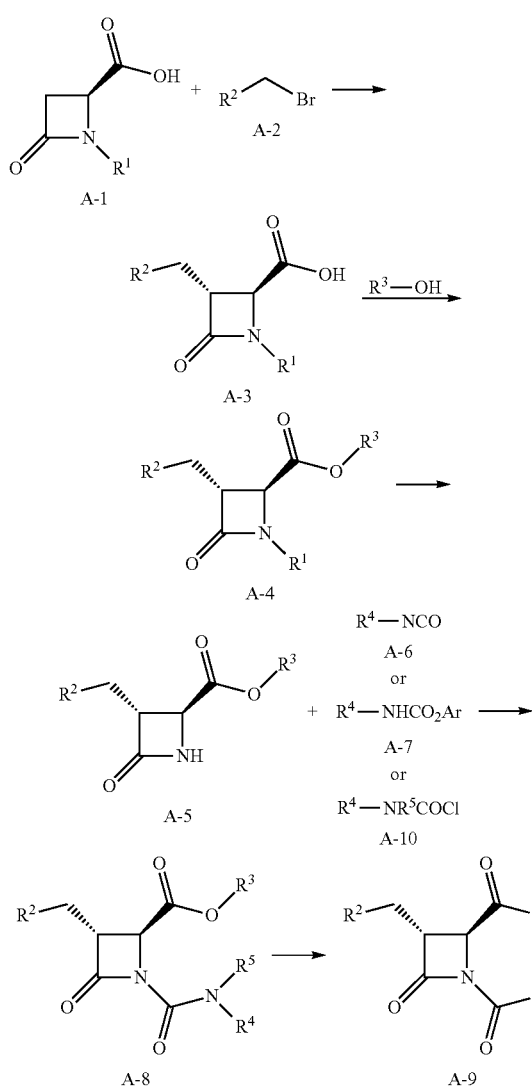

Scheme 1.
Synthesis of compounds of Structures A-8 and A-9 as shown on Chart A.

Scheme 1 describes a general method for the preparation of (2S,3R)-trans-disubstituted 4-oxoazetidine-2-carboxylates of general structure A-8 and A-9. Alkylation of the dianion of N-protected azetidinone A-1 (for example, $R^1$=TBS) with a commercially available or readily prepared alkyl halide of general structure A-2 affords the desired intermediate as predominately the trans product and with retention of the stereochemistry at the 2-position (Baldwin, J. E., et al., Tetrahedron, 1990 46, 4733). For aminopyridine containing compounds, the bromide described in the preparation of Intermediate 1 is preferred as alkylating agent. Further, the synthetic sequence described for the preparation of Intermediate 1 is of general utility for the preparation of a number of requisite bromides of general structure A-2 from commercially available esters and alcohols. Esterification of the carboxylic acid under standard condensation conditions affords intermediate A-4 which is readily purified by normal phase chromatography. For the temporary protection of the carboxylic acid, the benzyl and 4-methoxybenzyl esters are particularly useful. Removal of the N-protecting group of the beta lactam affords the intermediate A-5 which is readily acylated with a commercially available or readily prepared isocyanate A-6 (for example, Tsai, M. H., Takaoka, L. R., Powell, N. A., Nowick, J. S. *Org. Syn.* 2002, 78, 220) to afford the beta lactam intermediate A-8. Intermediate A-5 can also be converted to A-8 by its reaction with a number of other reagents known to react with amines to afford ureas such as phenyl carbamates (A-7 where Ar=phenyl, for example: Thavonekham, B. *Synthesis,* 1997, 1189) and 4-nitrophenyl carbamates (A-7 where Ar is 4-nitrophenyl, for example: Hutchins, S. M., Chapman, K. T. *Tet. Lett.* 1994, 35, 4055). Additionally, reaction of A-5 with a carbamoyl chloride (A-10 where $R^5$=Me, for example: Holmes, D. L., Smith, E. M., Nowick, J. S. *J. Am. Chem. Soc.* 1997, 119(33), 7665) affords tetra-substituted ureas A-8 ($R^5$=Me). Commercially available or readily prepared amines, $R^4$—$NH_2$, (for a recent review on the asymmetric synthesis of amines of particular interest see, Robak, M. T., Herbage, M. A., Ellman, J. A. *Chem. Rev.* 2010, 110, 3600) serve as suitable starting materials for the preparation of isocyanates, A-6 and carbamates, A-7. Removal of the temporary protecting group of the carboxylate (either by hydrogenation in the cases where $R^3$ is benzyl or via acidolysis with TFA when $R^3$ is 4-methoxybenzyl) and removal of any other protecting groups present in the molecule affords the examples of general structure A-9. In those examples where the ester $CO_2R^3$ is retained, removal of any other protecting groups present in the molecules affords examples of general structure A-8. For some structures A-9, the carboxylic acid can also be esterified using methods known to one skilled in the art to afford additional examples of general structure A-8. Exemplary compounds of the present invention synthesized according to the route described in Scheme 1 are summarized in Chart A (FIGS. 1A-1M).

Scheme 2.
Synthesis of compounds of Structure B-5 as shown on Chart B.

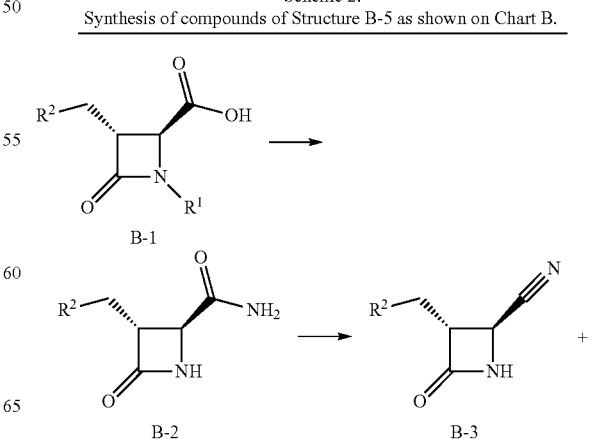

187
-continued

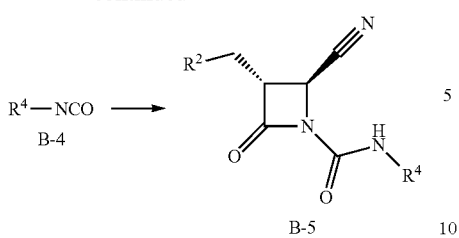

Scheme 2 describes a general method for the preparation of 2,3-disubstituted 4-oxoazetidines containing a 2-cyano group. Conversion of the carboxylic acid in intermediate B-1 (prepared as described for intermediate A-3 in Scheme 1) to the carboxamide (for example by the action of di-tert-butyldicarbonate and ammonium bicarbonate in the presence of pyridine as described by Pozdnev, V., *Tet. Lett.*, 1995, 36, 7115) affords intermediate B-2 with concomitant removal of the silyl protecting group at N-1. Dehydration of the aliphatic amide provides the nitrile intermediate B-3 (for a general review, see Mowry, D., *Chem. Rev.* 1948, 42, 189). Reaction with an isocyanate B-4 and, if necessary, removal of any protecting groups remaining affords examples of the general formula B-5. Exemplary compounds of the present invention synthesized according to the route described in Scheme 2 are summarized in Chart B (FIG. 2).

Scheme 3.
Synthesis of compounds of Structure C-8 as shown on Chart C and D.

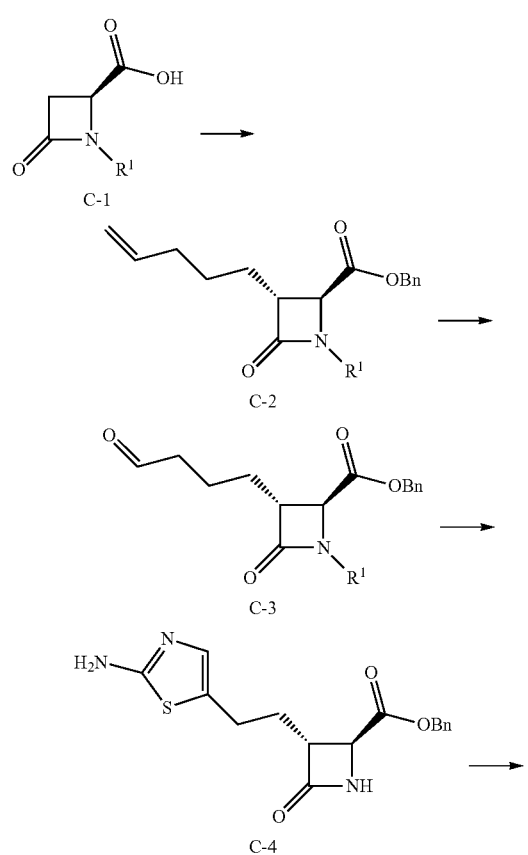

188
-continued

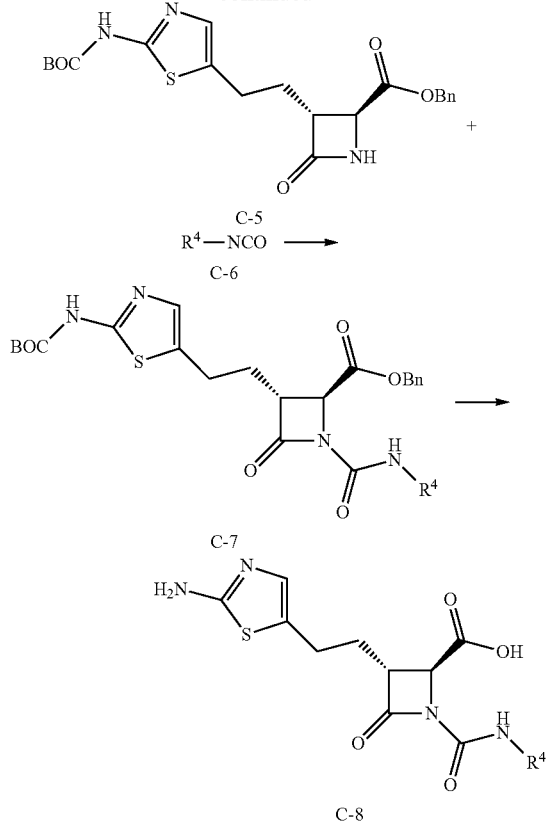

Scheme 3 describes the synthesis of 3-[2-(2-amino-1,3-thiazol-5-yl)ethyl]azetidine-2-ones of general structure C-8. Oxidation of alkene C-2 (readily prepared by the methods described in Scheme 1) affords aldehyde C-3 which is treated successively with tetrabutylammonium bromide followed by thiourea to afford the aminothiazole intermediate C-4 with concomitant removal of the protecting group at N-1. Protection of the aminothiazole with a suitable protecting group such as BOC affords intermediate C-5. Reaction with an isocyanate C-6 followed by removal of any protecting groups affords examples of the general formula C-8. Exemplary compounds of the present invention synthesized according to the route described in Scheme 3 are summarized in Chart C and D (FIG. 3).

Scheme 4. Synthesis of compounds of Structure D-8 as shown on Chart C and D.

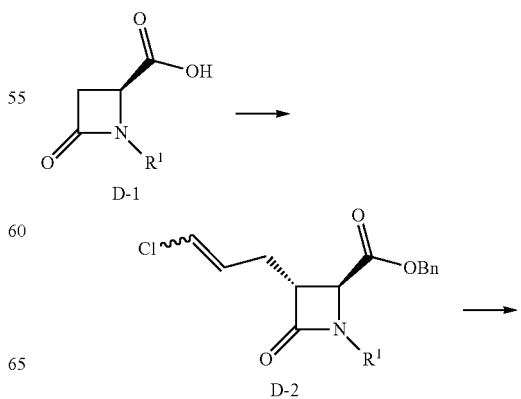

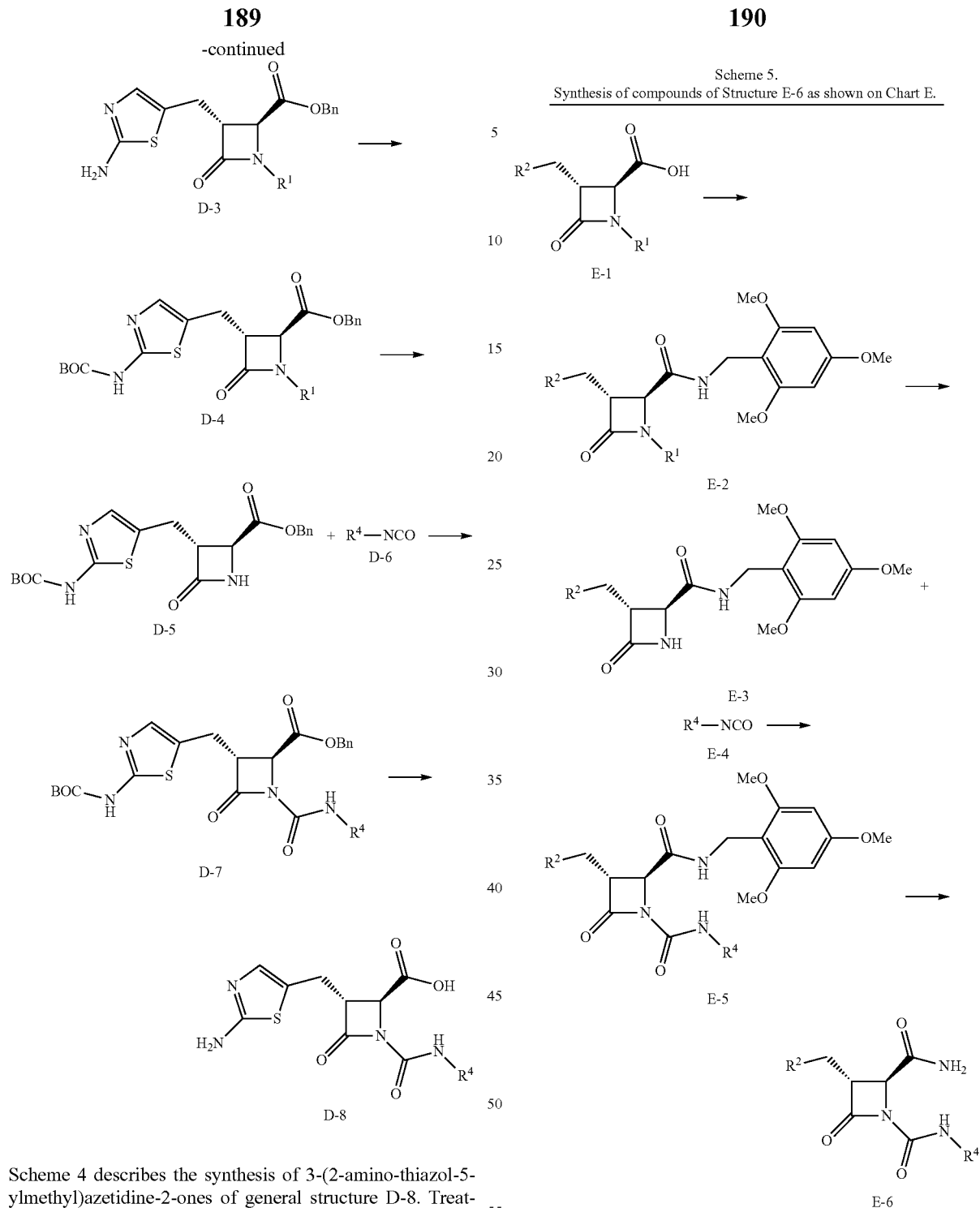

Scheme 4 describes the synthesis of 3-(2-amino-thiazol-5-ylmethyl)azetidine-2-ones of general structure D-8. Treatment of vinyl halide D-2 (readily prepared by the methods described in Scheme 1) with MCPBA followed by condensation of the intermediate chloro epoxide with thiourea affords the aminothiazole intermediate D-3. Protection of the aminothiazole with a suitable group such as BOC affords intermediate D-4. Deprotection of the beta lactam nitrogen and reaction with an isocyanate D-6 affords intermediate D-7. Removal of any remaining protecting groups affords examples of the general formula D-8. Exemplary compounds of the present invention synthesized according to the route described in Scheme 4 are summarized in Charts C and D (FIG. 3).

Scheme 5 describes a general method for the preparation of 2-carboxamides of general structure E-6. Condensation of acid E-1 (prepared as described for A-3 of Scheme 1) affords amide E-2. Removal of the N-1 protecting group followed by condensation of isocyanate E-4 affords intermediate E-5. Removal of the amide protecting group and any other protecting groups present in the molecule affords examples of general formula E-6. Exemplary compounds of the present invention synthesized according to the route described in Scheme 5 are summarized in Chart E (FIG. 4).

Scheme 6.
Synthesis of compounds of Structure F-8 as shown on Chart F.

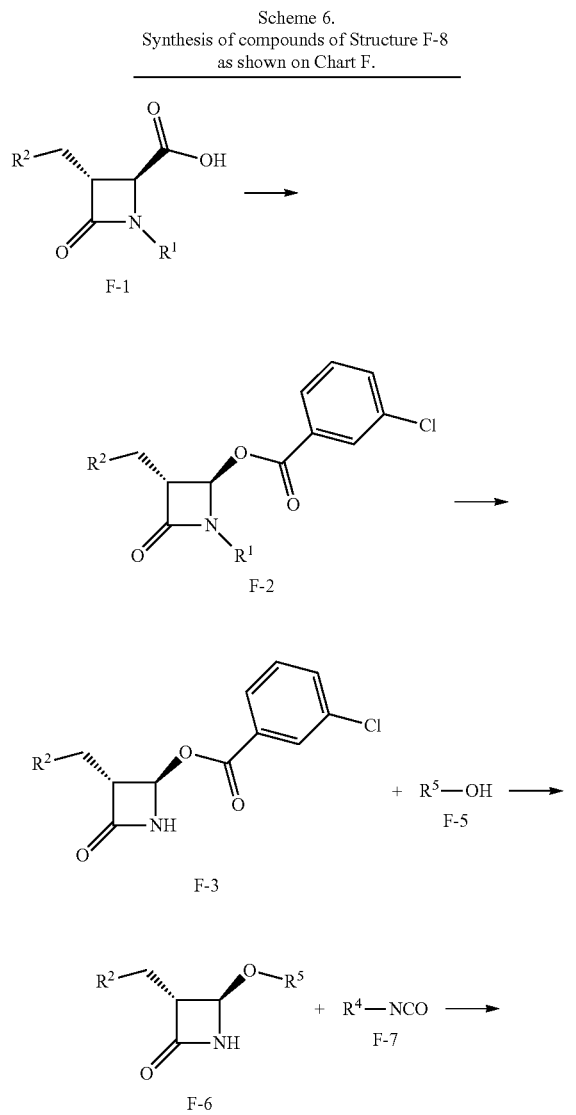

Scheme 7.
Synthesis of compounds of Structure G-4 as shown on Chart G.

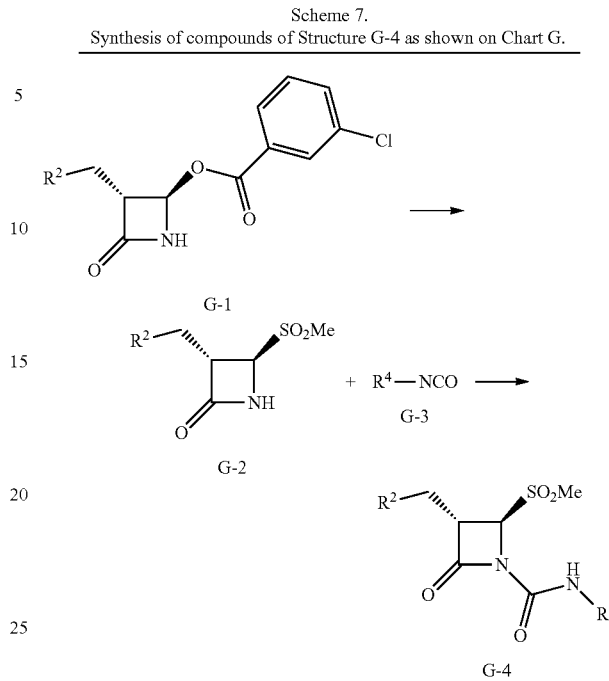

Scheme 7 describes the synthesis of sulfones of general formula G-4. Reaction of benzoate G-1 (prepared as described for F-3, Scheme 6) with sodium methanesulfinate affords the sulfone G-2 (Clauss, K., et. al. Liebigs Ann. Chem. 1974, 539). Reaction with an isocyanate G-3 and subsequent removal of any protecting groups present in the molecule affords examples of general formula G-4. Exemplary compounds of the present invention synthesized according to the route described in Scheme 7 are summarized in Chart G (FIG. 6).

Scheme 8.
Synthesis of compounds of Structure H-9 as shown on Chart H.

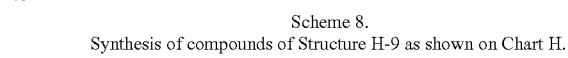

Scheme 6 describes the synthesis of (2R,3R)-trans-disubstituted ethers of the general formula F-8. Oxidative decarboxylation of F-1 (prepared as described for A-3 of Scheme 1) affords the benzoate F-2 (for example, see Shiozaki, M., *Synthesis,* 1990, 691). Removal of the N-1 protecting group followed by displacement of the benzoate with an oxygen nucleophile, F-5, affords ether F-6. Reaction with an isocyanate F-7 and removal of any protecting groups present in the molecule affords examples of general formula F-8. Exemplary compounds of the present invention synthesized according to the route described in Scheme 6 are summarized in Chart F (FIG. 5).

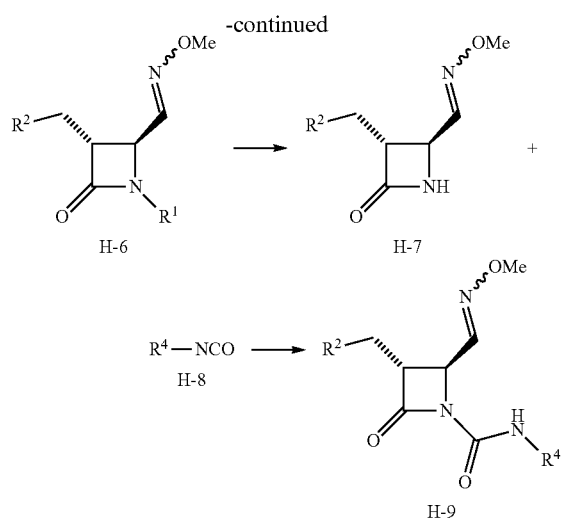

Scheme 8 describes a general method for the preparation of oximes of general structure H-9.

Reduction of N-protected azetidinone H-1 (for example, $R^1$=TBDPS) affords the hydroxymethyl intermediate H-2 which is readily oxidized to the aldehyde H-3. Condensation with methoxyamine affords the oxime H-4 as a mixture of geometric isomers. Alkylation of the anion of oxime H-4 with a commercially available or readily prepared alkyl halide of general structure H-5 affords the 2,3-trans product H-6. Removal of the N-protecting group of the beta lactam affords the intermediate H-7. Reaction with an isocyanate H-8 and removal of any protecting groups present in the molecule affords examples of general formula H-9. Exemplary compounds of the present invention synthesized according to the route described in Scheme 8 are summarized in Chart H (FIG. 7).

Scheme 9. Synthesis of compounds of Structures I-4 through I-7 as shown on Chart I.

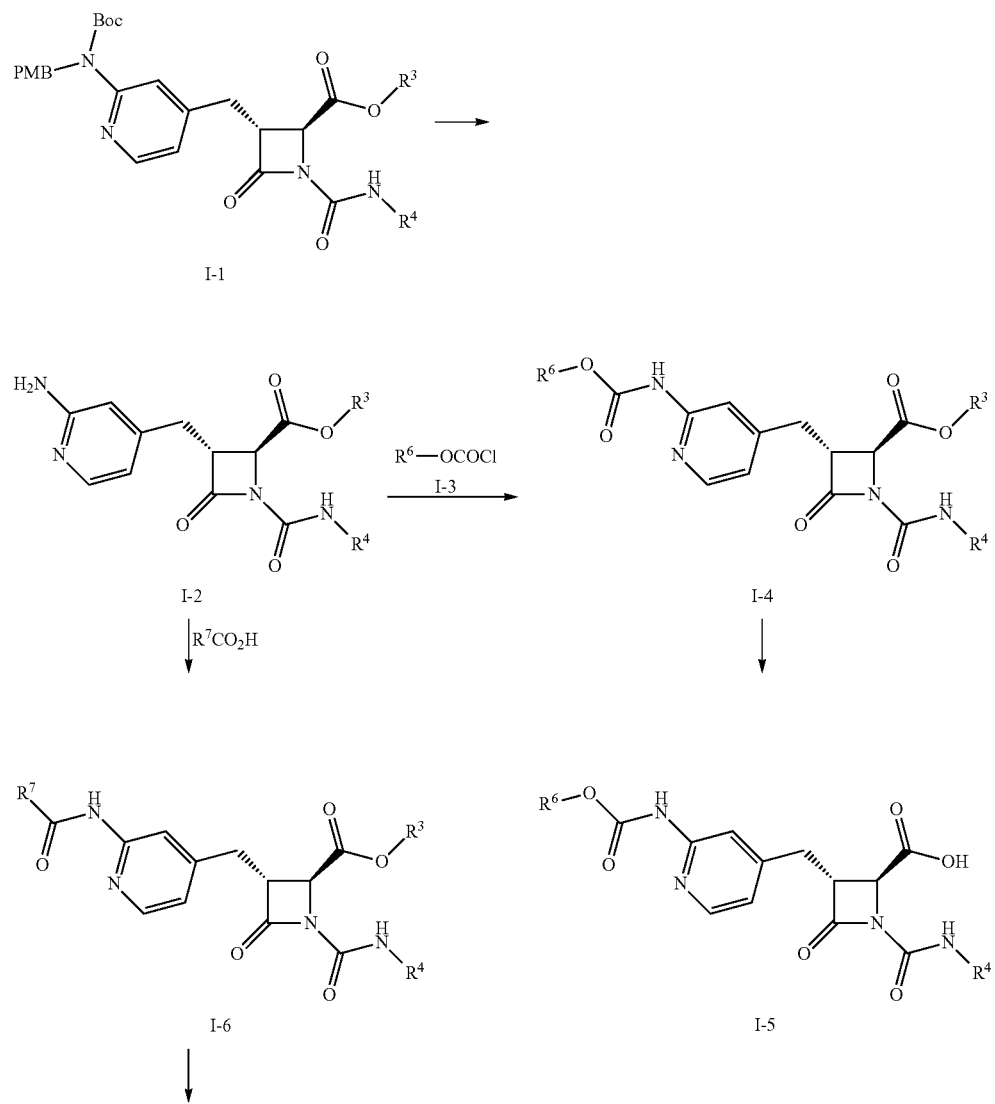

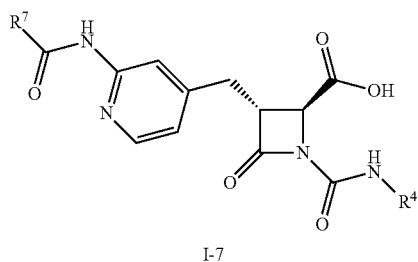

I-7

Scheme 9 describes a general method for the preparation of examples of general structure I-4 through I-7. Removal of the Boc and PMB protecting groups of I-1 (prepared as described for A-8, Scheme 1) affords the aminopyridine I-2. Reaction with a chloroformate or other suitable carbonic acid derivative affords carbamate of general structure I-4. Removal of the carboxylic acid group, if desired, affords compounds of general structure I-5. Further, reaction of I-2 with a carboxylic acid $R^7CO_2H$ in the presence of a suitable condensation agent affords compounds of general structure I-6. Removal of the carboxylic acid protecting group and condensing with a different alcohol $R^3OH$ in the presence of a suitable condensing agent allows for the interconversion of the $R^3$ group of I-6. In those cases where the free carboxylic acid is desired, removal of the carboxylic acid protecting group and any other protecting groups present in the molecule affords compounds of general structure I-7. Exemplary compounds of the present invention synthesized according to the route described in Scheme 9 are summarized in Chart I (FIG. 8).

Scheme 10.
Synthesis of compounds of Structures J-3 and J-4 as shown on Chart J.

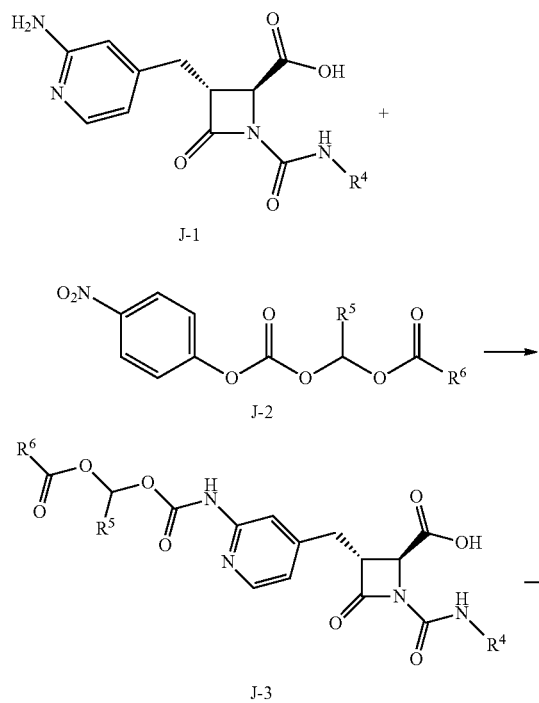

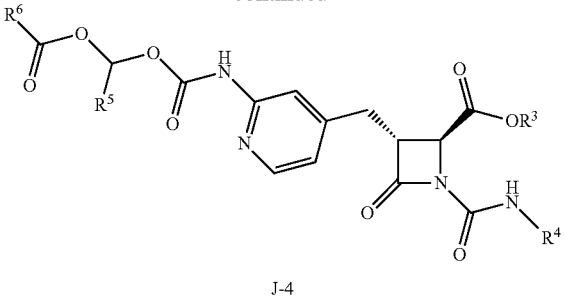

J-4

Scheme 10 describes a general method for the preparation of examples of general structure J-3 and J-4. Transient silylation of compounds of general structure J-1 (prepared as described in Scheme 1) followed by reaction with nitrophenyl carbonate J-2 ($R^5$=H or Me) affords the compound of general structure J-3. Reaction of J-3 with an alcohol ($R^3$—OH) in the presence of a suitable condensing agent or a bromide ($R^3$—Br) in the presence of a suitable base provides esters of general structure J-4. Exemplary compounds of the present invention synthesized according to the route described in Scheme 10 are summarized in Chart J (FIGS. 9A-9B).

Scheme 11.
Synthesis of compounds of Structure K-9 as shown on Chart K.

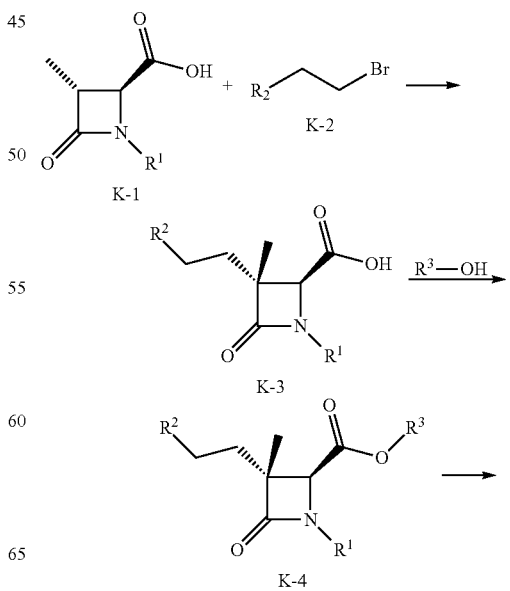

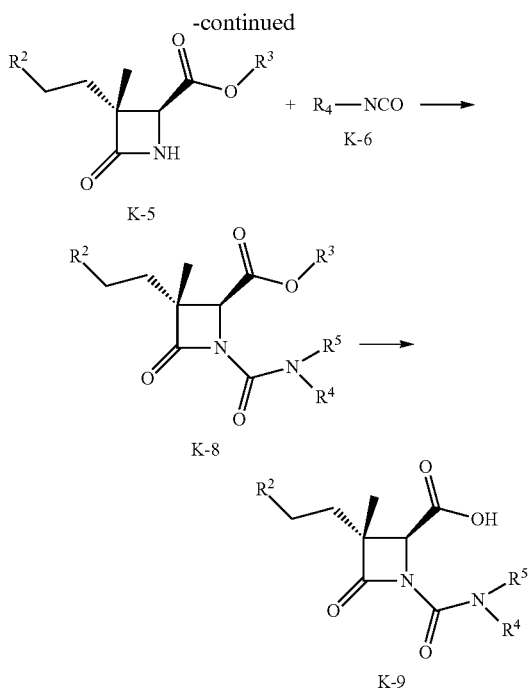

Figure 10B:
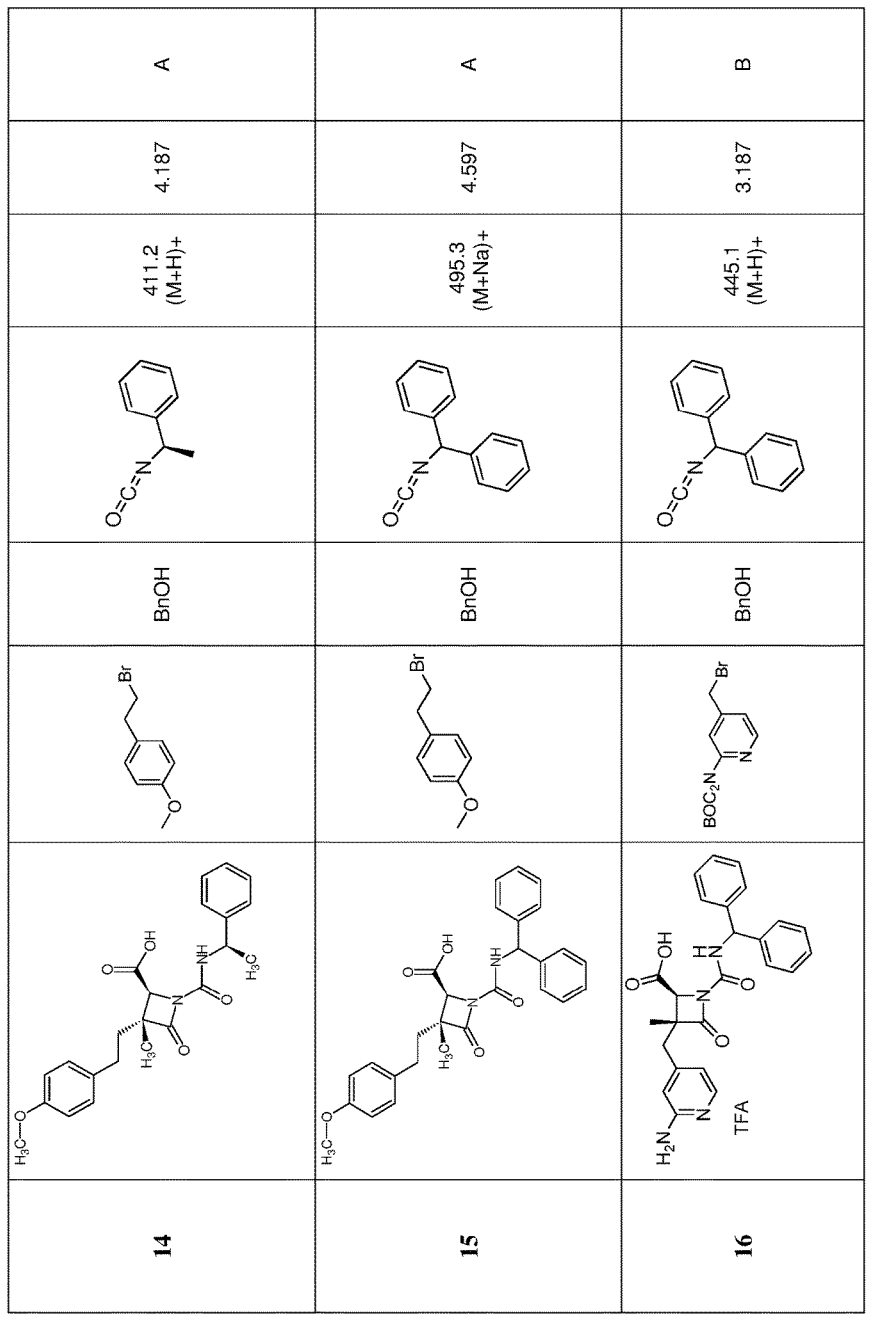

Scheme 11 describes a general method for the preparation of (2S,3R)-trisubstituted 4-oxoazetidine-2-carboxylates of general structure K-9. The chemistry is completely analogous to the method described in Scheme 1 in which the starting material utilized is the known lactam K-1 (see Finke, P. E., et. al., J. Med. Chem. 1995, 38, 2449). Exemplary compounds of the present invention synthesized according to the route described in Scheme 11 are summarized in Chart K (FIGS. 10A-10B).

Example 2. Preparation of Intermediates

Intermediate 1: tert-Butyl [4-(bromomethyl)pyridin-2-yl](4-methoxybenzyl)carbamate

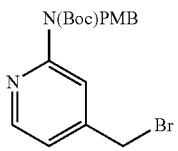

Step 1. Preparation of Methyl 2-[(tert-butoxycarbonyl)amino]isonicotinate

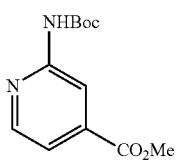

A solution of di-tert-butyldicarbonate (47.8 g, 219 mmol) in t-BuOH (650 mL, 6.80 mol) was warmed at 33° C. and treated with methyl 2-aminoisonicotinate (30.4 g, 200 mmol) in portions over 1 h [~5 g added every 10 min]. The reaction mixture was stirred at 33° C. overnight (18 h); HPLC/LC MS indicated nearly complete conversion. The solids were collected by vacuum filtration [course frit sintered glass funnel] and washed with Et$_2$O (~200 mL). The light tan solid was dried on high vac for 3.5 h until constant weight was achieved (39.65 g, 79%): MS (ESI+) for C$_{12}$H$_{16}$N$_2$O$_4$ m/z 253.2 [M+H]$^+$, 275.2 [M+Na]$^+$; HPLC retention time: 3.25 min (Method B).

Step 2. Preparation of tert-butyl [4-(hydroxymethyl)pyridin-2-yl](4-methoxybenzyl)carbamate

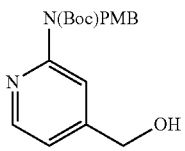

A slurry of methyl 2-[(tert-butoxycarbonyl)amino]isonicotinate (41.5 g, 164 mmol) in DMF (610 mL, 7.90 mol) was cooled to ~0° C. (ice/NaCl) and treated with a 1.0 M solution of NaHMDS in THF (197 mL, 197 mmol) dropwise over 2 h to afford a clear, brown solution. The reaction mixture was stirred for 30 min at 0° C. and treated with PMBCl (24.5 mL, 181 mmol) dropwise over 11 min. The reaction mixture was stirred for 10 min to afford a yellow/brown mixture, the cold bath was removed, and the reaction mixture stirred at rt for 1 h 40 min; HPLC indicated nearly complete conversion. The reaction mixture was cooled to ~0° C. (ice/NaCl) and the reaction was quenched by the addition of saturated aqueous NH$_4$Cl (100 mL). The mixture was allowed to warm to rt and was extracted with Et$_2$O (1×200 mL). The separated aqueous layer was diluted with water (100 mL) and extracted with Et$_2$O (2×100 mL). The combined organics were washed with saturated aqueous NaHCO$_3$ (1×400 mL) and the separated aqueous layer was filtered [course sintered glass] and extracted with Et$_2$O (2×100 mL). The combined organics were washed with 10% aqueous LiCl (2×600 mL), dried (Na$_2$SO$_4$), and concentrated in vacuo to afford an orange oil. The crude material was further dried on high vac overnight to afford a light colored solid/orange oil (80.86 g), which was carried on without further manipulation: MS (ESI+) for C$_{20}$H$_{24}$N$_2$O$_5$ m/z 373.2 [M+H]$^+$; HPLC retention time: 4.53 min (Method B); 1H NMR indicated the material was contaminated with hexamethyldisilazane. The above crude methyl 2-[(tert-butoxycarbonyl)(4-methoxybenzyl)amino]isonicotinate (80.86 g) was divided into two equal portions and each was treated as follows: A solution of crude material in THF (400 mL) was cooled to ~0° C. (ice/NaCl) and treated with LiBH$_4$ (3.94 g, 181 mmol) in one portion. The reaction mixture was stirred for 5 min, the cold bath was removed, and the reaction mixture was allowed to warm to rt with stirring over 30 min. The flask was transferred to a preheated 50° C. oil bath and the reaction mixture was stirred at 40° C. for 2.5 h; HPLC indicated complete conversion. The reaction mixture was cooled to ~0° C. and the reaction was carefully quenched by the slow, dropwise addition of saturated aqueous NaHCO$_3$ (100 mL). The mixture was diluted with water (150 mL) and extracted with EtOAc (1×200 mL, 2×100 mL). The combined organics were washed with saturated aqueous NH$_4$Cl (1×200 mL), water (1×200 mL), and brine (1×200 mL), dried (Na$_2$SO$_4$), and concentrated in vacuo to afford the title compound as a viscous yellow oil (55.6 g, 89%), which was carried on without further manipulation: MS (ESI+) for $C_{19}H_{24}N_2O_4$ m/z 345.3 [M+H]$^+$; HPLC retention time: 3.19 min (Method B).

Step 3. Preparation of tert-Butyl [4-(bromomethyl) pyridin-2-yl](4-methoxybenzyl)carbamate

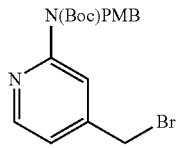

To a stirring solution of tert-butyl [4-(hydroxymethyl) pyridin-2-yl](4-methoxybenzyl)carbamate (23.14 g, 67.19 mmol) in THF (300 mL) cooled in an ice/water bath was added Et$_3$N (13.6 mL, 97.8 mmol). MsCl (7.20 mL, 93.1 mmol) was added slowly over 15 min and the reaction mixture was stirred for 1 h at 0° C.; HPLC indicated nearly complete conversion. LiBr (8.54 g, 98.3 mmol) was added in one portion and the cold bath was removed. The reaction mixture was stirred overnight at rt; HPLC indicated complete conversion to the desired product. The reaction mixture was partitioned between EtOAc (250 mL) and water (250 mL). The separated aqueous phase was extracted with EtOAc (200 mL) and the combined organic phases were washed with water (300 mL), dried (MgSO$_4$), and evaporated in vacuo to afford a viscous orange oil (12.05 g). The crude mixture was adsorbed onto silica and purified by flash column chromatography (500 g silica, packed with hexanes, eluted with 15% EtOAc/hexanes) to afford the title compound as a pale yellow oil (11.59 g, 42%): MS (ESI+) for $C_{19}H_{23}BrN_2O_3$/z 407.1, 409.1 [M+H]$^+$; HPLC ret. time: 4.48 min (Method B); 1H NMR (CDCl$_3$, 300 MHz) δ 8.42-8.30 (m, 1H), 7.73 (br s, 1H), 7.26-7.19 (m, 2H), 7.07-6.9.9 (m, 1H), 6.85-6.77 (m, 2H), 5.14 (s, 2H), 4.38 (s, 2H), 3.78 (s, 3H), 1.44 (s, 9H).

Intermediate 2: 1-[(1R)-1-isocyanatoethyl]-3-(trifluoromethoxy)benzene

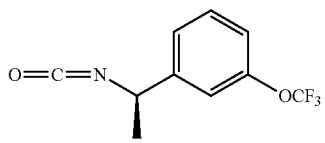 [SMILES: C[C@@H](N=C=O)c1cccc(OC(F)(F)F)c1]

To a cooled (0-5° C.), vigorously stirred solution of (1R)-1-[3-(trifluoromethoxy)phenyl]ethanamine hydrochloride (prepared as described in steps 1 through 3 in Example 4 from 3-trifluoromethoxy-benzaldehyde) (0.197 g, 0.815 mmol) in methylene chloride (4 mL) and sat NaHCO$_3$ (4 ml) was added triphosgene (0.080 g, 0.269 mmol) in one portion. After 30 min, the mixture was transferred to a separatory funnel and the organic layer collected. The aqueous layer was washed with DCM and the combined organic layers were dried with anhydrous sodium sulfate, filtered and concentrated to afford the title compound (155 mg, 82%) as a viscous oil which was used immediately without further purification. $^1$H NMR (300 MHz, CDCl$_3$) δ 1.63 (d, J=7 Hz, 3H), 4.82 (q, J=7 Hz, 1H), 7.16-7.29 (m, 3H), 7.41 (t, J=8 Hz, 1H).

Intermediate 3. 4-methoxybenzyl (2S,3R)-3-({2-[(tert-butoxycarbonyl)(4-methoxybenzyl)amino] pyridin-4-yl}methyl)-4-oxo-1-{[(1S)-2,2,2-trifluoro-1-phenylethyl]carbamoyl}azetidine-2-carboxylate

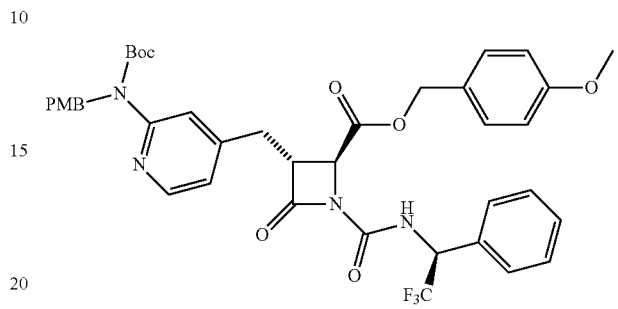

To a solution of 4-nitrophenylchloroformate (0.378 g, 2.22 mmol) in tetrahydrofuran (20 mL) at ambient temperature was added a solution of (S)-2,2,2-trifluoro-1-phenylethylamine (0.390 g, 2.22 mmol) and pyridine (0.180 mL, 2.22 mmol) in THF (20 mL) dropwise over 45 min. After 15 min, the mixture was diluted with ethyl acetate and washed with 0.1 N aqueous HCl, brine, dried with anhydrous sodium sulfate, filtered, and concentrated to afford 4-nitrophenyl [(1S)-2,2,2-trifluoro-1-phenylethyl]carbamate which was used without further purification. MS (ESI+) for $C_{15}H_{11}F_3N_2O_4$ m/z 341.3 (M+H)$^+$; HPLC retention time: 4.4 min (Method C). To a solution of the carbamate described above in THF (5 mL) was added 4-methoxybenzyl (2S,3R)-3-({2-[(tert-butoxycarbonyl)(4-methoxybenzyl) amino]pyridin-4-yl}methyl)-4-oxoazetidine-2-carboxylate (185 mg, 0.329 mmol), triethylamine (0.080 mL, 0.57 mmol) and 4-dimethylaminopyridine (0.002 g, 0.016 mmol) at ambient temperature. After 3 days, volatiles were removed at reduced pressure and the residue purified by flash chromatography using hexanes and ethyl acetate (15-30%) as eluent to afford the title compound (220 mg, 74%) as a white solid which contained approximately 15% of (S,S)-1,3-bis-(2,2,2-trifluoro-1-phenyl-ethyl)-urea that was readily removed by chromatography after removal of the protecting groups. $^1$H NMR (300 MHz, CDCl$_3$) δ 1.43 (s, 9H), 3.02-3.24 (m, 2H), 3.50-3.56 (m, 1H), 3.78 (s, 3H), 3.80 (s, 3H), 4.29 (d, J=3 Hz, 1H), 5.50-5.62 (m, 1H), 6.79-6.85 (overlapping m, 5H), 7.10 (d, J=9 Hz, 2H), 7.21-7.23 (overlapping m, 3H), 7.39-7.45 (overlapping m, 6H), 7.64 (s, 1H), 8.27 (d, J=5 Hz, 1H); MS (ESI+) for $C_{40}H_{41}F_3N_4O_8$ m/z 763.0 (M+H)$^+$; HPLC retention time: 5.54 min (Method C).

Intermediate 4. tert-Butyl [4-(2-bromoethyl)pyridin-2-yl](4-methoxybenzyl)carbamate

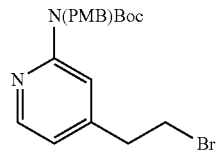

Step 1. Preparation of tert-butyl (4-methylpyridin-2-yl)carbamate

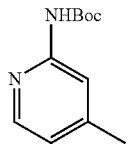

A solution of 2-pyridinamine, 4-methyl-(0.60 g, 5.5 mmol) in t-BuOH (35 mL) was treated with di-tert-butyldicarbonate (1.3 g, 6.1 mmol). The reaction mixture was stirred at 30° C. for 2 d 17 h; HPLC/TLC indicated conversion to product. The solvent was removed in vacuo to afford a tan crystalline solid, which was recrystallized from hot isopropanol to give the title compound as a white crystalline solid (0.87 g, 75%): ($^1$H NMR consistent, does not show any contamination, which agrees with the LC MS though HPLC shows two peaks) MS (ESI+) for $C_{11}H_{16}N_2O_2$ m/z 153.2 [M−tBu+H]$^+$; HPLC retention time: 2.24 min (second peak at 2.11 min) (Method B).

Step 2. Preparation of tert-butyl (4-methoxybenzyl)(4-methylpyridin-2-yl)carbamate

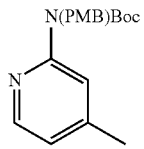

A solution of tert-butyl (4-methylpyridin-2-yl)carbamate (81 mg, 0.39 mmol) in DMF (1.2 mL) was cooled to −10° C. (ice/brine) and treated with sodium hydride (60% in mineral oil, 22 mg, 0.55 mmol). The reaction mixture was vigorously stirred for 20 min at −10° C. to afford a nearly homogeneous solution, which was treated with PMBCl (0.07 mL, 0.5 mmol). The reaction mixture was stirred for 40 min to afford a pink mixture, the cold bath was removed, and the mixture was stirred at rt for 17 h to afford an orange mixture; HPLC/LC MS indicated complete conversion to product. The reaction was quenched by the addition of water (1 mL) and diluted with water (5 mL) and Et$_2$O (40 mL). The separated organic layer was washed with water (10 mL), 0.1 N aqueous HCl (10 mL), saturated aqueous NaHCO$_3$ (10 mL), and brine (10 mL), dried (Na$_2$SO$_4$), and concentrated in vacuo to afford a light orange oil. Purification by column chromatography (2×8 cm silica; Hex, 5%, 10%, 20% EtOAc/Hex) afforded the title compound as a clear, colorless oil (91 mg, 71%); MS (ESI+) for $C_{19}H_{24}N_2O_3$ m/z 329.2 [M+H]$^+$; HPLC retention time: 3.66 min (Method B).

Step 3. Preparation of ethyl {2-[(tert-butoxycarbonyl)(4-methoxybenzyl)amino]pyridin-4-yl}acetate and tert-butyl 2-[(4-methoxybenzyl)amino]-4-methylnicotinate

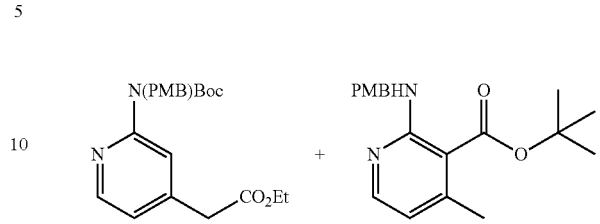

A solution of tert-butyl (4-methoxybenzyl)(4-methylpyridin-2-yl)carbamate (3.3 g, 10.0 mmol) and diethyl carbonate (6.1 mL, 50.0 mmol) in THF (82 mL) was cooled to −78° C. (acetone/CO$_2$) and treated dropwise with a 1.33 M solution of LDA in hexanes/THF/ethylbenzene (9.1 mL, 12 mmol) over 15 min. The yellow-orange reaction mixture was stirred for 30 min at −78° C.; HPLC indicated a 1.1:1:0.5 mixture of tert-butyl (4-methoxybenzyl)(4-methylpyridin-2-yl)carbamate, desired product ethyl {2-[(tert-butoxycarbonyl)(4-methoxybenzyl)amino]pyridin-4-yl}acetate and side product tert-butyl 2-[(4-methoxybenzyl)amino]-4-methylnicotinate. At 45 min the reaction was quenched by the addition of acetic acid (0.68 mL, 12 mmol) and the mixture was diluted with water (75 mL) and EtOAc (36 mL). The mixture was allowed to warm to rt and the separated aqueous layer was extracted with EtOAc (2×36 mL). The combined organics were dried (Na$_2$SO$_4$) and concentrated in vacuo to afford a yellow oil. Purification by column chromatography (5×18 cm silica; Hex, 5%, 10%, 15%, 20% EtOAc/Hex) afforded a 70:30 mixture of ethyl {2-[(tert-butoxycarbonyl)(4-methoxybenzyl)amino]pyridin-4-yl}acetate and tert-butyl 2-[(4-methoxybenzyl)amino]-4-methylnicotinate as a clear, colorless oil (1.77 g, 33%) and recovered tert-butyl (4-methoxybenzyl)(4-methylpyridin-2-yl)carbamate as a clear, colorless oil (1.78 g, 54%): $^1$H NMR indicated a 2.9:1 mixture of ethyl {2-[(tert-butoxycarbonyl)(4-methoxybenzyl)amino]pyridin-4-yl}acetate and tert-butyl 2-[(4-methoxybenzyl)amino]-4-methylnicotinate; MS (ESI+) for $C_{22}H_{28}N_2O_5$ m/z 401.3 [M+H]$^+$, MS (ESI+) for $C_{19}H_{24}N_2O_3$ n/z 329.3 [M+H]$^+$; HPLC ret. time for ethyl {2-[(tert-butoxycarbonyl)(4-methoxybenzyl)amino]pyridin-4-yl}acetate: 4.22 min (Method B), HPLC retention time for tert-butyl 2-[(4-methoxybenzyl)amino]-4-methylnicotinate: 3.24 min (Method B).

Step 4. Preparation of tert-butyl [4-(2-hydroxyethyl)pyridin-2-yl](4-methoxybenzyl)carbamate

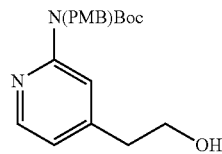

A ~2:1 mixture of ethyl {2-[(tert-butoxycarbonyl)(4-methoxybenzyl)amino]pyridin-4-yl}acetate (1.77 g, 3.27 mmol) and tert-butyl 2-[(4-methoxybenzyl)amino]-4-methylnicotinate in THF (16 mL) was cooled to 0° C. (ice/brine) and treated with LiBH$_4$ (0.21 g, 9.6 mmol). The cold bath was removed and the reaction mixture was allowed to warm to rt over 20 min, followed by heating at 50° C. for 3 h; HPLC/LC MS indicated complete consumption of {2-[(tert-butoxycarbonyl)(4-methoxybenzyl)amino]pyridin-4-yl}acetate. The reaction mixture was allowed to cool to rt and the reaction was carefully quenched by the addition of saturated aqueous NaHCO₃ (30 mL). The mixture was diluted with water (60 mL) and extracted with EtOAc (3×60 mL). The combined organics were dried (Na₂SO₄) and concentrated in vacuo to afford a bright yellow oil. Purification by column chromatography (4×14 cm silica; Hex, 10%, 30%, 50% EtOAc/Hex) afforded the title compound as a clear, colorless oil (0.91 g, 78%): MS (ESI+) for $C_{20}H_{26}N_2O_4$ m/z 359.3 [M+H]⁺; HPLC retention. time: 3.17 min (Method B).

Step 5. Preparation of tert-Butyl [4-(2-bromoethyl)pyridin-2-yl](4-methoxybenzyl)carbamate

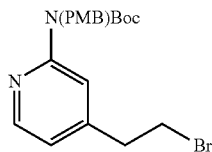

A mixture of tert-butyl [4-(2-hydroxyethyl)pyridin-2-yl](4-methoxybenzyl)carbamate (0.91 g, 2.5 mmol) and carbon tetrabromide (0.93 g, 2.8 mmol) in CH₂Cl₂ (15 mL) was cooled to 0° C. (ice/water). Triphenylphosphine (0.73 g, 2.8 mmol) was added in one portion and the bright yellow reaction mixture was stirred for 30 min at 0° C. The cold bath was removed and reaction mixture was stirred at rt for 1 h; HPLC indicated nearly complete conversion to product. At 2 h, HPLC indicated no change. The reaction mixture was diluted with CH₂Cl₂ (120 mL) and washed with saturated aqueous NaHCO₃ (70 mL). The separated aqueous phase was extracted with CH₂Cl₂ (2×70 mL) and the combined organics were dried (Na₂SO₄) and concentrated in vacuo to afford a clear, colorless oil. Purification by column chromatography (4×16 cm silica; Hex, 10%, 20%, 30% EtOAc/Hex) afforded the title compound as a clear, colorless oil (0.69 g, 64%): MS (ESI+) for $C_{20}H_{25}BrN_2O_3$ m/z 421.2 [M+H]⁺; HPLC retention. time: 4.29 min (Method B); 1H NMR (CDCl₃, 300 MHz) δ 8.37-8.28 (m, 1H), 7.54 (br s, 1H), 7.26-7.16 (m, 2H), 6.90-6.84 (m, 1H), 6.84-6.74 (m, 2H), 5.38-4.88 (m, 2H), 3.77 (s, 3H), 3.62-3.51 (m, 2H), 3.19-3.09 (m, 2H), 1.44 (s, 9H).

Intermediate 5: tert-Butyl [4-(bromomethyl)pyridin-2-yl]methylcarbamate

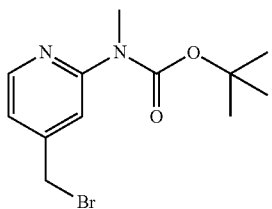 [SMILES: CN(C(=O)OC(C)(C)C)c1cc(CBr)ccn1]

Step 1. Preparation of methyl 2-[(tert-butoxycarbonyl)(methyl)amino]isonicotinate

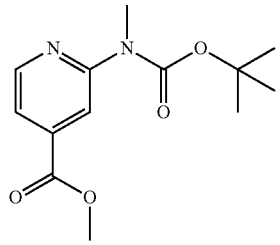 [SMILES: COC(=O)c1ccnc(N(C)C(=O)OC(C)(C)C)c1]

A slurry of methyl 2-[(tert-butoxycarbonyl)amino]isonicotinate (5.0 g, 2.0E1 mmol) in DMF (75 mL) was cooled to ~0° C. (ice/NaCl) and treated with a 1.0 M solution of sodium hexamethyldisilazane in THF (24 mL, 24 mmol) dropwise over 25 min to afford a clear, yellow/brown solution. The reaction mixture was stirred for 30 min at 0° C. and treated with methyl iodide (1.4 mL, 22 mmol). The reaction mixture was stirred for 20 min, the cold bath was removed, and the reaction mixture stirred at rt for 2 h; HPLC/LC MS indicated complete conversion to product. The reaction mixture was cooled to ~0° C. and the reaction was quenched by the addition of saturated aqueous NH₄Cl (25 mL). The mixture was allowed to warm to rt and was extracted with Et₂O (3×50 mL). The combined organics were washed with saturated aqueous NaHCO₃ (1×50 mL) and 10% aqueous LiCl (2×50 mL), dried (Na₂SO₄), and concentrated in vacuo to afford a bright yellow oil with precipitate. The crude material was further dried on high vacuum overnight to afford the crude title compound as a light colored solid/yellow oil (5.29 g). MS (ESI+) for $C_{13}H_{18}N_2O_4$LC m/z 267.1 (M+H)⁺; HPLC retention time: 3.78 min (Method B).

Step 2. Preparation of tert-Butyl [4-(hydroxymethyl)pyridin-2-yl]methylcarbamate

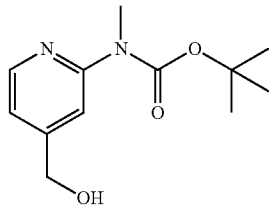 [SMILES: CN(C(=O)OC(C)(C)C)c1cc(CO)ccn1]

A solution of crude methyl 2-[(tert-butoxycarbonyl)(methyl)amino]isonicotinate (5.29 g) in THF (50 mL) was cooled to ~0° C. (ice/brine) and treated with lithium tetrahydroborate (0.47 g, 22 mmol) in one portion. The reaction mixture was stirred for 10 min, the cold bath was removed, and the reaction mixture was allowed to warm to rt over 30 min. The flask was transferred to a preheated 40° C. oil bath and the reaction mixture was stirred at 40° C. for 3.5 h; HPLC indicated a mixture of product and starting material. The oil bath temperature was increased to 50° C. for 50 min; HPLC indicated nearly complete conversion to product. The reaction mixture was allowed to cool to rt and was stored at 0-5° C. overnight. The reaction mixture was cooled to ~0° C. and the reaction was carefully quenched by the slow, dropwise addition of saturated aqueous NaHCO₃ (15 mL). The mixture was diluted with water (20 mL) and extracted with EtOAc (3×20 mL). The combined organics were washed with saturated aqueous NH₄Cl (1×20 mL), water (1×20 mL), and brine (1×30 mL), dried (Na₂SO₄), and concentrated in vacuo to afford the crude title compound as a tan oil (4.49 g). MS (ESI+) for C₁₂H₁₈N₂O₃LC m/z 239.2 (M+H)⁺; HPLC retention time: 2.10 min (Method B).

Step 3. Preparation of tert-Butyl [4-(bromomethyl)pyridin-2-yl]methylcarbamate

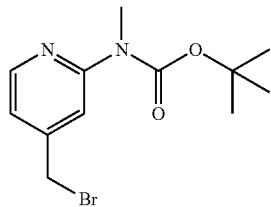 [SMILES: CN(C(=O)OC(C)(C)C)c1cc(CBr)ccn1]

A mixture of crude tert-butyl [4-(hydroxymethyl)pyridin-2-yl]methylcarbamate (4.49 g) and carbon tetrabromide (7.2 g, 22 mmol) was taken up in CH₂Cl₂ (110 mL) and cooled to ~0° C. (ice water). Triphenylphosphine (5.7 g, 22 mmol) was added in one portion and the bright yellow reaction mixture was stirred for 20 min, the cold bath was removed, and the orange-red mixture was stirred at rt for 1 h; HPLC/LC MS indicated complete conversion to product. The reaction mixture was diluted with CH₂Cl₂ (50 mL) and washed with saturated aqueous NaHCO₃ (1×50 mL). The separated aqueous layer was extracted with CH₂Cl₂ (2×20 mL) and the combined organics were dried (Na₂SO₄) and concentrated in vacuo to afford a red-orange oil, which was stored at 0-5° C. overnight. Purification by column chromatography (5×14 cm silica; Hex, 10%, 20%, 30% EtOAc/Hex) afforded the title compound as a clear, nearly colorless oil (4.74 g, 80%). MS (ESI+) for C₁₂H₁₇BrN₂O₂ m/z 301.1, 303.1 (M+H)⁺; HPLC retention time: 3.52 min (Method B); ¹H NMR (300 MHz, CDCl₃) δ 8.43-8.27 (m, 1H), 7.84-7.66 (m, 1H), 7.12-6.92 (m, 1H), 4.39 (br s, 2H), 3.41 (s, 3H), 1.54 (s, 9H).

Example 3

Scheme 1: (2S,3R)-3-[(2-Aminopyridin-4-yl)methyl]-1-{[(1R-1-cyclohexylethyl]carbamoyl}-4-oxoazetidine-2-carboxylic acid trifluoroacetate

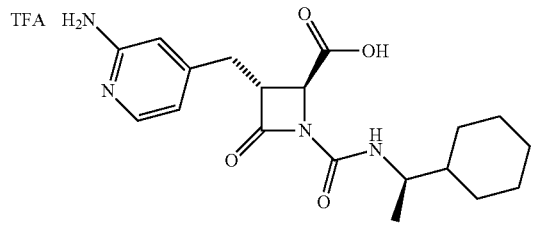

Step 1. Preparation of (2S,3R)-3-({2-[(tert-butoxycarbonyl)(4-methoxybenzyl)amino]pyridin-4-yl}methyl)-1-[tert-butyl(dimethyl)silyl]-4-oxoazetidine-2-carboxylic acid

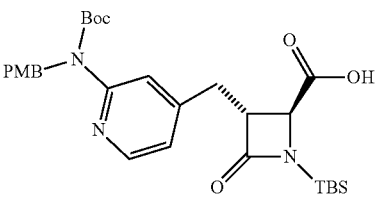

An oven-dried, 3-neck flask was cooled under nitrogen, charged with (2S)-1-[tert-butyl(dimethyl)silyl]-4-oxoazetidine-2-carboxylic acid (3.00 g, 13.1 mmol) and dry THF (110 mL), and the mixture was cooled to −70° C. Lithium diisopropylamide in THF [1.25 M (titrated), 21.4 mL, 26.8 mmol] was added dropwise over 8 min., keeping the internal temperature below −55° C., and the resulting tan mixture was stirred at −78° C. for 35 min and then placed in an ice-brine-MeOH bath and stirred below −15° C. for an additional 30 min. A solution of tert-butyl [4-(bromomethyl)pyridin-2-yl](4-methoxybenzyl)carbamate (5.86 g, 14.4 mmol) in dry THF (21 mL) which had been cooled to 0° C. was then added over 5 min., keeping the internal temperature below −5° C., and the resulting dark mixture was stirred at this temperature for 1 h, quenched with aqueous citric acid (0.5 M, 120 mL), diluted with water (120 mL) and extracted with EtOAc (3×100 mL). The combined organic phase was washed with brine (60 mL), dried over anhydrous magnesium sulfate, filtered and concentrated under reduced pressure to give the crude product as a clear, tacky residue which was used as is in the next step. MS (ESI+) for C₂₉H₄₁N₃O₆Si m/z 556.5 (M+H)⁺.

Step 2. Preparation of benzyl (2S,3R)-3-({2-[(tert-butoxycarbonyl)(4-methoxybenzyl)amino]pyridin-4-yl}methyl)-1-[tert-butyl(dimethyl)silyl]-4-oxoazetidine-2-carboxylate

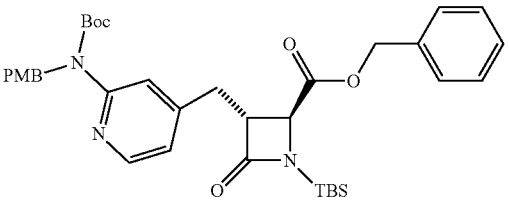

A stirred solution of crude (2S,3R)-3-({2-[(tert-butoxycarbonyl)(4-methoxybenzyl)amino]pyridin-4-yl}methyl)-1-[tert-butyl(dimethyl) silyl]-4-oxoazetidine-2-carboxylic acid in DCM (60 mL) under nitrogen was treated with N-(3-dimethylaminopropyl)-N'-ethylcarbodiimide hydrochloride (3.26 g, 17.0 mmol), followed by benzyl alcohol (1.62 mL, 15.7 mmol) and 4-dimethylaminopyridine (160 mg, 1.31 mmol), and the resulting brown mixture was stirred at rt for 2 h, at which point HPLC indicated the reaction was complete. The mixture was diluted with water (60 mL) and extracted with DCM (2×60 mL), and the combined organic phase was washed with water (60 mL) and brine (50 mL), dried over Na$_2$SO$_4$, filtered and concentrated under reduced pressure. Purification by silica gel chromatography [120 g cartridge; elution with a gradient of 10-20% EtOAc/hexanes] provided 4.16 g of the title compound (contaminated with ~15 wt % benzyl alcohol; 42% yield over first two steps) as a tan, viscous oil which was used without further purification. MS (ESI+) for C$_{36}$H$_{47}$N$_3$O$_6$Si m/z 646.7 (M+H)$^+$.

Step 3. Preparation of benzyl (2S,3R)-3-({2-[(tert-butoxycarbonyl)(4-methoxybenzyl)amino]pyridin-4-yl}methyl)-4-oxoazetidine-2-carboxylate

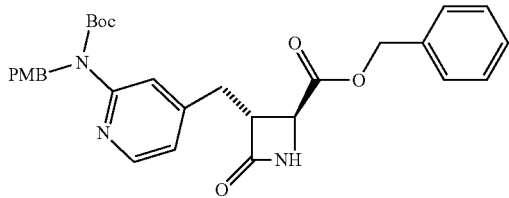

A stirred solution of benzyl (2S,3R)-3-({2-[(tert-butoxycarbonyl)(4-methoxybenzyl)amino]pyridin-4-yl}methyl)-1-[tert-butyl(dimethyl) silyl]-4-oxoazetidine-2-carboxylate (2.98 g, 3.92 mmol) in MeOH (39 mL) under nitrogen was treated with acetic acid (0.780 mL, 13.7 mmol) followed by a solution of ammonium fluoride in MeOH (0.5 M, 10.2 mL, 5.10 mmol), and the resulting homogeneous mixture was stirred at rt for 1 h, at which point HPLC indicated the reaction was complete. The mixture was concentrated under reduced pressure, and the residue was taken up in DCM (120 mL), washed with sat aqueous NaHCO$_3$ (80 mL), water (60 mL) and brine (40 mL), dried over Na$_2$SO$_4$, filtered and concentrated under reduced pressure. Purification by silica gel chromatography [40 g cartridge; elution with 20-50% EtOAc/hexanes] afforded 1.95 g (94%) of the title compound as a white solid. MS (ESI+) for C$_{30}$H$_{33}$N$_3$O$_6$ m/z 532.4 (M+H)$^+$.

Step 4. Preparation of benzyl (2S,3R)-3-({2-[(tert-butoxycarbonyl)(4-methoxybenzyl)amino]pyridin-4-yl}methyl)-1-{[(1R)-1-cyclohexylethyl]carbamoyl}-4-oxoazetidine-2-carboxylate

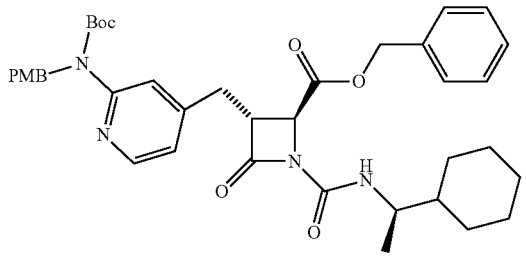

A stirred solution of benzyl (2S,3R)-3-({2-[(tert-butoxycarbonyl)(4-methoxybenzyl)amino]pyridin-4-yl}methyl)-4-oxoazetidine-2-carboxylate (2.72 g, 5.12 mmol) in DCM (51 mL) under nitrogen was treated with Et$_3$N (2.50 mL, 17.9 mmol) followed by a solution of commercial [(1R)-1-isocyanatoethyl]cyclohexane (1.02 g, 6.65 mmol) in DCM (5 mL), and the mixture was stirred at rt overnight, at which point HPLC indicated starting material was nearly consumed. At 17 h, the mixture was concentrated under reduced pressure, and the residue was purified by silica gel chromatography [120 g; elution with 15-25% EtOAc/hexanes] to give 2.31 g (66%) of the title compound as a white foam. MS (ESI+) for C$_{39}$H$_{48}$N$_4$O$_7$ m/z 685.7 (M+H)$^+$.

Step 5. Preparation of (2S,3R)-3-({2-[(tert-butoxycarbonyl)(4-methoxybenzyl)amino]pyridin-4-yl}methyl)-1-{[(1R)-1-cyclohexylethyl]carbamoyl}-4-oxoazetidine-2-carboxylic acid

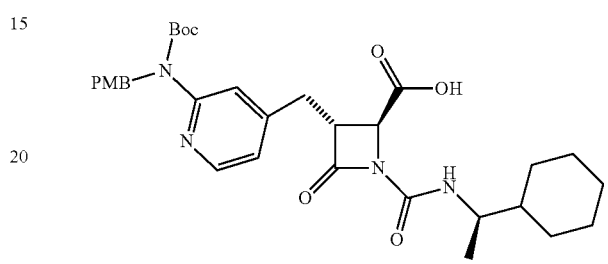

A mixture of benzyl (2S,3R)-3-({2-[(tert-butoxycarbonyl)(4-methoxybenzyl)amino]pyridin-4-yl}methyl)-1-{[(1R)-1-cyclohexylethyl]carbamoyl}-4-oxoazetidine-2-carboxylate (1.94 g, 2.83 mmol) in 1:1 MeOH/EtOAc (56 mL) under nitrogen was treated with 10% palladium-on-carbon (301 mg, 0.283 mmol Pd), and the mixture was evacuated and filled with nitrogen twice and then stirred under a hydrogen atmosphere (double-layer balloon) for 70 min, at which point HPLC indicated the reaction was complete. The catalyst was filtered off through solka floc, rinsing with 1:1 MeOH/EtOAc, and the filtrate was concentrated under reduced pressure to give 1.67 g (99%) of the title compound as a white, tacky solid. MS (ESI+) for C$_{32}$H$_{42}$N$_4$O$_7$ m/z 595.5 (M+H)$^+$.

Step 6. Preparation of (2S,3R)-3-[(2-aminopyridin-4-yl)methyl]-1-{[(1R)-1-cyclohexylethyl]carbamoyl}-4-oxoazetidine-2-carboxylic acid trifluoroacetate

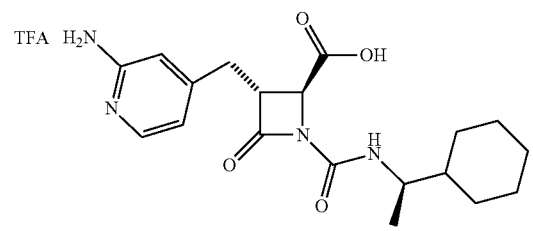 [SMILES: C[C@@H](NC(=O)N1C(=O)[C@H](Cc2ccnc(N)c2)[C@H]1C(=O)O)C1CCCCC1 ; "TFA"]

A stirred solution of (2S,3R)-3-({2-[(tert-butoxycarbonyl)(4-methoxybenzyl)amino]pyridin-4-yl}methyl)-1-{[(1R)-1-cyclohexylethyl]carbamoyl}-4-oxoazetidine-2-carboxylic acid (78.0 mg, 0.131 mmol) in DCM (2.1 mL) under nitrogen was cooled in an ice-water bath and treated dropwise with TFA (0.7 mL, 9 mmol). The resulting mixture was stirred at 0-5° C. for 30 min and then warmed to rt and stirred overnight, at which point HPLC indicated the reaction was complete. The mixture was concentrated under reduced pressure, and the residue was purified by preparative HPLC on a CombiFlash Rf system [30 g C18 Gold column; elution with a gradient of 10% acetonitrile (0.07% TFA)/water (0.1% TFA) to 100% acetonitrile (0.07% TFA)]. Lyophilization of product fractions afforded 45 mg (70%) of the title compound as a white amorphous solid. $^1$H NMR (400 MHz, MeOD) δ 7.79 (d, J=6.4 Hz, 1H), 6.98 (s, 1H), 6.91 (d, J=6.8 Hz, 1H), 6.64 (bd, J=9.2 Hz, 1H), 4.27 (d, J=2.8 Hz, 1H), 3.70 (m, 2H), 3.24 (m, 2H), 1.85-1.65 (m, 5H), 1.42 (m, 1H), 1.36-1.15 (m, 3H), 1.17 (d, J=6.8 Hz, 3H), 1.15-0.95 (m, 2H); MS (ESI+) for $C_{19}H_{26}N_4O_4$ (parent) m/z 375.3 (M+H)$^+$; HPLC retention time: 3.21 min (Method A).

Example 4

Scheme 1: (2S,3R)-3-[(2-aminopyridin-4-yl)methyl]-1-{[(1R-1-(2,2-difluoro-1,3-benzodioxol-5-yl)ethyl]carbamoyl}-4-oxoazetidine-2-carboxylic acid trifluoroacetate.

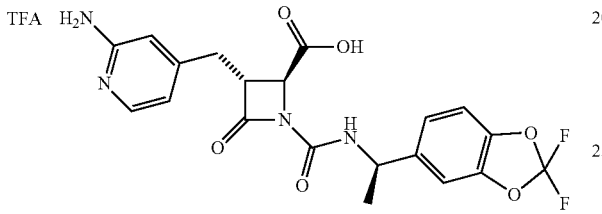

Step 1. Preparation of (S)—N-[(1E)-(2,2-difluoro-1,3-benzodioxol-5-yl)methylene]-2-methylpropane-2-sulfinamide

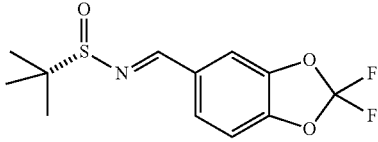 [SMILES: CC(C)(C)[S@](=O)/N=C/c1ccc2c(c1)OC(F)(F)O2]

To a solution of (S)-2-methyl-propane-2-sulfinic acid amide (0.207 g, 1.71 mmol) in DCM (5 mL) was added copper(II) sulfate (0.8186 g, 5.129 mmol) followed by a solution of 2,2-difluoro-1,3-benzodioxole-5-carbaldehyde (0.350 g, 1.88 mmol) in DCM (5 mL). The mixture was stirred at ambient temperature for 16 h, filtered through celite and concentrated at reduced pressure. The residue was purified by flash chromatography (hexane with ethyl acetate (2-8%) as eluent) to afford the title compound (0.468 g, 95%) as an oil. MS (ESI+) for $C_{13}H_{17}F_2NO_3S$ m/z 290.1 (M+H)$^+$; HPLC retention time: 4.73 min (Method C).

Step 2. Preparation of N-[(1R)-1-(2,2-difluoro-1,3-benzodioxol-5-yl)ethyl]-2-methylpropane-2-sulfinamide

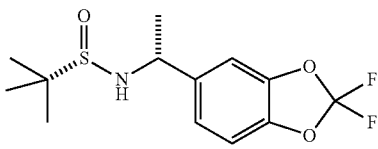 [SMILES: C[C@@H](N[S@@](=O)C(C)(C)C)c1ccc2c(c1)OC(F)(F)O2]

To a cooled (−20° C.) solution of (S)—N-[(1E)-(2,2-difluoro-1,3-benzodioxol-5-yl)methylene]-2-methylpropane-2-sulfinamide (0.274 g, 0.947 mmol) in THF (9 mL) was added 3 M methylmagnesium bromide (3 M in ethyl ether, 3.157 mL, 9.471 mmol) over 15 min at a rate sufficiently slow to maintain the reaction temperature below −15° C. After 60 min at −20° C., the reaction was quenched by the addition of sat aqueous NH$_4$Cl. The mixture was diluted with ethyl acetate and washed with sat NaHCO$_3$, brine, dried with anhydrous sodium sulfate, filtered and concentrated. The residue was purified by flash chromatography (hexanes with ethyl acetate 20-30% as eluent) to afford the title product (the major and slower eluting diastereomer, 0.234 g, 81%) as an oil: MS (ESI+) for $C_{13}H_{17}F_2NO_3S$ m/z 306.2 (M+H)$^+$; HPLC retention time: 4.20 min (Method C).

Step 3. Preparation of (1R)-1-(2,2-difluoro-1,3-benzodioxol-5-yl)ethanamine hydrochloride

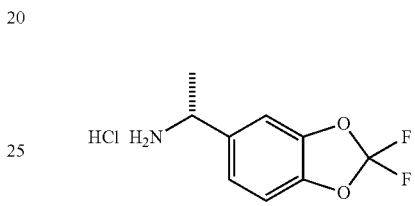

To a cooled (0-5° C.) solution of N-[(1R)-1-(2,2-difluoro-1,3-benzodioxol-5-yl)ethyl]-2-methylpropane-2-sulfinamide (0.234 g, 0.766 mmol) in methanol (4.6 mL) was added hydrogen chloride in 1,4-dioxane (4 M, 0.958 mL, 3.83 mmol). After 5 min, the ice bath was removed and the reaction mixture stirred at ambient temperature for 1 h. Volatiles were removed in vacuo and the residue concentrated twice from methanol, twice from ethyl ether and dried in vacuo to afford the title compound (0.175 g, 96%) as a white solid: 1H NMR (300 MHz, CD$_3$OD) δ 1.67 (t, J=7 Hz, 3H), 4.55 (q, J=7 Hz, 2H), 7.29-7.36 (m, 2H), 7.43-7.44 (m, 1H); HPLC retention time: 2.69 min (Method C).

Step 4. Preparation of phenyl [(1R)-1-(2,2-difluoro-1,3-benzodioxol-5-yl)ethyl]carbamate

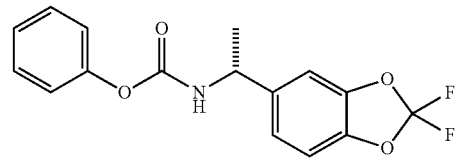 [SMILES: C[C@@H](NC(=O)Oc1ccccc1)c1ccc2c(c1)OC(F)(F)O2]

To a cooled (0-5° C.) solution of (1R)-1-(2,2-difluoro-1,3-benzodioxol-5-yl)ethanamine hydrochloride (100 mg, 0.421 mmol) in methylene chloride (2 mL) was added triethylamine (0.132 mL, 0.947 mmol) followed by phenyl chloroformate (0.054 mL, 0.433 mmol) dropwise. After 15 min the ice bath was removed and the reaction mixture stirred at ambient temperature for 3 h. The mixture is diluted with ethyl acetate and washed with 0.1 N HCl, sat NaHCO$_3$, brine, dried with anhydrous sodium sulfate, filtered and concentrated. The residue was purified by flash chromatography (hexanes with ethyl acetate 5% as eluent) to afford the title compound (140 mg, 93%) as a white solid: MS (ESI+) for $C_{16}H_{13}F_2NO_4$ m/z 322.2 (M+H)$^+$; HPLC retention time: 4.75 min (Method C).

Step 5. Preparation of 4-methoxybenzyl (2S,3R)-3-({2-[(tert-butoxycarbonyl)(4-methoxybenzyl)amino]pyridin-4-yl}methyl)-1-{[(1R)-1-(2,2-difluoro-1,3-benzodioxol-5-yl)ethyl]carbamoyl}-4-oxoazetidine-2-carboxylate

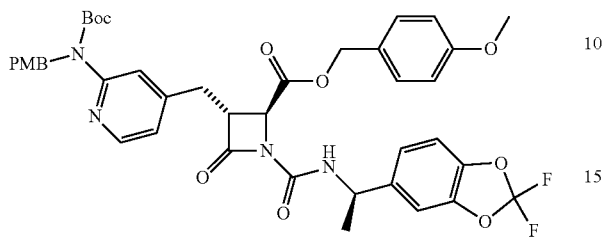

To a solution of 4-methoxybenzyl (2S,3R)-3-({2-[(tert-butoxycarbonyl)(4-methoxybenzyl)amino]pyridin-4-yl}methyl)-4-oxoazetidine-2-carboxylate (prepared as described for Example 3 substituting 4-methoxybenzyl alcohol for benzyl alcohol in step 2, 0.161 g, 0.287 mmol) in dimethyl sulfoxide (2 mL) was added phenyl [(1R)-1-(2,2-difluoro-1,3-benzodioxol-5-yl)ethyl]carbamate (0.120 g, 0.374 mmol). After 16 h, the mixture was diluted with ethyl acetate and washed with 0.1 N HCl, sat NaHCO$_3$, brine, dried with anhydrous sodium sulfate, filtered and concentrated. The residue was purified by flash chromatography (hexanes with ethyl acetate 5-20% as eluent) to afford the title compound (156 mg, 69%) as a white solid: MS (ESI+) for C$_{41}$H$_{42}$F$_2$N$_4$O$_{10}$ m/z 789.5 (M+H)$^+$; HPLC retention time: 5.71 min (Method C).

Step 6. Preparation of (2S,3R)-3-[(2-aminopyridin-4-yl)methyl]-1-{[(1R)-1-(2,2-difluoro-1,3-benzodioxol-5-yl)ethyl]carbamoyl}-4-oxoazetidine-2-carboxylic acid trifluoroacetate

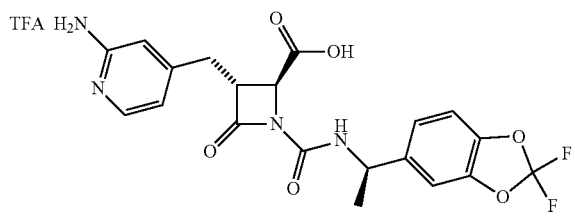

To a cooled (0-5° C.) solution of 4-methoxybenzyl (2S,3R)-3-({2-[(tert-butoxycarbonyl)(4-methoxybenzyl)amino]pyridin-4-yl}methyl)-1-{[(1R)-1-(2,2-difluoro-1,3-benzodioxol-5-yl)ethyl]carbamoyl}-4-oxoazetidine-2-carboxylate (0.160 g, 0.203 mmol) in methylene chloride (6 mL) was added triethylsilane (1 mL) followed by trifluoroacetic acid (3 mL). After 2 h, the ice bath was removed and the reaction mixture stirred at ambient temperature for 16 h. The volatiles were removed and the residue purified by CombiFlash chromatography [30 g RediSep C-18 gold silica gel cartridge, solvent gradient: 10% acetonitrile (0.07% TFA)/ water (0.1% TFA) to 100% acetonitrile (0.07% TFA)] and lyophilized to afford the title compound (80 mg, 70%) as a white solid: 1H NMR (300 MHz, CD$_3$OD) δ 1.54 (d, J=7 Hz, 3H), 3.20-3.29 (m, 2H), 3.69-3.75 (m, 1H), 4.30 (d, J=3 Hz, 1H), 4.94-5.00 (m, 1H), 6.90-6.98 (m, 2H), 7.13-7.26 (m, 3H); MS (ESI+) for C$_{20}$H$_{18}$F$_2$N$_4$O$_6$ m/z 449.2 (M+H)$^+$; HPLC retention time: 3.39 min (Method C).

Example 5

Scheme 1: (2S,3R)-3-[(2-aminopyridin-4-yl)methyl]-1-{[(1S)-1-cyclohexyl-2,2,2-trifluoroethyl]carbamoyl}-4-oxoazetidine-2-carboxylic acid trifluoroacetate

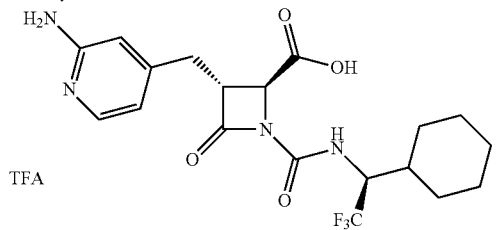

Step 1. Preparation of benzyl (2S,3R)-3-({2-[(tert-butoxycarbonyl)(4-methoxybenzyl)amino]pyridin-4-yl}methyl)-1-{[(1S)-1-cyclohexyl-2,2,2-trifluoroethyl]carbamoyl}-4-oxoazetidine-2-carboxylate

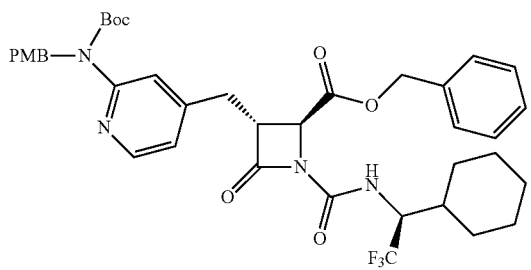

To a solution of benzyl (2S,3R)-3-({2-[(tert-butoxycarbonyl)(4-methoxybenzyl)amino]pyridin-4-yl}methyl)-4-oxoazetidine-2-carboxylate (100 mg, 0.19 mmol, prepared by the general methods described in Scheme 1) in dimethyl sulfoxide (0.58 mL) was added phenyl [(1S)-1-cyclohexyl-2,2,2-trifluoroethyl]carbamate (74 mg, 0.24 mmol) followed by triethylamine (28 μL, 0.21 mol). The mixture was stirred at ambient temperature overnight, diluted with ethyl acetate, washed with water, dried with anhydrous sodium sulfate, filtered and concentrated. The residue was purified by flash chromatography using hexanes/ethyl acetate (5-15%) as eluent to afford the title compound (70 mg, 50%) as a tan solid: 1H NMR (CDCl$_3$) δ 0.97-1.33 (m, 5H), 1.42 (s, 9H), 1.59-1.86 (m, 6H), 3.05-3.25 (m, 2H), 3.53-3.59 (m, 1H), 3.78 (s, 3H), 4.31-4.39 (overlapping m, 2H), 5.09-5.25 (overlapping, 4H), 6.64 (d, J=10 Hz, 1H), 6.78-6.86 (overlapping m, 3H), 7.19-7.23 (m, 4H), 7.32-7.36 (m, 3H), 7.65 (s, 1H), 8.27 (d, J=5 Hz, 1H); MS (ESI+) for C$_{39}$H$_{45}$F$_3$N$_4$O$_7$ m/z 739.3 (M+H)$^+$. HPLC retention time: 5.99 min (Method C).

Step 2. Preparation of (2S,3R)-3-[(2-aminopyridin-4-yl)methyl]-1-{[(1S)-1-cyclohexyl-2,2,2-trifluoroethyl]carbamoyl}-4-oxoazetidine-2-carboxylic acid trifluoroacetate

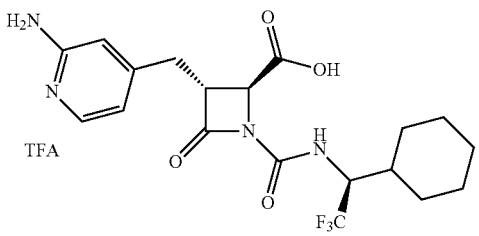 [SMILES: Nc1cc(C[C@H]2C(=O)N(C(=O)N[C@@H](C3CCCCC3)C(F)(F)F)[C@@H]2C(=O)O)ccn1]

To a flask containing Pd/C (10%, 10 mg) was added a solution of benzyl (2S,3R)-3-({2-[(tert-butoxycarbonyl)(4-methoxybenzyl)amino]pyridin-4-yl}methyl)-1-{[(1 S)-1-cyclohexyl-2,2,2-trifluoroethyl]carbamoyl}-4-oxoazetidine-2-carboxylate (70 mg, 0.095 mmol) in ethanol (40 mL). The mixture was stirred under 1 atmosphere of $H_2$ for 3 h, filtered through a pad of solka floc and concentrated under reduced pressure. To a cooled (0-5° C.) solution of the residue obtained above in methylene chloride (3 mL) was added triethylsilane (0.5 mL) followed by trifluoroacetic acid (1.5 mL). After 2 h, the ice bath was removed and the reaction mixture stirred at ambient temperature for 16 h. The volatiles were removed under reduced pressure and the residue purified by CombiFlash chromatography [30 g RediSep C-18 gold silica gel cartridge, solvent gradient: 10% acetonitrile (0.07% TFA)/water (0.1% TFA) to 100% acetonitrile (0.07% TFA)] and lyophilized to afford the title compound (40 mg, 78%) as a white solid: 1H NMR (CDCl$_3$) δ 1.08-1.39 (m, 5H), 1.68-1.92 (m, 6H), 3.23-3.29 (m, 2H), 3.76-3.82 (m, 1H), 4.34-4.39 (overlapping m, 2H), 6.90-6.93 (m, 1H), 6.98 (s, 1H), 7.78-7.80 (m, 1H); MS (ESI+) for $C_{19}H_{23}F_3N_4O_4$ m/z 429.1 (M+H)$^+$; HPLC retention time: 3.89 min (Method C).

Example 6

Scheme 1: (2S,3R)-1-{[(1S)-1-cyclohexyl-2,2,2-trifluoroethyl]carbamoyl}-4-oxo-3-(pyridin-4-ylmethyl)azetidine-2-carboxylic acid trifluoroacetate

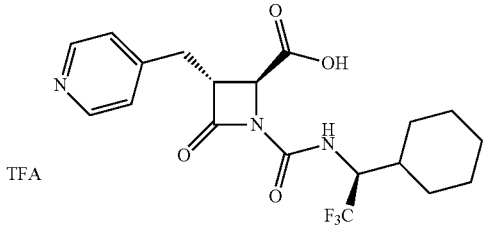

To a cooled (0-5° C.) solution of 4-methoxybenzyl (2S,3R)-3-[(2-chloropyridin-4-yl)methyl]-1-{[(1 S)-1-cyclohexyl-2,2,2-trifluoroethyl]carbamoyl}-4-oxoazetidine-2-carboxylate (0.190 g, 0.33 mmol, prepared by the general methods described in Scheme 1) in $CH_2Cl_2$ (6 mL) was added trifluoroacetic acid (3 mL). After 5 min, the ice bath was removed and the reaction stirred at ambient temperature for an additional 30 min. Volatiles were removed at reduced pressure and the residue concentrated twice from ether. The residue was dissolved in ethanol (20 mL) and added to a flask containing Pd/C (10%, 20 mg). Triethylamine (0.102 mL, 0.74 mmol) was added and the mixture stirred under 1 atmosphere of $H_2$ for 30 min. The mixture was filtered through celite and concentrated under reduced pressure. The residue was purified by CombiFlash chromatography [30 g RediSep C-18 gold silica gel cartridge, solvent gradient: 10% acetonitrile (0.07% TFA)/water (0.1% TFA) to 100% acetonitrile (0.07% TFA)] and lyophilized to afford the title compound (39 mg, 22%) as a white solid. $^1$H NMR (CD$_3$OD) δ 1.07-1.39 (m, 5H), 1.68-1.93 (m, 6H), 3.46-3.61 (m, 2H), 3.89-3.95 (m, 1H), 4.36-4.44 (overlapping m, 2H), 8.02 (d, J=7 Hz, 2H), 8.76 (d, J=7 Hz, 2H); MS (ESI+) for $C_{19}H_{22}F_3N_3O_4$ m/z 414.0 (M+H)$^+$; HPLC retention time: 3.45 min (Method C).

Example 7

Scheme 2: (2S,3R)-3-[(2-Aminopyridin-4-yl)methyl]-2-cyano-4-oxo-N-[(1R)-1-phenylethyl]azetidine-1-carboxamide trifluoroacetate.

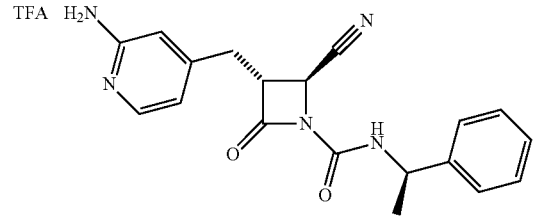

Step 1. Preparation of (2S,3R)-3-({2-[(tert-butoxycarbonyl)(4-methoxybenzyl)amino]pyridin-4-yl}methyl)-1-[tert-butyl(dimethyl)silyl]-4-oxoazetidine-2-carboxylic acid

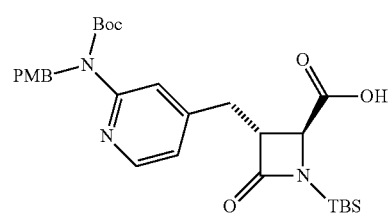

The title compound was prepared from benzyl (2S,3R)-3-({2-[(tert-butoxycarbonyl)(4-methoxybenzyl)amino]pyridin-4-yl}methyl)-1-[tert-butyl(dimethyl) silyl]-4-oxoazetidine-2-carboxylate according to the general procedure described in step 5 of Example 3 in 98% yield as a white tacky solid. MS (ESI+) for $C_{29}H_{41}N_3O_6Si$ m/z 556.5 (M+H)$^+$.

Step 2. Preparation of tert-butyl (4-{[(2S,3R)-2-carbamoyl-4-oxoazetidin-3-yl]methyl}pyridin-2-yl)(4-methoxybenzyl)carbamate

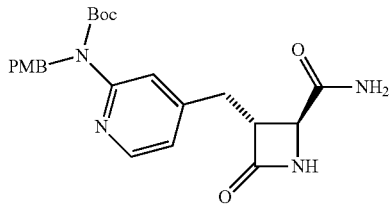

A stirred solution of (2S,3R)-3-({2-[(tert-butoxycarbonyl)(4-methoxybenzyl)amino]pyridin-4-yl}methyl)-1-[tert-butyl(dimethyl) silyl]-4-oxoazetidine-2-carboxylic acid (Step 1, 417 mg, 0.750 mmol) in dry DMF (3.5 mL) under nitrogen was treated sequentially with pyridine (38 μL, 0.47 mmol), di-tert-butyldicarbonate (205 mg, 0.938 mmol) and ammonium bicarbonate (71.2 mg, 0.900 mmol), and the resulting tan mixture was stirred at rt overnight. HPLC at 24 h indicated the reaction was complete, so the mixture was diluted with water (30 mL) and extracted with DCM (3×30 mL). The combined organic phase was washed with brine (15 mL), dried over $Na_2SO_4$ and concentrated under reduced pressure. Purification by radial chromatography [2000 micron silica gel rotor; 5-10% MeOH/DCM eluent] gave 225 mg (68%) of the title compound as a glassy solid. MS (ESI+) for $C_{23}H_{28}N_4O_5$ m/z 441.4 (M+H)$^+$.

Step 3. Preparation of tert-butyl (4-{[(2S,3R)-2-cyano-4-oxoazetidin-3-yl]methyl}pyridin-2-yl)(4-methoxybenzyl)carbamate

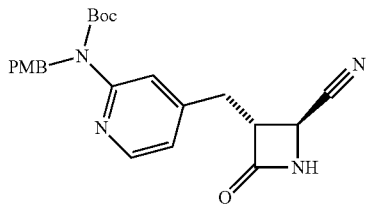

A stirred solution of tert-butyl (4-{[(2S,3R)-2-carbamoyl-4-oxo azetidin-3-yl]methyl}pyridin-2-yl)(4-methoxybenzyl)carbamate (Step 2, 75.0 mg, 0.170 mmol) and pyridine (33.0 μL, 0.409 mmol) in dry THF (2 mL) under nitrogen was cooled in an ice-brine-MeOH bath at −10° C. and treated with trifluoroacetic anhydride (28.8 μL, 0.204 mmol) slowly dropwise over ~3 min. The resulting homogeneous mixture was allowed to slowly warm to 0° C. over 25 min, at which point HPLC indicated the reaction was essentially complete. The mixture was diluted with water (15 mL) and extracted with EtOAc (3×15 mL), and the combined organic phase was washed with brine (10 mL), dried over $MgSO_4$ and concentrated under reduced pressure to give 75 mg of a clear film. This crude product was combined with another 72 mg crude product from an additional reaction and purified by radial chromatography [2000 micron silica gel rotor; 5% MeOH/DCM eluent] to give 119 mg (86% for combined reactions) of the title compound as a white solid. MS (ESI+) for $C_{23}H_{26}N_4O_4$ m/z 423.4 (M+H)$^+$.

Step 4. Preparation of tert-butyl (4-{[(2S,3R)-2-cyano-4-oxo-1-{[(1R)-1-phenylethyl]-carbamoyl}azetidin-3-yl]methyl}pyridin-2-yl)(4-methoxybenzyl)carbamate

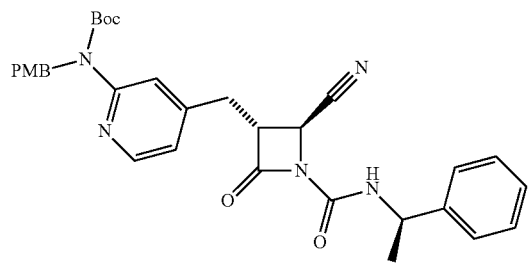

The title compound was prepared from tert-butyl (4-{[(2S,3R)-2-cyano-4-oxoazetidin-3-yl]methyl}pyridin-2-yl)(4-methoxybenzyl)carbamate and [(1R)-1-isocyanatoethyl]benzene according to the general procedure of Step 4 of Example 3 in 52% as a glassy solid. MS (ESI+) for $C_{32}H_{35}N_5O_5$ m/z 570.5 (M+H)$^+$.

Step 5. Preparation of (2S,3R)-3-[(2-aminopyridin-4-yl)methyl]-2-cyano-4-oxo-N-[(1R)-1-phenylethyl] azetidine-1-carboxamide trifluoroacetate

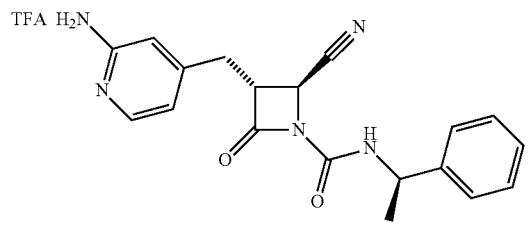

The title compound was prepared from tert-butyl (4-{[(2S,3R)-2-cyano-4-oxo-1-{[(1R)-1-phenylethyl] carbamoyl}azetidin-3-yl]methyl}pyridin-2-yl)(4-methoxybenzyl)carbamate according to the general procedure described in Step 6 of Example 3 in 51% as a white solid. $^1$H NMR (400 MHz, MeOD) δ 7.82 (d, J=6.8 Hz, 1H), 7.38 (m, 4H), 7.29 (m, 1H), 7.09 (bd, J=7.6 Hz, 1H), 6.97 (s, 1H), 6.91 (dd, J=6.8, 1.6 Hz, 1H), 5.00 (m, 1H), 4.70 (d, J=3.2 Hz, 1H), 4.17 (td, J=8.0, 3.2 Hz, 1H), 3.27 (d, J=8.0 Hz, 2H), 1.55 (d, J=6.8 Hz, 3H); MS (ESI+) for $C_{19}H_{19}N_5O_2$ (parent) m/z 350.3 (M+H)$^+$; HPLC retention time: 2.85 min (Method A).

Example 8

Scheme 2: (2S,3R)-3-[(2-Aminopyridin-4-yl)methyl]-2-cyano-N-(diphenylmethyl)-4-oxoazetidine-1-carboxamide trifluoroacetate.

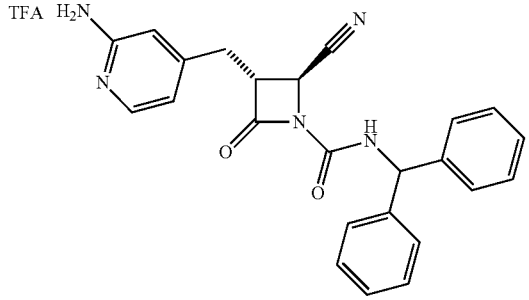

Step 1. Preparation of tert-butyl [4-({(2S,3R)-2-cyano-1-[(diphenylmethyl)carbamoyl]-4-oxoazetidin-3-yl}methyl)pyridin-2-yl](4-methoxybenzyl)carbamate

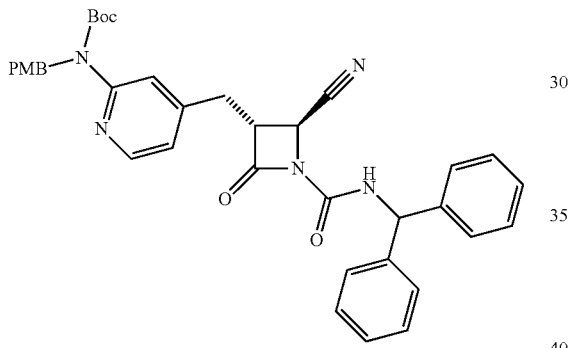

The title compound was prepared from tert-butyl (4-{[(2S,3R)-2-cyano-4-oxoazetidin-3-yl]methyl}pyridin-2-yl)(4-methoxybenzyl)carbamate and 1,1'-(isocyanatomethylene)dibenzene according to the general procedure of step 4 of Example 3 using a 1.5 h reaction time in 84% as a glassy solid. MS (ESI+) for $C_{37}H_{37}N_5O_5$ m/z 632.7 (M+H)$^+$.

Step 2. Preparation of (2S,3R)-3-[(2-aminopyridin-4-yl)methyl]-2-cyano-N-(diphenylmethyl)-4-oxoazetidine-1-carboxamide trifluoroacetate

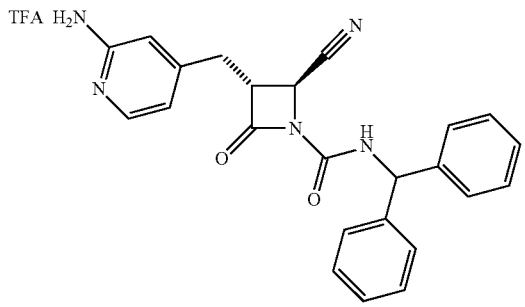

The title compound was prepared from tert-butyl [4-({(2S,3R)-2-cyano-1-[(diphenylmethyl)carbamoyl]-4-oxoazetidin-3-yl}methyl)pyridin-2-yl](4-methoxybenzyl)carbamate according to the general procedure of Step 6 of Example 3 in 54% as a white solid. $^1$H NMR (400 MHz, MeOD) δ 7.81 (d, J=6.8 Hz, 1H), 7.44 (bd, J=7.6 Hz, 1H), 7.28-7.40 (m, 10H), 6.96 (m, 1H), 6.91 (dd, J=6.8, 1.6 Hz, 1H), 6.15 (d, J=8.0 Hz, 1H), 4.73 (d, J=3.2 Hz, 1H), 4.22 (td, J=8.0, 3.2 Hz, 1H), 3.27 (d, J=8.0 Hz, 2H); MS (ESI+) for $C_{24}H_{21}N_5O_2$ (parent) m/z 412.4 (M+H)$^+$; HPLC retention time: 3.36 min (Method A).

Example 9

Scheme 3: (2S,3R)-3-[2-(2-Amino-1,3-thiazol-5-yl)ethyl]-1-(diphenylmethyl)carbamoyl]-4-oxoazetidine-2-carboxylic acid trifluoroacetate.

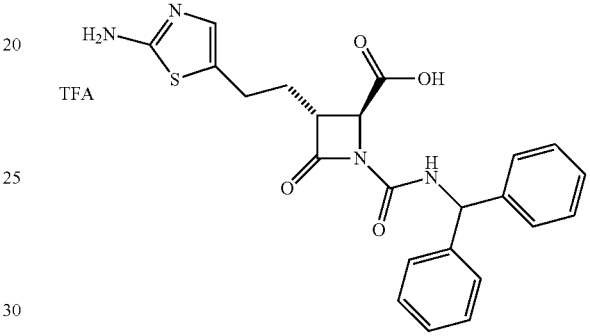

Step 1. Preparation of benzyl (2S,3R)-1-[tert-butyl(dimethyl)silyl]-4-oxo-3-pent-4-en-1-ylazetidine-2-carboxylate

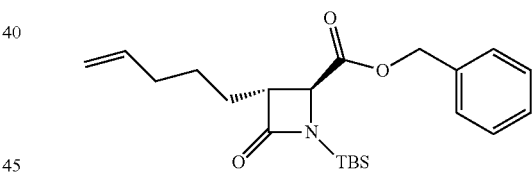

The title compound was prepared following the general procedure of steps 1 and 2 of Example 3 but using 5-bromopent-1-ene in step 1 and allowing the alkylation to warm to 0° C. The title compound was obtained in 29% as a viscous oil. MS (ESI+) for $C_{22}H_{33}NO_3Si$ m/z 388.3 (M+H)$^+$.

Step 2. Preparation of benzyl (2S,3R)-1-[tert-butyl(dimethyl)silyl]-4-oxo-3-(4-oxobutyl)azetidine-2-carboxylate

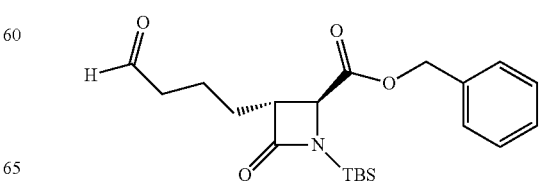

A stirred mixture of benzyl (2S,3R)-1-[tert-butyl(dimethyl)silyl]-4-oxo-3-pent-4-en-1-ylazetidine-2-carboxylate (412 mg, 1.06 mmol) in 1,4-dioxane (12 mL)/water (3 mL) was treated with N-methylmorpholine N-oxide (156 mg, 1.33 mmol) followed by osmium tetroxide (2.5 wt % in 2-methyl-2-propanol, 670 µL, 0.053 mmol), and the resulting mixture was stirred at rt under nitrogen for 2.5 h, at which point conversion to the benzyl (2S,3R)-1-[tert-butyl (dimethyl)silyl]-3-(4,5-dihydroxypentyl)-4-oxoazetidine-2-carboxylate intermediate [MS (ESI+) for $C_{22}H_{35}NO_5Si$ m/z 422.2 $(M+H)^+$] appeared complete by HPLC. Sodium metaperiodate (284 mg, 1.33 mmol) was added, and the resulting heterogeneous white mixture was stirred at rt for 2.5 h, at which point HPLC indicated the intermediate was consumed. The mixture was quenched with half-sat aqueous sodium thiosulfate (15 mL), diluted with water (15 mL) and extracted with EtOAc (2×40 mL). The combined organic phase was washed with brine (15 mL), dried over $MgSO_4$, filtered, concentrated and dried under reduced pressure to give 418 mg (100%) of the title compound as a viscous oil which was used without further purification. MS (ESI+) for $C_{21}H_{31}NO_4Si$ m/z 390.3 $(M+H)^+$.

Step 3. Preparation of benzyl (2S,3R)-3-[2-(2-amino-1,3-thiazol-5-yl)ethyl]-4-oxoazetidine-2-carboxylate

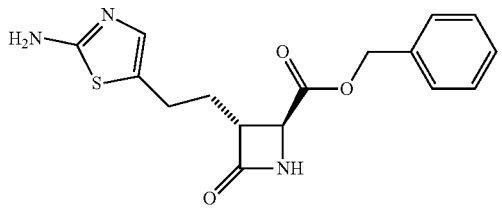 [SMILES: Nc1ncc(CC[C@H]2C(=O)N[C@@H]2C(=O)OCc2ccccc2)s1]

A stirred solution of benzyl (2S,3R)-1-[tert-butyl(dimethyl)silyl]-4-oxo-3-(4-oxobutyl)azetidine-2-carboxylate (414 mg, 1.06 mmol) in acetonitrile (11 mL) under nitrogen was treated with tetrabutylammonium tribromide (512 mg, 1.06 mmol) in one portion, and the resulting deep yellow, homogeneous mixture was stirred at rt for 75 min., at which point HPLC indicated starting material was consumed. The mixture was diluted with water (40 mL) and extracted with EtOAc (2×40 mL), and the combined organic phase was washed with water (2×40 mL) and brine (20 mL), dried over $MgSO_4$, filtered and concentrated under reduced pressure to give 302 mg of the crude benzyl (2S,3R)-3-(3-bromo-4-oxobutyl)-1-[tert-butyl(dimethyl)silyl]-4-oxoazetidine-2-carboxylate intermediate [MS (ESI+) for $C_{21}H_{30}BrNO_4Si$ m/z 468 $(M+H)^+$] as a tan viscous oil. A solution of this intermediate in EtOH (11 mL) was treated with thiourea (89.0 mg, 1.17 mmol), and the mixture was heated at gentle reflux for 2 h, cooled to rt, diluted with DCM (45 mL), washed with sat aqueous $NaHCO_3$ (30 mL), water (30 mL) and brine (20 mL), dried over $Na_2SO_4$, filtered and concentrated under reduced pressure. Purification by silica gel chromatography [40 g, 2.5-7.5% MeOH/DCM eluent] gave 60 mg (17%) of the title compound as a tan solid. MS (ESI+) for $C_{16}H_{17}N_3O_3S$ m/z 332.2 $(M+H)^+$. The TBS-protected by-product, benzyl (2S,3R)-3-[2-(2-amino-1,3-thiazol-5-yl)ethyl]-1-[tert-butyl(dimethyl)silyl]-4-oxoazetidine-2-carboxylate, was also isolated (145 mg, 24%, 80% purity). MS (ESI+) for $C_{22}H_{31}N_3O_3SSi$ m/z 446.2 $(M+H)^+$.

Step 4. Preparation of benzyl (2S,3R)-3-(2-{2-[(tert-butoxycarbonyl)amino]-1,3-thiazol-5-yl}ethyl)-4-oxoazetidine-2-carboxylate

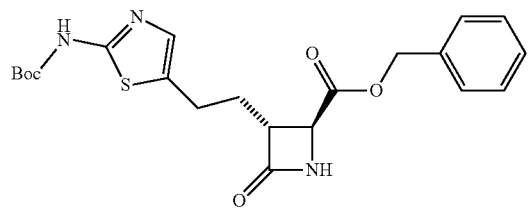 [SMILES: CC(C)(C)OC(=O)Nc1ncc(CC[C@H]2C(=O)N[C@@H]2C(=O)OCc2ccccc2)s1]

A stirred solution of benzyl (2S,3R)-3-[2-(2-amino-1,3-thiazol-5-yl)ethyl]-4-oxoazetidine-2-carboxylate (57.0 mg, 0.172 mmol) in acetonitrile (5 mL) under nitrogen was treated with di-tert-butyldicarbonate (48.8 mg, 0.224 mmol) and stirred at rt for approximately 2 days, during which time additional di-tert-butyldicarbonate (13 mg, 0.060 mmol) was added in one portion. The mixture was concentrated under reduced pressure and purified by radial chromatography [2000 micron silica gel rotor, 2.5-10% MeOH/DCM eluent] to give 74 mg (81%) of the title compound as a glassy film (contaminated with the bis-BOC by-product benzyl (2S,3R)-3-(2-{2-[bis(tert-butoxycarbonyl)amino]-1,3-thiazol-5-yl}ethyl)-4-oxoazetidine-2-carboxylate). MS (ESI+) for $C_{21}H_{25}N_3O_5S$ m/z 432.2 $(M+H)^+$.

Step 5. Preparation of benzyl (2S,3R)-3-(2-{2-[(tert-butoxycarbonyl)amino]-1,3-thiazol-5-yl}ethyl)-1-[(diphenylmethyl)carbamoyl]-4-oxoazetidine-2-carboxylate

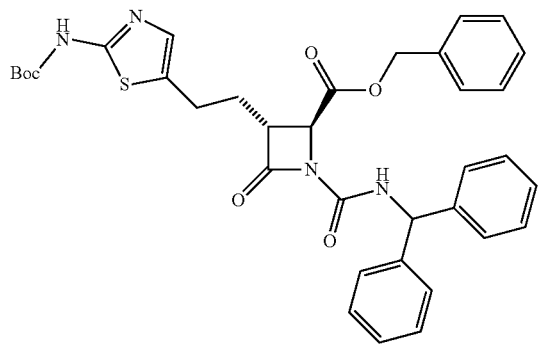 [SMILES: CC(C)(C)OC(=O)Nc1ncc(CC[C@H]2C(=O)N(C(=O)NC(c3ccccc3)c3ccccc3)[C@@H]2C(=O)OCc2ccccc2)s1]

The title compound was prepared from (2S,3R)-3-(2-{2-[(tert-butoxycarbonyl)amino]-1,3-thiazol-5-yl}ethyl)-4-oxoazetidine-2-carboxylate and 1,1'-(isocyanatomethylene)dibenzene following the general procedure of step 4 of Example 3 and using a 5 h reaction time in 82% as a glassy solid. MS (ESI+) for $C_{35}H_{36}N_4O_6S$ m/z 641.3 $(M+H)^+$.

Step 6. Preparation of (2S,3R)-3-(2-{2-[(tert-butoxycarbonyl)amino]-1,3-thiazol-5-yl}ethyl)-1-[(diphenylmethyl)carbamoyl]-4-oxoazetidine-2-carboxylic acid

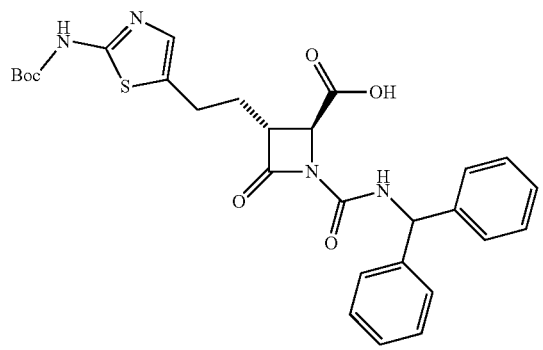 [SMILES: CC(C)(C)OC(=O)Nc1ncc(CC[C@H]2C(=O)N(C(=O)NC(c3ccccc3)c3ccccc3)[C@@H]2C(=O)O)s1]

A mixture of benzyl (2S,3R)-3-(2-{2-[(tert-butoxycarbonyl)amino]-1,3-thiazol-5-yl}ethyl)-1-[(diphenylmethyl)carbamoyl]-4-oxoazetidine-2-carboxylate (85.0 mg, 0.133 mmol) in 1:1 MeOH/EtOAc (6 mL) under nitrogen was treated with 10% palladium-on-carbon (35 mg, 0.013 mmol Pd), and the mixture was evacuated and filled with nitrogen twice and then stirred under a hydrogen atmosphere (double-layer balloon) for approximately 6 h, during which additional 10% palladium-on-carbon (35 mg, 0.013 mmol Pd) was added in one portion. The catalyst was filtered off through solka floc, rinsing with 1:1 MeOH/EtOAc, and the filtrate was concentrated under reduced pressure to give 71 mg (97%) of the title compound as an off-white foam which was used without further purification. MS (ESI+) for $C_{28}H_{30}N_4O_6S$ m/z 551.2 (M+H)+.

Step 7. Preparation of (2S,3R)-3-[2-(2-amino-1,3-thiazol-5-yl)ethyl]-1-[(diphenylmethyl)carbamoyl]-4-oxoazetidine-2-carboxylic acid trifluoroacetate

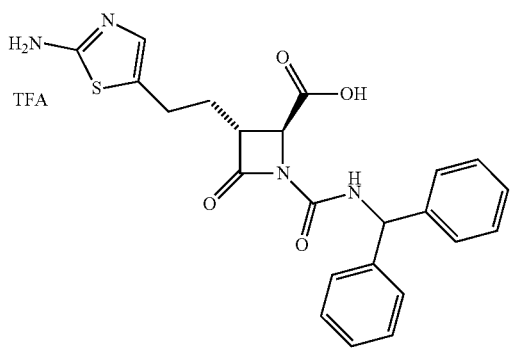 [SMILES: Nc1ncc(CC[C@H]2C(=O)N(C(=O)NC(c3ccccc3)c3ccccc3)[C@@H]2C(=O)O)s1]

The title compound was prepared from (2S,3R)-3-(2-{2-[(tert-butoxycarbonyl)amino]-1,3-thiazol-5-yl}ethyl)-1-[(diphenylmethyl)carbamoyl]-4-oxoazetidine-2-carboxylic acid following the general procedure of step 6 of Example 3 and using a 5 h reaction time in 47% as a white solid. $^1$H NMR (400 MHz, MeOD) δ 7.26-7.39 (m, 10H), 6.96 (br s, 1H), 6.11 (br s, 1H), 4.31 (br s, 1H), 3.40 (m, 1H), 2.88 (m, 2H), 2.16 (m, 2H); MS (ESI+) for $C_{23}H_{22}N_4O_4S$ (parent) m/z 451.0 (M+H)+; HPLC retention time: 3.25 min (Method A).

Example 10

Scheme 3: (2S,3R)-3-[2-(2-Amino-1,3-thiazol-5-yl)ethyl]-4-oxo-1-{[(1R)-1-phenylethyl]carbamoyl}azetidine-2-carboxylic acid trifluoroacetate.

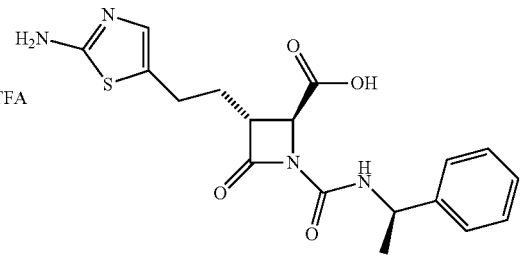

Step 1. Preparation of benzyl (2S,3R)-3-(2-{2-[(tert-butoxycarbonyl)amino]-1,3-thiazol-5-yl}ethyl)-4-oxo-1-{[(1R)-1-phenylethyl]carbamoyl}azetidine-2-carboxylate

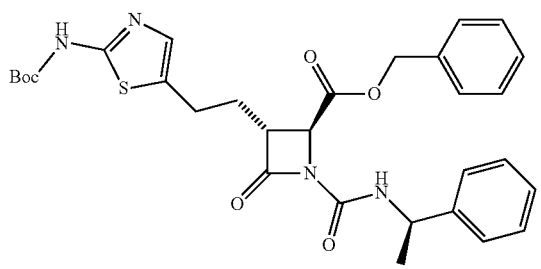 [SMILES: C[C@@H](NC(=O)N1C(=O)[C@H](CCc2cnc(NC(=O)OC(C)(C)C)s2)[C@H]1C(=O)OCc1ccccc1)c1ccccc1]

The title compound was prepared from benzyl (2S,3R)-3-(2-{2-[(tert-butoxycarbonyl)amino]-1,3-thiazol-5-yl}ethyl)-4-oxoazetidine-2-carboxylate and [(1R)-1-isocyanatoethyl]benzene following the general procedure of step 4 of Example 3 in 66% as a glassy solid. MS (ESI+) for $C_{30}H_{34}N_4O_6S$ m/z 579.3 (M+H)+.

Step 2. Preparation of (2S,3R)-3-(2-{2-[(tert-butoxycarbonyl)amino]-1,3-thiazol-5-yl}ethyl)-4-oxo-1-{[(1R)-1-phenlethyl]carbamoyl}azetidine-2-carboxylic acid

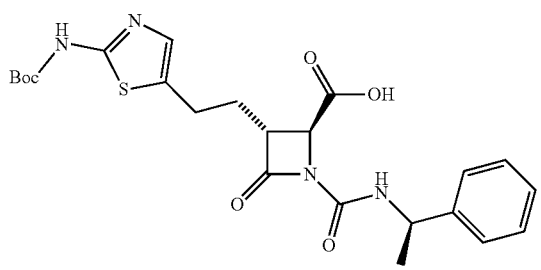 [SMILES: C[C@@H](NC(=O)N1C(=O)[C@H](CCc2cnc(NC(=O)OC(C)(C)C)s2)[C@H]1C(=O)O)c1ccccc1]

The title compound was prepared from benzyl (2S,3R)-3-(2-{2-[(tert-butoxycarbonyl)amino]-1,3-thiazol-5-yl}ethyl)-4-oxo-1-{[(1R)-1-phenylethyl]carbamoyl}azetidine-2-carboxylate following the general procedure of step 6 of Example 9 in 82% as a white solid. MS (ESI+) for C$_{23}$H$_{28}$N$_4$O$_6$S m/z 489.1 (M+H)+.

Step 3. Preparation of (2S,3R)-3-[2-(2-amino-1,3-thiazol-5-yl)ethyl]-4-oxo-1-{[(1R)-1-phenylethyl]carbamoyl}azetidine-2-carboxylic acid trifluoroacetate

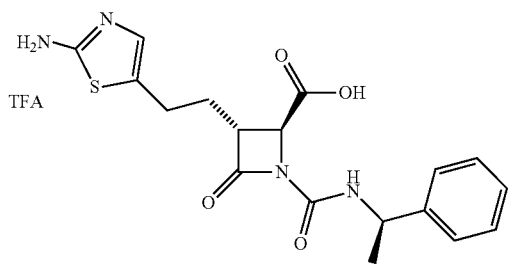 [SMILES: C[C@@H](NC(=O)N1C(=O)[C@H](CCc2cnc(N)s2)[C@H]1C(=O)O)c1ccccc1]

The title compound was prepared from (2S,3R)-3-(2-{2-[(tert-butoxycarbonyl)amino]-1,3-thiazol-5-yl}ethyl)-4-oxo-1-{[(1R)-1-phenylethyl]carbamoyl}azetidine-2-carboxylic acid following the general procedure of Step 6 of Example 3 and using a 5 h reaction time in 66% as a white solid. $^1$H NMR (400 MHz, MeOD) δ 7.36 (m, 4H), 7.27 (m, 1H), 6.96 (br s, 1H), 4.98 (q, J=6.8 Hz, 1H), 4.26 (br s, 1H), 3.35 (m, 1H), 2.89 (t, J=7.2 Hz, 2H), 2.16 (m, 2H), 1.53 (d, J=6.8 Hz, 3H); MS (ESI+) for C$_{18}$H$_{20}$N$_4$O$_4$S (parent) m/z 389.1 (M+H)$^+$; HPLC retention time: 2.71 min (Method A).

Example 11

Scheme 4: (2S,3R)-3-[2-(2-Amino-1,3-thiazol-5-yl)methyl]-1-[(diphenylmethyl)carbamoyl]-4-oxoazetidine-2-carboxylic acid trifluoroacetate

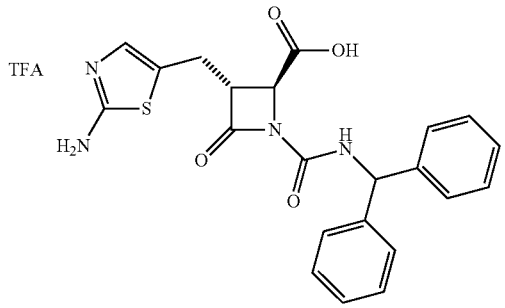

Step 1. Preparation of benzyl (2S,3R)-1-[tert-butyl(dimethyl)silyl]-3-[(2E)-3-chloroprop-2-en-1-yl]-4-oxoazetidine-2-carboxylate

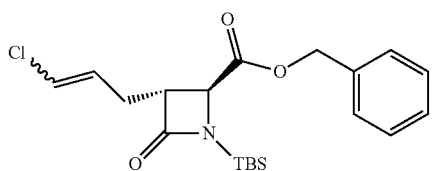

The title compound was prepared following the general procedures of steps 1-2 of Example 3 but using (1E)-1,3-dichloroprop-1-ene for tert-butyl [4-(bromomethyl)pyridin-2-yl](4-methoxybenzyl)carbamate in step 1 and allowing the reaction temperature to warm to 0° C. The title compound was obtained in 39% (mixture of E/Z isomers) as a viscous oil. MS (ESI+) for C$_{20}$H$_{28}$ClNO$_3$Si m/z 394.2 (M+H)$^+$.

Step 2. Preparation of benzyl (2S,3R)-3-[(2-amino-1,3-thiazol-5-yl)methyl]-1-[tert-butyl(dimethyl)silyl]-4-oxoazetidine-2-carboxylate

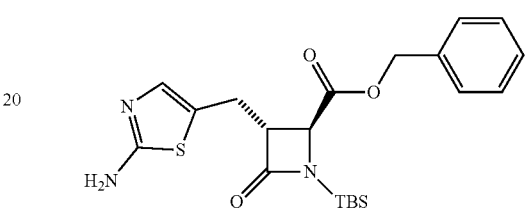

A stirred solution of benzyl (2S,3R)-1-[tert-butyl(dimethyl)silyl]-3-[(2E)-3-chloroprop-2-en-1-yl]-4-oxoazetidine-2-carboxylate (220 mg, 0.558 mmol) in dry 1,2-dichloroethane (2.8 mL) in a screw-cap vial was treated with m-chloroperbenzoic acid (289 mg, 1.68 mmol, washed and dried, >90% purity) and 2,6-di-tert-butyl-4-methylphenol (7.0 mg, 0.032 mmol), heated quickly to 60° C. and stirred at this temperature for 18 h. The mixture was cooled to rt, diluted with EtOAc (20 mL), washed with sat aqueous NaHCO$_3$ (2×20 mL), half-sat aqueous sodium thiosulfate (2×15 mL), water (20 mL) and brine (10 mL), dried over MgSO$_4$ and concentrated under reduced pressure to give the crude benzyl (2S,3R)-1-[tert-butyl(dimethyl)silyl]-3-[(3-chlorooxiran-2-yl)methyl]-4-oxoazetidine-2-carboxylate intermediate [MS (ESI+) for C$_{20}$H$_{28}$ClNO$_4$Si m/z 410.2 (M+H)$^+$] as a viscous oil which was used without further purification. A stirred mixture of this intermediate in dry 1,2-dimethoxyethane (5.5 mL) under nitrogen was treated with thiourea (53.1 mg, 0.698 mmol), heated to 60° C. and stirred at this temperature for 2.5 h, at which point HPLC and LC-MS indicated the intermediate was consumed. The mixture was cooled to rt, diluted with EtOAc (30 mL), water (8 mL) and sat aqueous NaHCO$_3$ (8 mL), and the layers were separated. The organic phase was washed with sat aqueous NaHCO$_3$ (15 mL), water (15 mL) and brine (10 mL), dried over MgSO$_4$ and concentrated under reduced pressure to give 240 mg of the crude product, which was combined with 100 mg crude product from a previous reaction. Purification by radial chromatography [2000 micron silica gel rotor; 5-10% MeOH/DCM eluent] gave 172 mg (49% for combined reactions) of the title compound as a viscous oil. MS (ESI+) for C$_{21}$H$_{29}$N$_3$O$_3$SSi m/z 432.3 (M+H)$^+$.

Step 3. Preparation of benzyl (2S,3R)-3-({2-[(tert-butoxycarbonyl)amino]-1,3-thiazol-5-yl}methyl)-1-[tert-butyl(dimethyl)silyl]-4-oxoazetidine-2-carboxylate

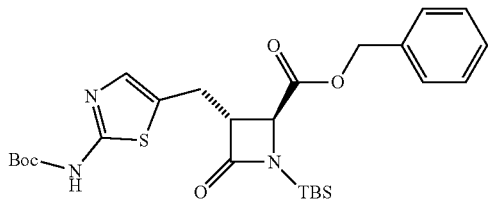

A stirred solution of benzyl (2S,3R)-3-[(2-amino-1,3-thiazol-5-yl)methyl]-1-[tert-butyl(dimethyl)silyl]-4-oxoazetidine-2-carboxylate (168 mg, 0.389 mmol) in acetonitrile (6 mL) under nitrogen was treated with di-tert-butyldicarbonate (170 mg, 0.778 mmol), and the resulting mixture was stirred at rt for approx. 24 h, at which point HPLC indicated reaction was complete. The mixture was concentrated under reduced pressure and purified by radial chromatography [2000 micron silica gel rotor; 30-50% EtOAc/hexanes eluent] to give the 242 mg (100%) of the title compound as an oily film (contaminated with the bis-BOC by-product benzyl (2S,3R)-3-({2-[bis(tert-butoxycarbonyl)amino]-1,3-thiazol-5-yl}methyl)-1-[tert-butyl(dimethyl)silyl]-4-oxoazetidine-2-carboxylate). MS (ESI+) for $C_{26}H_{37}N_3O_5SSi$ m/z 532.3 (M+H)$^+$.

Step 4. Preparation of benzyl (2S,3R)-3-({2-[(tert-butoxycarbonyl)amino]-1,3-thiazol-5-yl}methyl)-4-oxoazetidine-2-carboxylate

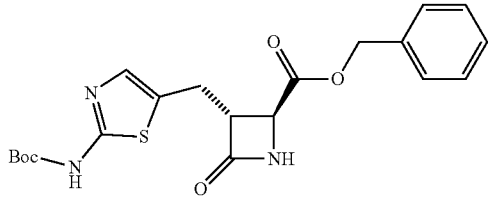 [SMILES: CC(C)(C)OC(=O)Nc1ncc(C[C@H]2C(=O)N[C@@H]2C(=O)OCc2ccccc2)s1]

The title compound was prepared from benzyl (2S,3R)-3-({2-[(tert-butoxycarbonyl)amino]-1,3-thiazol-5-yl}methyl)-1-[tert-butyl(dimethyl)silyl]-4-oxoazetidine-2-carboxylate following the general procedure of step 3 of Example 3 in 99% (contaminated with bis-BOC by-product benzyl (2S,3R)-3-({2-[bis(tert-butoxycarbonyl)amino]-1,3-thiazol-5-yl}methyl)-4-oxoazetidine-2-carboxylate). MS (ESI+) for $C_{20}H_{23}N_3O_5S$ m/z 418.2 (M+H)$^+$.

Step 5. Preparation of benzyl (2S,3R)-3-({2-[(tert-butoxycarbonyl)amino]-1,3-thiazol-5-yl}methyl)-1-[(diphenylmethyl)carbamoyl]-4-oxoazetidine-2-carboxylate

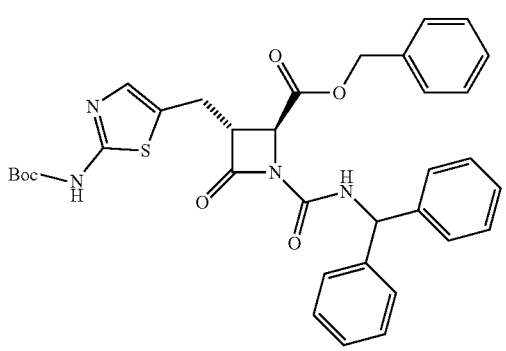 [SMILES: CC(C)(C)OC(=O)Nc1ncc(C[C@H]2C(=O)N(C(=O)NC(c3ccccc3)c3ccccc3)[C@@H]2C(=O)OCc2ccccc2)s1]

The title compound was prepared from benzyl (2S,3R)-3-({2-[(tert-butoxycarbonyl)amino]-1,3-thiazol-5-yl}methyl)-4-oxoazetidine-2-carboxylate and 1,1'-(isocyanatomethylene)dibenzene following the general procedure of step 4 of Example 3 using a 3 h reaction time in 88% as a glassy solid. MS (ESI+) for $C_{34}H_{34}N_4O_6S$ m/z 627.4 (M+H)+.

Step 6. Preparation of (2S,3R)-3-({2-[(tert-butoxycarbonyl)amino]-1,3-thiazol-5-yl}methyl)-1-[(diphenylmethyl)carbamoyl]-4-oxoazetidine-2-carboxylic acid

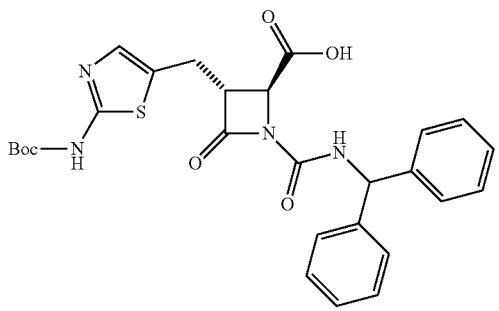

The title compound was prepared from benzyl (2S,3R)-3-({2-[(tert-butoxycarbonyl)amino]-1,3-thiazol-5-yl}methyl)-1-[(diphenylmethyl)carbamoyl]-4-oxoazetidine-2-carboxylate following the general procedure of step 6 of Example 9 in quantitative yield as a white solid. MS (ESI+) for $C_{27}H_{28}N_4O_6S$ n/z 537.3 (M+H)$^+$.

Step 7. Preparation of (2S,3R)-3-[(2-amino-1,3-thiazol-5-yl)methyl]-1-[(diphenylmethyl)carbamoyl]-4-oxoazetidine-2-carboxylic acid trifluoroacetate

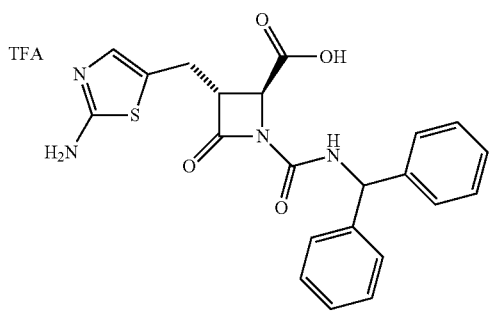

The title compound was prepared from (2S,3R)-3-({2-[(tert-butoxycarbonyl)amino]-1,3-thiazol-5-yl}methyl)-1-[(diphenylmethyl)carbamoyl]-4-oxoazetidine-2-carboxylic acid following the general procedure of step 6 of Example 3 and using a 3 h reaction time in 53% as a white solid. $^1$H NMR (400 MHz, MeOD) δ 7.49 (d, J=8.4 Hz, 1H), 7.40-7.27 (m, 10H), 7.14 (s, 1H), 6.12 (m, 1H), 4.34 (d, J=2.8 Hz, 1H), 3.69 (td, J=7.2, 2.8 Hz, 1H), 3.25 (m, 2H); MS (ESI+) for $C_{22}H_{20}N_4O_4S$ (parent) n/z 437.1 (M+H)$^+$; HPLC retention time: 3.11 min (Method A).

Example 12

Scheme 4: (2S,3R)-3-[(2-Amino-1,3-thiazol-5-yl)methyl]-4-oxo-1-{[(1R)-1-phenylethyl]carbamoyl}azetidine-2-carboxylic acid trifluoroacetate

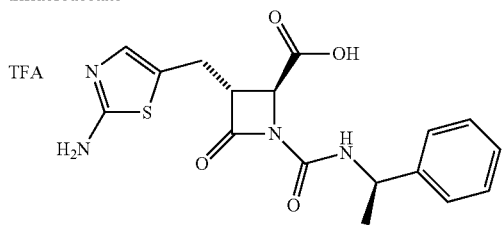

Step 1. Preparation of benzyl (2S,3R)-3-({2-[(tert-butoxycarbonyl)amino]-1,3-thiazol-5-yl}methyl)-4-oxo-1-{[(1R)-1-phenylethyl]carbamoyl}azetidine-2-carboxylate

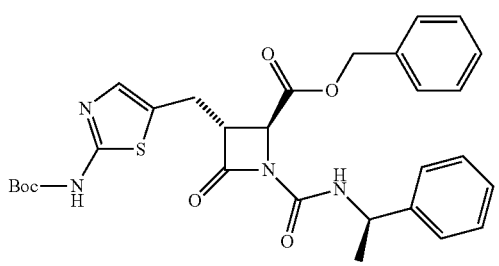

The title compound was prepared from benzyl (2S,3R)-3-({2-[(tert-butoxycarbonyl)amino]-1,3-thiazol-5-yl}methyl)-4-oxoazetidine-2-carboxylate and [(1R)-1-isocyanatoethyl]benzene following the general procedure of step 4 of Example 3, in approx. 95% as a glassy solid. MS (ESI+) for $C_{29}H_{32}N_4O_6S$ m/z 565.2 (M+H)$^+$.

Step 2. Preparation of (2S,3R)-3-({2-[(tert-butoxycarbonyl)amino]-1,3-thiazol-5-yl}methyl)-4-oxo-1-{[(1R)-1-phenylethyl]carbamoyl}azetidine-2-carboxylic acid

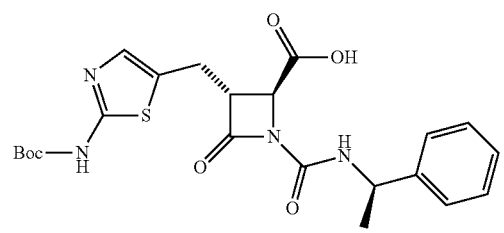

The title compound was prepared from benzyl (2S,3R)-3-({2-[(tert-butoxycarbonyl)amino]-1,3-thiazol-5-yl}methyl)-4-oxo-1-{[(1R)-1-phenylethyl]carbamoyl}azetidine-2-carboxylate following the general procedure of step 6 of Example 9 in 75% as a white solid. MS (ESI+) for $C_{22}H_{26}N_4O_6S$ m/z 475.2 (M+H)$^+$.

Step 3. Preparation of (2S,3R)-3-[(2-amino-1,3-thiazol-5-yl)methyl]-4-oxo-1-{[(1R)-1-phenylethyl]carbamoyl}azetidine-2-carboxylic acid trifluoroacetate

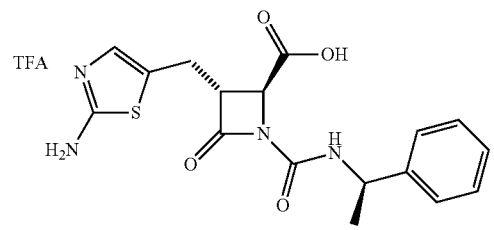

The title compound was prepared from (2S,3R)-3-({2-[(tert-butoxycarbonyl)amino]-1,3-thiazol-5-yl}methyl)-4-oxo-1-{[(1R)-1-phenylethyl]carbamoyl}azetidine-2-carboxylic acid following the general procedure of step 6 of Example 3 using a 5 h reaction time in 54% as a white solid. $^1$H NMR (400 MHz, MeOD) δ 7.37 (m, 4H), 7.28 (m, 1H), 7.16 (s, 1H), 4.98 (q, J=6.8 Hz, 1H), 4.32 (d, J=2.8 Hz, 1H) 3.65 (td, J=7.2, 2.8 Hz, 1H), 3.25 (m, 2H), 1.54 (d, J=7.2H, 3H); MS (ESI+) for $C_{17}H_{18}N_4O_4S$ (parent) m/z 375.3 (M+H)$^+$; HPLC retention time: 2.58 min (Method A).

Example 13

Scheme 5: (2S,3R)-3-[(2-aminopyridin-4-yl)methyl]-4-oxo-N-1-[(1R)-1-phenylethyl]azetidine-1,2-dicarboxamide trifluoroacetate

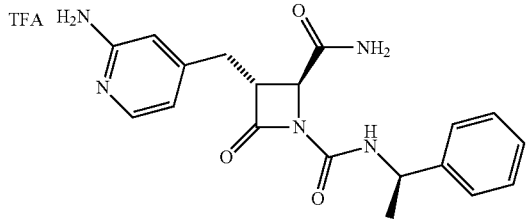

Step 1. Preparation of di-tert-butyl [4-({(3R,4S)-1-[tert-butyl(dimethyl)silyl]-2-oxo-4-[(2,4,6-trimethoxybenzyl)carbamoyl]azetidin-3-yl}methyl)pyridin-2-yl]imidodicarbonate

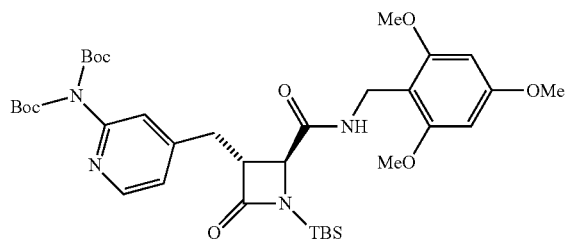

A solution of (2S,3R)-3-({2-[bis(tert-butoxycarbonyl)amino]pyridin-4-yl}methyl)-1-[tert-butyl(dimethyl)silyl]-4-oxoazetidine-2-carboxylic acid (170 mg, 0.32 mmol) in N,N-dimethylformamide (2.0 mL) was treated with (2,4,6-trimethoxyphenyl)methanamine hydrochloride (81.6 mg, 0.349 mmol) and N,N,N',N'-tetramethyl-O-(7-azabenzotriazol-1-yl)uronium hexafluorophosphate (145 mg, 0.381 mmol) followed by dropwise addition of N,N-diisopropylethylamine (182 µL, 1.05 mmol), and the reaction mixture was stirred at 0° C. HPLC analysis after 15 min indicated the starting material had been consumed. The reaction mixture was diluted with 25 mL H$_2$O, extracted with two 25 mL portions of CH$_2$Cl$_2$ and the combined organic phase was washed with 20 mL portions of H$_2$O and brine. The organic phase was dried over Na$_2$SO$_4$, filtered and concentrated to yield a slightly tan liquid that was placed on high vac to remove DMF. The crude material was purified by flash chromatography (60 g silica gel, 15-50% EtOAc/CH$_2$Cl$_2$) to yield the title compound (130 mg, 60%) as a slightly yellow glass: HPLC retention time: 5.05 min (Method A); MS (ESI+) for C$_{36}$H$_{54}$N$_4$O$_9$Si m/z 715.5 (M+H)$^+$.

Step 2. Preparation of di-tert-butyl [4-({(3R,4S)-2-oxo-4-[(2,4,6-trimethoxybenzyl)carbamoyl]azetidin-3-yl}methyl)pyridin-2-yl]imidodicarbonate

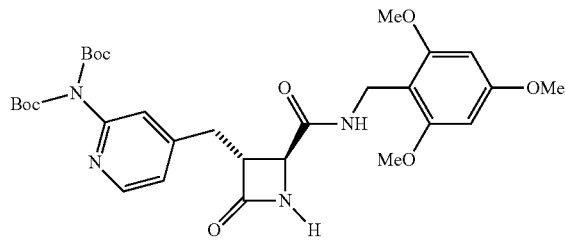

A solution of di-tert-butyl [4-({(3R,4S)-1-[tert-butyl(dimethyl)silyl]-2-oxo-4-[(2,4,6-trimethoxybenzyl)carbamoyl]azetidin-3-yl}methyl)pyridin-2-yl]imidodicarbonate (137 mg, 0.192 mmol) in methanol (3.3 mL) was treated dropwise with acetic acid (38 µL, 0.67 mmol) followed by 0.5 M ammonium fluoride in methanol (0.46 mL, 0.23 mmol) and the reaction mixture was stirred at room temperature. HPLC after 1.5 h indicated the reaction was complete. The reaction mixture was concentrated, the residue diluted with 7 mL toluene and concentrated. The residue was taken up in 20 mL CH$_2$Cl$_2$ and washed with 10 mL portions of H$_2$O and sat NaHCO$_3$. The organic phase was dried over Na$_2$SO$_4$, filtered and concentrated to yield the title compound (70 mg, 95%) as a light yellow stiff foam: HPLC retention time, 3.84 min (Method A); MS (ESI+) for C$_{30}$H$_{40}$N$_4$O$_9$ m/z 601.3 (M+H)$^+$.

Step 3. Preparation of di-tert-butyl [4-({(3R,4S)-2-oxo-1-{[(1R)-1-phenylethyl]carbamoyl}-4-[(2,4,6-trimethoxybenzyl)carbamoyl]azetidin-3-yl}methyl)pyridin-2-yl]imidodicarbonate

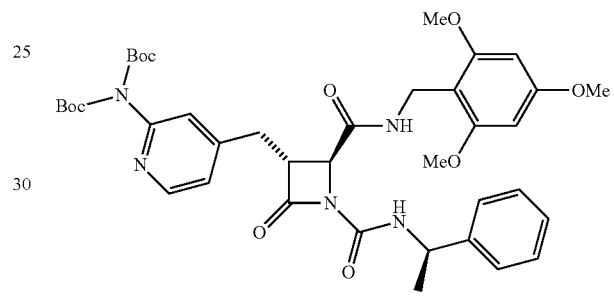

A solution of di-tert-butyl [4-({(3R,4S)-2-oxo-4-[(2,4,6-trimethoxybenzyl)carbamoyl]azetidin-3-yl}methyl)pyridin-2-yl]imidodicarbonate (94 mg, 0.16 mmol) in methylene chloride (2.5 mL) was treated dropwise with triethylamine (87 µL, 0.63 mmol) followed by [(1R)-1-isocyanatoethyl]benzene (29 µL, 0.20 mmol) and the reaction mixture was stirred at room temperature. After 4 h, HPLC indicated the reaction was complete. The reaction mixture was concentrated and the residue was taken up in 5 mL CH$_2$Cl$_2$ and concentrated to a slightly yellow glass. The crude material was purified by flash chromatography (30 g silica gel, 40-70% EtOAc/hex) to yield the title compound (94 mg, 80%) as a colorless glass: HPLC retention time, 4.88 min (Method A); MS (ESI+) for C$_{39}$H$_{49}$N$_5$O$_{10}$ m/z 748.9 (M+H)$^+$; MS (ESI−) for C$_{39}$H$_{49}$N$_5$O$_{10}$ m/z 746.5 (M−H)$^-$.

Step 4. Preparation of (2S,3R)-3-[(2-aminopyridin-4-yl)methyl]-4-oxo-N-1-[(1R)-1-phenylethyl]azetidine-1,2-dicarboxamide trifluoroacetate

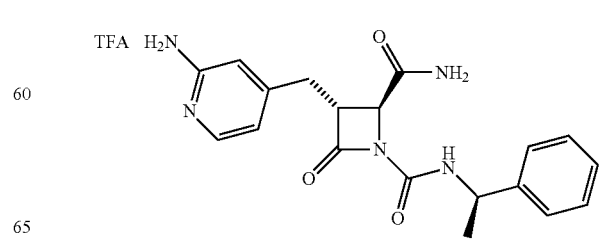

A solution of di-tert-butyl [4-({(3R,4S)-2-oxo-1-{[(1R)-1-phenylethyl]carbamoyl}-4-[(2,4,6-trimethoxybenzyl)carbamoyl]azetidin-3-yl}methyl)pyridin-2-yl]imidodicarbonate (94 mg, 0.12 mmol) in methylene chloride (4.0 mL) was cooled at 0° C., treated dropwise with trifluoroacetic acid (1.0 mL, 13 mmol) and the mixture was stirred at 0° C. for 60 minutes at which time the reaction was allowed to warm to room temperature. After stirring for 24 h, the reaction was found to be complete by HPLC. The reaction mixture was concentrated and the crude material was purified by CombiFlash chromatography [30 g RediSep C-18 gold silica gel cartridge, solvent gradient: 10% acetonitrile (0.07% TFA)/water (0.1% TFA) to 100% acetonitrile (0.07% TFA)] to yield the title compound (31 mg, 51%) as a white solid after lyophilization: HPLC retention time: 2.58 min (Method A); MS (ESI+) for $C_{19}H_{21}N_5O_3$ m/z 368.1 (M+H)+; $^1$H NMR (400 MHz, MeOD) δ 7.96 (1H, br. s.) 7.77 (1H, d, J=6.6 Hz) 7.40 (1H, br. s.) 7.35 (4H, m) 7.26 (1H, m) 7.09 (1H, d, J=7.8 Hz) 6.96 (1H, s) 6.89 (1H, dd, J=6.7, 1.6 Hz) 4.96 (1H, m) 4.28 (1H, d, J=2.8 Hz) 3.67 (1H, dt, J=8.0, 2.8 Hz) 3.23 (2H, m) 1.52 (3H, d, J=7.1 Hz).

Example 14

Scheme 6: 4-{[(2R,3R)-3-[(2-aminopyridin-4-yl)methyl]-4-oxo-1-{[(1R)-1-phenylethyl]carbamoyl}azetidin-2-yl]oxy}benzoic acid trifluoroacetate

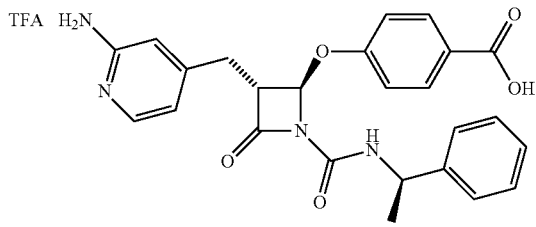

Step 1. Preparation of (2R,3R)-3-({2-[bis(tert-butoxycarbonyl)amino]pyridin-4-yl}methyl)-1-[tert-butyl(dimethyl)silyl]-4-oxoazetidin-2-yl 3-chlorobenzoate

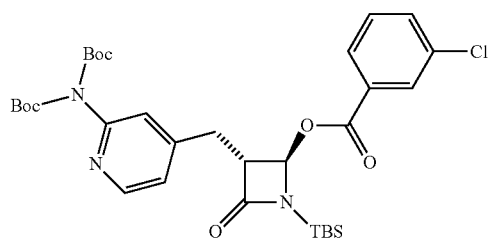

A solution of (2S,3R)-3-({2-[bis(tert-butoxycarbonyl)amino]pyridin-4-yl}methyl)-1-[tert-butyl(dimethyl)silyl]-4-oxoazetidine-2-carboxylic acid (201 mg, 0.375 mmol) in methylene chloride (7.0 mL) was cooled at 0° C. with an ice bath and treated with m-chloroperbenzoic acid (79 mg, 0.41 mmol) followed by N,N'-dicyclohexylcarbodiimide (85 mg, 0.41 mmol) and the reaction mixture was stirred at 0° C. for 25 min at which point HPLC indicated the starting material had been consumed. The reaction mixture was filtered, the solid was washed with 20 mL of 1/1 Et$_2$O/CH$_2$Cl$_2$ and the filtrate was washed with 15 mL H$_2$O and brine. The organic phase was dried over Na$_2$SO$_4$, filtered and concentrated to yield a light yellow glass. The crude material was purified by flash chromatography (45 g silica gel, 10-30% EtOAc/hex) to yield the title compound (131 mg, 54%) as a colorless glass: HPLC retention time, 5.95 min (Method A); MS (ESI+) for $C_{32}H_{44}ClN_3O_7Si$ m/z 646.3/648.3 (M+H)+.

Step 2. Preparation of (2R,3R)-3-({2-[bis(tert-butoxycarbonyl)amino]pyridin-4-yl}methyl)-4-oxoazetidin-2-yl 3-chlorobenzoate

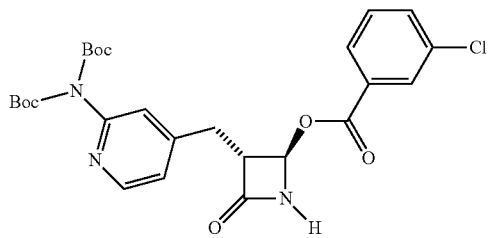

A solution of (2R,3R)-3-({2-[bis(tert-butoxycarbonyl)amino]pyridin-4-yl}methyl)-1-[tert-butyl(dimethyl)silyl]-4-oxoazetidin-2-yl 3-chlorobenzoate (130.0 mg, 0.201 mmol) in methanol (3.0 mL, 74 mmol) was treated with acetic acid (40 µL, 0.70 mmol) followed by 0.5 M ammonium fluoride in methanol (0.48 mL, 0.24 mmol) and the reaction mixture was stirred at room temperature for 1 h at which point HPLC indicated the starting material had been consumed. The reaction mixture was concentrated in vacuo, the residue was taken up in 5 mL toluene and the solution was concentrated. This process was repeated once, the residue was taken up in 25 mL CH$_2$Cl$_2$ and the solution was washed with 15 mL H$_2$O and sat. NaHCO$_3$ solution. The organic phase was dried over Na$_2$SO$_4$, filtered and concentrated to yield the title compound (106 mg, 96%) as a slightly yellow glass: HPLC retention time: 4.43 min (Method A); MS (ESI+) for $C_{26}H_{30}ClN_3O_7$ m/z 532.1/534.2 (M+H)+.

Step 3. Preparation of benzyl 4-{[(2R,3R)-3-({2-[bis(tert-butoxycarbonyl)amino]pyridin-4-yl}methyl)-4-oxoazetidin-2-yl]oxy}benzoate

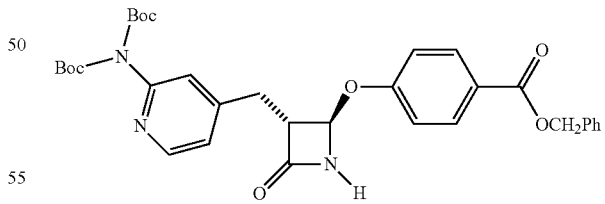

A solution of (2R,3R)-3-({2-[bis(tert-butoxycarbonyl)amino]pyridin-4-yl}methyl)-4-oxoazetidin-2-yl 3-chlorobenzoate (105 mg, 0.197 mmol) in acetonitrile (13 mL) and water (1 mL) was treated with benzyl p-hydroxybenzoate (45 mg, 0.20 mmol) followed by cesium carbonate (96 mg, 0.30 mmol) and the mixture was stirred at room temperature for 70 min, at which point HPLC indicated the starting material had been consumed. The reaction mixture was diluted with 25 mL H$_2$O and extracted with three 25 mL portions of EtOAc. The organic phase was washed with 25 mL brine and dried over Na$_2$SO$_4$. The solution was filtered and concentrated to yield a colorless glass which was purified by flash chromatography (30 g silica gel, 50-60% EtOAc/hex) to yield the title compound (85 mg, 71%) as a colorless glass: HPLC retention time, 4.71 min (Method A); MS (ESI+) for C$_{33}$H$_{37}$N$_3$O$_8$ m/z 604.3 (M+H)$^+$; MS (ESI−) for C$_{33}$H$_{37}$N$_3$O$_8$ m/z 604.6 (M−H)$^−$.

Step 4. Preparation of benzyl 4-{[(2R,3R)-3-({2-[bis(tert-butoxycarbonyl)amino]pyridin-4-yl}methyl)-4-oxo-1-{[(1R)-1-phenylethyl]carbamoyl}azetidin-2-yl]oxy}benzoate

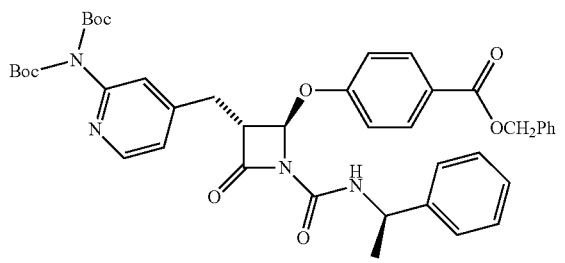

A solution of benzyl 4-{[(2R,3R)-3-({2-[bis(tert-butoxycarbonyl)amino]pyridin-4-yl}methyl)-4-oxoazetidin-2-yl]oxy}benzoate (82 mg, 0.14 mmol) in methylene chloride (2.2 mL) was treated dropwise with triethylamine (76 μL, 0.54 mmol) followed by [(1R)-1-isocyanatoethyl]benzene (25 μL, 0.18 mmol) and the reaction mixture was stirred at room temperature for 4 h, at which point HPLC indicated nearly all the starting material had been consumed. An additional 10 μL of isocyanate was added, and the reaction was continued for another hour. The reaction mixture was concentrated, the residue taken up in 5 mL CH$_2$Cl$_2$ and the solution concentrated to yield a white stiff foam. The crude material was purified by flash chromatography (25 g silica gel, 25-45 EtOAc/hex) to yield the title compound (87 mg, 85%) as a colorless glass: HPLC retention time: 5.54 min (Method A); MS (ESI+) for C$_{42}$H$_{46}$N$_4$O m/z 751.4 (M+H)$^+$.

Step 5. Preparation of 4-{[(2R,3R)-3-({2-[bis(tert-butoxycarbonyl)amino]pyridin-4-yl}methyl)-4-oxo-1-{[(1R)-1-phenylethyl]carbamoyl}azetidin-2-yl]oxy}benzoic acid

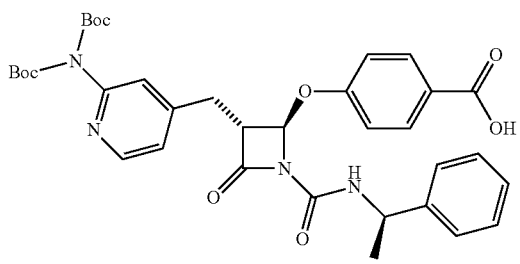

A solution of benzyl 4-{[(2R,3R)-3-({2-[bis(tert-butoxycarbonyl)amino]pyridin-4-yl}methyl)-4-oxo-1-{[(1R)-1-phenylethyl]carbamoyl}azetidin-2-yl]oxy}benzoate (87 mg, 0.12 mmol) in methanol (3.0 mL) and ethyl acetate (3.0 mL) was carefully treated with 10% palladium on carbon (12 mg). The reaction flask was evacuated and filled with hydrogen gas three times and the mixture was stirred under an atmosphere of hydrogen for 4.5 h at which point TLC had indicated the starting material had been consumed. The reaction mixture was filtered through a pad of solka floc and the pad was washed with 40 mL 1/1 EtOAc/MeOH. The filtrate was concentrated to yield the title compound (77 mg, 100%) as a colorless glass: HPLC retention time, 4.56 min (Method A); MS (ESI+) for C$_{35}$H$_{40}$N$_4$O$_9$ m/z 661.3 (M+H)$^+$; MS (ESI−) for C$_{35}$H$_{40}$N$_4$O$_9$ m/z 559.8 (M−H)$^−$.

Step 6. Preparation of 4-{[(2R,3R)-3-[(2-aminopyridin-4-yl)methyl]-4-oxo-1-{[(1R)-1-phenylethyl]carbamoyl}azetidin-2-yl]oxy}benzoic acid trifluoroacetate

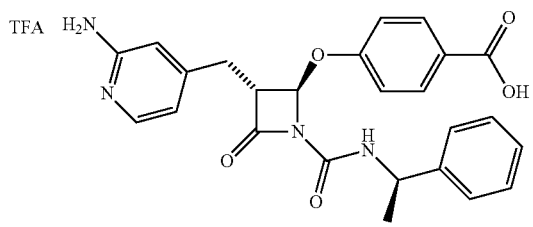

A solution of 4-{[(2R,3R)-3-({2-[bis(tert-butoxycarbonyl)amino]pyridin-4-yl}methyl)-4-oxo-1-{[(1R)-1-phenylethyl]carbamoyl}azetidin-2-yl]oxy}benzoic acid (76 mg, 0.12 mmol) in methylene chloride (3.3 mL) was cooled at 0° C. and treated dropwise with trifluoroacetic acid (0.66 mL, 8.6 mmol). The reaction mixture was stirred at 0° C. for 1 h, after which the ice bath was allowed to slowly expire. After 7 h, HPLC indicated the starting material had been consumed. The reaction mixture was concentrated in vacuo. The residue was taken up in 5 mL CH$_2$Cl$_2$ and concentrated to yield the crude product as a light pink glass. The material was purified by CombiFlash chromatography [30 g RediSep C-18 gold silica gel cartridge, solvent gradient: 10% acetonitrile (0.07% TFA)/water (0.1% TFA) to 100% acetonitrile (0.07% TFA)] to yield the title compound (32 mg, 48%) as a white powder: HPLC retention time: 3.13 min (Method A); MS (ESI+) for C$_{25}$H$_{24}$N$_4$O$_5$ m/z 461.1 (M+H)$^+$; $^1$H NMR (400 MHz, MeOD) δ 7.94 (2H, m) 7.72 (1H, d, J=6.6 Hz) 7.34 (4H, m) 7.27 (2H, m) 7.13 (2H, m) 6.91 (1H, s) 6.86 (1H, dd, J=6.8, 1.5 Hz) 6.08 (1H, d, J=1.5 Hz) 4.96 (1H, m) 3.79 (1H, dt, J=8.2, 1.5 Hz) 3.24 (2H, d, J=8.1 Hz) 1.53 (3H, d, J=7.1 Hz).

Example 15

Scheme 7: (2R,3S)-3-[(2-aminopyridin-4-yl)methyl]-2-(methylsulfonyl)-4-oxo-N-[(1R)-1-phenylethyl]azetidine-1-carboxamide trifluoroacetate

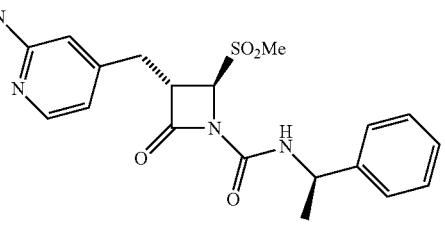

Step 1. Preparation of tert-butyl (4-methoxybenzyl) (4-{[(2R,3S)-2-(methylsulfonyl)-4-oxoazetidin-3-yl]methyl}pyridin-2-yl)carbamate

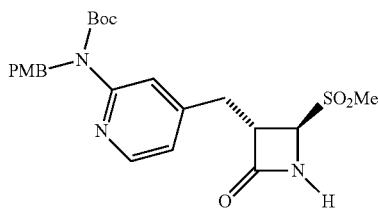

A solution of (2R,3R)-3-({2-[(tert-butoxycarbonyl)(4-methoxybenzyl)amino]pyridin-4-yl}methyl)-4-oxoazetidin-2-yl 3-chlorobenzoate (100 mg, 0.181 mmol) in acetonitrile (4.0 mL) and water (1.1 mL) was treated with sodium methanesulfinate (87 mg, 0.72 mmol). The mixture was stirred at room temperature for 4 h at which time HPLC indicated the starting material had been consumed. The reaction mixture was concentrated to remove most of the $CH_3CN$ and diluted with 10 mL $H_2O$. The aqueous phase was extracted with three 10 mL portions of EtOAc. The combined organic phase was dried over $MgSO_4$, filtered and concentrated to yield a colorless glass. The crude material was purified by prep TLC (20 cm×10 cm×1.0 mm prep TLC plate, 65% EtOAc/hex) to yield the title compound (52 mg, 60%) as a colorless glass: HPLC retention time, 3.50 min (Method A); MS (ESI+) for $C_{23}H_{29}N_3O_6S$ m/z 476.4 $(M+H)^+$; MS (ESI−) for $C_{23}H_{29}N_3O_6S$ m/z 474.3 $(M-H)^-$.

Step 2. Preparation of tert-butyl (4-methoxybenzyl) (4-{[(2R,3S)-2-(methylsulfonyl)-4-oxo-1-{[(1R)-1-phenylethyl]carbamoyl}azetidin-3-yl]methyl}pyridin-2-yl)carbamate

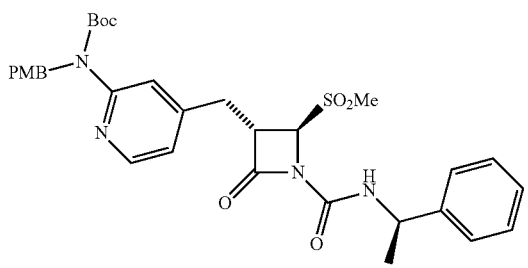

A solution of tert-butyl (4-methoxybenzyl)(4-{[(2R,3S)-2-(methylsulfonyl)-4-oxoazetidin-3-yl]methyl}pyridin-2-yl)carbamate (52.0 mg, 0.109 mmol) in methylene chloride (2.4 mL) was treated dropwise with triethylamine (61 µL, 0.44 mmol) followed by [(1R)-1-isocyanatoethyl]benzene (20 µL, 0.14 mmol) and the reaction mixture was stirred at room temperature for 2 h at which point HPLC indicated the starting material was consumed. The reaction mixture was concentrated to a colorless oil. The material was taken up in 5 mL $CH_2Cl_2$ and concentrated and the resultant crude product was purified by prep TLC (20 cm×20 cm×1.0 mm prep TLC plate, 50% EtOAc/hex) to yield the title compound (63 mg, 91%) as a colorless stiff foam: HPLC retention time: 5.02 min (Method A); MS (ESI+) for $C_{32}H_{38}N_4O_7S$ m/z 623.5 $(M+H)^+$; MS (ESI+) for $C_{32}H_{38}N_4O_7S$ m/z 621.5 $(M+H)^+$.

Step 3. Preparation of (2R,3S)-3-[(2-aminopyridin-4-yl)methyl]-2-(methylsulfonyl)-4-oxo-N-[(1R)-1-phenylethyl]azetidine-1-carboxamide trifluoroacetate

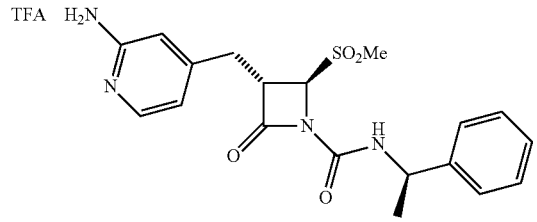 [SMILES: C[C@@H](NC(=O)N1C(=O)[C@H](Cc2ccnc(N)c2)[C@H]1S(C)(=O)=O)c1ccccc1 ; "TFA"]

A solution of tert-butyl (4-methoxybenzyl)(4-{[(2R,3S)-2-(methylsulfonyl)-4-oxo-1-{[(1R)-1-phenylethyl]carbamoyl}azetidin-3-yl]methyl}pyridin-2-yl)carbamate (62 mg, 0.10 mmol) in methylene chloride (3 mL) was cooled at 0° C. and treated with trifluoroacetic acid (1.0 mL, 13 mmol). The solution was stirred at 0° C. for 30 minutes then allowed to warm to room temperature. HPLC of the reaction mixture after 23 h indicated the starting material had been consumed. The crude reaction mixture was concentrated. The residue was taken up in 5 mL $CH_2Cl_2$ and concentrated to yield the crude product as a pink glass. The crude material was purified by CombiFlash chromatography [30 g RediSep C-18 gold silica gel cartridge, solvent gradient: 10% acetonitrile (0.07% TFA)/water (0.1% TFA) to 100% acetonitrile (0.07% TFA)] to yield the title compound (31 mg, 60%) as a white solid after lyophilization: HPLC retention time: 2.99 min (Method A); MS (ESI+) for $C_{19}H_{22}N_4O_4S$ m/z 403.2 $(M+H)^+$; $^1H$ NMR (400 MHz, MeOD) δ 7.77 (1H, d, J=6.8 Hz) 7.35 (4H, d, J=4.3 Hz) 7.27 (1H, m) 7.19 (1H, d, J=7.6 Hz) 6.98 (1H, s) 6.91 (1H, dd, J=6.8, 1.5 Hz) 5.30 (1H, d, J=2.8 Hz) 4.97 (1H, m) 4.02 (1H, m) 3.34 (1H, m) 3.21 (1H, m) 3.17 (3H, s) 1.54 (3H, d, J=7.1 Hz).

Example 16

Scheme 8: (2S,3R)-3-[(2-aminopyridin-4-yl)methyl]-2-[(methoxyimino)methyl]-4-oxo-N-[(1R)-1-phenylethyl]azetidine-1-carboxamide trifluoroacetate

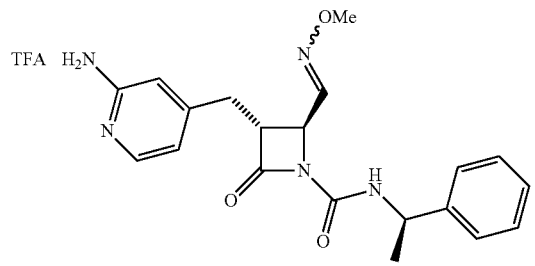

Step 1. Preparation of (4S)-1-[tert-butyl(diphenyl)silyl]-4-(hydroxymethyl)azetidin-2-one

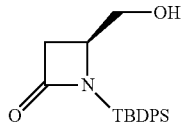

A solution of benzyl (2S)-1-[tert-butyl(diphenyl)silyl]-4-oxoazetidine-2-carboxylate (2.20 g, 4.96 mmol) in methanol (20 mL) was cooled to 0° C. (ice water) and treated with sodium tetrahydroborate (0.55 g, 15 mmol) in one portion. The reaction mixture was stirred and slowly warmed to room temperature. After 18 h, TLC indicated the starting material had been consumed. The reaction mixture was quenched with 10 mL sat $NaHCO_3$ solution and the mixture was concentrated to remove the solvent. The resultant milky suspension was diluted with 20 mL $H_2O$ and extracted with three 25 mL portions of MTBE. The organic phase was washed with 20 mL brine and dried over $MgSO_4$. The organic phase was filtered and concentrated to yield a colorless viscous oil. The crude material was purified by flash chromatography (110 g, 15-50% EtOAc/hex) to yield the title compound (0.82 g, 48%) as a white solid: HPLC retention time: 4.47 min (Method A).

Step 2. Preparation of (2S)-1-[tert-butyl(diphenyl)silyl]-4-oxoazetidine-2-carbaldehyde

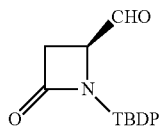

A solution of (4S)-1-[tert-butyl(diphenyl)silyl]-4-(hydroxymethyl)azetidin-2-one (530 mg, 1.56 mmol) in methylene chloride (39 mL) was treated with Dess-Martin periodinane (1.32 g, 3.12 mmol) and the reaction mixture was stirred at room temperature producing a clear solution. After 1.5 h at room temperature, the reaction mixture was diluted with 40 mL $Et_2O$ and concentrated in vacuo to afford a clear oil, which was taken up in 50 mL $Et_2O$ and a 1/1 mixture of 40 mL 10% aqueous $Na_2S_2O_3$ and 40 mL sat $NaHCO_3$ was added. The mixture was stirred vigorously until all solids had dissolved. The separated aqueous layer was extracted with two 20 mL portions of $Et_2O$ and the combined organic phase was dried over $Na_2SO_4$, filtered, and concentrated to afford the title compound (520 mg 99%) as a colorless viscous oil that was used as is in the next step: $^1$H NMR (300 MHz, $CDCl_3$) δ 9.12 (1H, d, J=4.1 Hz) 7.68 (2H, m) 7.59 (2H, m) 7.45 (6H, m) 3.76 (1H, m) 3.39 (1H, dd, J=15.8, 6.3 Hz) 3.02 (1H, dd, J=15.8, 3.1 Hz) 1.25 (9H, s).

Step 3. Preparation of (2S)-1-[tert-butyl(diphenyl)silyl]-4-oxoazetidine-2-carbaldehyde O-methyloxime

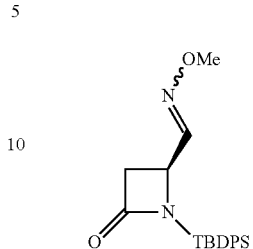

(2S)-1-[tert-butyl(diphenyl)silyl]-4-oxoazetidine-2-carbaldehyde (520 mg, 1.54 mmol) was taken up in ethanol (14 mL) and treated with pyridine (177 µL, 2.19 mmol) followed by methoxyamine hydrochloride (154 mg, 1.87 mmol) in one portion. The solution was stirred at room temperature for 19 h, at which point TLC (30% EA/hex) indicated the reaction was complete. The reaction mixture was concentrated to remove most of the solvent and the resultant colorless liquid was diluted with 20 mL $H_2O$ and extracted with three 20 mL portions of MTBE. The organic phase was washed with 20 mL $H_2O$, dried over $Na_2SO_4$, filtered and concentrated to yield a colorless viscous oil. The crude material was purified by flash chromatography (50 g, 10-20% EtOAc/hex) to yield the title compound (469 mg, 82%) as a colorless viscous oil which was a mixture of E/Z geometric isomers: HPLC retention time: 4.93 min (Method A); MS (ESI+) for $C_{21}H_{26}N_2O_2Si$ m/z 367.4 $(M+H)^+$, m/z 389.3 $(M+Na)^+$.

Step 4. Preparation of tert-butyl [4-({(2S,3R)-1-[tert-butyl(diphenyl)silyl]-2-[(methoxyimino)methyl]-4-oxoazetidin-3-yl}methyl)pyridin-2-yl](4-methoxybenzyl)carbamate

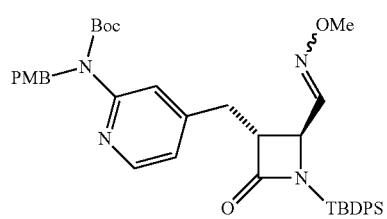

A solution of (2S)-1-[tert-butyl(diphenyl)silyl]-4-oxoazetidine-2-carbaldehyde O-methyloxime (469 mg, 1.28 mmol) in tetrahydrofuran (9.6 mL) was cooled to −78° C. and treated dropwise with a 1.2 M solution of lithium diisopropylamide in hexanes/THF/ethylbenzene (1.2 mL, 1.4 mmol). The pale yellow reaction mixture was stirred for 15 min and transferred via cannula to a precooled (−78° C.) solution of tert-butyl [4-(bromomethyl)pyridin-2-yl](4-methoxybenzyl)carbamate (570 mg, 1.4 mmol) in tetrahydrofuran (9.6 mL) dropwise over 15 min to afford a yellow-brown solution. The reaction mixture was stirred for 90 min at −78° C., at which time HPLC indicated the starting material had been consumed. The reaction was quenched by the addition of 10 mL saturated aqueous $NH_4Cl$. The cooling bath was removed and the mixture was stirred for 5 min. The reaction mixture was diluted with 20 mL $H_2O$ and extracted with two 40 mL portions of EtOAc. The combined organic phase was washed with 20 mL portions of H₂O and brine and dried over MgSO₄. The solution was filtered and concentrated to yield a maroon viscous oil. The crude material was purified by flash chromatography (80 g silica gel, 10-30% EtOAc/hex) to yield the title compound (553 mg, 62%) as a light yellow stiff foam which was a mixture of E/Z geometric isomers: HPLC retention time: 5.77/5.82 min (Method A); MS (ESI+) for C₄₀H₄₈N₄O₅Si m/z 693.6 (M+H)⁺.

Step 5. Preparation of tert-butyl (4-methoxybenzyl) [4-({(2S,3R)-2-[(methoxyimino)methyl]-4-oxoazetidin-3-yl}methyl)pyridin-2-yl]carbamate

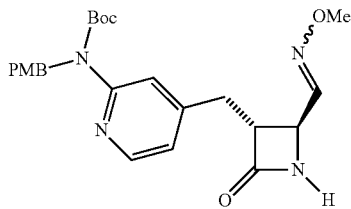

A solution of tert-butyl [4-({(2S,3R)-1-[tert-butyl(diphenyl) silyl]-2-[(methoxyimino)methyl]-4-oxoazetidin-3-yl}methyl)pyridin-2-yl](4-methoxybenzyl)carbamate (553 mg, 0.678 mmol) in methanol (10 mL) was treated dropwise with acetic acid (130 µL, 2.4 mmol) followed by 0.5 M ammonium fluoride in methanol (1.6 mL, 0.81 mmol). The solution was stirred at room temperature for 1 h, at which time HPLC indicated the starting material had been consumed. The reaction mixture was concentrated to remove the MeOH and the resultant oil was taken up in 50 mL CH₂Cl₂. The organic phase was washed with 25 mL portions of sat NaHCO₃ and H₂O, dried over Na₂SO₄, filtered and concentrated to a light yellow oil. The crude material was purified by flash chromatography (60 g silica gel, 40-80% EtOAc/hex) to yield the title compound (250 mg, 81%) as a slightly yellow glass which was a mixture of E/Z isomers: HPLC retention time: 3.59/3.66 min (Method A); MS (ESI+) for C₂₄H₃₀N₄O₅ m/z 455.3 (M+H)⁺; MS (ESI−) for C₂₄H₃₀N₄O₅ m/z 453.3 (M−H)⁻.

Step 6. Preparation of tert-butyl (4-methoxybenzyl) (4-{[(2S,3R)-2-[(methoxyimino)methyl]-4-oxo-1-{[(1R)-1-phenylethyl]carbamoyl}azetidin-3-yl]methyl}pyridin-2-yl)carbamate

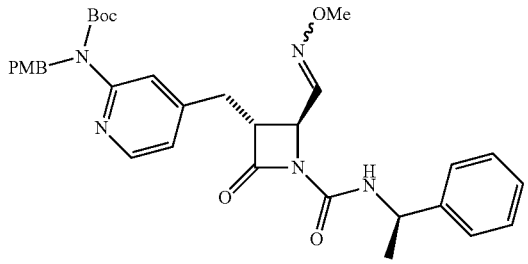

A solution of tert-butyl (4-methoxybenzyl) [4-({(2S,3R)-2-[(methoxyimino)methyl]-4-oxoazetidin-3-yl}methyl)pyridin-2-yl]carbamate (131 mg, 0.288 mmol) in methylene chloride (4.6 mL) was treated dropwise with triethylamine (160 µL, 1.2 mmol) followed by [(1R)-1-isocyanatoethyl]benzene (53 µL, 0.37 mmol) and the reaction mixture was stirred at room temperature for 21 h, at which point HPLC indicated the starting material had been consumed. The reaction was concentrated, the residue taken up in 5 mL CH₂Cl₂ and concentrated to a tan residue. The material was taken up in 1/1 Et₂O/hex and the suspension was filtered through a fine frit. The solids were washed with additional 1/1 Et₂O/hex and the filtrate concentrated to a tan stiff foam. The crude material was purified by flash chromatography (25 g silica gel, 25-40% EtOAc/hex) to yield the title compound (145 mg, 83%) as a colorless glass which was a mixture of E/Z isomers: HPLC retention time: 4.84 min (Method A); MS (ESI+) for C₃₃H₃₉N₅O₆ m/z 602.5 (M+H)⁺; MS (ESI−) for C₃₃H₃₉N₅O₆ m/z 600.4 (M−H)⁻.

Step 7. Preparation of (2S,3R)-3-[(2-aminopyridin-4-yl)methyl]-2-[(methoxyimino)methyl]-4-oxo-N-[(1R)-1-phenylethyl]azetidine-1-carboxamide trifluoroacetate

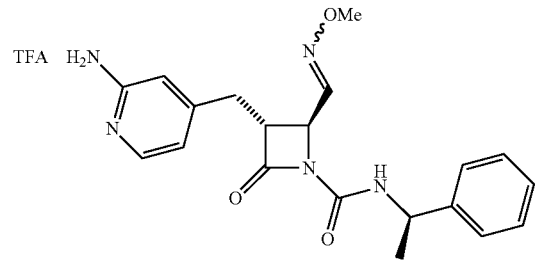 [SMILES: CON=C[C@@H]1[C@@H](Cc2ccnc(N)c2)C(=O)N1C(=O)N[C@H](C)c1ccccc1 ; "TFA"]

A solution of tert-butyl (4-methoxybenzyl)(4-{[(2S,3R)-2-[(methoxyimino)methyl]-4-oxo-1-{[(1R)-1-phenylethyl]carbamoyl}azetidin-3-yl]methyl}pyridin-2-yl)carbamate (145 mg, 0.241 mmol) in methylene chloride (4.5 mL) was cooled at 0° C. and treated with trifluoroacetic acid (1.5 mL, 20.0 mmol). The solution was stirred at 0° C. for 30 minutes then allowed to warm to room temperature. The reaction mixture was stirred for 24 h at which time HPLC indicated the starting material had been consumed. The reaction mixture was concentrated. The residue was taken up in 10 mL CH₂Cl₂ and concentrated to yield a tan glass. The crude material was purified by CombiFlash chromatography [30 g RediSep C-18 gold silica gel cartridge, solvent gradient: 10% acetonitrile (0.07% TFA)/water (0.1% TFA) to 100% acetonitrile (0.07% TFA)] to yield the title compound (71 mg, 59%) as a white solid after lyophilization: (data is for the E/Z mixture) HPLC retention time: 2.88/2.93 min (Method A); MS (ESI+) for C₂₀H₂₃N₅O₃ m/z 382.3 (M+H)⁺; ¹H NMR (400 MHz, MeOD) δ 7.78 (1H, m) 7.48 (0.6H, d, J=6.6 Hz) 7.34 (4H, m) 7.26 (1H, m) 6.96 (0.4H, d, J=4.8 Hz) 6.94 (1H, s) 6.88 (1H, m) 4.94 (1H, m) 4.73 (0.4H, dd, J=4.9, 3.2 Hz) 4.43 (0.6H, dd, J=6.4, 2.9 Hz) 3.79 (1.2H, s) 3.78 (1.8H, s) 3.73 (0.6H, dt, J=8.0, 3.0 Hz) 3.58 (0.4H, dt, J=7.6, 3.2 Hz) 3.21 (2H, m) 1.51 (3H, d, J=7.1 Hz)

Example 17

Scheme 9: Ethyl (2S,3R)-3-[(2-{[(hexyloxy)carbonyl]amino}pyridin-4-yl)methyl]-4-oxo-1-{[(1R)-1-phenylethyl]carbamoyl}azetidine-2-carboxylate

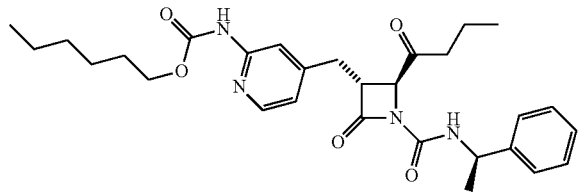

Step 1. Preparation of Ethyl (2S,3R)-3-[(2-aminopyridin-4-yl)methyl]-4-oxo-1-{[(1R)-1-phenylethyl]carbamoyl}azetidine-2-carboxylate

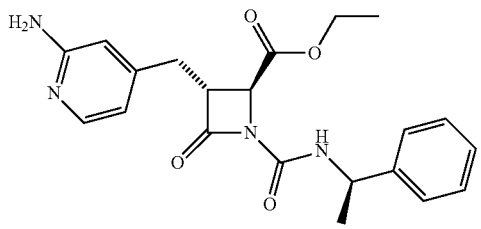 [SMILES: CCOC(=O)[C@@H]1[C@@H](Cc2ccnc(N)c2)C(=O)N1C(=O)N[C@H](C)c1ccccc1]

A solution of ethyl (2S,3R)-3-({2-[(tert-butoxycarbonyl)(4-methoxybenzyl)amino]-pyridin-4-yl}methyl)-4-oxo-1-{[(1R)-1-phenylethyl]carbamoyl}azetidine-2-carboxylate (474 mg, 0.715 mmol) in methylene chloride (9.0 mL) was cooled at 0° C. and treated dropwise with trifluoroacetic acid (3.0 mL). The solution was stirred at 0° C. for 60 min, followed by warming to room temperature. After 24 h, HPLC indicated that the starting material had been consumed. The purple oil was taken up in 15 mL CH$_2$Cl$_2$ and concentrated. The residue was dissolved in 11 mL CH$_2$Cl$_2$, treated with 10 mL sat NaHCO$_3$ and stirred at room temperature until the bubbling ceased. The mixture was poured into a separatory funnel and the phases separated. The aqueous phase was washed with 20 mL CH$_2$Cl$_2$ and the combined organic phases were dried over Na$_2$SO$_4$. The solution was filtered and concentrated to yield a stiff foam. The crude material was purified by flash chromatography (35 g silica gel, 6-8% MeOH/CH$_2$Cl$_2$) to yield the title compound (254 mg, 89%) as a colorless stiff foam: HPLC retention time: 3.01 min (Method A); MS (ESI+) for C$_{21}$H$_{24}$N$_4$O$_4$ m/z 397.3 (M+H)$^+$; MS (ESI−) for C$_{21}$H$_{24}$N$_4$O$_4$ m/z 395.3 (M−H)$^-$.

Step 2. Preparation of Ethyl (2S,3R)-3-[(2-{[(hexyloxy)carbonyl]amino}pyridin-4-yl)methyl]-4-oxo-1-{[(1R)-1-phenylethyl]carbamoyl}azetidine-2-carboxylate

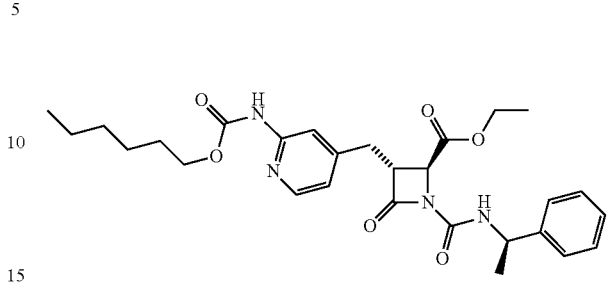

A stirred solution of ethyl (2S,3R)-3-[(2-aminopyridin-4-yl)methyl]-4-oxo-1-{[(1R)-1-phenylethyl]carbamoyl}azetidine-2-carboxylate (50.0 mg, 0.126 mmol) in dry methylene chloride (0.50 mL) under nitrogen was cooled in an ice water bath and treated with pyridine (22 µL, 0.28 mmol) followed by hexyl chloroformate (23 µL, 0.14 mmol) dropwise. The reaction mixture was stirred at 0-5° C. for 1 h followed by slow warming (over 2.5 h) to room temperature. The reaction mixture was diluted with 10 mL H$_2$O and extracted with two 15 mL portions of CH$_2$Cl$_2$. The organic phase was washed with 15 mL portions of H$_2$O and brine and was dried over Na$_2$SO$_4$. The solution was concentrated to nearly colorless viscous oil. The crude material was purified by flash chromatography (25 g silica gel, 30-50% EtOAc/hex) to yield the title compound (43 mg, 66%) as a colorless glass: HPLC retention time: 4.27 min (Method A); MS (ESI+) for C$_{28}$H$_{36}$N$_4$O$_6$ m/z 525.3 (M+H)$^+$; MS (ESI−) for C$_{28}$H$_{36}$N$_4$O$_6$ m/z 523.4 (M−H)$^-$; $^1$H NMR (400 MHz, CDCl$_3$) δ 8.21 (1H, d, J=5.1 Hz) 7.93 (1H, s) 7.73 (1H, br. s.) 7.35 (4H, m) 7.28 (1H, m) 6.89 (1H, dd, J=5.1, 1.5 Hz) 6.67 (1H, d, J=8.1 Hz) 5.03 (1H, m) 4.16 (5H, m) 3.54 (1H, ddd, J=8.3, 6.8, 2.7 Hz) 3.20 (1H, m) 3.09 (1H, m) 1.70 (2H, m) 1.55 (3H, d, J=7.1 Hz) 1.37 (6H, m) 1.16 (3H, t, J=7.2 Hz) 0.91 (3H, m).

Example 18

Scheme 9: (2S,3R)-3-[(2-{[(hexyloxy)carbonyl]amino}pyridin-4-yl)methyl]-4-oxo-1-{[(1R)-1-phenylethyl]carbamoyl}azetidine-2-carboxylic acid

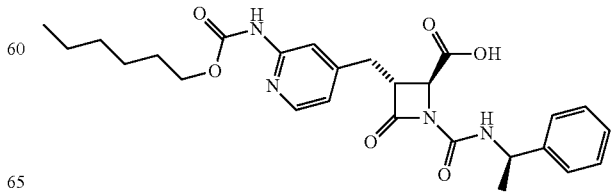

Step 1. Preparation of (2S,3R)-3-[(2-aminopyridin-4-yl)methyl]-4-oxo-1-{[(1R)-1-phenylethyl]carbamoyl}azetidine-2-carboxylate

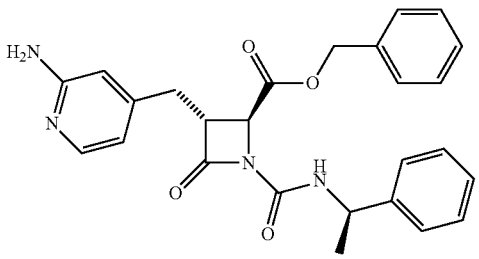 [SMILES: C[C@@H](NC(=O)N1C(=O)[C@H](Cc2ccnc(N)c2)[C@H]1C(=O)OCc1ccccc1)c1ccccc1]

A solution of benzyl (2S,3R)-3-({2-[(tert-butoxycarbonyl)(4-methoxybenzyl)amino]pyridin-4-yl}methyl)-4-oxo-1-{[(1R)-1-phenylethyl]carbamoyl}azetidine-2-carboxylate (344 mg, 0.507 mmol) in methylene chloride (6.4 mL) was cooled at 0° C. and treated dropwise with trifluoroacetic acid (2.1 mL, 28 mmol). The solution was stirred at 0° C. for 60 min, followed by warming to room temperature. After 24 h, HPLC indicated the reaction was complete. The purple oil was taken up in 15 mL $CH_2Cl_2$ and concentrated. The residue was dissolved in 20 mL $CH_2Cl_2$, treated with 10 mL sat $NaHCO_3$ and stirred at room temperature until the bubbling ceased. The mixture was poured into a separatory funnel and the phases separated. The aqueous phase was washed with 10 mL $CH_2Cl_2$ and the combined organic phases were dried over $Na_2SO_4$. The solution was filtered and concentrated to yield a light yellow stiff foam. The crude material was purified by flash chromatography (30 g silica gel, (4-6% $MeOH/CH_2Cl_2$) to yield the title compound (206 mg, 89%) as a colorless stiff foam: HPLC retention time: 3.48 min (Method A); MS (ESI+) for $C_{2-6}H_{26}N_4O_4$ m/z 459.3 (M+H)$^+$; MS (ESI−) for $C_{2-6}H_{26}N_4O_4$ m/z 457.2 (M−H)$^-$.

Step 2. Preparation of Benzyl (2S,3R)-3-[(2-{[(hexyloxy)carbonyl]amino}pyridin-4-yl)methyl]-4-oxo-1-{[(1R)-1-phenylethyl]carbamoyl}azetidine-2-carboxylate

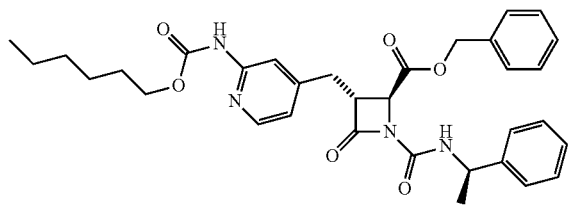 [SMILES: CCCCCCOC(=O)Nc1cc(C[C@H]2C(=O)N(C(=O)N[C@H](C)c3ccccc3)[C@@H]2C(=O)OCc2ccccc2)ccn1]

A stirred solution of benzyl (2S,3R)-3-[(2-aminopyridin-4-yl)methyl]-4-oxo-1-{[(1R)-1-phenylethyl]carbamoyl}azetidine-2-carboxylate (206 mg, 0.449 mmol) in dry methylene chloride (3.0 mL) under nitrogen was cooled in an ice water bath and treated with pyridine (95 µL, 1.2 mmol) followed by hexyl chloroformate (110 µL, 0.67 mmol) dropwise. The reaction mixture was stirred at 0-5° C. for 1 h at which point the cooling bath was allowed to slowly warm to room temperature over 2.5 h. At this time, HPLC indicated the starting material had been consumed. The reaction mixture was diluted with 20 mL $H_2O$ and extracted with two 20 mL portions of $CH_2Cl_2$. The organic phase was washed with 15 mL $H_2O$ and brine and was dried over $Na_2SO_4$. The solution was concentrated to a light yellow glass. The crude material was purified by flash chromatography (30 g silica gel, 30-50% EtOAc/hex) to yield the title compound (242 mg, 92%) as a colorless glass: HPLC retention time: 4.51 min (Method A); MS (ESI+) for $C_{33}H_{38}N_4O_6$ m/z 587.4 (M+H)$^+$.

Step 3. Preparation of (2S,3R)-3-[(2-{[(hexyloxy)carbonyl]amino}pyridin-4-yl)methyl]-4-oxo-1-{[(1R)-1-phenylethyl]carbamoyl}azetidine-2-carboxylic acid

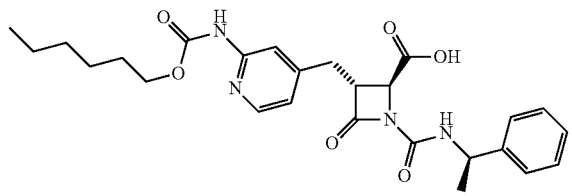 [SMILES: CCCCCCOC(=O)Nc1cc(C[C@H]2C(=O)N(C(=O)N[C@H](C)c3ccccc3)[C@@H]2C(=O)O)ccn1]

A solution of benzyl (2S,3R)-3-[(2-{[(hexyloxy)carbonyl]amino}pyridin-4-yl)methyl]-4-oxo-1-{[(1R)-1-phenylethyl]carbamoyl}azetidine-2-carboxylate (242 mg, 0.412 mmol) in methanol (4.0 mL) and ethyl acetate (4.0 mL) was carefully treated with 10% Pd—C catalyst (44 mg) The reaction flask was evacuated and filled with hydrogen gas three times and the reaction was stirred under an atmosphere of hydrogen for 1.5 h at which point HPLC indicated the starting material had been consumed. The reaction mixture was filtered through a pad of solka floc and the pad was washed with 40 mL 1/1 EtOAc/MeOH. The filtrate was concentrated to yield the title compound (197 mg, 96%) as a colorless solid: HPLC retention time: 3.77 min (Method A); MS (ESI+) for $C_{2-6}H_{32}N_4O_6$ m/z 497.3 (M+H)$^+$; MS (ESI−) for $C_{26}H_{32}N_4O_6$ m/z 495.2 (M−H)−; $^1$H NMR (400 MHz, CDCl$_3$) δ 9.34 (1H, br. s.) 8.04 (2H, s) 7.33 (4H, s) 7.28 (1H, m) 6.95 (1H, d, J=4.5 Hz) 6.78 (1H, d, J=7.8 Hz) 5.05 (1H, m) 4.31 (1H, br. s.) 4.15 (2H, t, J=6.7 Hz) 3.63 (1H, ddd, J=8.8, 6.1, 2.8 Hz) 3.22 (1H, m) 3.09 (1H, m) 1.67 (2H, m) 1.56 (3H, d, J=6.8 Hz) 1.33 (6H, m) 0.88 (3H, m).

Example 19

Scheme 9: Ethyl (2S,3R)-3-{[2-(L-alanylamino)pyridin-4-yl]methyl}-1-{[(1R)-1-(2,2-difluoro-1,3-benzodioxol-5-yl)ethyl]carbamoyl}-4-oxoazetidine-2-carboxylate trifluoroacetate

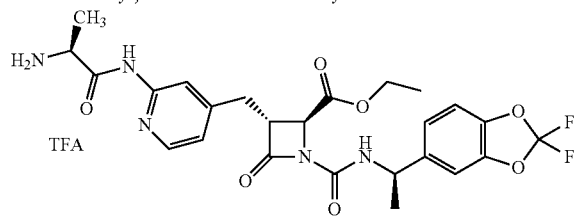

To a solution of benzyl (2S,3R)-3-[(2-aminopyridin-4-yl)methyl]-1-{[(1R)-1-(2,2-difluoro-1,3-benzodioxol-5-yl)ethyl]carbamoyl}-4-oxoazetidine-2-carboxylate (150 mg, 0.28 mmol) and N-(tert-butoxycarbonyl)-L-alanine (79 mg, 0.42 mmol) in N,N-dimethylformamide (1.7 mL) was added N,N-diisopropylethylamine (0.194 mL, 1.11 mmol) followed by N,N,N',N'-tetramethyl-O-(7-azabenzotriazol-1-yl) uronium hexafluorophosphate (159 mg, 0.42 mmol). After 72 h, the reaction was diluted with ethyl acetate and washed with sat NaHCO$_3$, brine, dried with anhydrous sodium sulfate, filtered and concentrated. The residue was partially purified by flash chromatography using hexanes/ethyl acetate (30-40%) as eluent to afford benzyl (2S,3R)-3-[(2-{[N-(tert-butoxycarbonyl)-L-alanyl]amino}pyridin-4-yl)methyl]-1-{[(1R)-1-(2,2-difluoro-1,3-benzodioxol-5-yl)ethyl]carbamoyl}-4-oxoazetidine-2-carboxylate (80 mg, approximately 80% pure, 40%) as a tan solid which was used without further purification. MS (ESI+) for C$_{35}$H$_{37}$F$_2$N$_5$O$_9$ m/z 710.2 (M+H)$^+$.

To a flask containing Pd/C (10%, 13 mg) was added a solution of the above intermediate (130 mg, a combination of two lots of similar purity) in ethanol (5 mL). The mixture was stirred under 1 atmosphere of H$_2$ for 5 h. Additional Pd/C (10%, 5 mg) was added under an atmosphere of nitrogen and the mixture stirred an additional 3 h under 1 atmosphere of H$_2$. The mixture was filtered through celite and concentrated under reduced pressure to afford (2S,3R)-3-[(2-{[N-(tert-butoxycarbonyl)-L-alanyl]amino}pyridin-4-yl)methyl]-1-{[(1R)-1-(2,2-difluoro-1,3-benzodioxol-5-yl)ethyl]carbamoyl}-4-oxoazetidine-2-carboxylic acid (100 mg) as a off white solid which was used without further purification. MS (ESI+) for C$_{28}$H$_{31}$F$_2$N$_5$O$_9$ m/z 620.2 (M+H)$^+$.

To a solution of afford (2S,3R)-3-[(2-{[N-(tert-butoxycarbonyl)-L-alanyl]amino}pyridin-4-yl)methyl]-1-{[(1R)-1-(2,2-difluoro-1,3-benzodioxol-5-yl)ethyl]carbamoyl}-4-oxoazetidine-2-carboxylic acid (100 mg, 0.16 mmol) in CH$_2$Cl$_2$ (1 mL) was added ethanol (0.28 mL, 4.84 mmol) followed by N-(3-dimethylaminopropyl)-N'-ethylcarbodiimide hydrochloride (0.120 g, 0.62 mmol) and DMAP (1 mg). After 16 h, the mixture was diluted with ethyl acetate and washed with 0.1 aqueous HCl, sat NaHCO$_3$, brine, dried with anhydrous sodium sulfate, filtered and concentrated. The residue was dissolved in CH$_2$Cl$_2$ (4 mL) and cooled to 0-5° C. To the cooled solution was added trifluoroacetic acid (2 mL). The reaction was stirred at 0-5° C. for 30 min then at ambient temperature for 1 h. Volatiles were removed under reduced pressure and the residue purified by Combi-Flash chromatography [30 g RediSep C-18 gold silica gel cartridge, solvent gradient: 10% acetonitrile (0.07% TFA)/water (0.1% TFA) to 100% acetonitrile (0.07% TFA)] and lyophilized to afford the title compound (24 mg, 22%) as a white solid. $^1$H NMR (CD$_3$OD) δ 1.09 (t, J=7 Hz, 3H), 1.54 (d, J=7 Hz, 3H), 1.62 (d, J=7 Hz, 3H), 3.15-3.29 (m, 2H), 3.69-3.74 (m, 1H), 4.05-4.18 (m, 3H), 4.28 (d, J=3 Hz, 1H), 4.95-4.98 (m, 1H), 7.14-7.24 (overlapping m, 4H), 8.07 (br s, 1H), 8.28 (d, J=5 Hz, 1H); MS (ESI+) for C$_{25}$H$_{27}$F$_2$N$_5$O$_7$ m/z 548.1 (M+H)$^+$; HPLC retention time: 3.58 min (Method C).

Example 20

Scheme 10: Ethyl (2S,3R)-1-{[(1R)-1-(2,2-difluoro-1,3-benzodioxol-5-yl)ethyl]carbamoyl}-3-{[2-({[(isobutyryloxy)methoxy]carbonyl}-amino)pyridin-4-yl]methyl}-4-oxoazetidine-2-carboxylate

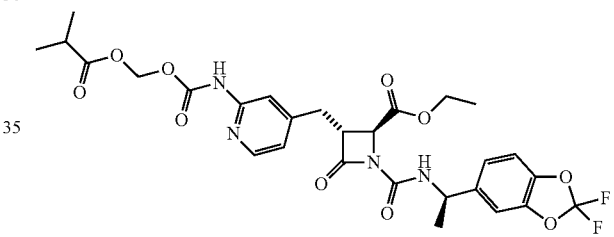

Step 1. Preparation of carbonic acid chloromethyl ester 4-nitro-phenyl ester

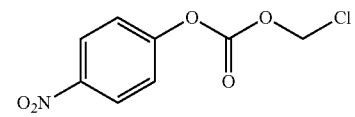 [SMILES: O=C(OCCl)Oc1ccc([N+](=O)[O-])cc1]

To a solution of 4-nitrophenol (3.81 g, 0.027 mol) in THF (50 mL) was added chloromethyl chloroformate (4.00 g, 0.030 mol) followed by N,N-diisopropylethylamine (5.29 mL, 0.030 mol). The mixture was stirred for 2 h, diluted with ethyl acetate and washed with sat NaHCO$_3$, brine, dried with anhydrous MgSO$_4$, filtered and concentrated to afford the title compound (6.10 g, 96%) as a yellow solid that was used without further purification. $^1$H NMR (CDCl$_3$) δ 5.88 (s, 2H), 7.44 (d, J=9 Hz, 2H), 8.32 (d, J=9 Hz, 2H).

Step 2. Preparation of carbonic acid iodomethyl ester 4-nitro-phenyl ester

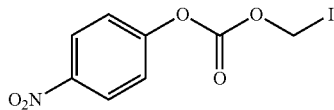 [SMILES: O=C(OCI)Oc1ccc([N+](=O)[O-])cc1]

To a solution of carbonic acid chloromethyl ester 4-nitrophenyl ester (3.00 g, 0.013 mol) in acetone (60 mL) was added sodium iodide (5.82 g, 0.039 mol) and 4 Å molecular sieves (3.00 g). The mixture was heated at 40° C. until judged complete by examination of an aliquot of the reaction mixture by $^1$H NMR (approx. 6 h). The mixture was cooled to ambient temperature and through a pad of celite. The volatiles removed at reduced pressure and the residue was dissolved in $CH_2Cl_2$, washed with sat $NaHCO_3$, water, brine, dried with anhydrous sodium sulfate, filtered and concentrated to afford the title compound (3.82 g, 91%) as a solid that was used without further purification. $^1$H NMR ($CDCl_3$) δ 6.08 (s, 2H), 7.44 (d, J=9 Hz, 2H), 8.32 (d, J=9 Hz, 2H).

Step 3. Preparation of silver 2-methylpropionate

To a solution of 2-methylpropionic acid (2.65 g, 0.030 mol) in acetonitrile (100 mL) was added silver(I) oxide (4.12 g, 0.018 mol). The flask was protected from light and heated at 70° C. for 90 min. The mixture was cooled to ambient temperature and filtered through a pad of celite. The volatiles were removed in vacuo to afford the title compound (5.65 g, 96%) as a tan solid that was used without further purification or characterization.

Step 4. Preparation of 2-methylpropionic acid 4-nitro-phenoxycarbonyloxymethyl ester

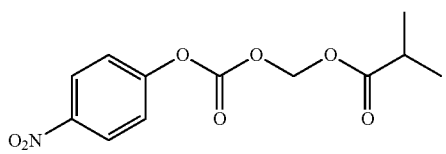 [SMILES: CC(C)C(=O)OCOC(=O)Oc1ccc([N+](=O)[O-])cc1]

To a solution of carbonic acid iodomethyl ester 4-nitrophenyl ester (2.10 g, 6.50 mmol) in toluene (30 mL) was added silver 2-methylpropanoate (2.53 g, 13.0 mmol). The mixture was heated at 55° C. until judged complete by examination of an aliquot of the reaction mixture by 1H NMR (approx. 5 h). The mixture was cooled to ambient temperature, filtered through a pad of celite and washed with 10% aqueous $K_2CO_3$, water, brine, dried with anhydrous sodium sulfate, filtered and concentrated. The residue was purified by flash chromatography using hexanes and ethyl acetate (5%) as eluent to afford the title compound (1.51 g, 82%) as an oil: 1H NMR ($CDCl_3$) δ 1.25 (d, J=7 Hz, 6H), 2.68 (heptet, J=7 Hz, 1H), 5.91 (s, 2H), 7.42 (d, J=9 Hz, 2H), 8.31 (d, J=9 Hz, 2H).

Step 5. Preparation of (2S,3R)-1-{[(1R)-1-(2,2-difluoro-1,3-benzodioxol-5-yl)ethyl]carbamoyl}-3-{[2-({[(isobutyryloxy)methoxy]carbonyl}amino)pyridin-4-yl]methyl}-4-oxoazetidine-2-carboxylic acid

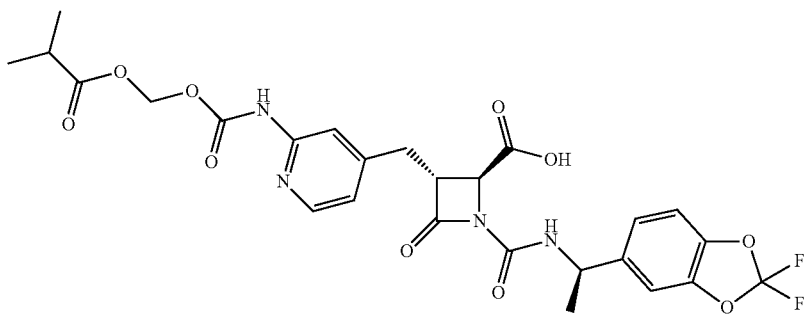 [SMILES: CC(C)C(=O)OCOC(=O)Nc1cc(C[C@H]2C(=O)N(C(=O)N[C@H](C)c3ccc4c(c3)OC(F)(F)O4)[C@@H]2C(=O)O)ccn1]

To a stirred mixture of (2S,3R)-3-[(2-aminopyridin-4-yl)methyl]-1-{[(1R)-1-(2,2-difluoro-1,3-benzodioxol-5-yl)ethyl]carbamoyl}-4-oxoazetidine-2-carboxylic acid trifluoroacetate (0.200 g, 0.36 mmol) in $CH_2Cl_2$ (0.5 mL) was added chlorotrimethylsilane (0.180 mL, 1.42 mmol) and N,N-diisopropylethylamine (0.217 mL, 1.24 mmol). The mixture was heated at 40° C. for 1 h then cooled to ambient temperature. A solution of 2-methylpropionic acid 4-nitrophenoxycarbonyloxymethyl ester (0.201 g, 0.72 mmol) in $CH_2Cl_2$ (0.36 mL) was added followed by N,N-diisopropylethylamine (0.124 mL, 0.72 mmol). The mixture was heated at 40° C. for 2 d then cooled to ambient temperature. The reaction was quenched by the addition of 0.1 aqueous HCL (pH approx. 3), stirred for 15 min then extracted with ethyl acetate. The combined organic layers were washed with brine, dried with anhydrous sodium sulfate, filtered and concentrated. The residue was purified by flash chromatography using hexanes and ethyl acetate (20%) followed by $CH_2Cl_2$/methanol (1-2%) as eluent to afford the title compound (0.080 g, 38%) as a glassy white solid: 1H NMR ($CDCl_3$) δ 1.19 (d, J=6 Hz, 6H), 1.56 (d, J=8 Hz, 3H), 2.61 (heptet, J=7 Hz, 1H), 3.11-3.31 (m, 2H), 3.68-3.74 (m, 1H), 4.32 (d, J=2 Hz, 1H), 5.01 (pentet, J=7 Hz, 1H), 5.83-5.88 (m, 2H), 6.75 (d, J=8 Hz, 1H), 7.04-7.08 (m, 4H), 8.06-8.12 (overlapping m, 2H), 9.79 (very br s, 1H); MS (ESI+) for $C_{2-6}H_{26}F_2N_4O_{10}$ m/z 593.2 (M+H)$^+$; HPLC retention time: 3.98 min (Method C).

Step 6. Preparation of ethyl (2S,3R)-1-{[(1R)-1-(2,2-difluoro-1,3-benzodioxol-5-yl)ethyl]carbamoyl}-3-{[2-({[(isobutyryloxy)methoxy]carbonyl}amino)pyridin-4-yl]methyl}-4-oxoazetidine-2-carboxylate

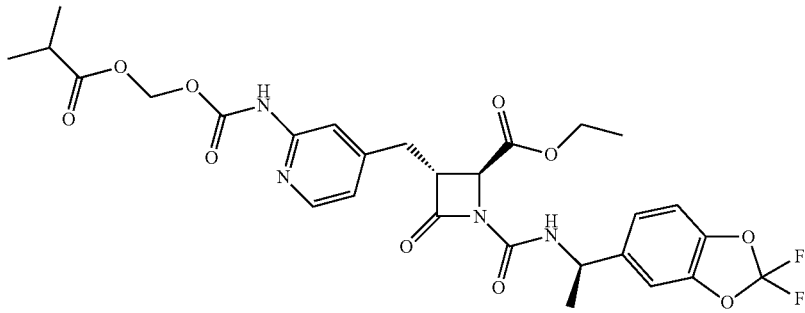 [SMILES: CCOC(=O)[C@@H]1[C@@H](Cc2ccnc(NC(=O)OCOC(=O)C(C)C)c2)C(=O)N1C(=O)N[C@H](C)c1ccc2c(c1)OC(F)(F)O2]

To a solution of (2S,3R)-1-{[(1R)-1-(2,2-difluoro-1,3-benzodioxol-5-yl)ethyl]carbamoyl}-3-{[2-({[(isobutyryloxy)methoxy]carbonyl}amino)pyridin-4-yl]methyl}-4-oxoazetidine-2-carboxylic acid (60 mg, 0.10 mmol) in $CH_2Cl_2$ (1 mL) was added ethanol (0.118 mL, 2.02 mmol), followed by N-(3-dimethylaminopropyl)-N'-ethylcarbodiimide hydrochloride (23 mg, 0.12 mmol) and 4-dimethylaminopyridine (0.6 mg, 0.006 mmol). The mixture was stirred at ambient temperature overnight, diluted with ethyl acetate and washed with 0.25 N aqueous HCl, water, brine, dried with anhydrous sodium sulfate, filtered and concentrated. The residue was purified by flash chromatography using hexanes/ethyl acetate (20-40%) as eluent to afford the title compound (35 mg, 60%) as a white solid: 1H NMR ($CDCl_3$) δ 1.14-1.22 (overlapping triplets, 9H), 1.54 (d, J=7 Hz, 3H), 2.63 (heptet, J=7 Hz, 1H), 3.10-3.27 (m, 2H), 3.54-3.60 (m, 1H), 4.13-4.24 (overlapping m, 3H), 4.99 (pentet, J=6 Hz, 1H), 5.89 (s, 2H), 6.65 (d, J=7 Hz, 1H), 6.98-7.07 (overlapping m, 4H), 8.02 (s, 1H), 8.31 (d, J=5 Hz, 1H), 9.66 (s, 1H); MS (ESI+) for $C_{28}H_{30}F_2N_4O_{10}$ m/z 621.1 (M+H)$^+$; HPLC retention time: 5.01 min (Method C).

Example 21

Scheme 11: (2S,3R)-3-[(2-(4-methoxyphenyl)ethyl]-3-methyl-4-oxo-1-{[(1R)-1-phenylethyl]carbamoyl}azetidine-2-carboxylic acid

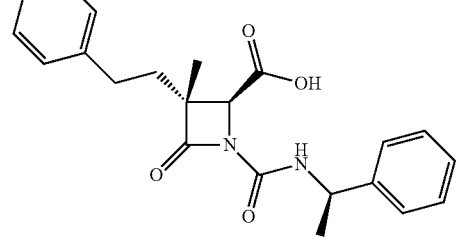

Step 1: Preparation of benzyl-(2S,3R)-1-[tert-butyl(dimethyl)silyl]-3-[2-(4-methoxyphenyl)ethyl]-3-methyl-4-oxoazetidine-2-carboxylate

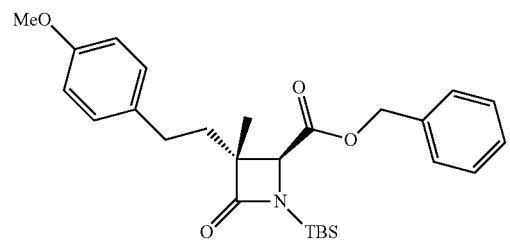

A 50 mL 2-neck round bottom flask was charged with (2S,3R)-1-[tert-butyl(dimethyl)silyl]-3-methyl-4-oxoazetidine-2-carboxylic acid (450.0 mg, 1.849 mmol) prepared by the method of Finke, P. E., et. al., J. Med. Chem. 1995, 38, 2449. The flask was evacuated and filled with nitrogen three times. Tetrahydrofuran (4.2 mL) was added and the solution was cooled at 0° C. in an ice bath. A 1.45M solution of LDA in heptane/THF/ethylbenzene (2.8 mL, 1.76 mmol) was added dropwise and the solution was stirred for 55 min at 0° C. A solution of 1-bromo-2-(4-methoxyphenyl)ethane (0.54 mL, 3.5 mmol) in tetrahydrofuran (2 mL) was added dropwise and stirring was continued at 0° C. for 2 h, followed by warming the reaction mixture to rt. After 6 h at rt, the reaction mixture was diluted with 25 mL ethyl acetate and poured into 14 mL of ice cold 0.5M $KHSO_4$ solution which was in a separatory funnel. The mixture was extracted and the phases separated. The aqueous phase was washed with two 20 mL portions of ethyl acetate and the combined organic phase was washed with 20 mL brine. The organic phase was dried over $Na_2SO_4$, filtered and concentrated to yield a tan oil. The crude product was taken up in methylene chloride (11 mL) and treated with N-(3-dimethylaminopropyl)-N'-ethylcarbodiimide hydrochloride (390 mg, 2.03 mmol) followed by benzyl alcohol (210 μL, 2.03 mmol) and 4-dimethylaminopyridine (11 mg, 0.094 mmol) and the reaction mixture was stirred at rt for 7 h. The reaction mixture was diluted with 35 mL $CH_2Cl_2$ and washed with two 25 mL portions of $H_2O$ and 20 mL brine. The organic phase was dried over $Na_2SO_4$, filtered and concentrated to yield a tan oil. The crude material was purified by flash chromatography (75 g silica gel; 5-20% ethyl acetate/hex) to yield 168 mg of the title compound contaminated with an unidentified impurity as a yellow oil. Purity was 57-62% by HPLC; HPLC retention time 5.77 min (Method A).

Step 2: Preparation of benzyl (2S,3R)-3-[2-(4-methoxyphenyl)ethyl]-3-methyl-4-oxoazetidine-2-carboxylate

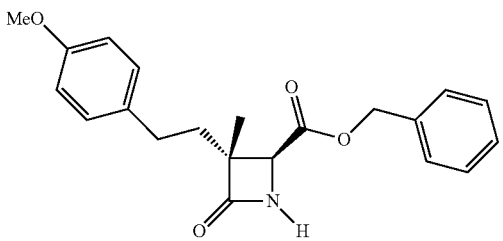 [SMILES: COc1ccc(CC[C@@]2(C)C(=O)N[C@@H]2C(=O)OCc2ccccc2)cc1]

A solution of benzyl (2S,3R)-3-[2-(4-methoxyphenyl)ethyl]-3-methyl-4-oxoazetidine-2-carboxylate (260 mg, 0.35 mmol) in methanol (5.3 mL) was treated with acetic acid (72 µL, 1.3 mmol) followed by 0.5 M NH$_4$F in methanol (1.0 mL, 0.52 mmol) dropwise and the mixture was stirred at rt for 20 h at which time HPLC indicated the starting material was still present. The reaction mixture was treated with 16 µL of HOAc and 190 µL of 0.5M NH$_4$F solution and allowed to stir at rt for an additional 20 h at which point HPLC indicated the reaction was complete. The reaction mixture was concentrated and the residue taken up in 10 mL toluene and concentrated. The process was repeated once and the residue was taken up in 25 mL CH$_2$Cl$_2$ and washed with 20 mL portions of H$_2$O and NaHCO$_3$ solution. The organic phase was dried over Na$_2$SO$_4$, filtered and concentrated to yield a light yellow viscous oil. The crude product was purified by flash chromatography (25 g silica gel; 20-40% ethyl acetate/hex) to yield the title compound (80 mg) as a colorless glass: HPLC retention time 3.81 min (Method A); $^1$H NMR (400 MHz, CDCl$_3$) δ 7.39 (m, 5H), 7.11 (d, J=8.59 Hz, 2H), 6.83 (m, 2H), 6.22 (br. s., 1H), 5.23 (m, 2H), 4.08 (s, 1H), 3.79 (s, 3H), 2.68 (m, 2H), 2.00 (m, 2H), 1.19 (s, 3H).

Step 3: Preparation of benzyl (2S,3R)-3-[2-(4-methoxyphenyl)ethyl]-3-methyl-4-oxo-1-{[(1R)-1-phenylethyl]carbamoyl}azetidine-2-carboxylate

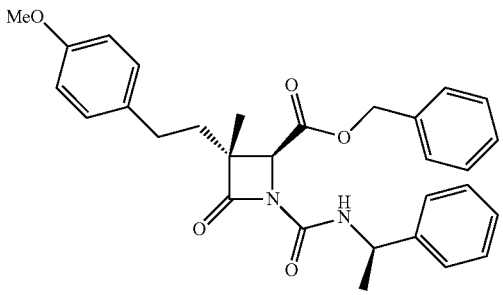 [SMILES: COc1ccc(CC[C@@]2(C)C(=O)N(C(=O)N[C@H](C)c3ccccc3)[C@@H]2C(=O)OCc2ccccc2)cc1]

A solution of benzyl (2S,3R)-3-[2-(4-methoxyphenyl)ethyl]-3-methyl-4-oxoazetidine-2-carboxylate (60.0 mg, 0.170 mmol) in methylene chloride (1.8 mL) was treated with triethylamine (95 µL, 0.679 mmol) followed by [(1R)-1-isocyanatoethyl]benzene (31 µL, 0.221 mmol) dropwise and the mixture was stirred at rt for 18 h at which point HPLC indicated the starting material had been consumed. The reaction mixture was concentrated, the residue taken up in 10 mL CH$_2$Cl$_2$ and concentrated to a colorless viscous oil/solid. The crude product was purified by prep TLC (20 cm×20 cm×1.0 mm prep TLC plate; 30% ethyl acetate/hex) to yield the title compound (72 mg) as a colorless glass: HPLC retention time 4.84 min (Method A); $^1$H NMR (400 MHz, CDCl$_3$) δ 7.35 (m, 9H), 7.29 (m, 1H), 7.10 (d, J=8.59 Hz, 2H), 6.84 (m, 2H), 6.71 (d, J=7.83 Hz, 1H), 5.27 (m, 1H), 5.18 (m, 1H), 5.09 (m, 1H), 4.43 (s, 1H), 3.80 (s, 3H), 2.72 (m, 1H), 2.62 (m, 1H), 2.04 (m, 2H), 1.57 (d, J=6.82 Hz, 3H), 1.17 (s, 3H).

Step 4: Preparation of (2S,3R)-3-[2-(4-methoxyphenyl)ethyl]-3-methyl-4-oxo-1-{[(1R)-1-phenylethyl]carbamoyl}azetidine-2-carboxylic acid

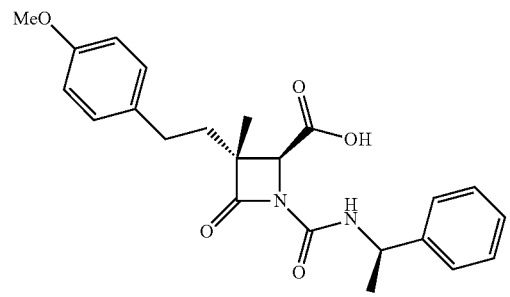 [SMILES: COc1ccc(CC[C@@]2(C)C(=O)N(C(=O)N[C@H](C)c3ccccc3)[C@@H]2C(=O)O)cc1]

A solution of benzyl (2S,3R)-3-[2-(4-methoxyphenyl)ethyl]-3-methyl-4-oxo-1-{[(1R)-1-phenylethyl]carbamoyl}azetidine-2-carboxylate (72 mg, 0.14 mmol) in methanol (2.3 mL) and ethyl acetate (2.3 mL) was carefully treated with 10% palladium on carbon (13 mg). The reaction flask was evacuated and filled with hydrogen gas three times and the reaction mixture was stirred at rt under an atmosphere of hydrogen for 3.5 h at which point TLC (25% ethyl acetate/hex) indicated the SM had been consumed. The reaction mixture was filtered through a pad of solka floc and the pad was washed with 30 mL 1/1 ethyl acetate/MeOH. The filtrate was concentrated to a colorless glass that was taken up in aqueous methanol and lyophilized to yield the title compound (56 mg) as a white solid: HPLC retention time 4.19 min (Method A); MS (ESI+) for C$_{23}$H$_{26}$N$_2$O$_5$ m/z 411.2 (M+H)$^+$; MS (ESI−) for C$_{23}$H$_{26}$N$_2$O$_5$ m/z 409.2 (M−H); $^1$H NMR (400 MHz, MeOD) δ 7.35 (m, 4H), 7.26 (m, 1H), 7.15 (m, 2H), 7.11 (d, J=7.83 Hz, 1H), 6.84 (m, 2H), 4.97 (m, 1H), 4.43 (s, 1H), 3.76 (s, 3H), 2.77 (m, 1H), 2.65 (m, 1H), 2.05 (m, 2H), 1.52 (d, J=7.07 Hz, 3H), 1.31 (s, 3H).

Example 22. Dose Response Assay for Protease Inhibitors

Materials:
Assay buffer: 20 mM Hepes, pH 7.4; 150 mM NaCl; 0.02% Tween 20
Compounds: 10 mM stocks in DMSO
Substrate: 20 mM Glp-Pro-Arg-AMC, 25 mg/2.3 mL H$_2$O (store at +4° C.) [Factor XIa, thrombin, and trypsin]

20 mM Pro-Phe-Arg-AMC (Bachem I-1295), 25 mg/2.2 mL H$_2$O (store at +4° C.) [Factor Xa]

Enzyme: Factor XIa; 0.25 μM in 50% glycerol (20 gg/mL)
Trypsin; 0.2 μM in 50% glycerol (4.8 gg/mL)
Thrombin; 0.2 μM in 50% glycerol (7.34 gg/mL)
Factor Xa; 0.2 μM in 50% glycerol (9.2 gg/mL)
These stocks are aliquoted (~100 μL/aliquot) and stored at −20° C.

Methods:
1. Dilute the substrate to 100 μM in assay buffer (30 μL/6 mL). The enzyme is diluted to 0.5 nM just prior to use (12 μL/6 mL for Factor XIa; 15 μL/6 mL for all of the rest.)
2. Pipette 50 μL of substrate into each well of the 96 well (12×8) microtiter plate. (Column 1 is used as the 100% activity control and receives no compound, and Column 12 is the blank and receives no enzyme.) Add an additional 46 μL to column 2.
3. Pipette 4 μL of each compound into the appropriate well in column 2 of the plate (unknowns assayed in triplicate, standard assayed in duplicate). The final compound concentration will be 1/50$^{th}$ of the stock.
4. Serially two-fold dilute the compound by mixing the sample in column 2, removing 50 μL to the next well (column 3), mix and remove to column 4, etc. until column 11. After mixing column 11, remove 50 μL and discard.
5. Pipette 50 μL of buffer into column 12. Initiate the reaction by adding 50 μL of enzyme solution to each well of columns 1-11 as rapidly as possible.
6. Read the plate in a spectrophotometer (SpectraMax) at 30° C., wherein each well is measured every 60 s for 30 min. For Factor Xa assays, each well is measured every 1 min for a total of 60 min.
7. For Factor XIa assays, the compounds are assayed, in duplicate, at 3 different starting concentrations, 20, 2, and 0.2 μM; 1:10, 1:100, and 1:1000 dil'n of 10 mM stock. All data sets are combined for graphing and data fitting.
8. Data can be used both for estimation of IC$_{50}$ and for estimation of K$_{on}$.

Example 23. β-lactam Stability in Rat Plasma

Stock Reagents:
Normal rat plasma, stored at −80° C.
Protocol:
1. Place 6 μL of each compound into 0.5 mL microcentrifuge tubes or 96-well U-bottom, polypropylene microtiter plate
2. Place 40 μL of acetonitrile (AcN) into 0.5 mL microcentrifuge tubes labeled 1-9
3. Add 114 μL of plasma to each compound
4. Sample 10 μL of compound/plasma into AcN at 2, 10, 20, 30, 60, 90, 120, 240, and 480 min of incubation at room temperature
5. Mix each time point after adding sample and place on ice.
6. Centrifuge time points (12,000 rpm, 3 min), remove 15 μL of the supernatant and mix with 15 μL 0.1% TFA in a V-bottom microtiter plate.
7. Place microtiter plate in autosampler of HPLC and analyze on Restek Pinnacle C18 column (2.1×100 mm).
8. Generate extracted ion chromatogram for parent compound and parent compound+18 (H$_2$O). Integrate extracted ion chromatograms (EIC) and plot % total peak area for parent and adduct versus time. Fit to a model of single phase exponential decay [Y=A$_0$*exp(-k*x)+C]. T½ is equal to ln(2)/k.

Example 24. Factor XIa Enzyme Inhibition Assays

The ability of compounds of the present invention to inhibit Factor XIa was evaluated by determining the concentration of inhibitor which resulted in a 50% reduction in enzyme activity (IC$_{50}$) using purified enzyme. Potential inhibitors of Factor XIa were evaluated using the following assay.

S-2366, pyroGlu-Pro-Arg-7-methylaminocourin (AMC), available from CPC Scientific, Inc., is based on the substrate pyro-Glu-Pro-Arg-pNA, available from Diapharma Group, Inc. (Columbus, Ohio), where the p-nitroanaline group is replaced with 7-methylaminocoumarin (AMC).

The final concentration of the substrate in the assay was 50 μM, and the final concentration of the enzyme was 0.25 nM. Inhibitors were tested by serial dilution over an appropriate range to yield a dose response curve for determination of the inhibitors' IC$_{50}$ value. The assay mixture was read every minute for 30 minutes in order to generate progress curves. The plates were read in a Spectramax m5 Multimode Plate Reader (Molecular Devices LLC, Sunnyvale, Calif.). Dose response curves were fit to Equation 1 below in which A is the maximum inhibition, B is the minimum inhibition, C is the IC$_{50}$, and D is the Hill coefficient.

$$[(A-B)/(1+(X/C)^D)]+B \quad \text{(Equation 1)}$$

Desirable compounds have an IC$_{50}$ value for inhibiting Factor XIa of less than 1 micromolar, 100 nanomolar, 10 nanomolar, or 1 nanomolar (in order of increasing preference).

TABLE 2

Potency, Selectivity, and Stability of Exemplary Compounds

| Compound | Potency hFXIa IC$_{50}$ (nM) | FXIa Fold Selectivity | | | Rat Plasma Stability (T$_{1/2}$; min) |
|---|---|---|---|---|---|
| | | FXa | Thrombin | Trypsin | |
| 1 | A | G | G | G | M |
| 2 | D | J | G | G | L |
| 3 | D | J | J | J | M |
| 4 | D | J | J | J | M |
| 5 | D | J | J | J | K |
| 6 | D | J | J | J | L |
| 7 | D | J | J | J | M |
| 8 | D | J | J | J | M |
| 9 | D | J | J | J | M |
| 10 | D | J | J | J | M |
| 11 | D | J | J | J | M |
| 12 | D | J | J | J | M |
| 13 | D | J | J | J | M |
| 14 | D | J | J | J | M |
| 15 | D | J | J | J | M |
| 16 | D | G | G | J | M |
| 17 | C | G | G | G | M |
| 18 | B | G | G | G | K |
| 19 | A | H | G | G | K |
| 20 | D | G | G | G | M |
| 21 | D | G | G | G | M |
| 22 | A | I | H | I | L |
| 23 | C | G | G | G | M |
| 24 | D | J | G | G | M |
| 25 | C | G | G | G | M |
| 26 | A | H | I | I | K |
| 27 | B | H | G | G | K |
| 28 | B | I | I | G | K |
| 29 | A | I | I | G | L |
| 31 | C | G | G | G | L |
| 32 | B | G | G | G | L |
| 33 | D | F | G | G | L |
| 34 | A | I | I | G | K |
| 35 | C | G | G | G | K |

TABLE 2-continued

Potency, Selectivity, and Stability of Exemplary Compounds

| Compound | Potency hFXIa IC$_{50}$ (nM) | FXIa Fold Selectivity FXa | Thrombin | Trypsin | Rat Plasma Stability (T$_{1/2}$; min) |
|---|---|---|---|---|---|
| 36 | A | I | I | G | M |
| 37 | A | H | I | I | M |
| 38 | A | I | I | H | L |
| 39 | C | G | G | G | K |
| 40 | B | I | I | I | L |
| 42 | A | I | I | H | L |
| 43 | B | G | G | G | L |
| 44 | A | I | I | G | L |
| 45A | C | G | G | G | L |
| 45B | B | H | H | G | L |
| 46 | B | I | G | G | M |
| 47 | A | I | I | H | L |
| 48 | C | G | G | G | L |
| 49 | A | H | I | G | L |
| 50A | B | G | I | G | L |
| 50B | C | G | G | G | K |
| 51 | D | J | J | J | M |
| 52 | B | H | I | G | L |
| 53 | B | G | G | G | K |
| 54 | B | H | I | G | M |
| 55 | D | G | G | G | L |
| 56 | D | J | J | J | L |
| 57 | D | J | J | J | K |
| 68 | A | G | I | I | L |
| 88 | A | I | I | G | L |
| 89 | A | G | I | G | L |
| 91 | A | I | I | G | L |
| 92 | B | H | I | I | K |
| 95 | D | J | J | J | M |
| 96 | D | J | J | J | M |
| 97 | D | J | J | J | K |
| 98 | A | G | I | I | L |
| 99 | A | I | I | G | K |
| 100 | C | G | G | G | M |
| 102 | D | J | J | J | L |
| 103 | A | I | H | G | K |
| 104 | A | I | I | I | L |
| 107 | D | J | J | J | M |
| 108 | D | J | J | J | M |
| 114 | D | J | J | J | M |
| 123 | C | G | G | G | L |
| 128 | D | J | J | J | L |
| 130 | C | G | G | G | L |
| 131 | D | J | J | J | M |
| 132 | C | G | G | G | K |
| 133 | D | J | J | J | M |
| 134 | C | G | G | G | L |
| 135 | C | G | G | G | L |
| 136 | C | J | J | J | M |
| 137 | B | H | I | I | K |
| 138 | D | J | J | J | M |
| 139 | D | J | J | J | M |
| 140 | B | I | I | G | K |
| 144 | D | J | J | J | M |
| 145 | D | J | J | J | M |
| 147 | D | J | J | J | M |
| 148 | C | G | G | G | K |
| 149 | B | J | J | J | M |
| 150 | B | J | J | J | K |
| 151 | B | J | J | J | K |
| 152 | D | J | J | J | M |
| 153 | D | J | J | J | M |
| 154 | D | J | J | J | M |
| 155 | C | J | J | J | M |
| 156 | C | H | I | I | L |
| 157 | D | J | J | J | M |
| 158 | C | J | J | J | M |
| 159 | C | J | J | J | M |
| 160 | C | J | J | J | K |
| 166 | A | H | I | G | K |
| 168 | A | I | I | I | L |
| 169 | C | G | H | G | L |
| 170 | B | G | G | G | K |
| 171 | D | J | J | J | K |
| 175 | D | J | J | J | L |
| 180 | B | J | J | J | K |
| 190 | D | J | J | J | M |
| 191 | D | J | J | J | M |
| 192 | D | J | J | J | M |
| 193 | D | J | J | J | M |
| 194 | D | J | J | J | M |
| 195 | D | J | J | J | M |
| 196 | D | J | J | J | M |
| 197 | C | J | J | J | M |
| 198 | C | J | J | J | M |
| 199 | C | J | J | J | M |
| 200 | D | J | J | J | M |

For Table 2: FXIa and hFXIa refer to Factor XIa and human Factor XIa, respectively.

Potency: "A" indicates <10 nM, "B" indicates 10-100 nM, "C" indicates 100-1000 nM, "D" indicates >1000 nM, and "E" indicates the data is not available or has not been determined.

Selectivity: "F" indicates <1, "G" indicates 1-500, "H" indicates 500-1000; "I" indicates >1000, and "J" indicates the data is not available or has not been determined.

Rat Plasma Stability: "K" indicates 0-100 min; "L" indicates >100 min; "M" indicates the data is not available or has not been determined.

Example 25. Solubility Assays

The following procedure was used to determine the aqueous solubility of a test compound in phosphate buffered saline (PBS-NaCl 137 mM, KCl 2.7 mM, Na$_2$HPO$_4$ 8.1 mM, KH$_2$PO$_4$ 1.5 mM, pH 7.4) in 96-well plate format by HPLC-UV/VIS analysis. The test compound was prepared at 200 µM in PBS from a 10 mM DMSO stock solution. The final DMSO concentration was 2%. The PBS buffer samples were mixed thoroughly followed by incubation at room temperature for 24 h. At the end of the incubation, the PBS buffer samples were centrifuged and supernatants analyzed by HPLC. The aqueous solubility (µM) of the test compound in PBS was determined by comparing the peak area of the principal peak in the calibration standard (200 µM) with the peak area of the corresponding peak in each of the PBS samples. The range of the assay was approximately 0.5 µM to 200 µM. The reference compounds used in each assay were metoprolol, rifampicin, ketoconazole, phenytoin, haloperidol, simvastatin, diethylstilbestrol, and tamoxifen ranking from fully soluble (200 µM) to poorly soluble (<1 µM).

Example 26. Metabolic Stability Assays

The following procedure was used to determine the stability of a test compound in pooled liver microsomes from human (mixed gender) in 96-well plate format. The test compound was quantified at five time points by HPLC-MS/MS analysis. The final microsomal protein concentration in the assay was 0.1 mg/mL. Each compound was tested at 0.1 µM with 0.01% DMSO, 0.25% acetonitrile and 0.25% methanol. The test compound was pre-incubated with human liver microsomes in phosphate buffer (pH 7.4) for 5 min in a 37° C. shaking waterbath. The reaction was initiated by adding NADPH-generating system and incubated for 0, 15, 30, 45, and 60 minutes. The reaction was stopped by transferring the incubation mixture to acetonitrile/methanol. Samples were then mixed and centrifuged and the supernatants used for HPLC-MS/MS analysis. Peak areas corresponding to the test compound were recorded. The compound remaining was calculated by comparing the peak area at each time point to time zero. Four reference compounds were tested in each assay; propranolol and imipramine are relatively stable, whereas verapamil and terfenadine are readily metabolized in human liver microsomes.

Example 27. Plasma Protein Binding Assays

The following procedure was used to determine the plasma protein binding of a test compound in pooled plasma from human (mixed gender) via equilibrium dialysis in a 96-well plate format.

The dialysate compartment is loaded with phosphate-buffered saline (pH 7.4) and the sample side is loaded with plasma spiked with the test compound at a concentration of 10 μM. After loading, samples are covered and incubated for 4 hours at 37° C. After incubation, each compartment is sampled, diluted with acetonitrile/buffer and centrifuged. The supernatants are analyzed by HPLC-MS/MS. The amount measured in the plasma compartment includes both free and bound drug, while that on the buffer side represents free drug only; the differences are used to calculate the percentage plasma protein bound. Three reference compounds were tested in each assay; acebutolol, quinidine and warfarin. These compounds yield protein binding values that represent low, medium, and high binding to human plasma proteins, respectively.

TABLE 3

Plasma Protein Binding, Solubility and Metabolic Stability of Exemplary Compounds

| Compound | Protein Binding Human plasma: % bound; 10 μM: 4 h incubation @ 37 C. | Aqueous Solubility (μM in PBS); 10 mM: 4 h incubation @ 37 C. | Metabolic Stability Human microsomes: half-life (mins) 0.1 μM: time points: 0, 15, 30, 45, 60 min @ 37 C. |
|---|---|---|---|
| 38 | P | R | V |
| 88 | P | R | V |
| 91 | O | R | V |
| 92 | Q | T | Y |
| 100 | N | R | X |
| 128 | N | R | V |
| 134 | N | R | W |
| 158 | P | U | W |
| 169 | O | R | V |

N indicates >98%; O indicates 90-98%; P indicates <90%; Q indicates the data is not available, not detectable, or has not been determined.
R indicates >100 μM; S indicates 10-100 μM; T indicates 1-10 μM; U indicates <1 μM
V indicates >60 minutes; W indicates 30-60 minutes; X indicates <30 minutes; Y indicates the data is not available, not detectable, or has not been determined.

The invention claimed is:

1. A method of reducing the risk of deep vein thrombosis comprising administering to a subject that has suffered an ischemic event an effective amount of (1) a compound of formula (II) or (2) a pharmaceutically acceptable salt thereof pharmaceutical composition comprising a compound of formula (II) or a pharmaceutically acceptable salt thereof:

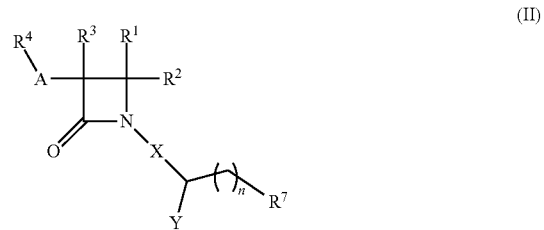

(II)

wherein
R$^1$ is H or —C$_{1-6}$ alkyl;
R$^2$ is H, C$_{1-6}$ alkyl, —CO$_2$R$^5$, —C(O)NR$^9$R$^{10}$, —CN, —CHN(OR$^5$) or a heteroaryl;
R$^3$ is H or —C$_{1-6}$ alkyl;
A is a bond, C$_{1-6}$ alkylene, C$_{2-6}$ alkenylene or C$_{2-6}$ alkynylene;
R$^4$ is cycloalkyl, aryl, heteroaryl or heterocyclyl, each of which is substituted with 0-3 occurrences of —NH$_2$ or R$^6$;
each R$^5$ is independently H, —C$_{1-6}$ alkyl, aralkyl, or aryl substituted with 0-3 occurrences of —NH$_2$ or R$^6$;
X is —C(O)O—, —OC(O)—, —C(O)S(O)$_2$—, —S(O)$_2$C(O)—, —C(O)N(R$^5$)— or —N(R$^5$)C(O)—;
Y is cycloalkyl, heteroaryl, or heterocyclyl, each of which is substituted with 0-3 occurrences of —NH$_2$ or R$^6$; or substituted —C$_{1-6}$ alkyl or phenyl substituted with 1-2 occurrences of R$^6$;
R$^7$ is H, —C$_{1-6}$ alkyl, cycloalkyl, aryl, heteroaryl or heterocyclyl, each of which is substituted with 0-3 occurrences of —NH$_2$ or R$^6$;
wherein when R$^6$ is a substituent for any of R$^4$, R$^5$, or R$^7$, then each R$^6$ is independently halo, hydroxy, cyano, nitro, C$_{1-6}$ alkyl, C$_{1-6}$ alkoxy, —NR$^9$R$^{10}$, —NHR$^{10}$, —C(O)R$^{11}$, —C(O)OR$^{11}$, —C(O)NR$^9$R$^{10}$, —C(NR$^8$)(N(R$^8$)$_2$), —SO$_q$R$^{11}$, —SO$_2$NR$^9$R$^{10}$, —NHC(O)OR$^{11}$, —NHC(O)R$^{11}$, aryl, heteroaryl, aralkyl, cycloalkyl, heteroaralkyl, heterocyclyl or heterocyclylalkyl; or
two R$^6$ groups taken together with the atoms to which they are attached form a 5-7-membered ring; and
when R$^6$ is a substituent for Y, each R$^6$ is independently halo, haloalkoxy; or
two R$^6$ groups taken together with the atoms to which they are attached form:

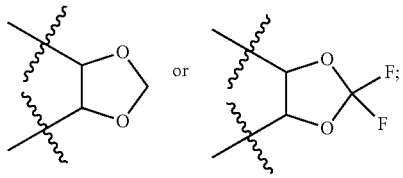 [SMILES: *C1OCOC1* ; "or" ; *C1OC(F)(F)OC1*]

each R$^8$ is independently H, —C$_{1-6}$ alkyl, —C(O)R$^5$, —C(O)OR$^5$, aryl, heteroaryl, aralkyl, heteroaralkyl, heterocyclyl or heterocyclylalkyl;
each of R$^9$ and R$^{10}$ is independently —C$_{1-6}$ alkyl, cycloalkyl, heterocyclyl, aryl, or heteroaryl, or
R$^9$ and R$^{10}$ together form an optionally substituted 5-7-membered ring;
each R$^{11}$ is independently H, —C$_{1-10}$ alkyl, aralkyl, or aryl;
q is an integer from 0 to 2; and
n is an integer from 0 to 2.

2. A method of inhibiting Factor XIa in a subject, comprising administering to the subject that has suffered ischemia an effective amount of (1) a compound of formula (II) or (2) a pharmaceutically acceptable salt thereof pharmaceutical composition comprising a compound of formula (II) or a pharmaceutically acceptable salt thereof:

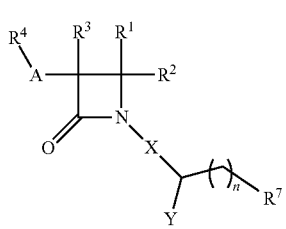

(II)

or a pharmaceutically acceptable salt thereof, wherein
$R^1$ is H or —$C_{1-6}$ alkyl;
$R^2$ is H, —$C_{1-6}$ alkyl, —$CO_2R^5$, —$C(O)NR^9R^{10}$, —CN, —$CHN(OR^5)$ or a heteroaryl;
$R^3$ is H or —$C_{1-6}$ alkyl;
A is a bond, $C_{1-6}$ alkylene, $C_{2-6}$ alkenylene or $C_{2-6}$ alkynylene;
$R^4$ is cycloalkyl, aryl, heteroaryl or heterocyclyl, each of which is substituted with 0-3 occurrences of —$NH_2$ or $R^6$;
each $R^5$ is independently H, —$C_{1-6}$ alkyl, aralkyl, or aryl substituted with 0-3 occurrences of —$NH_2$ or $R^6$;
X is —C(O)O—, —OC(O)—, —C(O)S(O)$_2$—, —S(O)$_2$C(O)—, —C(O)N($R^5$)— or —N($R^5$)C(O)—;
Y is cycloalkyl, heteroaryl, or heterocyclyl, each of which is substituted with 0-3 occurrences of —$NH_2$ or $R^6$; or substituted —$C_{1-6}$ alkyl or phenyl substituted with 1-2 occurrences of $R^6$;
$R^7$ is H, —$C_{1-6}$ alkyl, cycloalkyl, aryl, heteroaryl or heterocyclyl, each of which is substituted with 0-3 occurrences of —$NH_2$ or $R^6$;
wherein when $R^6$ is a substituent for any of $R^4$, $R^5$, or $R^7$, then each $R^6$ is independently halo, hydroxy, cyano, nitro, $C_{1-6}$ alkyl, $C_{1-6}$ alkoxy, —$NR^9R^{10}$, —$NHR^{10}$, —$C(O)R^{11}$, —$C(O)OR^{11}$, —$C(O)NR^9R^{10}$, —$C(NR^8)(N(R^8)_2)$, —$SO_qR^{11}$, —$SO_2NR^9R^{10}$, —$NHC(O)OR^{11}$, —$NHC(O)R^{11}$, aryl, heteroaryl, aralkyl, cycloalkyl, heteroaralkyl, heterocyclyl or heterocyclylalkyl; or
two $R^6$ groups taken together with the atoms to which they are attached form a 5-7-membered ring; and
when $R^6$ is a substituent for Y, each $R^6$ is independently halo, haloalkoxy; or
two $R^6$ groups taken together with the atoms to which they are attached form:

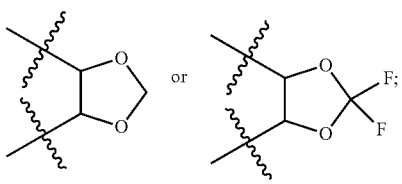 [SMILES: *C1OCOC1* ; "or" ; *C1OC(F)(F)OC1*]

each $R^8$ is independently H, —$C_{1-6}$ alkyl, —$C(O)R^5$, —$C(O)OR^5$, aryl, heteroaryl, aralkyl, heteroaralkyl, heterocyclyl or heterocyclylalkyl;

each of $R^9$ and $R^{10}$ is independently —$C_{1-6}$ alkyl, cycloalkyl, heterocyclyl, aryl, or heteroaryl, or
$R^9$ and $R^{10}$ together form an optionally substituted 5-7-membered ring;
each $R^{11}$ is independently H, —$C_{1-10}$ alkyl, aralkyl, or aryl;
q is an integer from 0 to 2; and
n is an integer from 0 to 2.

3. The method of claim 2, wherein the subject is a mammal.

4. The method of claim 2, wherein the subject is a human.

5. The method of claim 2, wherein the subject is undergoing surgery.

6. The method of claim 2, wherein the subject is undergoing hip or knee replacement surgery.

7. The method of claim 2, wherein the subject is a subject with nonvalvular atrial fibrillation.

8. The method of claim 2, wherein the subject has hypertension.

9. The method of claim 1, wherein the compound is

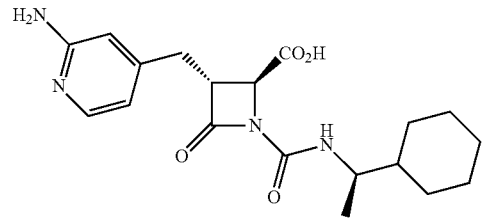 [SMILES: C[C@@H](NC(=O)N1C(=O)[C@H](Cc2ccnc(N)c2)[C@H]1C(=O)O)C1CCCCC1]

or a pharmaceutically acceptable salt thereof.

10. The method of claim 1, wherein the compound is

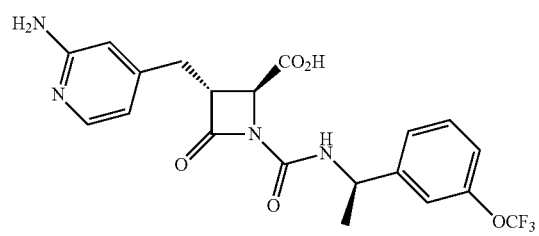 [SMILES: C[C@@H](NC(=O)N1C(=O)[C@H](Cc2ccnc(N)c2)[C@H]1C(=O)O)c1cccc(OC(F)(F)F)c1]

or a pharmaceutically acceptable salt thereof.

11. The method of claim 1, wherein the compound is

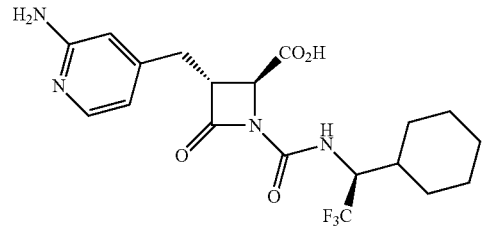 [SMILES: Nc1cc(C[C@H]2C(=O)N(C(=O)N[C@@H](C3CCCCC3)C(F)(F)F)[C@@H]2C(=O)O)ccn1]

or a pharmaceutically acceptable salt thereof.

12. The method of claim 1, wherein the compound is

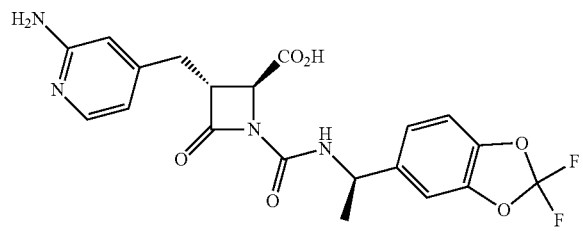 [SMILES: C[C@@H](NC(=O)N1C(=O)[C@H](Cc2ccnc(N)c2)[C@H]1C(=O)O)c1ccc2c(c1)OC(F)(F)O2]

or a pharmaceutically acceptable salt thereof.

13. The method of claim 1, wherein the compound is

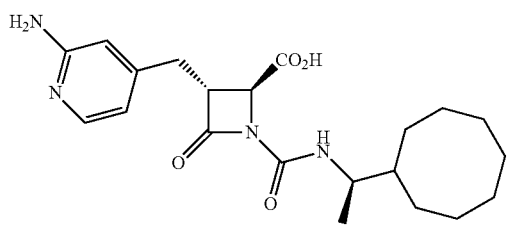 [SMILES: C[C@@H](NC(=O)N1C(=O)[C@H](Cc2ccnc(N)c2)[C@H]1C(=O)O)C1CCCCCCC1]

or a pharmaceutically acceptable salt thereof.

14. The method of claim 2, wherein the compound is

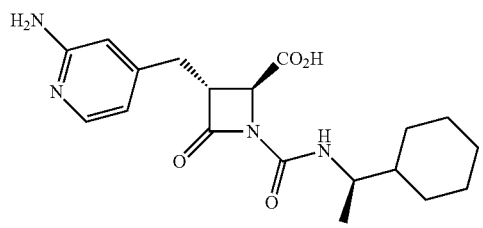 [SMILES: C[C@@H](NC(=O)N1C(=O)[C@H](Cc2ccnc(N)c2)[C@H]1C(=O)O)C1CCCCC1]

or a pharmaceutically acceptable salt thereof.

15. The method of claim 2, wherein the compound is

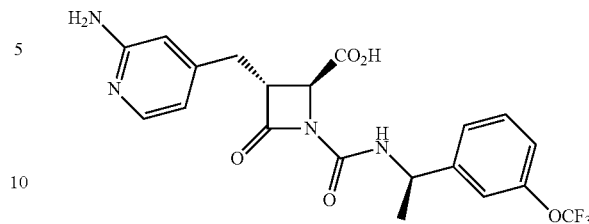

or a pharmaceutically acceptable salt thereof.

16. The method of claim 2, wherein the compound is

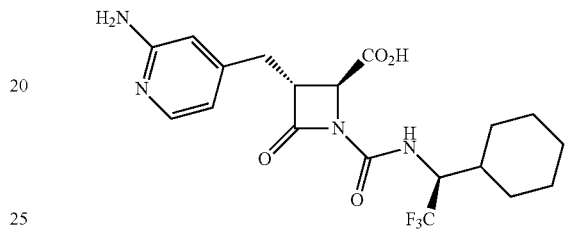

or a pharmaceutically acceptable salt thereof.

17. The method of claim 2, wherein the compound is

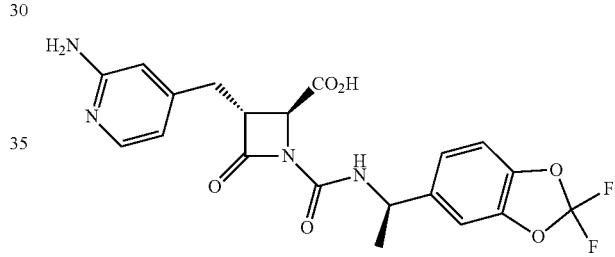

or a pharmaceutically acceptable salt thereof.

18. The method of claim 2, wherein the compound is

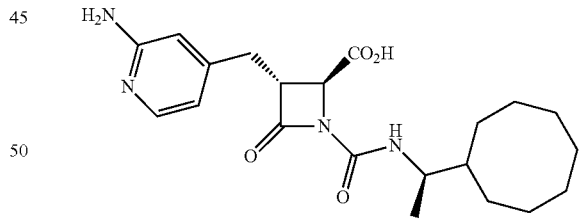

or a pharmaceutically acceptable salt thereof.

* * * * *